(12) United States Patent
Blumberg et al.

(10) Patent No.: US 7,098,212 B2
(45) Date of Patent: Aug. 29, 2006

(54) PIPERAZINE DERIVATIVES

(76) Inventors: Laura C. Blumberg, 5 Division St., Waterford, CT (US) 06385; Matthew F. Brown, 443 Wheeler Rd., Stonington, CT (US) 06378; Matthew M. Hayward, 3 Pyrus Ct., Old Lyme, CT (US) 06371; Gregory D. Lundquist, 374 Forsyth Rd., Salem, CT (US) 06420; Christopher S. Poss, 231 Wyassup Rd., North Stonington, CT (US) 06379; Andrei Shavnya, 48 Dean Rd., East Lyme, CT (US) 06333

( * ) Notice: Subject to any disclaimer, the term of this patent is extended or adjusted under 35 U.S.C. 154(b) by 336 days.

(21) Appl. No.: 10/273,658

(22) Filed: Oct. 18, 2002

(65) Prior Publication Data

US 2004/0034034 A1 Feb. 19, 2004

Related U.S. Application Data

(60) Provisional application No. 60/338,601, filed on Oct. 22, 2001.

(51) Int. Cl.
*A61K 31/506* (2006.01)
*A61K 31/495* (2006.01)
*A61K 31/496* (2006.01)
*C07D 295/00* (2006.01)
*C07D 403/12* (2006.01)

(52) U.S. Cl. ............... 514/252.14; 514/253.13; 514/254.01; 514/254.02; 514/254.05; 514/255.01; 544/295; 544/365; 544/369; 544/372; 544/391; 544/366

(58) Field of Classification Search ............ 544/391, 544/295, 365, 369, 372, 366; 514/255.01, 514/252.14, 253.13, 254.01, 254.02, 254.05
See application file for complete search history.

(56) References Cited

U.S. PATENT DOCUMENTS

| 3,119,742 | A | 1/1964 | Heimlich et al. | 167/82 |
| 3,492,397 | A | 1/1970 | Peters et al. | 424/20 |
| 3,538,214 | A | 11/1970 | Polli et al. | 424/19 |
| 4,060,598 | A | 11/1977 | Groppenbächer et al. | 424/33 |
| 4,173,626 | A | 11/1979 | Dempski et al. | 424/19 |
| 5,607,930 | A | 3/1997 | Long et al. | 514/235.8 |
| 5,780,472 | A | 7/1998 | Cho et al. | 514/252 |
| 6,207,665 | B1 | 3/2001 | Bauman et al. | 514/235.8 |
| 6,649,611 | B1 | 11/2003 | Blumberg et al. | 514/235.8 |
| 2002/0119961 | A1 | 8/2002 | Blumberg et al. | |

FOREIGN PATENT DOCUMENTS

| WO | WO 9501343 | 1/1995 |
| WO | WO 9856771 | 12/1998 |
| WO | WO 0172728 | 10/2001 |
| WO | WO 0236581 | 5/2002 |

OTHER PUBLICATIONS

Trivedi et al. Annual Reports in Medicinal Chemistry, vol. 35, p. 191-200 (2000).*
Combadiere et al. J. Biol. Chem., 270 (50) 29671-29675, 1995.
Teran et al., J. Immunol., 1806-1812, 1996.
Smith et al., J. Immunol, 153, 4704, 1994.
Cook et al., Science, 269, 1583, 1995.
Belperio et al., J. Immunol., 165, 461, 2000.
Gao et al., J. Clin Invest, 105, 35, 2000.
Rottman et al., Eur. J. Imm, 30, 2372, 2000.
Kuna et al., J. Allergy Clinical Immunology, (1994), Abstract 321.
Maryanoff et al., Journal of American Chemical Society, (1985), vol. 107, pp. 217-226.
Giasl et al., Helvetica Chimica Acta, (1997), vol. 80, pp. 671-683.
LeBerre et al., Bulletin De La Société Chimique France, (1975), N° 150, pp. 807-811.
Boros et al., Synthetic Communications, (2001), vol. 31, No. 4, pp. 505-510.
Cignarella et al, Eur. J. Med. Chem., (1990), vol. 25, pp. 749-756.
Merck Index, 13th ed., Merck & Co., vol. 201, p. 772, Fipexide, No. 4114.

* cited by examiner

*Primary Examiner*—Emily Bernhardt

(57) ABSTRACT

The present invention relates to compounds of the formula I

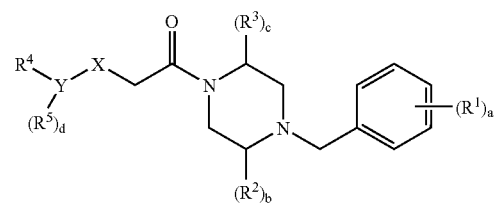

and the pharmaceutically acceptable forms thereof; wherein X, Y, a, b, c, d, $R^1$, $R^2$, $R^3$, $R^4$ and $R^5$ are as defined herein. Moreover, the present invention is also directed at pharmaceutical compositions comprising a compound of the formula I and a pharmaceutically acceptable carrier. Furthermore, the present invention is directed at methods of using the herein described compounds and compositions for treating or preventing a disorder or condition that can be treated or prevented by antagonizing the CCR1 receptor in a mammal.

20 Claims, No Drawings

PIPERAZINE DERIVATIVES

This application claims the benefit of priority of provisional Patent Application Ser. No. 60/338,601 filed Oct. 22, 2001, which is incorporated herein in its entirety for all purposes.

BACKGROUND OF THE INVENTION

The present invention relates to novel piperazine derivatives, methods of use and pharmaceutical compositions containing them.

The compounds of the invention are potent and selective inhibitors of MIP-1α (CCL3) binding to its receptor CCR1 found on inflammatory and immunomodulatory cells (preferably leukocytes and lymphocytes). The CCR1 receptor is also sometimes referred to as the CC-CKR1 receptor. These compounds also inhibit MIP-1α (and the related chemokines shown to interact with CCR1 (e.g., RANTES (CCL5), MCP-2 (CCL8), MCP-3 (CCL7), HCC-1 (CCL14) and HCC-2 (CCL15))) induced chemotaxis of THP-1 cells and human leukocytes and are potentially useful for the treatment or prevention of autoimmune diseases (such as rheumatoid arthritis, type I diabetes (recent onset), lupus, inflammatory bowel disease, optic neuritis, psoriasis, multiple sclerosis, polymyalgia rheumatica, uveitis, and vasculitis), acute and chronic inflammatory conditions (such as osteoarthritis, adult Respiratory Distress Syndrome, Respiratory Distress Syndrome of infancy, ischemia reperfusion injury, and glomerulonephritis), allergic conditions (such as asthma and atopic dermatitis), inflammation associated with infection (such as viral inflammation (including influenza and hepatitis) and Guillian-Barre syndrome syndrome), chronic bronchitis, xeno-transplantation, transplantation tissue rejection (chronic and acute), organ rejection (chronic and acute), atherosclerosis, restenosis (including, but not limited to, restenosis following balloon and/or stent insertion), HIV infectivity (co-receptor usage), and granulomatous diseases (including sarcoidosis, leprosy and tuberculosis) and sequelae associated with certain cancers such as multiple myeloma. Compounds in this series may also have utility for the prevention of cancer metastasis. Compounds in this series may also limit the production of cytokines at inflammatory sites, including but not limited to TNF and IL-1, as a consequence of decreasing cell infiltration, providing benefit for diseases linked to TNF and IL-1, including congestive heart failure, pulmonary emphysema or dyspnea associated therewith, emphysema; HIV-1, HIV-2, HIV-3; cytomegalovirus (CMV), adenoviruses, Herpes viruses (*Herpes zoster* and *Herpes simplex*). They may also provide benefit for the sequelae associated with infection where such infection induces production of detrimental inflammatory cytokines such as TNF e.g, fungal meningitis, joint tissue damage, hyperplasia, pannus formation and bone resorption, psoriatic arthritis, hepatic failure, bacterial meningitis, Kawasaki syndrome, myocardial infarction, acute liver failure, lyme disease, septic shock, cancer, trauma, and malaria, etc.

MIP-1α and RANTES are soluble chemotactic peptides (chemokines) which are produced by a variety of cell types, including inflammatory cells, such as CD8+ lymphocytes, polymorphonuclear leukocytes (PMNs) and macrophages, *J. Biol. Chem.*, 270 (30) 29671–29675 (1995). These chemokines act by inducing the migration and activation of key inflammatory and immunomodulatory cells. Elevated levels of chemokines have been found in the synovial fluid of rheumatoid arthritis patients, chronic and rejecting tissue from transplant patients and in the nasal secretions of allergic rhinitis patients following allergen exposure (Teran , et al., *J. Immunol.*, 1806–1812 (1996), and Kuna et al., *J. Allergy Clin. Immunol.* 321 (1994)). Antibodies which interfere with chemokine/receptor interaction by neutralizing MIP1α or RANTES have provided indirect evidence for the role of CCR1 in cell infiltration and in disease. (Smith et al., *J. Immunol*, 153, 4704 (1994) and Cook et al., *Science*, 269, 1583 (1995), Belperio et. al. *J. Immunol*, 165, 461 (2000). A more direct role for CCR1 has been demonstrated in transgenic mice lacking this receptor which have shown decreased inflammatory responses, prolonged survival of allogeneic tissue transplants (Gao et. al. *J. Clin Invest* 105; 35 (2000)), and decreased disease in a model of multiple sclerosis (Rottman et al *Eur. J. Imm* 30; 2372 (2000). Together this data demonstrates that CCR1 receptor antagonists would be an effective treatment of several immune based diseases. The compounds described within are potent and selective antagonists of the CCR1 receptor.

Different piperazine derivatives have been recently described as anti-inflammatory agents in U.S. Pat. No. 6,207,665, which is incorporated herein in its entirety for all purposes. These agents are also described as inhibiting the activity of the chemokines, MIP-1α and RANTES.

SUMMARY OF THE INVENTION

In one aspect, the present invention relates to compounds of the formula I

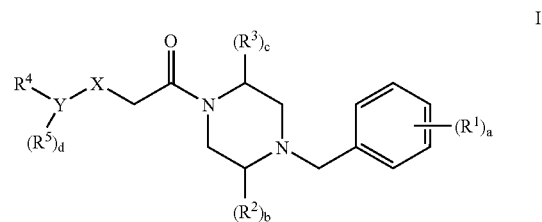

and the pharmaceutically acceptable forms thereof; wherein a is 0, 1, 2, 3, 4, or 5;

b is 0, 1 or 2;

c is 0, 1, or 2;

d is 0, 1, 2, 3, or 4;

X is —O—, —S—, —$CH_2$—, or —$NR^6$—;

Y is $(C_6–C_{10})$aryl, or $(C_2–C_9)$heteroaryl;

each $R^1$ is independently H—, HO—, halo-, $(C_1–C_8)$alkyl-, $(C_1–C_8)$alkyl-O—, HO—$(C_1–C_8)$alkyl-, NC—, $H_2N$—, $H_2N$—$(C_1–C_8)$alkyl-, HO—(C=O)—, $(C_1–C_8)$alkyl-(C=O)—, $(C_1–C_8)$alkyl-(C=O)—$(C_1–C_8)$alkyl-, $H_2N$—(C=O)—, or $H_2N$—(C=O)—$(C_1–C_8)$alkyl-;

each $R^2$ and $R^3$ are independently H—, oxo, $(C_1–C_8)$alkyl-, $(C_3–C_8)$cycloalkyl-$(C_1–C_8)$alkyl-, $(C_6–C_{10})$aryl-, $(C_6–C_{10})$aryl-$(C_1–C_8)$alkyl-, HO—$(C_1–C_8)$alkyl-, $(C_1–C_8)$alkyl-O—$(C_1–C_8)$alkyl-, $H_2N$—$(C_1–C_8)$alkyl-, $(C_1–C_8)$alkyl-NH—$(C_1–C_8)$alkyl-, [$(C_1–C_8)$alkyl]$_2N$—$(C_1–C_8)$alkyl-, $(C_2–C_9)$heterocyclyl-$(C_1–C_8)$alkyl-, $(C_3–C_8)$cycloalkyl-NH—$(C_1–C_8)$alkyl-, $(C_1–C_8)$alkyl-(C=O)—NH—$(C_1–C_8)$alkyl-, $(C_1–C_8)$alkyl-O—(C=O)—NH—$(C_1–C_8)$alkyl-, $H_2N$—(C=O)—NH—$(C_1–C_8)$alkyl-, $(C_1–C_8)$alkyl-$SO_2$—NH—$(C_1–C_8)$alkyl-, $(C_2–C_9)$heteroaryl-$(C_1–C_8)$alkyl-, $H_2N$—(C=O)—, or $H_2N$—(C=O)—$(C_1–C_8)$alkyl-;

$R^4$ is [HO—(C=O)—][$H_2N$—]($C_1$–$C_8$)alkyl-, [HO—(C=O)—][($C_1$–$C_8$)alkyl)NH—]($C_1$–$C_8$)alkyl-, [HO—(C=O)—][(($C_1$–$C_8$)alkyl)$_2$N—]($C_1$–$C_8$)alkyl-, [HO—(C=O)—($C_1$–$C_8$)alkyl][($C_1$–$C_8$)alkyl]N—, [HO—(C=O)—($C_1$–$C_8$)alkyl][($C_1$–$C_8$)alkyl]N—($C_1$–$C_8$)alkyl-, [HO—(C=O)—($C_1$–$C_8$)alkyl][($C_1$–$C_8$)alkyl-SO$_2$]N—, [HO—(C=O)—($C_1$–$C_8$)alkyl][($C_1$–$C_8$)alkyl-SO$_2$]N—($C_1$–$C_8$)alkyl-, [HO—(C=O)—($C_1$–$C_8$)alkyl][($C_1$–$C_8$)alkyl-(C=O)—]N—, [HO—(C=O)—($C_1$–$C_8$)alkyl][($C_1$–$C_8$)alkyl-(C=O)—]N—($C_1$–$C_8$)alkyl-, [HO—(C=O)—($C_1$–$C_8$)alkyl][($C_1$–$C_8$)alkyl-O—(C=O)—]N—, [HO—(C=O)—($C_1$–$C_8$)alkyl][($C_1$–$C_8$)alkyl-O—(C=O)—]N—($C_1$–$C_8$)alkyl-, [HO—(C=O)—($C_1$–$C_8$)alkyl][($C_1$–$C_8$)alkylN—(C=O)—]N—, [HO—(C=O)—($C_1$–$C_8$)alkyl][($C_1$–$C_8$)alkyl-NH—(C=O)—]N—($C_1$–$C_8$)alkyl-, HO—(C=O)—($C_1$–$C_8$)alkyl-O—N=($C_1$–$C_8$)alkyl-, HO—(C=O)—($C_1$–$C_8$)alkyl-SO$_2$—, HO—(C=O)—($C_1$–$C_8$)alkyl-SO$_2$—($C_1$–$C_8$)alkyl-, HO—(C=O)—($C_1$–$C_8$)alkyl-SO$_2$—NH—, HO—(C=O)—($C_1$–$C_8$)alkyl-SO$_2$—NH—($C_1$–$C_8$)alkyl-, HO—(C=O)—($C_1$–$C_8$)alkyl-NH—SO$_2$—, HO—(C=O)—($C_1$–$C_8$)alkyl-NH—SO$_2$-($C_1$–$C_8$)alkyl-, HO—(C=O)—(C=O)—NH—SO$_2$—, HO—(C=O)—(C=O)—NH—SO$_2$—($C_1$–$C_8$)alkyl-, HO—(C=O)—($C_1$–$C_8$)alkyl-NH—(C=O)—NH—, HO—(C=O)—($C_1$–$C_8$)alkyl-NH—(C=O)—NH—($C_1$–$C_8$)alkyl-, HO—(C=O)—($C_1$–$C_8$)alkyl-O—, HO—(C=O)—($C_1$–$C_8$)alkyl-O—($C_1$–$C_8$)alkyl-, HO—(C=O)—($C_1$–$C_8$)alkyl substituted with hydroxy, HO—(C=O)—($C_2$–$C_8$)alkenyl-, ($C_1$–$C_9$)heterocyclyl-($C_1$–$C_8$)alkyl-O—, ($C_1$–$C_9$)heterocyclyl-($C_1$–$C_8$)alkyl-O—($C_1$–$C_8$)alkyl-, ($C_1$–$C_9$)heteroaryl-($C_1$–$C_8$)alkyl-O—, ($C_1$–$C_9$)heteroaryl-($C_1$–$C_8$)alkyl-O—($C_1$–$C_8$)alkyl-, ($C_1$–$C_9$)heterocyclyl-O—, ($C_1$–$C_9$)heterocyclyl-O—($C_1$–$C_8$)alkyl-, ($C_1$–$C_9$)heteroaryl-O—, ($C_1$–$C_9$)heteroaryl-O—($C_1$–$C_8$)alkyl-, HO—(C=O)—($C_1$–$C_8$)alkyl-S—, HO—(C=O)—($C_1$–$C_8$)alkyl-S—($C_1$–$C_8$)alkyl-, ($C_1$–$C_9$)heterocyclyl-($C_1$–$C_8$)alkyl-S—, ($C_1$–$C_9$)heterocyclyl-($C_1$–$C_8$)alkyl-S—($C_1$–$C_8$)alkyl-, ($C_1$–$C_9$)heteroaryl-($C_1$–$C_8$)alkyl-S—, ($C_1$–$C_9$)heteroaryl-($C_1$–$C_8$)alkyl-S—($C_1$–$C_8$)alkyl-, ($C_1$–$C_9$)heterocyclyl-S—, ($C_1$–$C_9$)heterocyclyl-S—($C_1$–$C_8$)alkyl-, ($C_1$–$C_9$)heteroaryl-S—, ($C_1$–$C_9$)heteroaryl-S—($C_1$–$C_8$)alkyl-, HO—(C=O)—($C_1$–$C_8$)alkyl-NH—SO$_2$—NH—, HO—(C=O)—($C_1$–$C_8$)alkyl-NH—SO$_2$—NH—($C_1$–$C_8$)alkyl-, HO—(C=O)—($C_1$–$C_8$)alkyl-SO$_2$—NH—(C=O)—, HO—(C=O)—($C_1$–$C_8$)alkyl-SO$_2$—NH—(C=O)—($C_1$–$C_8$)alkyl-, HO—(C=O)—($C_1$–$C_8$)alkyl-(C=O)—NH—SO$_2$—, HO—(C=O)—($C_1$–$C_8$)alkyl-(C=O)—NH—SO$_2$—($C_1$–$C_8$)alkyl-, HO—(C=O)—(C=O)—, HO—(C=O)—(C=O)—($C_1$–$C_8$)alkyl-, HO—(C=O)—($C_1$–$C_8$)alkyl-(C=O)—, HO—(C=O)—($C_1$–$C_8$)alkyl-(C=O)—($C_1$–$C_8$)alkyl-, HO—(C=O)—($C_1$–$C_9$)heterocyclyl-(C=O)—, HO—(C=O)—($C_1$–$C_9$)heteroaryl-(C=O)—, NC—NH—(C=O)—, NC—NH—(C=O)—($C_1$–$C_8$)alkyl, [($C_1$–$C_8$)alkyl-SO$_2$—NH—(C=O)—][$H_2N$—]($C_1$–$C_8$)alkyl-, ($C_1$–$C_8$)alkyl-SO$_2$—NH—(C=O)—($C_1$–$C_8$)alkyl-, ($C_1$–$C_8$)alkyl-SO$_2$—NH—(C=O)—($C_1$–$C_8$)alkyl-NH—, ($C_1$–$C_8$)alkyl-SO$_2$—NH—(C=O)—($C_1$–$C_8$)alkyl-NH—($C_1$–$C_8$)alkyl-, [($C_1$–$C_8$)alkyl-SO$_2$—NH—(C=O)—($C_1$–$C_8$)alkyl][($C_1$–$C_8$)alkyl]N—, [($C_1$–$C_8$)alkyl-SO$_2$—NH—(C=O)—($C_1$–$C_8$)alkyl][($C_1$–$C_8$)alkyl]N—($C_1$–$C_8$)alkyl-, ($C_1$–$C_8$)alkyl-SO$_2$—NH—(C=O)—($C_1$–$C_8$)alkyl-NH—SO$_2$—, ($C_1$–$C_8$)alkyl-SO$_2$—NH—(C=O)—($C_1$–$C_8$)alkyl-NH—SO$_2$—($C_1$–$C_8$)alkyl-, ($C_1$–$C_8$)alkyl-SO$_2$—NH—(C=O)—($C_1$–$C_8$)alkyl-SO$_2$—NH—, ($C_1$–$C_8$)alkyl-SO$_2$—NH—(C=O)—($C_1$–$C_8$)alkyl-SO$_2$—NH—($C_1$–$C_8$)alkyl-, ($C_1$–$C_8$)alkyl-SO$_2$—NH—(C=O)—($C_1$–$C_8$)alkyl-SO$_2$—, ($C_1$–$C_8$)alkyl-SO$_2$—NH—(C=O)—($C_1$–$C_8$)alkyl-SO$_2$—($C_1$–$C_8$)alkyl-, ($C_1$–$C_8$)alkyl-SO$_2$—NH—(C=O)—(C=O)—, ($C_1$–$C_8$)alkyl-SO$_2$—NH—(C=O)—(C=O)—($C_1$–$C_8$)alkyl-, ($C_1$–$C_8$)alkyl-SO$_2$—NH—(C=O)—($C_1$–$C_8$)alkyl-(C=O)—, ($C_1$–$C_8$)alkyl-SO$_2$—NH—(C=O)—($C_1$–$C_8$)alkyl-(C=O)—($C_1$–$C_8$)alkyl-, NC—($C_1$–$C_8$)alkyl-SO$_2$—NH—(C=O)—, NC—($C_1$–$C_8$)alkyl-SO$_2$—NH—(C=O)—($C_1$–$C_8$)alkyl-, HO—($C_1$–$C_8$)alkyl-SO$_2$—NH—(C=O)—, HO—($C_1$–$C_8$)alkyl-SO$_2$—NH—(C=O)—($C_1$–$C_8$)alkyl-, ($C_1$–$C_8$)alkyl-SO$_2$—NH—(C=O)—($C_2$–$C_8$)alkenyl-, ($C_1$–$C_9$)heterocyclyl-SO$_2$—NH—(C=O)—, ($C_1$–$C_9$)heterocyclyl-SO$_2$—NH—(C=O)—($C_1$–$C_8$)alkyl-, ($C_1$–$C_9$)heterocyclyl-($C_1$–$C_8$)alkyl-SO$_2$—NH—(C=O)—, ($C_1$–$C_9$)heterocyclyl-($C_1$–$C_8$)alkyl-SO$_2$—NH—(C=O)—($C_1$–$C_8$)alkyl-, ($C_6$–$C_{10}$)aryl-SO$_2$—NH—(C=O)—, ($C_6$–$C_{10}$)aryl-SO$_2$—NH—(C=O)—($C_1$–$C_8$)alkyl-, ($C_1$–$C_9$)heteroaryl-SO$_2$—NH—(C=O)—, ($C_1$–$C_9$)heteroaryl-SO$_2$—NH—(C=O)—($C_1$–$C_8$)alkyl-, $H_2N$—SO$_2$—NH—(C=O)—, $H_2N$—SO$_2$—NH—(C=O)—($C_1$–$C_8$)alkyl-, ($C_1$–$C_8$)alkyl-NH—SO$_2$—NH—(C=O)—, ($C_1$–$C_8$)alkyl-NH—SO$_2$—NH—(C=O)—($C_1$–$C_8$)alkyl-, [($C_1$–$C_8$)alkyl]$_2$N—SO$_2$—NH—(C=O)—, [($C_1$–$C_8$)alkyl]$_2$N—SO$_2$—NH—(C=O)—($C_1$–$C_8$)alkyl-, ($C_1$–$C_8$)alkyl-SO$_2$—NH—(C=O)—O—, ($C_1$–$C_8$)alkyl-SO$_2$—NH—(C=O)—($C_1$–$C_8$)alkyl-O—($C_1$–$C_8$)alkyl-, $H_2N$—SO$_2$—($C_1$–$C_8$)alkyl-, ($C_1$–$C_8$)alkyl-(C=O)—NH—SO$_2$—($C_1$–$C_8$)alkyl-, NC—($C_1$–$C_8$)alkyl-(C=O)—NH—SO$_2$—($C_1$–$C_8$)alkyl-, HO—($C_1$–$C_8$)alkyl-(C=O)—NH—SO$_2$—($C_1$–$C_8$)alkyl-, ($C_6$–$C_{10}$)aryl—(C=O)—NH—SO$_2$—, ($C_6$–$C_{10}$)aryl-(C=O)—NH—SO$_2$—($C_1$–$C_8$)alkyl-, ($C_1$–$C_9$)heteroaryl-(C=O)—NH—SO$_2$—, ($C_1$–$C_9$)heteroaryl-(C=O)—NH—SO$_2$—($C_1$–$C_8$)alkyl-, ($C_1$–$C_9$)heterocyclyl-(C=O)—NH—SO$_2$—, ($C_1$–$C_9$)heterocyclyl-(C=O)—NH—SO$_2$—($C_1$–$C_8$)alkyl-, $H_2N$—(C=O)—NH—SO$_2$—, $H_2N$—(C=O)—NH—SO$_2$—($C_1$–$C_8$)alkyl-, ($C_1$–$C_8$)alkyl-NH—(C=O)—NH—SO$_2$—($C_1$–$C_8$)alkyl-, [($C_1$–$C_8$)alkyl]$_2$—N—(C=O)—NH—SO$_2$—($C_1$–$C_8$)alkyl-, ($C_6$–$C_{10}$)aryl-NH—(C=O)—NH—SO$_2$—, ($C_6$–$C_{10}$)aryl-NH—(C=O)—NH—SO$_2$—($C_1$–$C_8$)alkyl-, ($C_1$–$C_9$)heteroaryl-NH—(C=O)—NH—SO$_2$—, ($C_1$–$C_9$)heteroaryl-NH—(C=O)—NH—SO$_2$—($C_1$–$C_8$)alkyl-, ($C_1$–$C_8$)alkyl-O—(C=O)—NH—SO$_2$—, ($C_1$–$C_8$)alkyl-O—(C=O)—NH—SO$_2$—($C_1$–$C_8$)alkyl-, ($C_6$–$C_{10}$)aryloxy-(C=O)—NH—SO$_2$—, ($C_6$–$C_{10}$)aryloxy-(C=O)—NH—SO$_2$—($C_1$–$C_8$)alkyl-, ($C_1$–$C_8$)alkyl-SO$_2$—NH—(C=O)—O—, ($C_1$–$C_8$)alkyl-SO$_2$—NH—(C=O)—O—($C_1$–$C_8$)alkyl-, ($C_1$–$C_8$)alkyl-SO$_2$—NH—(C=O)—NH—($C_1$–$C_8$)alkyl-, ($C_6$–$C_{10}$)aryl-SO$_2$—NH—(C=O)—O—, ($C_6$–$C_{10}$)aryl-SO$_2$—NH—(C=O)—O—($C_1$–$C_8$)alkyl-, ($C_6$–$C_{10}$)aryl-SO$_2$—NH—(C=O)—NH—, ($C_6$–$C_{10}$)aryl-SO$_2$—NH—(C=O)—NH—($C_1$–$C_8$)alkyl-, ($C_1$–$C_9$)heteroaryl-SO$_2$—NH—(C=O)—O—, ($C_1$–$C_9$)heteroaryl-SO$_2$—NH—(C=O)—O—($C_1$–$C_8$)alkyl-, $NH_2$—SO$_2$—NH—(C=O)—O—, $NH_2$—SO$_2$—NH—(C=O)—O—($C_1$–$C_8$)alkyl-, ($C_1$–$C_9$)heteroaryl-SO$_2$—NH—(C=O)—NH—, ($C_1$–$C_9$)heteroaryl-SO$_2$—NH—(C=O)—NH—($C_1$–$C_8$)alkyl-, $NH_2$—SO$_2$—NH—(C=O)—NH—, $NH_2$—SO$_2$—NH—(C=O)—NH—($C_1$–$C_8$)alkyl-, HO—(C=O)—($C_1$–$C_8$)alkyl-NH—(C=O)—O—, HO—(C=O)—($C_1$–$C_8$)alkyl-NH—(C=O)—O—($C_1$–$C_8$)alkyl-, HO—(C=O)—($C_1$–$C_8$)alkyl-O—(C=O)—NH—, HO—(C=O)—($C_1$–$C_8$)alkyl-O—(C=O)—NH—($C_1$–$C_8$)alkyl-, ($C_1$–$C_8$)alkyl-(C=O)—NH—SO$_2$—NH—, ($C_1$–$C_8$)alkyl-(C=O)—NH—SO$_2$—NH—($C_1$–$C_8$)alkyl, ($C_6$–$C_{10}$)aryl-(C=O)—NH—SO$_2$—NH—, ($C_6$–$C_{10}$)aryl-(C=O)—NH—SO$_2$—NH—($C_1$–$C_8$)alkyl, ($C_1$–$C_9$)heteroaryl-(C=O)—NH—SO$_2$—NH—, ($C_1$–$C_9$)heteroaryl-(C=O)—

NH—SO$_2$—NH—(C$_1$–C$_8$)alkyl, NH$_2$—(C=O)—NH—SO$_2$—NH—, NH$_2$—(C=O)—NH—SO$_2$—NH—(C$_1$–C$_8$)alkyl, (C$_1$–C$_9$)heteroaryl-(C$_1$–C$_8$)alkyl-(C=O)—, (C$_1$–C$_9$)heteroaryl-(C$_1$–C$_8$)alkyl-(C=O)—(C$_1$–C$_8$)alkyl-, (C$_1$–C$_9$eterocyclyl-(C$_1$–C$_8$)alkyl-(C=O)—(C$_1$–C$_8$)alkyl-, (C$_1$–C$_9$)heteroaryl-(C=O)—(C$_1$–C$_8$)alkyl-, or (C$_1$–C$_9$)heterocyclyl-(C=O)—(C$_1$–C$_8$)alkyl;

or, if Y is a (C$_2$–C$_9$)heteroaryl group, then R$^4$ can also be HO—(C=O)—(C$_1$–C$_8$)alkyl-, (C$_2$–C$_9$)heteroaryl-, (C$_2$–C$_9$)heterocyclyl-, (C$_2$–C$_9$)heteroaryl-(C$_1$–C$_8$)alkyl, or (C$_2$–C$_9$)heterocyclyl-(C$_1$–C$_8$)alkyl;

each R$^5$ is independently H—, HO—, halo-, NC—, HO—(C=O)—, H$_2$N—, (C$_1$–C$_8$)alkyl-NH—, [(C$_1$–C$_8$)alkyl]$_2$N—, (C$_1$–C$_8$)alkyl-, (C$_1$–C$_8$)alkyl-O—, HO—(C$_1$–C$_8$)alkyl-, (C$_1$–C$_8$)alkyl-O—(C$_1$–C$_8$)alkyl-, H$_2$N—(C$_1$–C$_8$)alkyl-, (C$_1$–C$_8$)alkyl-NH—(C$_1$–C$_8$)alkyl-, [(C$_1$–C$_8$)alkyl]$_2$N—(C$_1$–C$_8$)alkyl-, (C$_1$–C$_8$)alkyl-(C=O)—, (C$_1$–C$_8$)alkyl-(C=O)—(C$_1$–C$_8$)alkyl-, (C$_6$–C$_{10}$)aryl-, (C$_2$–C$_9$)heteroaryl-, (C$_6$–C$_{10}$)aryloxy-, H$_2$N—(C=O)—, H$_2$N—(C=O)—(C$_1$–C$_8$)alkyl-, (C$_1$–C$_8$)alkyl-NH—(C=O)—, (C$_1$–C$_8$)alkyl-NH—(C=O)—(C$_1$–C$_8$)alkyl-, [(C$_1$–C$_8$)alkyl]$_2$N—(C=O)—, [(C$_1$–C$_8$)alkyl]$_2$-N—(C=O)—(C$_1$–C$_8$)alkyl-, (C$_3$–C$_8$)cycloalkyl-, (C$_1$–C$_8$)alkyl-SO$_2$—, NC—(C$_1$–C$_8$)alkyl-, (C$_1$–C$_8$)alkyl-(C=O)—NH—, H$_2$N—(C=O)—NH—, or H$_2$N—(C=O)—NH—(C$_1$–C$_8$)alkyl-; and R$^6$ is H, (C$_1$–C$_8$)alkyl-, (C$_1$–C$_8$)alkyl-(C=O)—, (C$_6$–C$_{10}$)aryl-(C=O)—, (C$_2$–C$_9$)heteroaryl-(C=O)—, H$_2$N—(C=O)—, (C$_1$–C$_8$)alkyl-NH—(C=O)—, [(C$_1$–C$_8$)alkyl]$_2$N—(C=O)—, (C$_1$–C$_8$)alkyl-O—(C=O)—, or (C$_1$–C$_8$)alkyl-SO$_2$—.

In one embodiment, R$^4$ is [HO—(C=O)—][H$_2$N—](C$_1$–C$_8$)alkyl-, [HO—(C=O)—][(C$_1$–C$_8$)alkyl)NH—](C$_1$–C$_8$)alkyl-, [HO—(C=O)—][((C$_1$–C$_8$)alkyl)$_2$N—](C$_1$–C$_8$)alkyl-, [HO—(C=O)—(C$_1$–C$_8$)alkyl][(C$_1$–C$_8$)alkyl]N—, [HO—(C=O)—(C$_1$–C$_8$)alkyl][(C$_1$–C$_8$)alkyl]N—(C$_1$–C$_8$)alkyl-, [HO—(C=O)—(C$_1$–C$_8$)alkyl][(C$_1$–C$_8$)alkyl-SO$_2$]N—, [HO—(C=O)—(C$_1$–C$_8$)alkyl][(C$_1$–C$_8$)alkyl-SO$_2$]N—(C$_1$–C$_8$)alkyl-, [HO—(C=O)—(C$_1$–C$_8$)alkyl][(C$_1$–C$_8$)alkyl-(C=O)—]N—, [HO—(C=O)—(C$_1$–C$_8$)alkyl][(C$_1$–C$_8$)alkyl-(C=O)—]N—(C$_1$–C$_8$)alkyl-, [HO—(C=O)—(C$_1$–C$_8$)alkyl][(C$_1$–C$_8$)alkyl-O—(C=O)-]N—, [HO—(C=O)—(C$_1$–C$_8$)alkyl][(C$_1$–C$_8$)alkyl-O—(C=O)—]N—(C$_1$–C$_8$)alkyl-, [HO—(C=O)—(C$_1$–C$_8$)alkyl][(C$_1$–C$_8$)alkylN—(C=O)—]N—, [HO—(C=O)—(C$_1$–C$_8$)alkyl][(C$_1$–C$_8$)alkyl-NH—(C=O)—]N—(C$_1$–C$_8$)alkyl-, HO—(C=O)—(C$_1$–C$_8$)alkyl-O—N=(C$_1$–C$_8$)alkyl-, HO—(C=O)—(C$_1$–C$_8$)alkyl-SO$_2$—, HO—(C=O)—(C$_1$–C$_8$)alkyl-SO$_2$—(C$_1$–C$_8$)alkyl-, HO—(C=O)—(C$_1$–C$_8$)alkyl-SO$_2$—NH—, HO—(C=O)—(C$_1$–C$_8$)alkyl-SO$_2$—NH—(C$_1$–C$_8$)alkyl-, HO—(C=O)—(C$_1$–C$_8$)alkyl-NH—SO$_2$—, HO—(C=O)—(C$_1$–C$_8$)alkyl-NH—SO$_2$—(C$_1$–C$_8$)alkyl-, HO—(C=O)—(C=O)—NH—SO$_2$—, HO—(C=O)—(C=O)—NH—SO$_2$—(C$_1$–C$_8$)alkyl-, HO—(C=O)—(C$_1$–C$_8$)alkyl-NH—(C=O)—NH—, HO—(C=O)—(C$_1$–C$_8$)alkyl-NH—(C=O)—NH—(C$_1$–C$_8$)alkyl-, HO—(C=O)—(C$_1$–C$_8$)alkyl-O—, HO—(C=O)—(C$_1$–C$_8$)alkyl-O—(C$_1$–C$_8$)alkyl-, HO—(C=O)—(C$_2$–C$_8$)alkenyl-, (C$_2$–C$_9$)heterocyclyl-(C$_1$–C$_8$)alkyl-O—, (C$_2$–C$_9$)heterocyclyl-(C$_1$–C$_8$)alkyl-O—(C$_1$–C$_8$)alkyl-, (C$_2$–C$_9$)heteroaryl-(C$_1$–C$_8$)alkyl-O—(C$_1$–C$_8$)alkyl-O—(C$_2$–C$_9$)heteroaryl-(C$_1$–C$_8$)alkyl-O—(C$_1$–C$_8$)alkyl-, (C$_2$–C$_9$)heterocyclyl-O—, (C$_2$–C$_9$)heterocyclyl-O—(C$_1$–C$_8$)alkyl-, (C$_2$–C$_9$)heteroaryl-O—, (C$_2$–C$_9$)heteroaryl-O—(C$_1$–C$_8$)alkyl-, HO—(C=O)—(C$_1$–C$_8$)alkyl-S—, HO—(C=O)—(C$_1$–C$_8$)alkyl-S—(C$_1$–C$_8$)alkyl-, (C$_2$–C$_9$)heterocyclyl-(C$_1$–C$_8$)alkyl-S—, (C$_2$–C$_9$)heterocyclyl-(C$_1$–C$_8$)alkyl-S—(C$_1$–C$_8$)alkyl-, (C$_2$–C$_9$)heteroaryl-(C$_1$–C$_8$)alkyl-S—, (C$_2$–C$_9$)heteroaryl-(C$_1$–C$_8$)alkyl-S—(C$_1$–C$_8$)alkyl-, (C$_2$–C$_9$)heterocyclyl-S—, (C$_2$–C$_9$)heterocyclyl-S—(C$_1$–C$_8$)alkyl-, (C$_2$–C$_9$)heteroaryl-S—, (C$_2$–C$_9$)heteroaryl-S—(C$_1$–C$_8$)alkyl-, HO—(C=O)—(C$_1$–C$_8$)alkyl-NH—SO$_2$—NH—, HO—(C=O)—(C$_1$–C$_8$)alkyl-NH—SO$_2$—NH—(C$_1$–C$_8$)alkyl-, HO—(C=O)—(C$_1$–C$_8$)alkyl-SO$_2$—NH—(C=O)—, HO—(C=O)—(C$_1$–C$_8$)alkyl-SO$_2$—NH—(C=O)—(C$_1$–C$_8$)alkyl-, HO—(C=O)—(C$_1$–C$_8$)alkyl-(C=O)—NH—SO$_2$—, HO—(C=O)—(C$_1$–C$_8$)alkyl-(C=O)—NH—SO$_2$—(C$_1$–C$_8$)alkyl-, HO—(C=O)—(C=O)—, HO—(C=O)—(C=O)—(C$_1$–C$_8$)alkyl-, HO—(C=O)—(C$_1$–C$_8$)alkyl-(C=O)—, HO—(C=O)—(C$_1$–C$_8$)alkyl-(C=O)—(C$_1$–C$_8$)alkyl-, HO—(C=O)—(C$_2$–C$_9$)heterocyclyl-(C=O)—, HO—(C=O)—(C$_2$–C$_9$)heteroaryl-(C=O)—, NC—NH—(C=O)—, NC—NH—(C=O)—(C$_1$–C$_8$)alkyl, [(C$_1$–C$_8$)alkyl-SO$_2$—NH—(C=O)—][H$_2$N—](C$_1$–C$_8$)alkyl-, (C$_1$–C$_8$)alkyl-SO$_2$—NH—(C=O)—, (C$_1$–C$_8$)alkyl-SO$_2$—NH—(C=O)—(C$_1$–C$_8$)alkyl-, (C$_1$–C$_8$)alkyl-SO$_2$—NH—(C=O)—(C$_1$–C$_8$)alkyl-NH—, (C$_1$–C$_8$)alkyl-SO$_2$—NH—(C=O)—(C$_1$–C$_8$)alkyl-NH—(C$_1$–C$_8$)alkyl-, [(C$_1$–C$_8$)alkyl-SO$_2$—NH—(C=O)—(C$_1$–C$_8$)alkyl][(C$_1$–C$_8$)alkyl]N—, [(C$_1$–C$_8$)alkyl-SO$_2$—NH—(C=O)—(C$_1$–C$_8$)alkyl][(C$_1$–C$_8$)alkyl]N—(C$_1$–C$_8$)alkyl-, (C$_1$–C$_8$)alkyl-SO$_2$—NH—(C=O)—(C$_1$–C$_8$)alkyl-NH—SO$_2$—, (C$_1$–C$_8$)alkyl-SO$_2$—NH—(C=O)—(C$_1$–C$_8$)alkyl-NH—SO$_2$—(C$_1$–C$_8$)alkyl-, (C$_1$–C$_8$)alkyl-SO$_2$—NH—(C=O)—(C$_1$–C$_8$)alkyl-SO$_2$—NH—, (C$_1$–C$_8$)alkyl-SO$_2$—NH—(C=O)—(C$_1$–C$_8$)alkyl-SO$_2$—NH—(C$_1$–C$_8$)alkyl-, (C$_1$–C$_8$)alkyl-SO$_2$—NH—(C=O)—(C$_1$–C$_8$)alkyl-SO$_2$—, (C$_1$–C$_8$)alkyl-SO$_2$—NH—(C=O)—(C$_1$–C$_8$)alkyl-SO$_2$—(C$_1$–C$_8$)alkyl-, (C$_1$–C$_8$)alkyl-SO$_2$—NH—(C=O)—(C=O)—, (C$_1$–C$_8$)alkyl-SO$_2$—NH—(C=O)—(C=O)—(C$_1$–C$_8$)alkyl-, (C$_1$–C$_8$)alkyl-SO$_2$—NH—(C=O)—(C$_1$–C$_8$)alkyl-(C=O)—, (C$_1$–C$_8$)alkyl-SO$_2$—NH—(C=O)—(C$_1$–C$_8$)alkyl-(C=O)—(C$_1$–C$_8$)alkyl-, NC—(C$_1$–C$_8$)alkyl-SO$_2$—NH—(C=O)—, NC—(C$_1$–C$_8$)alkyl-SO$_2$—NH—(C=O)—(C$_1$–C$_8$)alkyl-, HO—(C$_1$–C$_8$)alkyl-SO$_2$—NH—(C=O)—(C$_1$–C$_8$)alkyl-, (C$_1$–C$_8$)alkyl-SO$_2$—NH—(C=O)—(C$_2$–C$_8$)alkenyl-, (C$_2$–C$_9$)heterocyclyl-SO$_2$—NH—(C=O)—, (C$_2$–C$_9$)heterocyclyl-SO$_2$—NH—(C=O)—(C$_1$–C$_8$)alkyl-, (C$_2$–C$_9$)heterocyclyl-(C$_1$–C$_8$)alkyl-SO$_2$—NH—(C=O)—, (C$_2$–C$_9$)heterocyclyl-(C$_1$–C$_8$)alkyl-SO$_2$—NH—(C=O)—(C$_1$–C$_8$)alkyl-, (C$_6$–C$_{10}$)aryl-SO$_2$—NH—(C=O)—, (C$_6$–C$_{10}$)aryl-SO$_2$—NH—(C=O)—(C$_1$–C$_8$)alkyl-, (C$_2$–C$_9$)heteroaryl-SO$_2$—NH—(C=O)—, (C$_2$–C$_9$)heteroaryl-SO$_2$—NH—(C=O)—(C$_1$–C$_8$)alkyl-, H$_2$N—SO$_2$—NH—(C=O)—, H$_2$N—SO$_2$—NH—(C=O)—(C$_1$–C$_8$)alkyl-, (C$_1$–C$_8$)alkyl-NH—SO$_2$—NH—(C=O)—, (C$_1$–C$_8$)alkyl-NH—SO$_2$—NH—(C=O)—(C$_1$–C$_8$)alkyl-, [(C$_1$–C$_8$)alkyl]$_2$N—SO$_2$—NH—(C=O)—, [(C$_1$–C$_8$)alkyl]$_2$N—SO$_2$—NH—(C=O)—(C$_1$–C$_8$)alkyl-, (C$_1$–C$_8$)alkyl-SO$_2$—NH—(C=O)—(C$_1$–C$_8$)alkyl-O—, (C$_1$–C$_8$)alkyl-SO$_2$—NH—(C=O)—(C$_1$–C$_8$)alkyl-O—(C$_1$–C$_8$)alkyl-, H$_2$N—SO$_2$—(C$_1$–C$_8$)alkyl-, (C$_1$–C$_8$)alkyl-(C=O)—NH—SO$_2$—(C$_1$–C$_8$)alkyl-, NC—(C$_1$–C$_8$)alkyl-(C=O)—NH—SO$_2$—(C$_1$–C$_8$)alkyl-, HO—(C$_1$–C$_8$)alkyl-(C=O)—NH—SO$_2$—(C$_1$–C$_8$)alkyl-, (C$_6$–C$_{10}$)aryl-(C=O)—NH—SO$_2$—, (C$_6$–C$_{10}$)aryl-(C=O)—NH—SO$_2$—(C$_1$–C$_8$)alkyl-, (C$_2$–C$_9$)heteroaryl-(C=O)—NH—SO$_2$—, (C$_2$–C$_9$)heteroaryl-(C=O)—NH—SO$_2$—(C$_1$–C$_8$)alkyl-, (C$_2$–C$_9$)heterocyclyl-(C=O)—NH—SO$_2$—, (C$_2$–C$_9$)heterocyclyl-(C=O)—NH—SO$_2$—(C$_1$–C$_8$)alkyl-, H$_2$N—(C=O)—NH—SO$_2$—, H$_2$N—(C=O)—NH—SO$_2$—(C$_1$–C$_8$)alkyl-, (C$_1$–C$_8$)alkyl-NH—(C=O)—NH—SO$_2$—(C$_1$–C$_8$)alkyl-, [(C$_1$–C$_8$)alkyl]$_2$—

N—(C=O)—NH—SO₂—(C₁–C₈)alkyl-, (C₆–C₁₀)aryl-NH—(C=O)—NH—SO₂—, (C₆–C₁₀)aryl-NH—(C=O)—NH—SO₂—(C₁–C₈)alkyl-, (C₂–C₉)heteroaryl-NH—(C=O)—NH—SO₂—, (C₂–C₉)heteroaryl-NH—(C=O)—NH—SO₂—(C₁–C₈)alkyl-, (C₁–C₈)alkyl-O—(C=O)—NH—SO₂—, (C₁–C₈)alkyl-O—(C=O)—NH—SO₂—(C₁–C₈)alkyl-, (C₆–C₁₀)aryloxy-(C=O)—NH—SO₂—, (C₆–C₁₀)aryloxy-(C=O)—NH—SO₂—(C₁–C₈)alkyl-, (C₁–C₈)alkyl-SO₂—NH—(C=O)—O—, (C₁–C₈)alkyl-SO₂—NH—(C=O)—O—(C₁–C₈)alkyl-, (C₁–C₈)alkyl-SO₂—NH—(C=O)—NH—(C₁–C₈)alkyl-, (C₆–C₁₀)aryl-SO₂—NH—(C=O)—O—, (C₆–C₁₀)aryl-SO₂—NH—(C=O)—O—(C₁–C₈)alkyl-, (C₆–C₁₀)aryl-SO₂—NH—(C=O)—NH—, (C₆–C₁₀)aryl-SO₂—NH—(C=O)—NH—(C₁–C₈)alkyl-, (C₂–C₉)heteroaryl-SO₂—NH—(C=O)—O—, (C₂–C₉)heteroaryl-SO₂—NH—(C=O)—O—(C₁–C₈)alkyl-, NH₂—SO₂—NH—(C=O)—O—, NH₂—SO₂—NH—(C=O)—O—(C₁–C₈)alkyl-, (C₂–C₉)heteroaryl-SO₂—NH—(C=O)—NH—, (C₂–C₉)heteroaryl-SO₂—NH—(C=O)—NH—(C₁–C₈)alkyl-, NH₂—SO₂—NH—(C=O)—NH—, NH₂—SO₂—NH—(C=O)—NH—(C₁–C₈)alkyl-, HO—(C=O)—(C₁–C₈)alkyl-NH—(C=O)—O—, HO—(C=O)—(C₁–C₈)alkyl-NH—(C=O)—O—(C₁–C₈)alkyl-, HO—(C=O)—(C₁–C₈)alkyl-O—(C=O)—NH—, HO—(C=O)—(C₁–C₈)alkyl-O—(C=O)—NH—(C₁–C₈)alkyl-, (C₁–C₈)alkyl-(C=O)—NH—SO₂—NH—, (C₁–C₈)alkyl-(C=O)—NH—SO₂—NH—(C₁–C₈)alkyl, (C₆–C₁₀)aryl-(C=O)—NH—SO₂—NH—, (C₆–C₁₀)aryl-(C=O)—NH—SO₂—NH—(C₁–C₈)alkyl, (C₂–C₉)heteroaryl-(C=O)—NH—SO₂—NH—, (C₂–C₉)heteroaryl-(C=O)—NH—SO₂—NH—(C₁–C₈)alkyl, NH₂—(C=O)—NH—SO₂—NH—, or NH₂—(C=O)—NH—SO₂—NH—(C₁–C₈)alkyl.

In another embodiment, the present invention includes compounds of formula I or the pharmaceutically acceptable salts or prodrugs thereof.

Preferred compounds of formula I include those wherein each R¹ is independently H—, HO—, halo, NC—, (C₁–C₈)alkyl-, or (C₁–C₈)alkyl-O—.

Other preferred compounds of formula I include those wherein each R² and R³ are independently H—, (C₁–C₈)alkyl-, (C₃–C₈)cycloalkyl-(C₁–C₈)alkyl-, (C₆–C₁₀)aryl-, (C₆–C₁₀)aryl-(C₁–C₈)alkyl-, HO—(C₁–C₈)alkyl-, H₂N—(C₁–C₈)alkyl-, (C₁–C₉)heterocyl-(C₁–C₈)alkyl-, (C₁–C₈)alkyl-O—(C=O)—NH—(C₁–C₈)alkyl-, H₂N—(C=O)—NH—(C₁–C₈)alkyl-, (C₁–C₈)alkyl-SO₂—NH—(C₁–C₈)alkyl-, (C₁–C₉)heteroaryl-(C₁–C₈)alkyl-, H₂N—(C=O)—, or H₂N—(C=O)—(C₁–C₈)alkyl-.

Other preferred compounds of formula I include those wherein X is —O— and Y is a phenyl ring.

Other preferred compounds of formula I include those wherein X is —O— and Y is a pyridyl ring.

Other preferred compounds of formula I include those wherein X is —NR⁶— and Y is a pyridyl ring.

Other preferred compounds of formula I include those wherein R⁴ is [HO—(C=O)—][H₂N—](C₁–C₈)alkyl-, [HO—(C=O)—][(C₁–C₈)alkyl)NH—](C₁–C₈)alkyl-, [HO—(C=O)—][)(C₁–C₈)alkyl)₂N—](C₁–C₈)alkyl-, [HO—(C=O)—(C₁–C₈)alkyl][(C₁–C₈)alkyl]N—, [HO—(C=O)—(C₁–C₈)alkyl][(C₁–C₈)alkyl]N—(C₁–C₈)alkyl-, (C₁–C₈)alkyl-SO₂—NH—(C=O)—(C₁–C₈)alkyl-, NC—(C₁–C₈)alkyl-SO₂—NH—(C=O)—(C₁–C₈)alkyl-, HO—(C₁–C₈)alkyl-SO₂—NH—(C=O)—(C₁–C₈)alkyl-, (C₁–C₉)heterocyclyl-SO₂—NH—(C=O)—(C₁–C₈)alkyl-, (C₁–C₉)heterocyclyl-(C₁–C₈)alkyl-SO₂—NH—(C=O)—(C₁–C₈)alkyl-, (C₁–C₉)heteroaryl-SO₂—NH—(C=O)—(C₁–C₈)alkyl-, H₂N—SO₂—NH—(C=O)—(C₁–C₈)alkyl-, (C₁–C₈)alkyl-NH—SO₂—NH—(C=O)—, (C₁–C₈)alkyl-SO₂—NH—(C=O)—(C₁–C₈)alkyl-O—, (C₁–C₈)alkyl-SO₂—NH—(C=O)—(C₁–C₈)alkyl-O—(C₁–C₈)alkyl-, H₂N—SO₂—(C₁–C₈)alkyl-, (C₁–C₈)alkyl-(C=O)—NH—SO₂—(C₁–C₈)alkyl-, NC—(C₁–C₈)alkyl-(C=O)—NH—SO₂—(C₁–C₈)alkyl-, HO—(C₁–C₈)alkyl-(C=O)—NH—SO₂—(C₁–C₈)alkyl-, (C₁–C₉)heteroaryl-(C=O)—NH—SO₂—(C₁–C₈)alkyl-, (C₁–C₉)heterocyclyl-(C=O)—NH—SO₂—(C₁–C₈)alkyl-, H₂N—(C=O)—NH—SO₂—(C₁–C₈)alkyl-, (C₁–C₈)alkyl-NH—(C=O)—NH—SO₂—(C₁–C₈)alkyl-, (C₁–C₈)alkyl-SO₂—NH—(C=O)—NH—(C₁–C₈)alkyl-, (C₁–C₈)alkyl-(C=O)—NH—SO₂—NH—(C₁–C₈)alkyl, HO—(C=O)—(C₁–C₈)alkyl-O—, HO—(C=O)—(C₁–C₈)alkyl-O—(C₁–C₈)alkyl-, (C₁–C₈)alkyl-SO₂—NH—(C=O)—(C₁–C₈)alkyl-O—, (C₁–C₉)heterocyclyl-(C₁–C₈)alkyl-O—, (C₁–C₉)heterocyclyl-(C₁–C₈)alkyl-O—(C₁–C₈)alkyl-, (C₁–C₉)heteroaryl-(C₁–C₈)alkyl-O—, (C₁–C₉)heteroaryl-(C₁–C₈)alkyl-O—(C₁–C₈)alkyl-, (C₁–C₉)heterocyclyl-O—, (C₁–C₉)heterocyclyl-O—(C₁–C₈)alkyl-, (C₁–C₉)heteroaryl-O—, (C₁–C₉)heteroaryl-O—(C₁–C₈)alkyl-, HO—(C=O)—(C₁–C₈)alkyl-S—, HO—(C=O)—(C₁–C₈)alkyl-S—(C₁–C₈)alkyl-, (C₁–C₉)heterocyclyl-(C₁–C₈)alkyl-S—, (C₁–C₉)heterocyclyl-(C₁–C₈)alkyl-S—(C₁–C₈)alkyl-, (C₁–C₉)heteroaryl-(C₁–C₈)alkyl-S—, (C₁–C₉)heteroaryl-(C₁–C₈)alkyl-S—(C₁–C₈)alkyl-, (C₁–C₉)heterocyclyl-S—, (C₁–C₉)heterocyclyl-S—(C₁–C₈)alkyl-, (C₁–C₉)heteroaryl-S—, (C₁–C₉)heteroaryl-S—(C₁–C₈)alkyl-, HO—(C=O)—(C₁–C₈)alkyl-SO₂—, HO—(C=O)—(C₁–C₈)alkyl-SO₂—(C₁–C₈)alkyl-, HO—(C=O)—(C=O)—(C₁–C₈)alkyl-, HO—(C=O)—(C₁–C₈)alkyl-(C=O)—, HO—(C=O)—(C₁–C₈)alkyl-(C=O)—(C₁–C₈)alkyl-, (C₁–C₉)heteroaryl-(C₁–C₈)alkyl-(C=O)—, HO—(C=O)—(C₁–C₈)alkyl-, (C₂–C₉)heteroaryl-, (C₂–C₉)heterocyclyl-, (C₂–C₉)heteroaryl-(C₁–C₈)alkyl, or (C₂–C₉)heterocyclyl-(C₁–C₈)alkyl.

Other preferred compounds of formula I include those wherein each R⁵ is independently H—, HO—, NC—, (C₁–C₈)alkyl-, (C₁–C₈)alkyl-O—, (C₁–C₈)alkyl-(C=O)— or halo.

Other preferred compounds of formula I include those wherein R⁶ is H—, (C₁–C₈)alkyl-, H₂N—(C=O)— or (C₁–C₈)alkyl-SO₂—.

Other preferred compounds of formula I include those wherein a is 1; X is —O—; Y is (C₆–C₁₀)aryl; R¹ is halo; R² and R³ are each independently H— or (C₁–C₈)alkyl-; and R⁵ is halo.

Other preferred compounds of the formula I include those with the absolute stereochemistry as depicted in formula Ia wherein b and c are each 1.

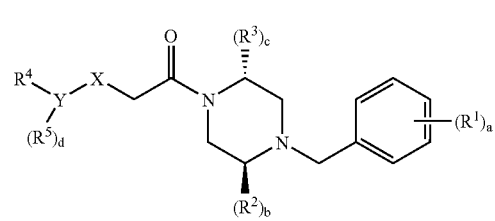

Ia

Examples of specific compounds of the formula I are the following:

(2-{2-[(2R)-2-Carbamoylmethyl-4-(4-fluoro-benzyl)-piperazin-1-yl]-2-oxo-ethoxy}-5-chloro-phenoxy)-acetic acid;

(2-{2-[(2R)-2-Ethyl-4-(4-fluoro-benzyl)-piperazin-1-yl]-2-oxo-ethoxy}-5-methyl-phenyl)-acetic acid;

(2-{2-[4-(4-Fluoro-benzyl)-(2R)-2-methyl-piperazin-1-yl]-2-oxo-ethoxy}-5-methyl-phenyl)-acetic acid;

(2-{2-[4-(4-Fluoro-benzyl)-(2R)-2-methyl-piperazin-1-yl]-2-oxo-ethoxy}-5-trifluoromethyl-phenyl)-methane-sulfonamide;

(2-{2-[4-(4-Fluoro-benzyl)-(2R,5S)-2,5-dimethyl-piperazin-1-yl]-2-oxo-ethoxy}-4-methoxy-phenyl)-acetic acid;

(2-{2-[4-(4-Fluoro-benzyl)-(2R,5S)-2,5-dimethyl-piperazin-1-yl]-2-oxo-ethoxy}-5-methyl-benzylideneaminooxy)-acetic acid;

(2-{2-[4-(4-Fluoro-benzyl)-(2R,5S)-2,5-dimethyl-piperazin-1-yl]-2-oxo-ethoxy}-5-methyl-phenyl)-acetic acid;

(2-{2-[4-(4-Fluoro-benzyl)-(2R,5S)-2,5-dimethyl-piperazin-1-yl]-2-oxo-ethoxy}-5-trifluoromethyl-phenyl)-methanesulfonamide;

(2-{3-[4-(4-Fluoro-benzyl)-(2R,5S)-2,5-dimethyl-piperazin-1-yl]-3-oxo-propyl}-5-methoxy-phenoxy)-acetic acid;

(2-{3-[4-(4-Fluoro-benzyl)-(2R,5S)-2,5-dimethyl-piperazin-1-yl]-3-oxo-propyl}-5-methyl-phenoxy)-acetic acid;

(2-Methylbenzenesulfonyl)-carbamic acid 5-chloro-2-{2-[4-(4-fluoro-benzyl)-(2R,5S)-2,5-dimethyl-piperazin-1-yl]-2-oxo-ethoxy}-benzyl ester;

(2R)-2-(5-Chloro-2-{2-[4-(4-fluoro-benzyl)-(2R)-2-methyl-piperazin-1-yl]-2-oxo-ethoxy}-phenoxy)-propionic acid;

(2R)-2-(5-Chloro-2-{2-[4-(4-fluoro-benzyl)-(2R,5S)-2,5-dimethyl-piperazin-1-yl]-2-oxo-ethoxy}-benzyloxy)-propionic acid;

(2R)-2-Amino-4-(5-chloro-2-{2-[4-(4-fluoro-benzyl)-(2R,5S)-2,5-dimethyl-piperazin-1-yl]-2-oxo-ethoxy}-phenoxy)-butyric acid;

(2S)-2-(5-Chloro-2-{2-[4-(4-fluoro-benzyl)-(2R)-2-methyl-piperazin-1-yl]-2-oxo-ethoxy}-phenoxy)-propionic acid;

(2S)-2-(5-Chloro-2-{2-[4-(4-fluoro-benzyl)-(2R,5S)-2,5-dimethyl-piperazin-1-yl]-2-oxo-ethoxy}-benzyloxy)-propionic acid;

(2S)-2-(5-Chloro-2-{2-[4-(4-fluoro-benzyl)-(2R,5S)-2,5-dimethyl-piperazin-1-yl]-2-oxo-ethoxy}-phenoxy)-propionic acid;

(2S)-2-Amino-4-(5-bromo-2-{2-[4-(4-fluoro-benzyl)-(2R,5S)-2,5-dimethyl-piperazin-1-yl]-2-oxo-ethoxy}-phenoxy)-butyric acid;

(2S)-2-Amino-4-(5-chloro-2-{2-[4-(4-fluoro-benzyl)-(2R)-2-methyl-piperazin-1-yl]-2-oxo-ethoxy}-phenoxy)-butyric acid;

(2S)-2-Amino-4-(5-chloro-2-{2-[4-(4-fluoro-benzyl)-(2R,5S)-2,5-dimethyl-piperazin-1-yl]-2-oxo-ethoxy}-phenoxy)-butyric acid;

(4-Chloro-2-{2-[4-(4-fluoro-benzyl)-(2R)-2-methyl-piperazin-1-yl]-2-oxo-ethoxy}-phenyl)-acetic acid;

(4-Chloro-2-{2-[4-(4-fluoro-benzyl)-(2R,5S)-2,5-dimethyl-piperazin-1-yl]-2-oxo-ethoxy}-phenyl)-acetic acid;

(4S)-4-(5-Bromo-2-{2-[4-(4-fluoro-benzyl)-(2R)-2-methyl-piperazin-1-yl]-2-oxo-ethoxy}-phenoxy)-pyrrolidine-(2S)-2-carboxylic acid;

(4S)-4-(5-Bromo-2-{2-[4-(4-fluoro-benzyl)-(2R,5S)-2,5-dimethyl-piperazin-1-yl]-2-oxo-ethoxy}-phenoxy)-pyrrolidine-(2S)-2-carboxylic acid;

(4S)-4-(5-Chloro-2-{2-[4-(4-fluoro-benzyl)-(2R,5S)-2,5-dimethyl-piperazin-1-yl]-2-oxo-ethoxy}-phenoxy)-1-methyl-pyrrolidine-(2S)-2-carboxylic acid;

(4S)-4-(5-Chloro-2-{2-[4-(4-fluoro-benzyl)-(2R,5S)-2,5-dimethyl-piperazin-1-yl]-2-oxo-ethoxy}-phenoxy)-pyrrolidine-(2S)-2-carboxylic acid;

(4S)-4-(5-Chloro-2-{2-[4-(4-fluoro-benzyl)-(2R,5S)-2,5-dimethyl-piperazin-1-yl]-2-oxo-ethoxy}-phenoxy)-pyrrolidine-2-carboxylic acid;

(5-Bromo-2-{2-[(2R)-2-ethyl-4-(4-fluoro-benzyl)-piperazin-1-yl]-2-oxo-ethoxy}-phenyl)-acetic acid;

(5-Bromo-2-{2-[(2R)-2-ethyl-4-(4-fluoro-benzyl)-piperazin-1-yl]-2-oxo-ethoxy}-phenyl)-methanesulfonamide;

(5-Bromo-2-{2-[4-(4-chloro-benzyl)-(2R)-2-methyl-piperazin-1-yl]-2-oxo-ethoxy}phenyl)methanesulfonamide;

(5-Bromo-2-{2-[4-(4-chloro-benzyl)-(2R,5S)-2,5-dimethyl-piperazin-1-yl]-2-oxo-ethoxy}-phenyl)-methanesulfonamide;

(5-Bromo-2-{2-[4-(4-fluoro-benzyl)-(2R)-2-methyl-piperazin-1-yl]-2-oxo-ethoxy}-phenoxy)-acetic acid;

(5-Bromo-2-{2-[4-(4-fluoro-benzyl)-(2R)-2-methyl-piperazin-1-yl]-2-oxo-ethoxy}-phenoxy)-difluoro-acetic acid;

(5-Bromo-2-{2-[4-(4-fluoro-benzyl)-(2R)-2-methyl-piperazin-1-yl]-2-oxo-ethoxy}-phenyl)-acetic acid;

(5-Bromo-2-{2-[4-(4-fluoro-benzyl)-(2R)-2-methyl-piperazin-1-yl]-2-oxo-ethoxy}-phenyl)-methanesulfonamide;

(5-Bromo-2-{2-[4-(4-fluoro-benzyl)-(2R,5S)-2,5-dimethyl-piperazin-1-yl]-2-oxo-ethoxy}-benzylideneaminooxy)-acetic acid;

(5-Bromo-2-{2-[4-(4-fluoro-benzyl)-(2R,5S)-2,5-dimethyl-piperazin-1-yl]-2-oxo-ethoxy}-phenoxy)-acetic acid;

(5-Bromo-2-{2-[4-(4-fluoro-benzyl)-(2R,5S)-2,5-dimethyl-piperazin-1-yl]-2-oxo-ethoxy}-phenoxy)-difluoro-acetic acid;

(5-Bromo-2-{2-[4-(4-fluoro-benzyl)-(2R,5S)-2,5-dimethyl-piperazin-1-yl]-2-oxo-ethoxy}-phenyl)-acetic acid;

(5-Bromo-2-{2-[4-(4-fluoro-benzyl)-(2R,5S)-2,5-dimethyl-piperazin-1-yl]-2-oxo-ethoxy}-phenyl)-methanesulfonamide;

(5-Chloro-2-{2-[(2R)-2-ethyl-4-(4-fluoro-benzyl)-piperazin-1-yl]-2-oxo-ethoxy}-phenoxy)-acetic acid;

(5-Chloro-2-{2-[(2R)-2-ethyl-4-(4-fluoro-benzyl)-piperazin-1-yl]-2-oxo-ethoxy}-phenyl)-acetic acid;

(5-Chloro-2-{2-[(2R)-2-ethyl-4-(4-fluoro-benzyl)-piperazin-1-yl]-2-oxo-ethoxy}-phenyl)-methanesulfonamide;

(5-Chloro-2-{2-[4-(3,4-difluoro-benzyl)-(2R)-2-methyl-piperazin-1-yl]-2-oxo-ethoxy}-phenyl)-acetic acid;

(5-Chloro-2-{2-[4-(3,4-difluoro-benzyl)-(2R)-2-methyl-piperazin-1-yl]-2-oxo-ethoxy}-phenyl)-methanesulfonamide;

(5-Chloro-2-{2-[4-(3,4-difluoro-benzyl)-(2R,5S)-2,5-dimethyl-piperazin-1-yl]-2-oxo-ethoxy}-phenyl)-acetic acid;

(5-Chloro-2-{2-[4-(3,4-difluoro-benzyl)-(2R,5S)-2,5-dimethyl-piperazin-1-yl]-2-oxo-ethoxy}-phenyl)-methanesulfonamide;

(5-Chloro-2-{2-[4-(4-chloro-benzyl)-(2R)-2-methyl-piperazin-1-yl]-2-oxo-ethoxy}-phenyl)-acetic acid;

(5-Chloro-2-{2-[4-(4-chloro-benzyl)-(2R)-2-methyl-piperazin-1-yl]-2-oxo-ethoxy}-phenyl)-methanesulfonamide;

(5-Chloro-2-{2-[4-(4-chloro-benzyl)-(2R,5S)-2,5-dimethyl-piperazin-1-yl]-2-oxo-ethoxy}-phenyl)-acetic acid;

(5-Chloro-2-{2-[4-(4-chloro-benzyl)-(2R,5S)-2,5-dimethyl-piperazin-1-yl]-2-oxo-ethoxy}-phenyl)-methanesulfonamide;

(5-Chloro-2-{2-[4-(4-fluoro-benzyl)-(2R,5S)-2,5-dimethyl-piperazin-1-yl]-2-oxo-ethoxy}-phenyl)-oxo-acetic acid;

(5-Chloro-2-{2-[4-(4-fluoro-benzyl)-(2R)-2-methyl-piperazin-1-yl]-2-oxo-ethoxy}-phenoxy)-acetic acid;

(5-Chloro-2-{2-[4-(4-fluoro-benzyl)-(2R)-2-methyl-piperazin-1-yl]-2-oxo-ethoxy}-phenoxy)-difluoro-acetic acid;

(5-Chloro-2-{2-[4-(4-fluoro-benzyl)-(2R)-2-methyl-piperazin-1-yl]-2-oxo-ethoxy}-phenyl)-acetic acid;

(5-Chloro-2-{2-[4-(4-fluoro-benzyl)-(2R)-2-methyl-piperazin-1-yl]-2-oxo-ethoxy}-phenyl)-methanesulfonamide;
(5-Chloro-2-{2-[4-(4-fluoro-benzyl)-(2R)-2-methyl-piperazin-1-yl]-2-oxo-ethoxy}-phenylmethanesulfonylamino)-oxo-acetic acid;
(5-Chloro-2-{2-[4-(4-fluoro-benzyl)-(2R,5S)-2,5-dimethyl-piperazin-1-yl]-2-oxo-ethoxy}-benzenesulfonylamino)-acetic acid;
(5-Chloro-2-{2-[4-(4-fluoro-benzyl)-(2R,5S)-2,5-dimethyl-piperazin-1-yl]-2-oxo-ethoxy}-benzenesulfonylamino)-oxo-acetic acid;
(5-Chloro-2-{2-[4-(4-fluoro-benzyl)-(2R,5S)-2,5-dimethyl-piperazin-1-yl]-2-oxo-ethoxy}-benzyloxy)-acetyl methanesulfonamide;
(5-Chloro-2-{2-[4-(4-fluoro-benzyl)-(2R,5S)-2,5-dimethyl-piperazin-1-yl]-2-oxo-ethoxy}-benzylsulfamoyl)-acetic acid;
(5-Chloro-2-{2-[4-(4-fluoro-benzyl)-(2R,5S)-2,5-dimethyl-piperazin-1-yl]-2-oxo-ethoxy}-phenoxy)-acetic acid;
(5-Chloro-2-{2-[4-(4-fluoro-benzyl)-(2R,5S)-2,5-dimethyl-piperazin-1-yl]-2-oxo-ethoxy}-phenoxy)-difluoro-acetic acid;
(5-Chloro-2-{2-[4-(4-fluoro-benzyl)-(2R,5S)-2,5-dimethyl-piperazin-1-yl]-2-oxo-ethoxy}-phenylmethanesulfonyl)-acetic acid;
(5-Chloro-2-{2-[4-(4-fluoro-benzyl)-(2R,5S)-2,5-dimethyl-piperazin-1-yl]-2-oxo-ethoxy}-phenylmethanesulfonylamino)-oxo-acetic acid;
(5-Chloro-2-{2-[4-(4-fluoro-benzyl)-(2R,5S)-2,5-dimethyl-piperazin-1-yl]-2-oxo-ethoxy}-phenylsulfamoyl)-acetic acid;
(5-Chloro-2-{3-[4-(4-fluoro-benzyl)-(2R,5S)-2,5-dimethyl-piperazin-1-yl]-3-oxo-propyl}-phenoxy)-acetic acid;
[(4-Chloro-2-{2-[4-(4-fluoro-benzyl)-(2R,5S)-2,5-dimethyl-piperazin-1-yl]-2-oxo-ethoxy}-phenyl)]-N-cyanoacetamide;
[(5-Chloro-2-{2-[4-(4-fluoro-benzyl)-(2R,5S)-2,5-dimethyl-piperazin-1-yl]-2-oxo-ethoxy}-benzyl)-methylamino]-acetic acid;
[(5-Chloro-2-{2-[4-(4-fluoro-benzyl)-(2R,5S)-2,5-dimethyl-piperazin-1-yl]-2-oxo-ethoxy}-phenyl)-phenyl-methyleneaminooxy]-acetic acid;
[(5-Chloro-2-{2-[4-(4-fluoro-benzyl)-(2R,5S)-2,5-dimethyl-piperazin-1-yl]-2-oxo-ethoxy}-pyridine-3-carbonyl)-amino]-acetic acid;
[(5-Chloro-2-{2-[4-(4-fluoro-benzyl)-(2R,5S)-2,5-dimethyl-piperazin-1-yl]-2-oxo-ethylamino}-pyridine-3-carbonyl)-amino]-acetic acid;
[1-(5-Bromo-2-{2-[4-(4-fluoro-benzyl)-(2R,5S)-2,5-dimethyl-piperazin-1-yl]-2-oxo-ethoxy}-phenyl)-ethylideneaminooxy]-acetic acid;
[1-(5-Chloro-2-{2-[4-(4-fluoro-benzyl)-(2R,5S)-2,5-dimethyl-piperazin-1-yl]-2-oxo-ethoxy}-phenyl)-ethylideneaminooxy]-acetic acid;
[3-(4-Chloro-2-{2-[4-(4-fluoro-benzyl)-(2R,5S)-2,5-dimethyl-piperazin-1-yl]-2-oxo-ethoxy}-phenyl)-ureido]-acetic acid;
[3-(5-Chloro-2-{2-[4-(4-fluoro-benzyl)-(2R,5S)-2,5-dimethyl-piperazin-1-yl]-2-oxo-ethoxy}-phenyl)-ureido]-acetic acid;
1-(5-Chloro-2-{2-[4-(4-fluoro-benzyl)-(2R,5S)-2,5-dimethyl-piperazin-1-yl]-2-oxo-ethoxy}-benzyl)-3-(2-methylbenzenesulfonyl)-urea;
1-(5-Chloro-2-{2-[4-(4-fluoro-benzyl)-(2R,5S)-2,5-dimethyl-piperazin-1-yl]-2-oxo-ethoxy}-benzyl)-3-(methylsulfonyl)-urea;
1-(5-Chloro-2-{2-[4-(4-fluoro-benzyl)-(2R,5S)-2,5-dimethyl-piperazin-1-yl]-2-oxo-ethoxy}-phenyl)-2-(1H-tetrazol-5-yl)-ethanone;
1-(5-Chloro-2-{2-[4-(4-fluoro-benzyl)-(2R,5S)-2,5-dimethyl-piperazin-1-yl]-2-oxo-ethoxy}-phenyl)-3-(1H-tetrazol-5-yl)-propan-1-one;
1-[(5-chloro-2-{2-[4-(4-fluoro-benzyl)-(2R,5S)-2,5-dimethyl-piperazin-1-oxo-ethoxy}-benzyl)]-3-(2-methylbenzoyl)sulfamide;
1-Acetyl-3-(5-chloro-2-{2-[4-(4-fluoro-benzyl)-(2R,5S)-2,5-dimethyl-piperazin-1-yl]-2-oxo-ethoxy}-benzyl)sulfamide;
2-(5-Bromo-2-{2-[4-(4-fluoro-benzyl)-(2R)-2-methyl-piperazin-1-yl]-2-oxo-ethoxy}-phenoxy)-2-methyl-propionic acid;
2-(5-Bromo-2-{2-[4-(4-fluoro-benzyl)-(2R,5S)-2,5-dimethyl-piperazin-1-yl]-2-oxo-ethoxy}-phenoxy)-2-methyl-propionic acid;
2-(5-Chloro-2-{2-[4-(4-fluoro-benzyl)-(2R)-2-methyl-piperazin-1-yl]-2-oxo-ethoxy}-phenoxy)-2-methyl-propionic acid;
2-(5-Chloro-2-{2-[4-(4-fluoro-benzyl)-(2R,5S)-2,5-dimethyl-piperazin-1-yl]-2-oxo-ethoxy}-benzenesulfonyl)-2-methyl-propionic acid;
2-(5-Chloro-2-{2-[4-(4-fluoro-benzyl)-(2R,5S)-2,5-dimethyl-piperazin-1-yl]-2-oxo-ethoxy}-benzyloxy)-2-methyl-propionic acid;
2-(5-Chloro-2-{2-[4-(4-fluoro-benzyl)-(2R,5S)-2,5-dimethyl-piperazin-1-yl]-2-oxo-ethoxy}-benzylsulfamoyl)-propionic acid;
2-(5-Chloro-2-{2-[4-(4-fluoro-benzyl)-(2R,5S)-2,5-dimethyl-piperazin-1-yl]-2-oxo-ethoxy}-phenoxy)-2-methyl-propionic acid;
2-(5-Chloro-2-{2-[4-(4-fluoro-benzyl)-(2R,5S)-2,5-dimethyl-piperazin-1-yl]-2-oxo-ethoxy}-phenoxy)-4-methyl-thiazole-5-carboxylic acid;
2-(5-Chloro-2-{2-[4-(4-fluoro-benzyl)-(2R,5S)-2,5-dimethyl-piperazin-1-yl]-2-oxo-ethoxy}-phenoxy)-6-methyl-pyrimidine-4-carboxylic acid;
2-(5-Chloro-2-{2-[4-(4-fluoro-benzyl)-(2R,5S)-2,5-dimethyl-piperazin-1-yl]-2-oxo-ethoxy}-phenoxy)-nicotinic acid;
2-(5-Chloro-2-{2-[4-(4-fluoro-benzyl)-(2R,5S)-2,5-dimethyl-piperazin-1-yl]-2-oxo-ethoxy}-phenoxy)-propionic acid;
2-(5-Chloro-2-{2-[4-(4-fluoro-benzyl)-(2R,5S)-2,5-dimethyl-piperazin-1-yl]-2-oxo-ethoxy}-phenoxymethyl)-furan-3-carboxylic acid;
2-(5-Chloro-2-{2-[4-(4-fluoro-benzyl)-(2R,5S)-2,5-dimethyl-piperazin-1-yl]-2-oxo-ethoxy}-phenoxymethyl)-nicotinic acid;
2-(5-Chloro-2-{2-[4-(4-fluoro-benzyl)-(2R,5S)-2,5-dimethyl-piperazin-1-yl]-2-oxo-ethoxy}-phenoxymethyl)-thiazole-4-carboxylic acid;
2-(5-Chloro-2-{2-[4-(4-fluoro-benzyl)-(2R,5S)-2,5-dimethyl-piperazin-1-yl]-2-oxo-ethoxy}-phenylsulfanyl)-2-methyl-propionic acid;
2-[4-Bromo-2-(2H-tetrazol-5-yloxy)-phenoxy]-1-[4-(4-fluoro-benzyl)-(2R)-2-methyl-piperazin-1-yl]-ethanone;
2-[4-Chloro-2-(2H-tetrazol-5-ylmethoxy)-phenoxy]-1-[4-(4-fluoro-benzyl)-(2R,5S)-2,5-dimethyl-piperazin-1-yl]-ethanone;
2-[4-Chloro-2-(2H-tetrazol-5-yloxy)-phenoxy]-1-[4-(4-fluoro-benzyl)-(2R)-2-methyl-piperazin-1-yl]-ethanone;
2-[4-Chloro-2-(2H-tetrazol-5-yloxy)-phenoxy]-1-[4-(4-fluoro-benzyl)-(2R,5S)-2,5-dimethyl-piperazin-1-yl]-ethanone;

2-[4-Chloro-2-(5-hydroxy-furan-2-yl)-phenoxy]-1-[4-(4-fluoro-benzyl)-(2R,5S)-2,5-dimethyl-piperazin-1-yl]-ethanone;

2-Amino-3-(5-chloro-2-{2-[4-(4-fluoro-benzyl)-(2R,5S)-2,5-dimethyl-piperazin-1-yl]-2-oxo-ethoxy}-phenyl)-propionic acid;

2-Amino-3-(5-chloro-2-{2-[4-(4-fluoro-benzyl)-(2R,5S)-2,5-dimethyl-piperazin-1-yl]-2-oxo-ethoxy}-pyridin-3-yl)-propionic acid;

2-Chloro-N-[(5-chloro-2-{2-[4-(4-fluoro-benzyl)-(2R,5S)-2,5-dimethyl-piperazin-1-yl]-2-oxo-ethoxy}-phenyl)-acetyl]-benzenesulfonamide;

3-(2-{2-[(2R)-2-Ethyl-4-(4-fluoro-benzyl)-piperazin-1-yl]-2-oxo-ethoxy}-5-methyl-phenyl)-propionic acid;

3-(2-{2-[4-(4-Fluoro-benzyl)-(2R)-2-methyl-piperazin-1-yl]-2-oxo-ethoxy}-5-methyl-phenyl)-propionic acid;

3-(2-{2-[4-(4-Fluoro-benzyl)-(2R,5S)-2,5-dimethyl-piperazin-1-yl]-2-oxo-ethoxy}-5-methyl-phenyl)-acrylic acid;

3-(2-{2-[4-(4-Fluoro-benzyl)-(2R,5S)-2,5-dimethyl-piperazin-1-yl]-2-oxo-ethoxy}-5-methyl-phenyl)-propionic acid;

3-(5-Bromo-2-{2-[4-(4-fluoro-benzyl)-(2R)-2-methyl-piperazin-1-yl]-2-oxo-ethoxy}-phenyl)-acrylic acid;

3-(5-Bromo-2-{2-[4-(4-fluoro-benzyl)-(2R)-2-methyl-piperazin-1-yl]-2-oxo-ethoxy}-phenyl)-propionic acid;

3-(5-Bromo-2-{2-[4-(4-fluoro-benzyl)-(2R,5S)-2,5-dimethyl-piperazin-1-yl]-2-oxo-ethoxy}-phenyl)-acrylic acid;

3-(5-Bromo-2-{2-[4-(4-fluoro-benzyl)-(2R,5S)-2,5-dimethyl-piperazin-1-yl]-2-oxo-ethoxy}-phenyl)-propionic acid;

3-(5-Bromo-2-{2-[4-(4-fluoro-benzyl)-2-methyl-piperazin-1-yl]-2-oxo-ethoxy}-phenoxymethyl)-furan-2-carboxylic acid;

3-(5-Chloro-2-{2-[4-(4-fluoro-benzyl)-(2R)-2-methyl-piperazin-1-yl]-2-oxo-ethoxy}-phenoxymethyl)-furan-2-carboxylic acid;

3-(5-Chloro-2-{2-[4-(4-fluoro-benzyl)-(2R)-2-methyl-piperazin-1-yl]-2-oxo-ethoxy}-phenyl)-acrylic acid;

3-(5-Chloro-2-{2-[4-(4-fluoro-benzyl)-(2R)-2-methyl-piperazin-1-yl]-2-oxo-ethoxy}-phenyl)-propionic acid;

3-(5-Chloro-2-{2-[4-(4-fluoro-benzyl)-(2R,5S)-2,5-dimethyl-piperazin-1-yl]-2-oxo-ethoxy}-phenoxy)-2,2-dimethyl-propionic acid;

3-(5-Chloro-2-{2-[4-(4-fluoro-benzyl)-(2R,5S)-2,5-dimethyl-piperazin-1-yl]-2-oxo-ethoxy}-phenoxymethyl)-furan-2-carboxylic acid;

3-(5-Chloro-2-{2-[4-(4-fluoro-benzyl)-(2R,5S)-2,5-dimethyl-piperazin-1-yl]-2-oxo-ethoxy}-phenoxymethyl)-thiophene-2-carboxylic acid;

3-(5-Chloro-2-{2-[4-(4-fluoro-benzyl)-(2R,5S)-2,5-dimethyl-piperazin-1-yl]-2-oxo-ethoxy}-phenyl)-acrylic acid;

3-(5-Chloro-2-{2-[4-(4-fluoro-benzyl)-(2R,5S)-2,5-dimethyl-piperazin-1-yl]-2-oxo-ethoxy}-pyridin-3-yl)-acrylic acid;

3-(5-Chloro-2-{2-[4-(4-fluoro-benzyl)-(2R,5S)-2,5-dimethyl-piperazin-1-yl]-2-oxo-ethoxy}-pyridin-3-yl)-propionic acid;

3-(5-Chloro-2-{2-[4-(4-fluoro-benzyl)-(2R,5S)-2,5-dimethyl-piperazin-1-yl]-2-oxo-ethylamino}-pyridin-3-yl)-propionic acid;

3,5-Dimethyl-isoxazole-4-sulfonic acid [(5-chloro-2-{2-[4-(4-fluoro-benzyl)-(2R,5S)-2,5-dimethyl-piperazin-1-yl]-2-oxo-ethoxy}-phenyl)-acetyl]-amide;

3-[3-(4-Chloro-2-{2-[4-(4-fluoro-benzyl)-(2R,5S)-2,5-dimethyl-piperazin-1-yl]-2-oxo-ethoxy}-phenyl)-ureido]-propionic acid;

3-[3-(5-Chloro-2-{2-[4-(4-fluoro-benzyl)-(2R,5S)-2,5-dimethyl-piperazin-1-yl]-2-oxo-ethoxy}-phenyl)-ureido]-propionic acid;

4-(5-Bromo-2-{2-[4-(4-fluoro-benzyl)-(2R)-2-methyl-piperazin-1-yl]-2-oxo-ethoxy}-phenyl)-4-oxo-butyric acid;

4-(5-Bromo-2-{2-[4-(4-fluoro-benzyl)-(2R,5S)-2,5-dimethyl-piperazin-1-yl]-2-oxo-ethoxy}-phenyl)-4-oxo-butyric acid;

4-(5-Chloro-2-{2-[4-(4-fluoro-benzyl)-(2R)-2-methyl-piperazin-1-yl]-2-oxo-ethoxy}-phenoxy)-butyric acid;

4-(5-Chloro-2-{2-[4-(4-fluoro-benzyl)-(2R)-2-methyl-piperazin-1-yl]-2-oxo-ethoxy}-phenyl)-4-oxo-butyric acid;

4-(5-Chloro-2-{2-[4-(4-fluoro-benzyl)-(2R,5S)-2,5-dimethyl-piperazin-1-yl]-2-oxo-ethoxy}-phenoxy)-butyric acid;

4-(5-Chloro-2-{2-[4-(4-fluoro-benzyl)-(2R,5S)-2,5-dimethyl-piperazin-1-yl]-2-oxo-ethoxy}-phenoxy)-pyridine-2-carboxylic acid;

4-(5-Chloro-2-{2-[4-(4-fluoro-benzyl)-(2R,5S)-2,5-dimethyl-piperazin-1-yl]-2-oxo-ethoxy}-phenyl)-4-hydroxy-but-3-enoic acid;

4-(5-Chloro-2-{2-[4-(4-fluoro-benzyl)-(2R,5S)-2,5-dimethyl-piperazin-1-yl]-2-oxo-ethoxy}-phenyl)-4-oxo-butyric acid;

4-(5-Chloro-2-{2-[4-(4-fluoro-benzyl)-(2R,5S)-2,5-dimethyl-piperazin-1-yl]-2-oxo-ethoxy}-phenyl)-4-hydroxy-butyric acid;

4-(5-Chloro-2-{2-[4-(4-fluoro-benzyl)-(2R,5S)-2,5-dimethyl-piperazin-1-yl]-2-oxo-ethoxy}-phenyl)-but-3-enoic acid;

4-(5-Chloro-2-{2-[4-(4-fluoro-benzyl)-(2R,5S)-2,5-dimethyl-piperazin-1-yl]-2-oxo-ethoxy}-pyridin-3-yl)-4-oxo-butyric acid;

4-[2-(5-Chloro-2-{2-[4-(4-fluoro-benzyl)-(2R,5S)-2,5-dimethyl-piperazin-1-yl]-2-oxo-ethoxy}-phenyl)-2-oxo-ethyl]-isoxazolidine-3,5-dione;

4-[2-(5-Chloro-2-{2-[4-(4-fluoro-benzyl)-(2R,5S)-2,5-dimethyl-piperazin-1-yl]-2-oxo-ethoxy}-phenyl)-2-oxo-ethyl]-pyrazolidine-3,5-dione;

5-(5-Chloro-2-{2-[4-(4-fluoro-benzyl)-(2R,5S)-2,5-dimethyl-piperazin-1-yl]-2-oxo-ethoxy}-phenoxy)-5-(2-methoxy-ethyl)-pyrimidine-2,4,6-trione;

5-(5-Chloro-2-{2-[4-(4-fluoro-benzyl)-(2R,5S)-2,5-dimethyl-piperazin-1-yl]-2-oxo-ethoxy}-phenoxy)-5-ethyl-pyrimidine-2,4,6-trione;

5-(5-Chloro-2-{2-[4-(4-fluoro-benzyl)-(2R,5S)-2,5-dimethyl-piperazin-1-yl]-2-oxo-ethoxy}-phenoxy)-5-methyl-pyrimidine-2,4,6-trione;

5-(5-Chloro-2-{2-[4-(4-fluoro-benzyl)-(2R,5S)-2,5-dimethyl-piperazin-1-yl]-2-oxo-ethoxy}-phenoxymethyl)-furan-2-carboxylic acid;

5-(5-Chloro-2-{2-[4-(4-fluoro-benzyl)-(2R,5S)-2,5-dimethyl-piperazin-1-yl]-2-oxo-ethoxy}-phenoxymethyl)-thiophene-2-carboxylic acid;

5-(5-Chloro-2-{2-[4-(4-fluoro-benzyl)-(2R,5S)-2,5-dimethyl-piperazin-1-yl]-2-oxo-ethoxy}-phenyl)-5-hydroxy-dihydro-furan-2-one;

5-(5-Chloro-2-{2-[4-(4-fluoro-benzyl)-(2R,5S)-2,5-dimethyl-piperazin-1-yl]-2-oxo-ethoxy}-phenyl)-5-oxo-pentanoic acid;

5-(5-Chloro-2-{2-[4-(4-fluoro-benzyl)-(2R,5S)-2,5-dimethyl-piperazin-1-yl]-2-oxo-ethoxy}-phenyl)-dihydro-furan-2-one;

5-[2-(5-Chloro-2-{2-[4-(4-fluoro-benzyl)-(2R,5S)-2,5-dimethyl-piperazin-1-yl]-2-oxo-ethoxy}-phenyl)-2-oxo-ethyl]-2-thioxo-dihydro-pyrimidine-4,6-dione;

5-[2-(5-Chloro-2-{2-[4-(4-fluoro-benzyl)-(2R,5S)-2,5-dimethyl-piperazin-1-yl]-2-oxo-ethoxy}-phenyl)-2-oxo-ethyl]-pyrimidine-2,4,6-trione;

(5-Chloro-2-{2-[4-(4-fluoro-benzyl)-(2R,5S)-2,5-dimethyl-piperazin-1-yl]-2-oxo-ethoxy}-benzylideneaminooxy)-acetic acid;

5-Chloro-2-{2-[4-(4-fluoro-benzyl)-(2R,5S)-2,5-dimethyl-piperazin-1-yl]-2-oxo-ethoxy}-N-(2-hydroxy-2-methyl-propionyl)-benzenesulfonamide;

5-Chloro-2-{2-[4-(4-fluoro-benzyl)-(2R,5S)-2,5-dimethyl-piperazin-1-yl]-2-oxo-ethoxy}-N-(2-methyl phenylamino)carbonyl]-benzenesulfonamide;

5-Chloro-2-{2-[4-(4-fluoro-benzyl)-(2R,5S)-2,5-dimethyl-piperazin-1-yl]-2-oxo-ethoxy}-N-(4-fluorophenylamino)carbonyl]-benzenesulfonamide;

5-Chloro-2-{2-[4-(4-fluoro-benzyl)-(2R,5S)-2,5-dimethyl-piperazin-1-yl]-2-oxo-ethoxy}-N-(ethoxycarbonyl]-benzenesulfonamide;

5-Chloro-2-{2-[4-(4-fluoro-benzyl)-(2R,5S)-2,5-dimethyl-piperazin-1-yl]-2-oxo-ethoxy}-N-(methoxycarbonyl]-benzenesulfonamide;

5-Chloro-2-{2-[4-(4-fluoro-benzyl)-(2R,5S)-2,5-dimethyl-piperazin-1-yl]-2-oxo-ethoxy}-N-(phenylamino)carbonyl]-benzenesulfonamide;

5-Chloro-2-{2-[4-(4-fluoro-benzyl)-(2R,5S)-2,5-dimethyl-piperazin-1-yl]-2-oxo-ethoxy}-N-hydroxyacetyl-benzenesulfonamide;

6-(5-Chloro-2-{2-[4-(4-fluoro-benzyl)-(2R,5S)-2,5-dimethyl-piperazin-1-yl]-2-oxo-ethoxy}-phenoxy)-nicotinic acid;

6-(5-Chloro-2-{2-[4-(4-fluoro-benzyl)-(2R,5S)-2,5-dimethyl-piperazin-1-yl]-2-oxo-ethoxy}-phenoxy)-pyridine-2-carboxylic acid;

6-(5-Chloro-2-{2-[4-(4-fluoro-benzyl)-(2R,5S)-2,5-dimethyl-piperazin-1-yl]-2-oxo-ethoxy}-phenoxymethyl)-nicotinic acid;

6-[(5-Chloro-2-{2-[4-(4-fluoro-benzyl)-(2R,5S)-2,5-dimethyl-piperazin-1-yl]-2-oxo-ethoxy}-pyridin-3-ylamino)-methyl]-nicotinic acid;

C-(2-{2-[4-(4-Fluoro-benzyl)-(2R)-2-methyl-piperazin-1-yl]-2-oxo-ethoxy}-5-trifluoromethyl-phenyl)-N-(2-hydroxy-2-methyl-propionyl)-methanesulfonamide;

C-(2-{2-[4-(4-Fluoro-benzyl)-(2R,5S)-2,5-dimethyl-piperazin-1-yl]-2-oxo-ethoxy}-5-trifluoromethyl-phenyl)-N-(2-hydroxy-2-methyl-propionyl)-methanesulfonamide;

C-(2-{2-[4-(4-Fluoro-benzyl)-(2R,5S)-2,5-dimethyl-piperazin-1-yl]-2-oxo-ethoxy}-5-trifluoromethyl-phenyl)-N-hydroxyacetyl-methanesulfonamide;

C-(5-Chloro-2-{2-[4-(3,4-difluoro-benzyl)-(2R)-2-methyl-piperazin-1-yl]-2-oxo-ethoxy}-phenyl)-N-cyclopropanecarbonyl-methanesulfonamide;

C-(5-Chloro-2-{2-[4-(3,4-difluoro-benzyl)-(2R,5S)-2,5-dimethyl-piperazin-1-yl]-2-oxo-ethoxy}-phenyl)-N-(2-hydroxy-2-methyl-propionyl)-methanesulfonamide;

C-(5-Chloro-2-{2-[4-(3,4-difluoro-benzyl)-(2R,5S)-2,5-dimethyl-piperazin-1-yl]-2-oxo-ethoxy}-phenyl)-N-(methoxycarbonyl)-methanesulfonamide;

C-(5-Chloro-2-{2-[4-(3,4-difluoro-benzyl)-(2R,5S)-2,5-dimethyl-piperazin-1-yl]-2-oxo-ethoxy}-phenyl)-N-cyclopropanecarbonyl-methanesulfonamide;

C-(5-Chloro-2-{2-[4-(3,4-difluoro-benzyl)-(2R,5S)-2,5-dimethyl-piperazin-1-yl]-2-oxo-ethoxy}-phenyl)-N-hydroxyacetyl-methanesulfonamide;

C-(5-Chloro-2-{2-[4-(4-chloro-benzyl)-(2R)-2-methyl-piperazin-1-yl]-2-oxo-ethoxy}-phenyl)-N-trifluoroacetyl-methanesulfonamide;

C-(5-Chloro-2-{2-[4-(4-chloro-benzyl)-(2R,5S)-2,5-dimethyl-piperazin-1-yl]-2-oxo-ethoxy}-phenyl)-N-(2-hydroxy-2-methyl-propionyl)-methanesulfonamide;

C-(5-Chloro-2-{2-[4-(4-chloro-benzyl)-(2R,5S)-2,5-dimethyl-piperazin-1-yl]-2-oxo-ethoxy}-phenyl)-N-(methoxycarbonyl)-methanesulfonamide;

C-(5-Chloro-2-{2-[4-(4-chloro-benzyl)-(2R,5S)-2,5-dimethyl-piperazin-1-yl]-2-oxo-ethoxy}-phenyl)-N-cyclopropanecarbonyl-methanesulfonamide;

C-(5-Chloro-2-{2-[4-(4-chloro-benzyl)-(2R,5S)-2,5-dimethyl-piperazin-1-yl]-2-oxo-ethoxy}-phenyl)-N-hydroxyacetyl-methanesulfonamide;

C-(5-Chloro-2-{2-[4-(4-chloro-benzyl)-(2R,5S)-2,5-dimethyl-piperazin-1-yl]-2-oxo-ethoxy}-phenyl)-N-trifluoroacetyl-methanesulfonamide;

C-(5-Chloro-2-{2-[4-(4-fluoro-benzyl)-(2R)-2-methyl-piperazin-1-yl]-2-oxo-ethoxy}-phenyl)-N-(1-hydroxy-cyclopropanecarbonyl)-methanesulfonamide;

C-(5-Chloro-2-{2-[4-(4-fluoro-benzyl)-(2R)-2-methyl-piperazin-1-yl]-2-oxo-ethoxy}-phenyl)-N-(2-hydroxy-2-methyl-propionyl)-methanesulfonamide;

C-(5-Chloro-2-{2-[4-(4-fluoro-benzyl)-(2R)-2-methyl-piperazin-1-yl]-2-oxo-ethoxy}-phenyl)-N-(3-hydroxy-3-methyl-butyryl)-methanesulfonamide;

C-(5-Chloro-2-{2-[4-(4-fluoro-benzyl)-(2R)-2-methyl-piperazin-1-yl]-2-oxo-ethoxy}-phenyl)-N-(methoxycarbonyl)-methanesulfonamide;

C-(5-Chloro-2-{2-[4-(4-fluoro-benzyl)-(2R)-2-methyl-piperazin-1-yl]-2-oxo-ethoxy}-phenyl)-N-hydroxyacetyl-methanesulfonamide;

C-(5-Chloro-2-{2-[4-(4-fluoro-benzyl)-(2R,5S)-2,5-dimethyl-piperazin-1-yl]-2-oxo-ethoxy}-phenyl)-N-(1-hydroxy-cyclopropanecarbonyl)-methanesulfonamide;

C-(5-Chloro-2-{2-[4-(4-fluoro-benzyl)-(2R,5S)-2,5-dimethyl-piperazin-1-yl]-2-oxo-ethoxy}-phenyl)-N-(2,2-dimethyl-propionyl)-methanesulfonamide;

C-(5-Chloro-2-{2-[4-(4-fluoro-benzyl)-(2R,5S)-2,5-dimethyl-piperazin-1-yl]-2-oxo-ethoxy}-phenyl)-N-(2-hydroxy-2-methyl-propionyl)-methanesulfonamide;

C-(5-Chloro-2-{2-[4-(4-fluoro-benzyl)-(2R,5S)-2,5-dimethyl-piperazin-1-yl]-2-oxo-ethoxy}-phenyl)-N-(3-hydroxy-3-methyl-butyryl)-methanesulfonamide;

C-(5-Chloro-2-{2-[4-(4-fluoro-benzyl)-(2R,5S)-2,5-dimethyl-piperazin-1-yl]-2-oxo-ethoxy}-phenyl)-N-(ethylaminocarbonyl)-methanesulfonamide;

C-(5-Chloro-2-{2-[4-(4-fluoro-benzyl)-(2R,5S)-2,5-dimethyl-piperazin-1-yl]-2-oxo-ethoxy}-phenyl)-N-(methoxycarbonyl)-methanesulfonamide;

C-(5-Chloro-2-{2-[4-(4-fluoro-benzyl)-(2R,5S)-2,5-dimethyl-piperazin-1-yl]-2-oxo-ethoxy}-phenyl)-N-hydroxyacetyl-methanesulfonamide;

C-(5-Chloro-2-{2-[4-(4-fluoro-benzyl)-(2R,5S)-2,5-dimethyl-piperazin-1-yl]-2-oxo-ethoxy}-phenyl)-N-methoxyacetyl-methanesulfonamide;

Ethanesulfonic acid [(5-chloro-2-{2-[4-(4-fluoro-benzyl)-(2R,5S)-2,5-dimethyl-piperazin-1-yl]-2-oxo-ethoxy}-phenyl)-acetyl]-amide;

methylsulfonyl-carbamic acid 5-chloro-2-{2-[4-(4-fluoro-benzyl)-(2R,5S)-2,5-dimethyl-piperazin-1-yl]-2-oxo-ethoxy}-benzyl ester;

N-(5-Chloro-2-{2-[4-(4-fluoro-benzyl)-(2R)-2-methyl-piperazin-1-yl]-2-oxo-ethoxy}-pyridin-3-yl)-2,2-dimethyl-succinamic acid;

N-(5-Chloro-2-{2-[4-(4-fluoro-benzyl)-(2R)-2-methyl-piperazin-1-yl]-2-oxo-ethoxy}-pyridin-3-yl)-succinamic acid;

N-(5-Chloro-2-{2-[4-(4-fluoro-benzyl)-(2R,5S)-2,5-dimethyl-piperazin-1-yl]-2-oxo-ethoxy}-pyridin-3-yl)-succinamic acid;

N-[(2-{2-[(2R)-2-Ethyl-4-(4-fluoro-benzyl)-piperazin-1-yl]-2-oxo-ethoxy}-5-methyl-phenyl)-acetyl]-methanesulfonamide;

N-[(2-{2-[4-(4-Fluoro-benzyl)-(2R,5S)-2,5-dimethyl-piperazin-1-yl]-2-oxo-ethoxy}-4-methoxy-phenyl)-acetyl]-methanesulfonamide;

N-[(2-{2-[4-(4-Fluoro-benzyl)-(2R,5S)-2,5-dimethyl-piperazin-1-yl]-2-oxo-methoxy}-phenyl)-acetyl]-methanesulfonamide;

N-[(2-{3-[4-(4-Fluoro-benzyl)-(2R,5S)-2,5-dimethyl-piperazin-1-yl]-3-oxo-propyl}-5-methoxy-phenoxy)-acetyl]-methanesulfonamide;

N-[(2-{3-[4-(4-Fluoro-benzyl)-(2R,5S)-2,5-dimethyl-piperazin-1-yl]-3-oxo-propyl}-5-methyl-phenoxy)-acetyl]-methanesulfonamide;

N-[(2R)-2-Amino-4-(5-chloro-2-{2-[4-(4-fluoro-benzyl)-(2R,5S)-2,5-dimethyl-piperazin-1-yl]-2-oxo-ethoxy}-phenoxy)-butyryl]-methanesulfonamide;

N-[(4-Chloro-2-{2-[4-(4-fluoro-benzyl)-(2R)-2-methyl-piperazin-1-yl]-2-oxo-ethoxy}-phenyl)-acetyl]-methanesulfonamide;

N-[(4-Chloro-2-{2-[4-(4-fluoro-benzyl)-(2R,5S)-2,5-dimethyl-piperazin-1-yl]-2-oxo-ethoxy}-phenyl)-acetyl]-methanesulfonamide;

N-[(4S)-4-(5-Chloro-2-{2-[4-(4-fluoro-benzyl)-(2R,5S)-2,5-dimethyl-piperazin-1-yl]-2-oxo-ethoxy}-phenoxy)-pyrrolidine-(2S)-2-carbonyl]-methanesulfonamide;

N-[(5-Bromo-2-{(2R)-2-[2-ethyl-4-(4-fluoro-benzyl)-piperazin-1-yl]-2-oxo-ethoxy}-phenyl)-acetyl]-methanesulfonamide;

N-[(5-Bromo-2-{2-[4-(4-fluoro-benzyl)-(2R)-2-methyl-piperazin-1-yl]-2-oxo-ethoxy}-phenoxy)-acetyl]-methanesulfonamide;

N-[(5-Bromo-2-{2-[4-(4-fluoro-benzyl)-(2R)-2-methyl-piperazin-1-yl]-2-oxo-ethoxy}-phenyl)-acetyl]-methanesulfonamide;

N-[(5-Bromo-2-{2-[4-(4-fluoro-benzyl)-(2R,5S)-2,5-dimethyl-piperazin-1-yl]-2-oxo-ethoxy}-phenoxy)-acetyl]-methanesulfonamide;

N-[(5-Bromo-2-{2-[4-(4-fluoro-benzyl)-(2R,5S)-2,5-dimethyl-piperazin-1-yl]-2-oxo-ethoxy}-phenyl)-acetyl]-methanesulfonamide;

N-[(5-Bromo-2-{2-[4-(4-fluoro-benzyl)-piperazin-1-yl]-2-oxo-ethoxy}-phenyl)-acetyl]-methanesulfonamide;

N-[(5-Chloro-2-{2-[(2R)-2-ethyl-4-(4-fluoro-benzyl)-piperazin-1-yl]-2-oxo-ethoxy}-phenoxy)-acetyl]-methanesulfonamide;

N-[(5-Chloro-2-{2-[(2R)-2-ethyl-4-(4-fluoro-benzyl)-piperazin-1-yl]-2-oxo-ethoxy}-phenyl)-acetyl]-methanesulfonamide;

N-[(5-Chloro-2-{2-[4-(3,4-difluoro-benzyl)-(2R)-2-methyl-piperazin-1-yl]-2-oxo-ethoxy}-phenyl)-acetyl]-methanesulfonamide;

N-[(5-Chloro-2-{2-[4-(3,4-difluoro-benzyl)-(2R,5S)-2,5-dimethyl-piperazin-1-yl]-2-oxo-ethoxy}-phenyl)-acetyl]-methanesulfonamide;

N-[(5-Chloro-2-{2-[4-(4-chloro-benzyl)-(2R)-2-methyl-piperazin-1-yl]-2-oxo-ethoxy}-phenyl)-acetyl]-methanesulfonamide;

N-[(5-Chloro-2-{2-[4-(4-chloro-benzyl)-(2R,5S)-2,5-dimethyl-piperazin-1-yl]-2-oxo-ethoxy}-phenyl)-acetyl]-methanesulfonamide;

N-[(5-Chloro-2-{2-[4-(4-fluoro-benzyl)-(2R)-2-methyl-piperazin-1-yl]-2-oxo-ethoxy}-phenoxy)-acetyl]-methanesulfonamide;

N-[(5-Chloro-2-{2-[4-(4-fluoro-benzyl)-(2R)-2-methyl-piperazin-1-yl]-2-oxo-ethoxy}-phenyl)-acetyl]-methanesulfonamide;

N-[(5-Chloro-2-{2-[4-(4-fluoro-benzyl)-(2R,5S)-2,5-dimethyl-piperazin-1-yl]-2-oxo-ethoxy}-phenoxy)-acetyl]-methanesulfonamide;

N-[(5-Chloro-2-{2-[4-(4-fluoro-benzyl)-(2R,5S)-2,5-dimethyl-piperazin-1-yl]-2-oxo-ethoxy}-phenyl)-acetyl]-2-fluoro-benzenesulfonamide;

N-[(5-Chloro-2-{2-[4-(4-fluoro-benzyl)-(2R,5S)-2,5-dimethyl-piperazin-1-yl]-2-oxo-ethoxy}-phenyl)-acetyl]-2-methyl-benzenesulfonamide;

N-[(5-Chloro-2-{2-[4-(4-fluoro-benzyl)-(2R,5S)-2,5-dimethyl-piperazin-1-yl]-2-oxo-ethoxy}-phenyl)-acetyl]-4-fluoro-benzenesulfonamide;

N-[(5-Chloro-2-{2-[4-(4-fluoro-benzyl)-(2R,5S)-2,5-dimethyl-piperazin-1-yl]-2-oxo-ethoxy}-phenyl)-acetyl]-4-methoxy-benzenesulfonamide;

N-[(5-Chloro-2-{2-[4-(4-fluoro-benzyl)-(2R,5S)-2,5-dimethyl-piperazin-1-yl]-2-oxo-ethoxy}-phenyl)-acetyl]-4-methyl-benzenesulfonamide;

N-[(5-Chloro-2-{2-[4-(4-fluoro-benzyl)-(2R,5S)-2,5-dimethyl-piperazin-1-yl]-2-oxo-ethoxy}-phenyl)-acetyl]-benzenesulfonamide;

N-[(5-Chloro-2-{2-[4-(4-fluoro-benzyl)-(2R,5S)-2,5-dimethyl-piperazin-1-yl]-2-oxo-ethoxy}-phenyl)-acetyl]-C,C,C-trifluoro-methanesulfonamide;

N-[(5-Chloro-2-{2-[4-(4-fluoro-benzyl)-(2R,5S)-2,5-dimethyl-piperazin-1-yl]-2-oxo-ethoxy}-phenyl)-acetyl]-C-phenyl-methanesulfonamide;

N-[(5-Chloro-2-{2-[4-(4-fluoro-benzyl)-(2R,5S)-2,5-dimethyl-piperazin-1-yl]-2-oxo-ethoxy}-phenyl)-acetyl]-methanesulfonamide;

N-[(5-Chloro-2-{2-[4-(4-fluoro-benzyl)-(2R,5S)-2,5-dimethyl-piperazin-1-yl]-2-oxo-ethoxy}-phenyl)-acetyl]-sulfamide;

N-[(5-Chloro-2-{2-[4-(4-fluoro-benzyl)-(2R,5S)-2,5-dimethyl-piperazin-1-yl]-2-oxo-ethoxy}-pyridin-3-yl)-acetyl]-methanesulfonamide;

N-[(5-Chloro-2-{2-[4-(4-fluoro-benzyl)-piperazin-1-yl]-2-oxo-ethoxy}-phenyl)-acetyl]-methanesulfonamide;

N-[3-(2-{2-[(2R)-2-Ethyl-4-(4-fluoro-benzyl)-piperazin-1-yl]-2-oxo-ethoxy}-5-methyl-phenyl)-propionyl]-methanesulfonamide;

N-[3-(2-{2-[4-(4-Fluoro-benzyl)-(2R)-2-methyl-piperazin-1-yl]-2-oxo-ethoxy}-5-methyl-phenyl)-propionyl]-methanesulfonamide;

N-[3-(2-{2-[4-(4-Fluoro-benzyl)-(2R,5S)-2,5-dimethyl-piperazin-1-yl]-2-oxo-ethoxy}-5-methyl-phenyl)-propionyl]-methanesulfonamide;

N-[3-(2-{2-[4-(4-Fluoro-benzyl)-(2R,5S)-2,5-dimethyl-piperazin-1-yl]-2-oxo-ethoxy}-phenyl)-propionyl]-methanesulfonamide;

N-[3-(3-{2-[4-(4-Fluoro-benzyl)-(2R,5S)-2,5-dimethyl-piperazin-1-yl]-2-oxo-ethoxy}-6-methyl-pyridin-2-yl)-propionyl]-methanesulfonamide;

N-[3-(5-Bromo-2-{2-[4-(4-fluoro-benzyl)-(2R)-2-methyl-piperazin-1-yl]-2-oxo-ethoxy}-phenyl)-propionyl]-methanesulfonamide;

N-[3-(5-Bromo-2-{2-[4-(4-fluoro-benzyl)-(2R,5S)-2,5-dimethyl-piperazin-1-yl]-2-oxo-ethoxy}-phenyl)-propionyl]-methanesulfonamide;
N-[3-(5-Chloro-2-{2-[4-(4-fluoro-benzyl)-(2R)-2-methyl-piperazin-1-yl]-2-oxo-ethoxy}-phenyl)-propionyl]-methanesulfonamide;
N-[3-(5-Chloro-2-{2-[4-(4-fluoro-benzyl)-(2R,5S)-2,5-dimethyl-piperazin-1-yl]-2-oxo-ethoxy}-phenyl)-propionyl]-methanesulfonamide;
N-[3-(5-Chloro-2-{2-[4-(4-fluoro-benzyl)-(2R,5S)-2,5-dimethyl-piperazin-1-yl]-2-oxo-ethoxy}-pyridin-3-yl)-propionyl]-methanesulfonamide;
N-Acetyl-C-(2-{2-[4-(4-fluoro-benzyl)-(2R)-2-methyl-piperazin-1-yl]-2-oxo-ethoxy}-5-trifluoromethyl-phenyl)-methanesulfonamide;
N-Acetyl-C-(2-{2-[4-(4-fluoro-benzyl)-(2R,5S)-2,5-dimethyl-piperazin-1-yl]-2-oxo-ethoxy}-5-trifluoromethyl-phenyl)-methanesulfonamide;
N-Acetyl-C-(5-bromo-2-{2-[(2R)-2-ethyl-4-(4-fluoro-benzyl)-piperazin-1-yl]-2-oxo-ethoxy}-phenyl)-methanesulfonamide;
N-Acetyl-C-(5-bromo-2-{2-[4-(4-chloro-benzyl)-(2R)-2-methyl-piperazin-1-yl]-2-oxo-ethoxy}-phenyl)-methanesulfonamide;
N-Acetyl-C-(5-bromo-2-{2-[4-(4-chloro-benzyl)-(2R,5S)-2,5-dimethyl-piperazin-1-yl]-2-oxo-ethoxy}-phenyl)-methanesulfonamide;
N-Acetyl-C-(5-bromo-2-{2-[4-(4-fluoro-benzyl)-(2R)-2-methyl-piperazin-1-yl]-2-oxo-ethoxy}-phenyl)-methanesulfonamide;
N-Acetyl-C-(5-bromo-2-{2-[4-(4-fluoro-benzyl)-(2R,5S)-2,5-dimethyl-piperazin-1-yl]-2-oxo-ethoxy}-phenyl)-methanesulfonamide;
N-Acetyl-C-(5-chloro-2-{2-[(2R)-2-ethyl-4-(4-fluoro-benzyl)-piperazin-1-yl]-2-oxo-ethoxy}-phenyl)-methanesulfonamide;
N-Acetyl-C-(5-chloro-2-{2-[4-(3,4-difluoro-benzyl)-(2R)-2-methyl-piperazin-1-yl]-2-oxo-ethoxy}-phenyl)-methanesulfonamide;
N-Acetyl-C-(5-chloro-2-{2-[4-(3,4-difluoro-benzyl)-(2R,5S)-2,5-dimethyl-piperazin-1-yl]-2-oxo-ethoxy}-phenyl)-methanesulfonamide;
N-Acetyl-C-(5-chloro-2-{2-[4-(4-chloro-benzyl)-(2R)-2-methyl-piperazin-1-yl]-2-oxo-ethoxy}-phenyl)-methanesulfonamide;
N-Acetyl-C-(5-chloro-2-{2-[4-(4-chloro-benzyl)-(2R,5S)-2,5-dimethyl-piperazin-1-yl]-2-oxo-ethoxy}-phenyl)-methanesulfonamide;
N-Acetyl-C-(5-chloro-2-{2-[4-(4-fluoro-benzyl)-(2R)-2-methyl-piperazin-1-yl]-2-oxo-ethoxy}-phenyl)-methanesulfonamide;
N-Acetyl-C-(5-chloro-2-{2-[4-(4-fluoro-benzyl)-(2R,5S)-2,5-dimethyl-piperazin-1-yl]-2-oxo-ethoxy}-phenyl)-methanesulfonamide;
Propane-1-sulfonic acid [(5-chloro-2-{2-[4-(4-fluoro-benzyl)-(2R,5S)-2,5-dimethyl-piperazin-1-yl]-2-oxo-ethoxy}-phenyl)-acetyl]-amide; and
Propane-2-sulfonic acid [(5-chloro-2-{2-[4-(4-fluoro-benzyl)-(2R,5S)-2,5-dimethyl-piperazin-1-yl]-2-oxo-ethoxy}-phenyl)-acetyl]-amide.
In one embodiment, the compound of formula I is:
(2-{2-[4-(4-Fluoro-benzyl)-(2R)-2-methyl-piperazin-1-yl]-2-oxo-ethoxy}-5-trifluoromethyl-phenyl)-methanesulfonamide;
(2-{3-[4-(4-Fluoro-benzyl)-(2R,5S)-2,5-dimethyl-piperazin-1-yl]-3-oxo-propyl}-5-methyl-phenoxy)-acetic acid;
(4-Chloro-2-{2-[4-(4-fluoro-benzyl)-(2R)-2-methyl-piperazin-1-yl]-2-oxo-ethoxy}-phenyl)-acetic acid;
(5-Bromo-2-{2-[(2R)-2-ethyl-4-(4-fluoro-benzyl)-piperazin-1-yl]-2-oxo-ethoxy}-phenyl)-methanesulfonamide;
(5-Bromo-2-{2-[4-(4-chloro-benzyl)-(2R)-2-methyl-piperazin-1-yl]-2-oxo-ethoxy}phenyl)methanesulfonamide;
(5-Chloro-2-{2-[(2R)-2-ethyl-4-(4-fluoro-benzyl)-piperazin-1-yl]-2-oxo-ethoxy}-phenyl)-acetic acid;
(5-Chloro-2-{2-[4-(4-chloro-benzyl)-(2R,5S)-2,5-dimethyl-piperazin-1-yl]-2-ethoxy}-phenyl)-acetic acid;
(5-Chloro-2-{2-[4-(4-fluoro-benzyl)-(2R,5S)-2,5-dimethyl-piperazin-1-yl]-2-ethoxy}-benzyloxy)-acetyl methanesulfonamide;
[(5-Chloro-2-{2-[4-(4-fluoro-benzyl)-(2R,5S)-2,5-dimethyl-piperazin-1-yl]-2-oxo-ethylamino}-pyridine-3-carbonyl)-amino]-acetic acid;
2-(5-Chloro-2-{2-[4-(4-fluoro-benzyl)-(2R,5S)-2,5-dimethyl-piperazin-1-yl]-2-oxo-ethoxy}-phenoxy)-4-methyl-thiazole-5-carboxylic acid;
3-(2-{2-[4-(4-Fluoro-benzyl)-(2R,5S)-2,5-dimethyl-piperazin-1-yl]-2-oxo-5-methyl}-phenyl)-propionic acid;
3-(5-Chloro-2-{2-[4-(4-fluoro-benzyl)-(2R)-2-methyl-piperazin-1-yl]-2-oxo-ethoxyl-ethoxy}-phenyl)-acrylic acid;
4-(5-Chloro-2-{2-[4-(4-fluoro-benzyl)-(2R)-2-methyl-piperazin-1-yl]-2-oxo-ethoxy}-phenyl)-4-oxo-butyric acid;
5-(5-Chloro-2-{2-[4-(4-fluoro-benzyl)-(2R,5S)-2,5-dimethyl-piperazin-1-yl]-2-oxo-ethoxy}-phenoxy)-5-methyl-pyrimidine-2,4,6-trione;
6-(5-Chloro-2-{2-[4-(4-fluoro-benzyl)-(2R,5S)-2,5-dimethyl-piperazin-1-yl]-2-oxo-ethoxy}-phenoxymethyl)-nicotinic acid;
C-(5-Chloro-2-{2-[4-(4-fluoro-benzyl)-(2R)-2-methyl-piperazin-1-yl]-2-oxo-ethoxy}-phenyl)-N-(3-hydroxy-3-methyl-butyryl)-methanesulfonamide;
C-(5-Chloro-2-{2-[4-(4-fluoro-benzyl)-(2R,5S)-2,5-dimethyl-piperazin-1-yl]-2-oxo-ethoxy}-phenyl)-N-hydroxyacetyl-methanesulfonamide;
N-[(2-{2-[4-(4-Fluoro-benzyl)-(2R,5S)-2,5-dimethyl-piperazin-1-yl]-2-oxo-ethoxy}-4-methoxy-phenyl)-acetyl]-methanesulfonamide; or
N-[(5-Chloro-2-{2-[4-(4-fluoro-benzyl)-(2R,5S)-2,5-dimethyl-piperazin-1-yl]-2-oxo-ethoxy}-phenyl)-acetyl]-4-fluoro-benzenesulfonamide.
In another embodiment, the compound of formula I is:
(2S)-2-Amino-4-(5-chloro-2-{2-[4-(4-fluoro-benzyl)-(2R,5S)-2,5-dimethyl-piperazin-1-yl]-2-oxo-ethoxy}-phenoxy)-butyric acid;
(4S)-4-(5-Chloro-2-{2-[4-(4-fluoro-benzyl)-(2R,5S)-2,5-dimethyl-piperazin-1-yl]-2-oxo-ethoxy}-phenoxy)-pyrrolidine-(2S)-2-carboxylic acid;
(5-Bromo-2-{2-[4-(4-fluoro-benzyl)-(2R,5S)-2,5-dimethyl-piperazin-1-yl]-2-oxo-ethoxy}-benzylideneaminooxy)-acetic acid;
(5-Bromo-2-{2-[4-(4-fluoro-benzyl)-(2R,5S)-2,5-dimethyl-piperazin-1-yl]-2-oxo-ethoxy}-phenoxy)-acetic acid;
(5-Chloro-2-{2-[4-(4-fluoro-benzyl)-(2R,5S)-2,5-dimethyl-piperazin-1-yl]-2-oxo-ethoxy}-benzylsulfamoyl)-acetic acid;
1-(5-Chloro-2-{2-[4-(4-fluoro-benzyl)-(2R,5S)-2,5-dimethyl-piperazin-1-yl]-2-oxo-ethoxy}-phenyl)-2-(1H-tetrazol-5-yl)-ethanone;
3-(5-Chloro-2-{2-[4-(4-fluoro-benzyl)-(2R,5S)-2,5-dimethyl-piperazin-1-yl]-2-oxo-ethoxy}-phenyl)-acrylic acid;
3-[3-(5-Chloro-2-{2-[4-(4-fluoro-benzyl)-(2R,5S)-2,5-dimethyl-piperazin-1-yl]-2-oxo-ethoxy}-phenyl)-ureido]-propionic acid;

4-(5-Chloro-2-{2-[4-(4-fluoro-benzyl)-(2R,5S)-2,5-dimethyl-piperazin-1-yl]-2-oxo-ethoxy}-phenoxy)-pyridine-2-carboxylic acid;

4-(5-Chloro-2-{2-[4-(4-fluoro-benzyl)-(2R,5S)-2,5-dimethyl-piperazin-1-yl]-2-oxo-ethoxy}-phenyl)-4-oxo-butyric acid;

4-(5-Chloro-2-{2-[4-(4-fluoro-benzyl)-(2R,5S)-2,5-dimethyl-piperazin-1-yl]-2-oxo-ethoxy}-pyridin-3-ylamino)-butyric acid;

5-(5-Chloro-2-{2-[4-(4-fluoro-benzyl)-(2R,5S)-2,5-dimethyl-piperazin-1-yl]-2-oxo-ethoxy}-phenyl)-5-oxo-pentanoic acid;

(5-Chloro-2-{2-[4-(4-fluoro-benzyl)-(2R,5S)-2,5-dimethyl-piperazin-1-yl]-2-oxo-ethoxy}-benzylideneaminooxy)-acetic acid;

6-(5-Chloro-2-{2-[4-(4-fluoro-benzyl)-(2R,5S)-2,5-dimethyl-piperazin-1-yl]-2-oxo-ethoxy}-phenoxy)-nicotinic acid;

C-(5-Chloro-2-{2-[4-(4-fluoro-benzyl)-(2R,5S)-2,5-dimethyl-piperazin-1-yl]-2-oxo-ethoxy}-phenyl)-N-hydroxy-acetyl-methanesulfonamide;

N-[(5-Bromo-2-{2-[4-(4-fluoro-benzyl)-(2R)-2-methyl-piperazin-1-yl]-2-oxo-ethoxy}-phenyl)-acetyl]-methanesulfonamide;

N-[(5-Chloro-2-{2-[4-(4-fluoro-benzyl)-(2R)-2-methyl-piperazin-1-yl]-2-oxo-ethoxy}-phenyl)-acetyl]-methanesulfonamide;

N-[(5-Chloro-2-{2-[4-(4-fluoro-benzyl)-(2R,5S)-2,5-dimethyl-piperazin-1-yl]-2-oxo-ethoxy}-phenyl)-acetyl]-methanesulfonamide; or N-[(5-Chloro-2-{2-[4-(4-fluoro-benzyl)-(2R,5S)-2,5-dimethyl-piperazin-1-yl]-2-oxo-ethoxy}-pyridin-3-yl)-acetyl]-methanesulfonamide.

In yet another embodiment, the compound of formula I is:

(2R)-2-(5-Chloro-2-{2-[4-(4-fluoro-benzyl)-(2R)-2-methyl-piperazin-1-yl]-2-oxo-ethoxy}-phenoxy)-propionic acid;

(4S)-4-(5-Chloro-2-{2-[4-(4-fluoro-benzyl)-(2R,5S)-2,5-dimethyl-piperazin-1-yl]-2-oxo-ethoxy}-phenoxy)-pyrrolidine-2-carboxylic acid;

(5-Chloro-2-{2-[4-(4-fluoro-benzyl)-(2R)-2-methyl-piperazin-1-yl]-2-oxo-ethoxy}-phenyl)-acetic acid;

(5-Chloro-2-{2-[4-(4-fluoro-benzyl)-(2R,5S)-2,5-dimethyl-piperazin-1-yl]-2-oxo-ethoxy}-phenylsulfamoyl)-acetic acid;

4-(5-Chloro-2-{2-[4-(4-fluoro-benzyl)-(2R,5S)-2,5-dimethyl-piperazin-1-yl]-2-oxo-ethoxy}-phenyl)-4-hydroxy-but-3-enoic acid;

4-(5-Chloro-2-{2-[4-(4-fluoro-benzyl)-(2R,5S)-2,5-dimethyl-piperazin-1-yl]-2-oxo-ethoxy}-phenyl)-4-hydroxy-butyric acid;

4-(5-Chloro-2-{2-[4-(4-fluoro-benzyl)-(2R,5S)-2,5-dimethyl-piperazin-1-yl]-2-oxo-ethoxy}-phenyl)-but-3-enoic acid;

4-[2-(5-Chloro-2-{2-[4-(4-fluoro-benzyl)-(2R,5S)-2,5-dimethyl-piperazin-1-yl]-2-oxo-ethoxy}-phenyl)-2-oxo-ethyl]-isoxazolidine-3,5-dione;

4-[2-(5-Chloro-2-{2-[4-(4-fluoro-benzyl)-(2R,5S)-2,5-dimethyl-piperazin-1-yl]-2-oxo-ethoxy}-phenyl)-2-oxo-ethyl]-1,1-dioxo-[1,2,6]thiadiazinane-3,5-dione;

5-[2-(5-Chloro-2-{2-[4-(4-fluoro-benzyl)-(2R,5S)-2,5-dimethyl-piperazin-1-yl]-2-oxo-ethoxy}-phenyl)-2-oxo-ethyl]-2-thioxo-dihydro-pyrimidine-4,6-dione;

5-[2-(5-Chloro-2-{2-[4-(4-fluoro-benzyl)-(2R,5S)-2,5-dimethyl-piperazin-1-yl]-2-oxo-ethoxy}-phenyl)-2-oxo-ethyl]-pyrimidine-2,4,6-trione;

5-[2-(5-Chloro-2-{2-[4-(4-fluoro-benzyl)-(2R,5S)-2,5-dimethyl-piperazin-1-yl]-2-oxo-ethoxy}-phenyl)-2-oxo-ethyl]-2-imino-dihydro-pyrimidine-4,6-dione;

6-[2-(5-Chloro-2-{2-[4-(4-fluoro-benzyl)-(2R,5S)-2,5-dimethyl-piperazin-1-yl]-2-oxo-ethoxy}-phenyl)-2-oxo-ethyl]-[1,4]diazepane-2,5,7-trione;

N-(5-Chloro-2-{2-[4-(4-fluoro-benzyl)-(2R,5S)-2,5-dimethyl-piperazin-1-yl]-2-oxo-ethoxy}-pyridin-3-yl)-succinamic acid;

N-[(5-Bromo-2-{2-[4-(4-fluoro-benzyl)-(2R,5S)-2,5-dimethyl-piperazin-1-yl]-2-oxo-ethoxy}-phenyl)-acetyl]-methanesulfonamide;

N-[(5-Chloro-2-{2-[4-(4-fluoro-benzyl)-(2R,5S)-2,5-dimethyl-piperazin-1-yl]-2-oxo-ethoxy}-phenyl)-acetyl]-sulfamide;

N-Acetyl-C-(5-bromo-2-{2-[4-(4-chloro-benzyl)-(2R)-2-methyl-piperazin-1-yl]-2-oxo-ethoxy}-phenyl)-methanesulfonamide;

N-Acetyl-C-(5-chloro-2-{2-[(2R)-2-ethyl-4-(4-fluoro-benzyl)-piperazin-1-yl]-2-oxo-ethoxy}-phenyl)-methanesulfonamide;

N-Acetyl-C-(5-chloro-2-{2-[4-(4-chloro-benzyl)-(2R,5S)-2,5-dimethyl-piperazin-1-yl]-2-oxo-ethoxy}-phenyl)-methanesulfonamide; or Propane-1-sulfonic acid [(5-chloro-2-{2-[4-(4-fluoro-benzyl)-(2R,5S)-2,5-dimethyl-piperazin-1-yl]-2-oxo-ethoxy}-phenyl)-acetyl]-amide.

In another aspect, the present invention also relates to pharmaceutical compositions comprising an amount of a compound of the formula I or a pharmaceutically acceptable form thereof and a pharmaceutically acceptable carrier.

Moreover, another aspect of the present invention relates to using the aforementioned compounds of formula I wherein the use comprises administering a pharmaceutically effective amount of a compound of formula I, or a pharmaceutically acceptable form thereof, to a mammal to treat or prevent a disorder or condition selected from autoimmune diseases, lupus, acute and chronic inflammatory conditions, allergic conditions, inflammation associated with infection, viral, chronic bronchitis, xeno-transplantation, transplantation tissue rejection, atherosclerosis, restenosis, HIV infectivity, and granulomatous diseases.

In another aspect, the present invention relates to the use of compounds according to formula I, wherein the use comprises administering a pharmaceutically effective amount of a compound of formula I, or a pharmaceutically acceptable form thereof, to a mammal to treat or prevent a disorder or condition that can be treated or prevented by antagonizing the CCR1 receptor in a mammal.

Furthermore, another aspect of the present invention relates to the use of compositions comprising compounds of formula I or pharmaceutically acceptable forms thereof, wherein the use comprises administering a pharmaceutically effective amount of the composition a mammal to treat or prevent a disorder or condition that can be treated or prevented by antagonizing the CCR1 receptor in a mammal.

It is to be understood that both the foregoing general description and the following detailed description are exemplary and explanatory only and are not restrictive of the invention, as claimed.

DETAILED DESCRIPTION OF THE INVENTION

The present invention may be understood more readily by reference to the following detailed description of exemplary embodiments of the invention and the examples included therein.

Before the present compounds, compositions and methods are disclosed and described, it is to be understood that this invention is not limited to specific synthetic methods of making that may of course vary. It is also to be understood that the terminology used herein is for the purpose of describing particular embodiments only and is not intended to be limiting.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate (i.e., 1,1'-methylene-bis-(2-hydroxy-3-naphthoate)) salts.

The invention also relates to base addition salts of formula I. The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

The compounds of this invention may contain olefin-like double bonds. When such bonds are present, the compounds of the invention exist as cis and trans configurations and as mixtures thereof.

This invention also includes isotopically-labeled compounds, which are identical to those described by Formula I, except for the fact that one or more atoms are replaced by one or more atoms having specific atomic mass or mass numbers. Examples of isotopes that can be incorporated into compounds of the invention include isotopes of hydrogen, carbon, nitrogen, oxygen, sulfur, and fluorine, such as $^2$H, $^3$H, $^{13}$C, $^{14}$C, $^{15}$N, $^{18}$O, $^{17}$O, and $^{18}$F, respectively. Compounds of the present invention, prodrugs thereof, and pharmaceutically acceptable salts of the compounds or of the prodrugs which contain the aforementioned isotopes and/or other isotopes of other atoms are within the scope of this invention. Certain isotopically-labeled compounds of the present invention, for example those into which radioactive isotopes such as $^3$H and $^{14}$C are incorporated, are useful in drug and/or substrate tissue distribution assays. Tritiated (i.e., $^3$H), and carbon-14 (ie., $^{14}$C), isotopes are particularly preferred for their ease of preparation and detectability. Further, substitution with heavier isotopes such as deuterium (i.e., $^2$H), can afford certain therapeutic advantages resulting from greater metabolic stability, for example increased in vivo half-life or reduced dosage requirements and, hence, may be preferred in some circumstances. Isotopically labeled compounds of Formula I of this invention and prodrugs thereof can generally be prepared by carrying out the procedures disclosed in the schemes and/or in the Examples below, by substituting a readily available isotopically labeled reagent for a non-isotopically labeled reagent.

In this specification and in the claims that follow, reference will be made to a number of terms that shall be defined to have the following meanings:

Unless otherwise indicated, "alkyl" referred to herein may be linear or branched, a and they may also be cyclic (e.g., cyclopropyl, cyclobutyl, cyclopentyl, cyclohexyl, cycloheptyl) or bicyclic (e.g., norbornanyl, bicyclo[3.2.1]octane) or contain cyclic groups. "Alkyl" includes alkyl radicals, generally known as alkylenes, including, but not limited to, methylene, ethylene, propylene, and the like. They may also contain zero to two levels of unsaturation and may be optionally substituted with 1, 2 or 3 substituents independently selected from the group consisting of but not limited to: halo-, HO—, NC—, $H_2N$—, $(C_1$–$C_8)$alkyl-NH—, [$(C_1$–$C_8)$alkyl]N—, HO—(C=O)—, $H_2N$—(C=O)—.

"Alkenyl" referred to herein may be linear or branched, and they may also be cyclic (e.g. cyclobutenyl, cyclopentenyl, cyclohexenyl) or bicyclic or contain cyclic groups. They contain 1–3 carbon-carbon double bonds, which can be cis or trans. "Alkenyl" includes alkenyl radicals, generally known as alkylidienes, including, but not limited to, ethylidene, proppylidene, and the like. Alkenyl groups may be optionally substituted with 1, 2 or 3 substituents independently selected from the group consisting of but not limited to: halo-, HO—, NC—, $H_2N$—, $(C_1$–$C_8)$alkyl-, $(C_1$–$C_8)$alkyl-NH—, [$(C_1$–$C_8)$alkyl]N—, HO—(C=O)—, $H_2N$—(C=O)—.

"Aryl" refers to phenyl or naphthyl which may be optionally substituted with 1, 2 or 3 substituents independently selected from the group consisting of but not limited to: H—, HO—, halo-, $(C_1$–$C_8)$alkyl-, $(C_1$–$C_8)$alkyl-O—, HO—$(C_1$–$C_8)$alkyl-, NC—, $H_2N$—, $(C_1$–$C_8)$alkyl-NH—, [$(C_1$–$C_8)$alkyl]N—, $H_2N$—$(C_1$–$C_8)$alkyl-, HO—(C=O)—, HO—(C=O)—$(C_1$–$C_8)$alkyl-, $(C_1$–$C_8)$alkyl-(C=O)—, $(C_1$–$C_8)$alkyl-(C=O)—$(C_1$–$C_8)$alkyl-, $H_2N$—(C=O)—, $H_2N$—(C=O)—$(C_1$–$C_8)$alkyl-, $H_2NSO_2$—, or $(C_1$–$C_8)$alkyl-$SO_2$—NH—.

Unless otherwise indicated, "halo" or "halogen" includes fluorine, chlorine, bromine, and iodine.

"Heterocyclyl" refers to but is not limited to lactone, lactam, diazepanyl, pyrrolidinyl, tetrahydrofuranyl, dihydrofuranyl, tetrahydropyranyl, pyranyl, thiopyranyl, aziridinyl, oxiranyl, methylenedioxyl, chromenyl, barbituryl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl and chromanyl. As such, a heterocyclyl group as used herein is a non-aromatic group containing at least one carbon atom and at least one heteroatom, wherein the heteroatom(s) may be any combination of N, O, or S. Preferably, the heterocyclyl group is attached through a carbon or a nitrogen atom and may be optionally substituted with 1 to 4 substituents independently selected from the group consisting of, but not limited to: H—, HO—, halo-, oxo-, HN=, $(C_1$–$C_8)$alkyl-, $(C_1$–$C_8)$alkyl-O—, HO—$(C_1$–$C_8)$alkyl-, NC—, $H_2N$—, $(C_1$–$C_8)$alkyl-NH—, [$(C_1$–$C_8)$alkyl]N—, $H_2N$—$(C_1$–$C_8)$alkyl-, HO—(C=O)—, HO—(C=O)—$(C_1$–$C_8)$alkyl-, $(C_1$–$C_8)$alkyl-(C=O)—, $(C_1$–$C_8)$alkyl-(C=O)—$(C_1$–$C_8)$alkyl-, $H_2N-(C=O)-$, $H_2N-(C=O)-(C_1-C_8)$alkyl-, $H_2NSO_2-$, $(C_1-C_8)$alkyl-$SO_2-NH-$.

"Heteroaryl" refers but is not limited to furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridyl, pyrimidyl, pyrazinyl, pyridazinyl, 1,2,4-triazinyl, 1,2,3-triazinyl, 1,3,5-triazinyl, pyrazolo[3,4-b]pyridinyl, cinnolinyl, pteridinyl, purinyl, 6,7-dihydro-5H-[1]pyrindinyl, benzo[b]thiophenyl, 5,6,7,8-tetrahydro-quinolin-3-yl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl and benzoxazinyl. As such, a heteroaryl group as used herein is an aromatic group containing at least one carbon atom and at least one heteroatom, wherein the heteroatom(s) may be any combination of N, O, or S. Preferably, the heteroaryl group is attached through a carbon or a nitrogen atom and may be optionally substituted with 1 to 4 substituents independently selected from the group consisting of, but not limited to: H—, HO—, halo-, oxo-, HN=, $(C_1-C_8)$alkyl-, $(C_1-C_8)$alkyl-O—, HO—$(C_1-C_8)$alkyl-, NC—, $H_2N-$, $(C_1-C_8)$alkyl-NH—, [$(C_1-C_8)$alkyl]N—, $H_2N-(C_1-C_8)$alkyl-, HO—$(C=O)$—, HO—$(C=O)$—$(C_1-C_8)$alkyl-, $(C_1-C_8)$alkyl-$(C=O)$—, $(C_1-C_8)$alkyl-$(C=O)$—$(C_1-C_8)$alkyl-, $H_2N-(C=O)$—, $H_2N-(C=O)$—$(C_1-C_8)$alkyl-, $H_2NSO_2-$, $(C_1-C_8)$alkyl-$SO_2-NH-$.

By "pharmaceutically acceptable" is meant a material that is not biologically or otherwise undesirable, i.e., the material may be administered to an individual without causing any substantially undesirable biological effects or interacting in a deleterious manner with any of the other components of a pharmaceutical composition in which it may be contained.

"Pharmaceutically acceptable forms" when used herein refers to the following pharmaceutically acceptable derivatives or variations: conformational isomers (e.g., cis and trans isomers) and all optical isomers (e.g., enantiomers and diastereamers), racemic, diastereomeric and other mixtures of such isomers, as well as tautomers, methyl, ethyl, t-butyl and 4-nitro-phenyl esters, and salt forms. By "tautomers" is meant chemical compounds that may exist in two or more forms of different structure (isomers) in equilibrium, the forms differing, usually, in the position of a hydrogen atom. Various types of tauromerism can occur, including keto-enol, ring-chain and ring-ring tautomerism.

The following reaction Schemes illustrate the preparation of the compounds of the present invention. Unless otherwise indicated a, b, c, d, and $R^1$ through $R^6$ and structural formula I in the reaction Schemes and the discussion that follow are defined as above. $R^7$ refers to an amino radical that can be unsubstituted, monosubstituted, disubstituted, cyclic or acyclic.

The reactions in the Preparations and Schemes are described in commonly assigned co-pending application Ser. No. U.S. Ser. No.: 09/821,322, filed Mar. 29, 2001, and provisional copending application Ser. No. 60/241,804 filed Oct. 19, 2000, the disclosures of which are incorporated herein by reference in their entirties for all purposes.

PREPARATION A

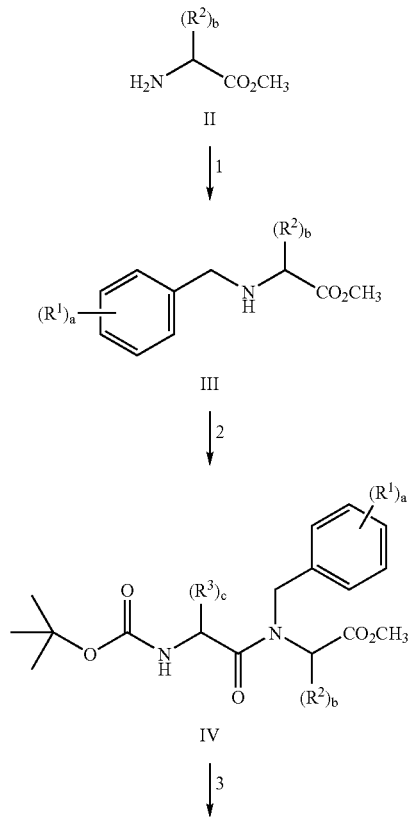

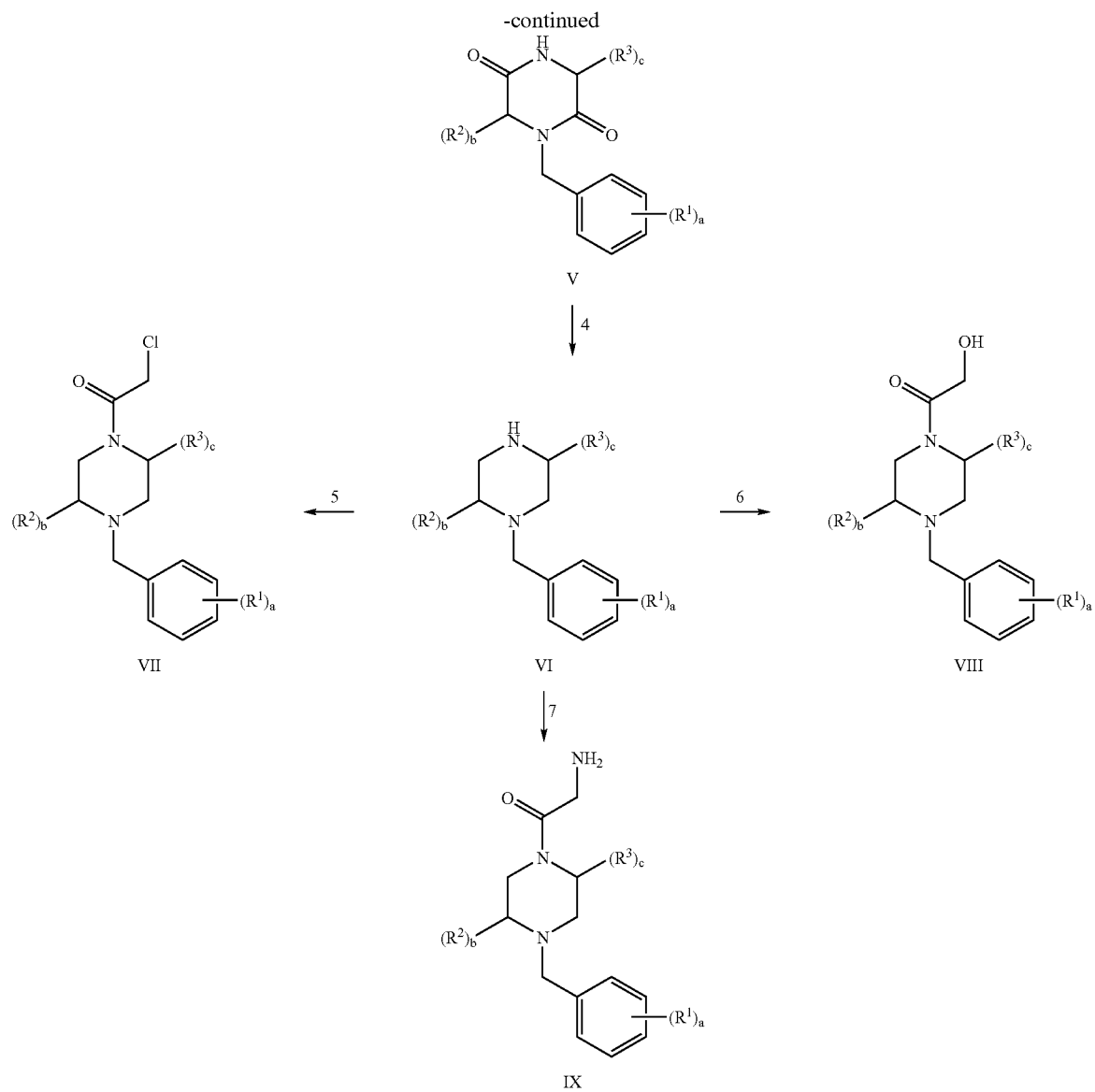
PREPARATION B
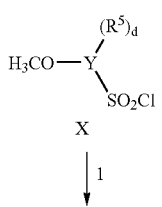
X
↓ 1
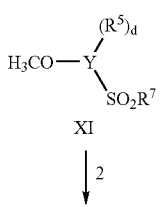
XI
↓ 2
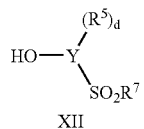
XII
PREPARATION C
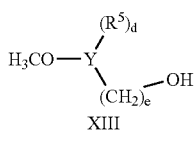
XIII
↓ 1

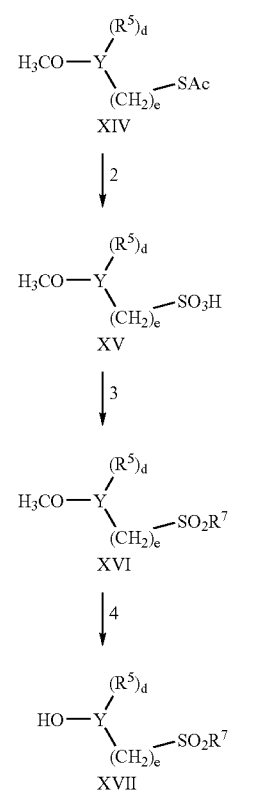

31
-continued
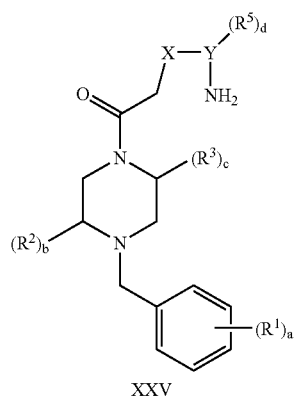
XXV
↓ 3
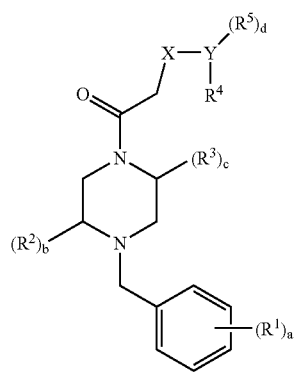
I
32
-continued
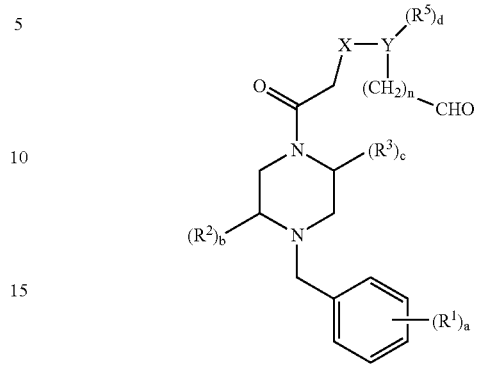
XXVI
↓ 2
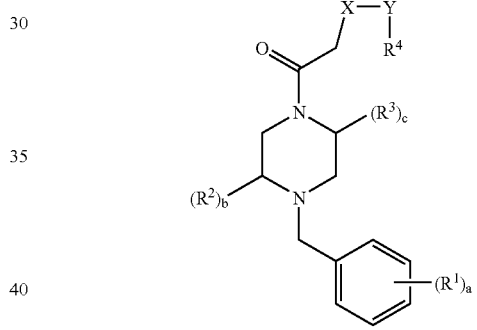
I
Scheme 3
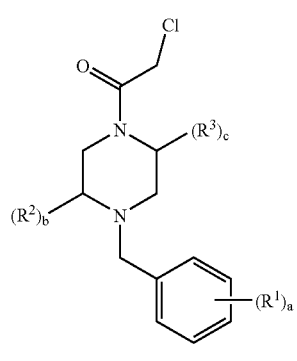
VII
↓ 1
Scheme 4
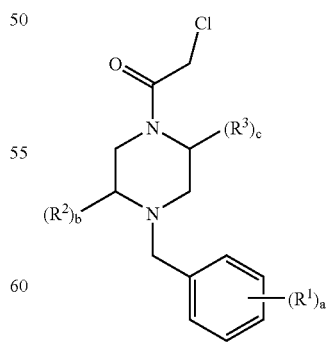
VII
↓ 1

33
-continued
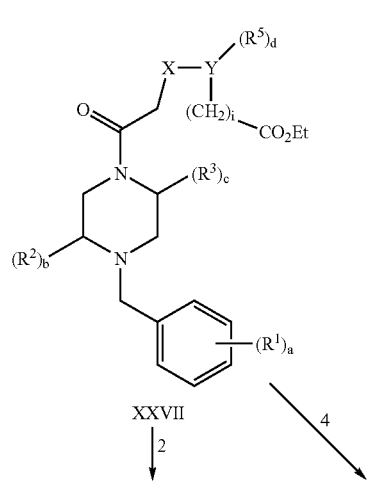
XXVII
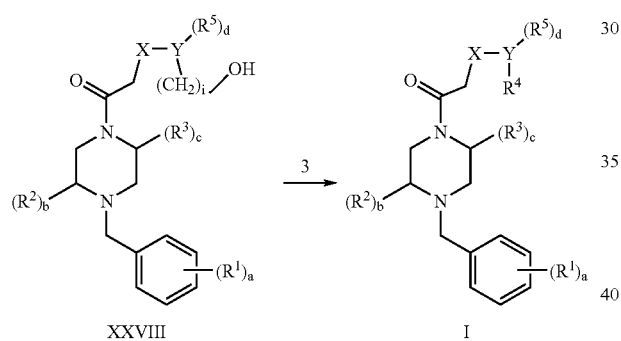
XXVIII     I
34
-continued
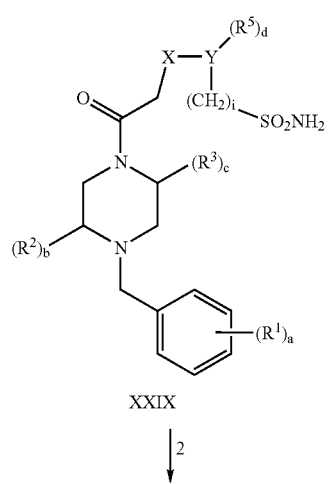
XXIX
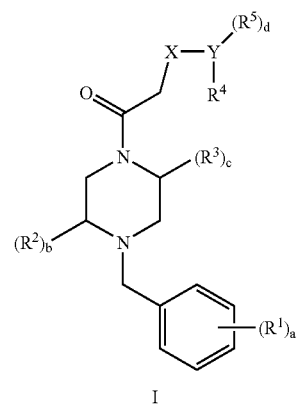
I
Scheme 5
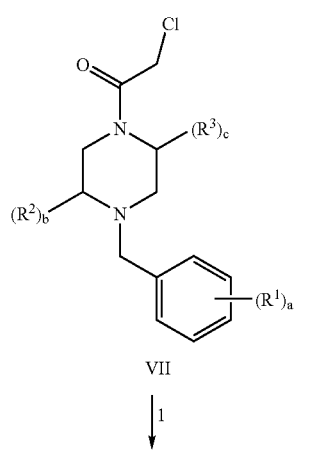
VII
Scheme 6
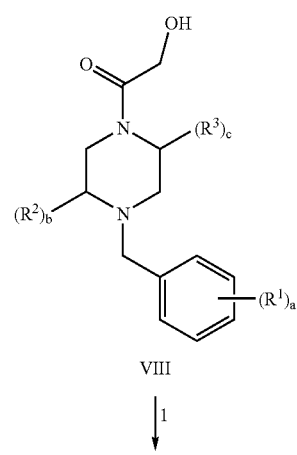
VIII -continued

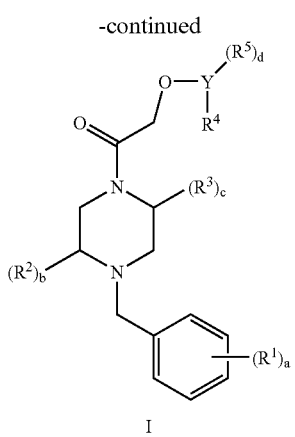

I

Scheme 7

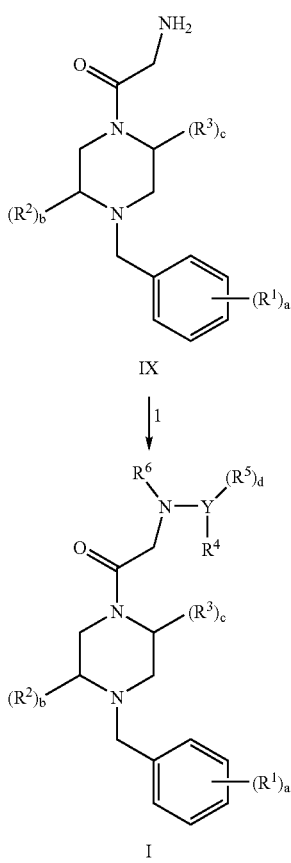

In reaction 1 of Preparation A, the compound of formula II wherein b is 0, 1 or 2, is converted to the corresponding compound of formula III by reacting II with a benzaldehyde compound of the formula

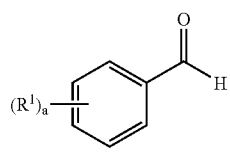

in the presence of a base, such as triethylamine, and a reducing agent, such as sodium triacetoxyborohydride, in an aprotic solvent, such as 1,2-dichloroethane. The reaction mixture is stirred at room temperature for a time period between about 1 hour to about 4 hours, preferably about 2 hours.

In reaction 2 of Preparation A, the compound of formula III is converted to the corresponding compound of formula IV by first reacting a compound of the formula

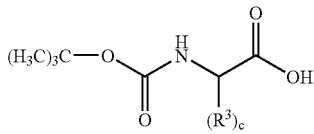

wherein c is 0, 1 or 2, with 4-methyl morpholine and isobutylchloroformate in the presence of a polar aprotic solvent, such as tetrahydrofuran, followed by reacting the intermediate so formed with the compound of formula III. The reaction mixture, so formed, is stirred overnight at ambient temperature.

In reaction 3 of Preparation A, the compound of formula IV is converted to the corresponding piperizine-2,5-dione compound of formula V by treating IV with trifluoroacetic acid in the presence of a polar aprotic solvent, such as methylene chloride. The reaction is stirred, at room temperature, for a time period between about 1 hour to about 4 hours, preferably about 2 hours.

In reaction 4 of Preparation A, the compound of formula V is converted to the corresponding compound of formula VI by reducing V with a reducing agent, such as lithium aluminum hydride. The reaction is conducted at a temperature between about −10° C. to about 10° C., preferably about 0° C., for a time period between about 10 minutes to about 90 minutes, preferably about 40 minutes.

In reaction 5 of Preparation A, the compound of formula VI is converted to the corresponding compound of formula VII by reacting VI with chloroacetyl chloride in the presence of a base, such as triethylamine, in a polar aprotic solvent, such as methylene chloride, at ambient temperature for a time period between 15 minutes and 3 hours, preferably about 30 minutes.

In reaction 6 of Preparation A, the compound of formula VI is converted to the corresponding compound of formula VIII by reacting VI with acetoxy acetylchloride in the presence of a base, such as triethylamine, in a polar aprotic solvent, such as methylene chloride, at ambient temperature for a time period between 15 minutes and 4 hours, preferably about 1 hour. The resulting acetyl-protected alcohol is reacted with lithium hydroxide hydrate in a solvent mixture including water, tetrahydrofuran and methanol, at ambient temperature for a time period between 1 hour and 8 hours, preferably about 2 hours.

In reaction 7 of Preparation A, the compound of formula VI is converted to the corresponding compound of formula IX by reacting VI with N-(t-butoxycarbonyl)glycine in the presence of a base, such as dimethylamino pyridine and a coupling reagent, such as 1-(3-dimethylaminopropyl)-3-ethylcarbodiimide, in a polar aprotic solvent, such as methylene chloride, at ambient temperature for a time period between 4 hours and 18 hours, preferably about 12 hours. The resulting compound containing an N-(t-butoxycarbonyl) protecting group is reacted with trifluoroacetic acid in a polar aprotic solvent, such as methylene chloride, at ambient temperature for a time period between 30 minutes and 6 hours, preferably about 2 hours.

One skilled in the art would recognize that Preparation A allows access to all the various isomers, diastereomers and enantiomers of formula VI. In particular, Preparation A can be utilized to prepare compounds with the preferred stereochemistry as depicted in the formula:

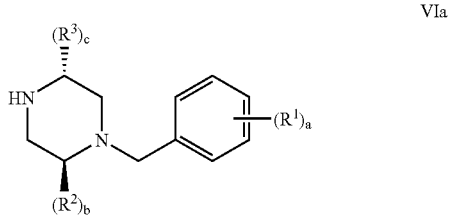

VIa

In reaction 1 of Preparation B, the compound of formula X is converted to the corresponding compound of formula XI by reacting X with an appropriate amine in the presence of a polar aprotic solvent, such as tetrahydrofuran. The reaction mixture is stirred at ambient temperature for a time period between about 1 hour to about 24 hours, preferably about 12 hours.

In reaction 2 of Preparation B, the compound of formula XI is converted to the corresponding compound of formula XII by reacting XI with thiophenol in the presence of a base, such as sodium hydride, and a polar aprotic solvent, such as dimethylformamide. The reaction is heated to reflux for a time period between about 1 hour to about 10 hours, preferably about 4 hours.

In reaction 1 of Preparation C the compound of formula XIII, where e is 1–4, is converted to the corresponding compound of formula XIV by first converting the hydroxyl group to a chloro group by reacting XIII with thionyl chloride, in the presence of an aprotic solvent, such as methylene chloride. The reaction is heated to reflux, for a time period between about 1 hour to about 10 hours, preferably about 3 hours. The resulting alkyl chloride is then treated with thioacetic acid in the presence of a base, such as cesium carbonate, in a polar aprotic solvent, such as dimethylformamide at ambient temperature for a time period between 6 hours and 24 hours, preferably about 12 hours.

In reaction 2 of Preparation C the compound of formula XIV is converted to the corresponding compound of formula XV by reacting XIV with hydrogen peroxide (aqueous solution) in acetic acid at ambient temperature for a time period between 6 hours and 24 hours, preferably about 12 hours.

In reaction 3 of Preparation C the compound of formula XV is converted to the corresponding compound of formula XVI by first reacting XV with phosphorous pentachloride in an aprotic solvent, such as toluene, at a temperature between ambient and reflux, preferably at reflux for a time period between 1 hour and 8 hours, preferably 3 hours to give the corresponding sulfonyl chloride. The sulfonyl chloride is then reacted with an appropriate amine in a polar aprotic solvent, such as tetrahydrofuran, at ambient temperature for a time period between 3 hours and 24 hours, preferably 12 hours.

In reaction 4 of Preparation C the compound of formula XVI is converted to the corresponding compound of formula XVII according to the procedure described in reaction 2 of Preparation B.

In reaction 1 of Preparation D the compound of formula XVIII is converted to the corresponding compound of the formula XIX by treating XVIII with a reducing agent, such as lithium aluminum hydride, in an aprotic solvent, such as tetrahydrofuran. The reaction mixture is heated to reflux for a time period between 1 hour and 6 hours, preferably about 2 hours.

In reaction 2 of Preparation D the compound of formula XIX is converted to the corresponding compound of the formula XX by first converting the hydroxyl group to a chloro group by reacting XIX with thionyl chloride, in the presence of an aprotic solvent, such as methylene chloride. The reaction is heated to reflux, for a time period between about 1 hour to about 10 hours, preferably about 3 hours. The resulting alkyl chloride is then treated with a cyanide source, such as potassium cyanide, in the presence of an aprotic solvent, such as acetonitrile and a crown ether, such as 18-crown-6. The reaction mixture is stirred at ambient temperature for a time period between about 1 hour to about 10 hours, preferably about 3 hours.

In reaction 3 of Preparation D the compound of formula XX is converted to the compound of formula XXI by treating XX with a hydroxide source, such as potassium hydroxide in a mixture of ethanol and water. The reaction mixture is heated to reflux for a time period between about 1 hour to about 10 hours, preferably about 8 hours.

In reaction 4 of Preparation D the compound of formula XXI is converted to the compound of formula XXII, wherein f is 1, by first demethylating the methyl ether by treatment with acid, such as 47% aqueous hydrogen bromide. The reaction mixture is heated to reflux for a time period between about 10 hours to about 30 hours, preferably about 24 hours. The phenolic acid is finally converted to the corresponding compound of formula XXII, wherein f is 1, by treating with ethanol in the presence of an acid, such as hydrochloric acid, at ambient temperature for a time period between about 8 hours to about 16 hours, preferably about 12 hours.

In reaction 5 of Preparation D the compound of formula XIX is converted to the corresponding compound of formula XXIII, by treating XIX with an oxidizing agent, such as Dess-Martin periodinane, in the presence of an aprotic solvent, such as tetrahydrofuran at ambient temperature for a time period between about 1 hour to about 16 hours, preferably about 4 hours.

In reaction 6 of Preparation D the compound of formula XXIII is converted to the corresponding compound of formula XXII wherein f is 2–8, by treating XXIII with a phosphonium ylide derived from the phosphonium salt of the formula:

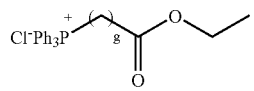

wherein g is 1–7, in the presence of an aprotic solvent, such as tetrahydrofuran. The reaction is conducted at a temperature between −78° C. and reflux, the preferred temperature is dependent on which phosphonium ylide is utilized, for a time period between about 4 hours to about 16 hours, preferably about 10 hours (for similar transformations, see: J. Am. Chem. Soc. 1985, 107, 217). The resulting olefinic ester is then hydrogenated by shaking under a positive pressure of hydrogen in the presence of a catalyst, such as platinum dioxide, in the presence of an aprotic solvent such as ethyl acetate. The methyl ether is then deprotected according to the procedure described in reaction 2 of Preparation B.

In reaction 1 of Scheme 1, the compound of formula VI is converted to the corresponding compound of formula I by reacting VI with a compound of the formula, HO—(C=O)—CH2-X—Y[($R^5$)$_d$]($R^4$), in the presence of a base, such as 4-dimethylaminopyridine, and a coupling reagent, such as 1-(3-dimethylaminopropyl)-3-ethylcarbodiimine, in a polar aprotic solvent, such as methylene chloride. The reaction is stirred at ambient temperature for a time period between 4 hours and 24 hours, preferably about 12 hours. Alternatively, the compound of formula VI is converted to the corresponding compound of formula I by first reacting VI with a compound of the formula:

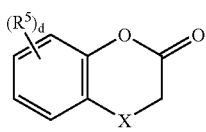

in the presence of an aprotic solvent, such as toluene, at a temperature between ambient and reflux, preferably reflux, for a time period between about 4 hours to 18 hours, preferably about 12 hours. The phenol thus formed can then be converted to compounds of formula I by reactions familiar to those skilled in the art.

In reaction 1 of Scheme 2, the compound of formula VII is converted to the corresponding compound of formula XXIV by reacting VII with a compound of the formula, H—X—Y[($R^5$)$_d$]($NO_2$) wherein X is —O—, —S—, or —NH— in the presence of potassium carbonate, potassium iodide and an aprotic solvent, such as butanone. The reaction is heated to reflux for a time period between about 4 hours to about 8 hours, preferably about 6 hours.

In reaction 2 of Scheme 2, the compound of formula XXIV is converted to the corresponding compound of formula XXV by hydrogenating XXIV in the presence of a catalyst, such as platinum on carbon, and a polar protic solvent, such as ethanol. The reaction is carried out under a pressure between about 30 psi to about 40 psi, preferably about 35 psi, for a time period between about 5 minutes to about 1 hour, preferably 30 minutes.

In reaction 3 of Scheme 2 the compound of formula XXV is converted to the corresponding urea of formula I, by first reacting XXV with 4-nitrophenyl chloroformate in the presence of a base, such as pyridine, and a polar aprotic solvent, such as methlyene chloride, followed by reacting the intermediate so formed with an appropriate amine or sulfonamide. The reaction mixture, so formed, is allowed to stir overnight at ambient temperature. The compound of formula XXV is reacted with an appropriate sulfonyl chloride to form the corresponding sulfonamides of formula I, in the presence of a base, such as triethylamine, and a polar aprotic solvent, such as methylene chloride. The reaction is stirred overnight at ambient temperature. For secondary amine formation of formula I, the compound of formula XXV is reacted with an appropriate aldehyde in the presence of a base, such as triethylamine, and a reducing agent, such as sodium triacetoxyborohydride, in an aprotic solvent, such as 1,2-dichloroethane. The reaction mixture is stirred at ambient temperature for a time period between about 1 hour to about 12 hours, preferably about 10 hours.

In reaction 1 of Scheme 3, the compound of formula VII is converted to the corresponding compound of formula XXVI where h is 0–3 according to the procedure described above in reaction 1 of Scheme 2.

In reaction 2 of Scheme 3, the compound of formula XXVI is converted to the corresponding amine of formula I by reacting XXVI with an appropriate amine in the presence of a 10:1 ratio solution of dichloroethane/acetic acid. The reaction mixture is stirred, at ambient temperature, for a time period between about 30 minutes to about 2 hours, preferably about 1 hour. A reducing agent, such as sodium cyanoborohydride is than added to the mixture and the reaction is allowed to stir overnight at ambient temperature. If the amine thus formed is primary or secondary, the compound of formula I may further be reacted according to the procedure described above in reaction 3 of Scheme 2, to provide ureas or sulfonamides. The compound of formula XXVI is converted to the corresponding oxime of formula I by reacting XXVI with an appropriate alkoxyamine in the presence of a base, such as triethylamine and a polar protic solvent, such as methanol, at a temperature between 0° C. and reflux, preferably at ambient temperature, for a time period between 1 hour and 8 hours, preferably about 3 hours.

In reaction 1 of Scheme 4, the compound of formula VII is converted to the corresponding compound of formula XXVII by reacting VII with a compound of the formula, H—X—Y[($R^5$)$_d$]($CH_2$)$_i$$CO_2$Et, wherein X is —O—, —S—, or —NH— and i is 0–3, according to the procedure described in reaction 1 of Scheme 2.

In reaction 2 of Scheme 4, the compound of formula XXVII is converted to the corresponding compound of formula XXVIII by reacting XXVII with a reducing agent, such as sodium borohydride, in a polar protic solvent, such as methanol, at ambient temperature for a time period between about 1 hour to about 10 hours, preferably about 3 hours.

In reaction 3 of Scheme 4, the compound of formula XXVIII is converted to the corresponding ether of formula I by first converting XXVIII to the corresponding alkyl chloride as described in reaction 2 of Preparation D. The alkyl chloride is then reacted with an appropriate alcohol which has previously been reacted with a strong base, such as NaH, in a polar aprotic solvent, such as dimethylformamide at a temperature between about −10° C. to about 10° C., preferably about 0° C., for a time period between about 10 minutes to about 90 minutes, preferably about 40 minutes. The alkyl chloride is stirred with the resulting alkoxide at ambient temperature for a period of about 3 hours to about 24 hours, preferably about 12 hours. The compound of formula XXVIII is converted to the corresponding carbamate of formula I by reacting XXVIII with an appropriate isocyanate in the presence of a base, such as triethylamine, in an aprotic solvent, such as toluene, at ambient temperature for a time period between 4 hours and 24 hours, preferably about 12 hours. The compound of formula XXVIII is converted to the corresponding acylsulfamide of formula I by first reacting XXVIII with a BOC-protected sulfamide, such as tert-butoxycarbonylsulfamide in the presence of triphenylphosphine and diethylazodicarboxylate in a polar aprotic solvent, such as tetrahydrofuran. The reaction is initially conducted at a temperature between −100° C. and 0° C., preferably about −60° C. for a time period of about 15 minutes, then slowly warmed to a temperature between 10° C. and ambient temperature for a time period between 1 hour and 8 hours, preferably about 2 hours. The resulting BOC-protected sulfamide is reacted with an acyl chloride in the presence of a base, such as triethyl amine and/or dimethylpyridine in a polar aprotic solvent, such as dichloromethane. The reaction is stirred at a temperature between 0° C. and 40° C., preferably at ambient temperature for a time period of 8 hours to 24 hours, preferably about 18 hours. The BOC-protected acylsulfamide thus formed is treated with a strong acid, such as trifluoracetic acid, in a polar aprotic solvent, such as dichloromethane, at ambient temperature for a time period between 1 hour and 6 hours, preferably about 3 hours, thus giving compounds of formula I.

In reaction 4 of Scheme 4, the compound of formula XXVII is converted to the corresponding compound of formula I by reacting XXVII with lithium hydroxide monohydrate in the presence of methanol, tetrahydrofuran and water to give the corresponding carboxylic acid. The reaction mixture is stirred at ambient temperature for a time period between 8 and 24 hours, preferably 12 hours. The carboxylic acid is converted to the corresponding acylsulfonamide of formula I by reacting the carboxylic acid with an appropriate sulfonamide in the presence of a base, such as 4-dimethylaminopyridine and coupling reagent, such as 1-(3-dimethylaminopropyl)-3-ethylcarbodiimine, in a polar aprotic solvent, such as methylene chloride. The reaction is stirred at ambient temperature for a time period between 4 hours and 24 hours, preferably about 12 hours. The carboxylic acid is converted to the corresponding acylsulfamide of formula I by reacting the carboxylic acid with chlorosulfonylisocyanate in a polar aprotic solvent, such as 1,2-dichloroethane, at a temperature between ambient and reflux, preferably ambient, for a time period between 8 and 24 hours, preferably about 12 hours, to give a compound of formula:

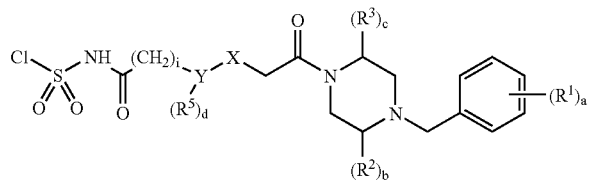

which is then reacted with an appropriate amine in a polar aprotic solvent, such as tetrahydrofuran, at ambient temperature for a time period between 4 hours and 24 hours, preferably about 12 hours.

In reaction 1 of Scheme 5, the compound of formula VII is converted to the corresponding compound of formula XXIX by reacting VII with a compound of the formula, H—X—Y[$(R^5)_d$]$(CH_2)_i$$SO_2NH_2$, wherein X is —O—, —S—, or —$NR^6$— and j is 0–4, according to the procedure described in reaction 1 of Scheme 2.

In reaction 2 of Scheme 5, the compound of formula XXIX is converted to the corresponding acylsulfonamide of formula I by reacting XXIX with an appropriate carboxylic acid in the presence of a base, such as 4-dimethylaminopyridine, and a coupling reagent, such as 1-(3-dimethylaminopropyl)-3-ethylcarbodiimine, in a polar aprotic solvent, such as methylene chloride. The reaction is stirred at ambient temperature for a time period between 4 hours and 24 hours, preferably about 12 hours. The compound of formula XXIX is converted to the corresponding sulfonylurea of formula I by reacting XXIX with an appropriate isocyanate in the presence of a base, such as 1,8-diazobicyclo[5.4.0]undec-7-ene and a polar aprotic solvent, such as tetrahydrofuran. The reaction is stirred at a temperature between ambient and reflux, preferably reflux for a time period of 6 hours to 24 hours, preferably about 12 hours. The compound of formula XXIX is converted to the corresponding sulfonylcarbamate of formula I by reacting XXIX with an appropriate chloroformate in the presence of a base, such as 1,8-diazobicyclo[5.4.0]undec-7-ene and a polar aprotic solvent, such as tetrahydrofuran. The reaction is stirred at a temperature between ambient and reflux, preferably reflux for a time period of 6 hours to 24 hours, preferably about 12 hours. The compound of formula XXIX is converted to the corresponding alkylated sulfonamide of formula I by first treating compound XXIX with di-t-butyl-dicarbonate in the presence of base such as triethylamine and 4-dimethylaminopyridine in a polar aprotic solvent such as dichloromethane. The resulting N-t-butyloxycarbonyl protected sulfonamide is then treated with an alkyl halide in the presence of a polar, aprotic solvent such as dimethylformamide. The N-t-butyloxycarbonyl protected secondary sulfonamide is then deprotected by treating with acid, such as trifluoroacetic acid in the presence of a polar solvent such as dichloromethane.

In reaction 1 of Scheme 6, the compound of formula VIII is converted to the corresponding compound of formula I by reacting VIII with a strong base, such as sodium hydride, in an aprotic solvent, such as toluene, at a temperature between about −10° C. and ambient temperature, preferably about 0° C. for a time period between 15 minutes and 90 minutes, preferably about 30 minutes. To this is added a compound of formula Cl—Y[$(R^5)_d$]$(R^4)$ where Y is a ($C_1$–$C_9$)heteroaryl wherein the chlorine is attached to a carbon atom that is adjacent to a heteroatom (for example, 2-pyridyl). The reactants are stirred at a temperature between ambient and reflux, preferably ambient temperature for a time period between 8 hours and 24 hours, preferably 12 hours.

In reaction 1 of Scheme 7, the compound of formula IX is converted to the corresponding compound of formula I where $R^6$ is H—, by reacting IX with a compound of formula Cl—Y[$(R^5)_d$]$(R^4)$ where Y is a ($C_1$–$C_9$)heteroaryl wherein the chlorine is attached to a carbon atom that is adjacent to a heteroatom (for example, 2-pyridyl). The reactants are stirred in a polar aprotic solvent, such as acetonitrile, in the presence of a base, such as triethylamine, at reflux temperature for a time period between about 4 hours and 24 hours, preferably about 12 hours. The compound of formula I where $R^6$ is H— is converted to the compound of formula I where $R^6$ is an alkyl group by reacting the compound of formula I where $R^6$ is H— with an appropriate alkyl halide in the presence of a base, such as triethylamine, and a polar aprotic solvent, such as tetrahydrofuran at a temperature between ambient and reflux, preferably at ambient temperature for a time period of 8 hours to 24 hours, preferably about 18 hours. The compound of formula I where $R^6$ is H— is converted to the compound of formula I where $R^6$ taken together with the nitrogen to which it is attached forms an amide, by reacting the compound of formula I where $R^6$ is H— with an appropriate carboxylic acid in the presence of a base, such as 4-dimethylaminopyridine, and a coupling reagent, such as 1-(3-dimethylaminopropyl)-3-ethylcarbodiimine, in a polar aprotic solvent, such as methylene chloride. The reaction is stirred at ambient temperature for a time period between 4 hours and 24 hours, preferably about 12 hours. The compound of formula I where $R^6$ is H— is converted to the compound of formula I where $R^6$ taken together with the nitrogen to which it is attached forms a urea, by reacting the compound of formula I where $R^6$ is H— with an appropriate isocyanate in the presence of a base, such as triethyamine, and a polar aprotic solvent, such as tetrahydrofuran. The reaction is stirred at a temperature between ambient and reflux, preferably reflux, for a time period of 4 hours to 18 hours, preferably about 12 hours. The compound of formula I where $R^6$ is H— is converted to the compound of formula I where $R^6$ taken together with the nitrogen to which it is attached forms a carbamate, by reacting the compound of formula I where $R^6$ is H— with an appropriate chloroformate in the presence of a base, such as triethyamine, and a polar aprotic solvent, such as tetrahydrofuran. The reaction is stirred at a temperature between ambient and reflux, preferably reflux, for a time period of 4 hours to 18 hours, preferably about 12 hours. The compound of formula I where $R^6$ is H— is converted to the compound of formula I where $R^6$ taken together with the nitrogen to which it is attached forms a sulfonamide, by reacting the compound of formula I where $R^6$ is H— with an appropriate sulfonylchloride in the presence of a base, such as triethyamine, and a polar aprotic solvent, such as tetrahydrofuran. The reaction is stirred at a temperature between ambient and reflux, preferably reflux, for a time period of 4 hours to 18 hours, preferably about 12 hours.

Unless indicated otherwise, the pressure of each of the above reactions is not critical. Generally, the reactions will be conducted at a pressure of about one to about three atmospheres, preferably at ambient pressure (about one atmosphere).

The compounds of the formula I which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, a solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate (i.e., 1,1'-methylene-bis-(2-hydroxy-3-naphthoate)) salts.

Those compounds of the formula I which are also acidic in nature, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula I. These non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum product yields.

Compounds of the formula I and their pharmaceutically acceptable salts (hereinafter also referred to, collectively, as "the active compounds") are potent antagonists of the CCR1 receptor. The active compounds are useful in the treatment or prevention of autoimmune diseases (such as rheumatoid arthritis, type I diabetes (recent onset), lupus, inflammatory bowel disease, optic neuritis, psoriasis, multiple sclerosis, polymyalgia rheumatica, uveitis, and vasculitis), acute and chronic inflammatory conditions (such as osteoarthritis, adult Respiratory Distress Syndrome, Respiratory Distress Syndrome of infancy, ischemia reperfusion injury, and glomerulonephritis), allergic conditions (such as asthma and atopic dermatitis), infection associated with inflammation (such as viral inflammation (including influenza and hepatitis) and Guillian-Barre syndrome syndrome), chronic bronchitis, xeno-transplantation, transplantation tissue rejection (chronic and acute), organ rejection (chronic and acute), atherosclerosis, restenosis (including, but not limited to, restenosis following balloon and/or stent insertion), HIV infectivity (co-receptor usage), and granulomatous diseases (including sarcoidosis, leprosy and tuberculosis) and sequelae associated with certain cancers such as multiple myeloma. Compounds in this series may also have utility for the prevention of cancer metastasis. Compounds in this series may also limit the production of cytokines at inflammatory sites, including but not limited to TNF and IL-1, as a consequence of decreasing cell infiltration, providing benefit for diseases linked to TNF and IL-1, including congestive heart failure, pulmonary emphysema or dyspnea associated therewith, emphysema; HIV-1, HIV-2, HIV-3; cytomegalovirus (CMV), adenoviruses, Herpes viruses (Herpes zoster and Herpes simplex). They may also provide benefit for the sequelae associated with infection where such infection induces production of detrimental inflammatory cytokines such as TNF e.g, fungal meningitis, joint tissue damage, hyperplasia, pannus formation and bone resorption, psoriatic arthritis, hepatic failure, bacterial meningitis, Kawasaki syndrome, myocardial infarction, acute liver failure, lyme disease, septic shock, cancer, trauma, and malaria, etc.

The activity of the compounds of the invention can be assessed according to procedures know to those of ordinary skill in the art. Examples of recognized methods for determining CCR1 induced migration can be found in Coligan, J. E., Kruisbeek, A. M., Margulies, D. H., Shevach, E. M., Strober, W. editors: *Current Protocols In Immunology*, 6.12.1–6.12.3. (John Wiley and Sons, NY, 1991). One specific example of how to determine the activity of a compound for inhibiting migration is described in detail below.

Chemotaxis Assay:

The ability of compounds to inhibit the chemotaxis to various chemokines can be evaluated using standard 48 or 96 well Boyden Chambers with a 5 micron polycarbonate filter. All reagents and cells can be prepared in standard RPMI (BioWhitikker Inc.) tissue culture medium supplemented with 1 mg/mL of bovine serum albumin. Briefly, MIP-1α (Peprotech, Inc., P.O. Box 275, Rocky Hill N.J.) or other test agonists, are placed into the lower chambers of the Boyden chamber. A polycarbonate filter is then applied and the upper chamber fastened. The amount of agonist chosen is that determined to give the maximal amount of chemotaxis in this system (e.g., 1 nM for MIP-1α should be adequate).

THP-1 cells (ATCC TIB-202), primary human monocytes, or primary lymphocytes, isolated by standard techniques can then be added to the upper chambers in triplicate together with various concentrations of the test compound. Compound dilutions can be prepared using standard serological techniques and are mixed with cells prior to adding to the chamber.

After a suitable incubation period at 37 degrees centigrade (e.g. 3.5 hours for THP-1 cells, 90 minutes for primary monocytes), the chamber is removed, the cells in the upper chamber aspirated, the upper part of the filter wiped and the number of cells migrating can be determined according to the following method.

For THP-1 cells, the chamber (a 96 well variety manufactured by Neuroprobe) can be centrifuged to push cells off the lower chamber and the number of cells can be quantitated against a standard curve by a color change of the dye fluorocein diacetate.

For primary human monocytes, or lymphocytes, the filter can be stained with Dif Quik® dye (American Scientific Products) and the number of cells migrating can be determined microscopically.

The number of cells migrating in the presence of the compound are divided by the number of cells migrating in control wells (without the compound). The quotant is the % inhibition for the compound which can then be plotted using standard graphics techniques against the concentration of compound used. The 50% inhibition point is then determined using a line fit analysis for all concentrations tested. The line fit for all data points must have an coefficient of correlation (R squared) of >90% to be considered a valid assay.

All of the compounds of the invention illustrated in the following examples had $IC_{50}$ of less than 10 μM, in the Chemotaxis assay.

The compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) or rectal administration or in a form suitable for administration by inhalation or insufflation. The active compounds of the invention may also be formulated for sustained delivery.

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (rmade, for example, from gelatin) for use in an inhaler or insufflator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., rheumatoid arthritis) is 0.1 to 1000 mg of the active ingredient per unit dose which could be administered, for example, 1 to 4 times per day.

Aerosol formulations for treatment of the conditions referred to above (e.g., rheumatoid arthritis) in the average adult human are preferably arranged so that each metered dose or "puff" of aerosol contains 20 μg to 1000 μg of the compound of the invention. The overall daily dose with an aerosol will be within the range 0.1 mg to 1000 mg. Administration may be several times daily, for example 2, 3, 4 or 8 times, giving for example, 1, 2 or 3 doses each time.

The active agents can be formulated for sustained delivery according to methods well known to those of ordinary skill in the art. Examples of such formulations can be found in U.S. Pat. Nos. 3,538,214, 4,060,598, 4,173,626, 3,119,742, and 3,492,397 all of which are incorporated herein in their entireties for all purposes.

The compounds of the invention may also be utilized in combination therapy with other therapeutic agents such as Cyclosporin A, ISAtx247, Rapamycin, Everolimus, FK-506, Azathioprine, Mycophenolate mofetil, Mycophenolic acid, Daclizumab, Basiliximab, Muromonab, Horse anti-thymocyte globulin, Polyclonal rabbit antithymocyte globulin, Leflunomide, FK-778 (MNA-715), FTY-720, BMS-188667 (CTLA4-Ig), RG-1046 (CTLA4-Ig), Prednisone, Prednisolone, Methylprednisolone suleptanate, Cortisone, Hydrocortisone, Methotrexate, Sulfasalazine, Etanercept, Infliximab, Adalimumab (D2E7), CDP-571, CDP-870, Anakinra, NSAIDS (aspirin, acetaminophen, naproxen, ibuprofen, ketoprofen, diclofenac and piroxicam), COX-2 inhibitors (Celecoxib, Valdecoxib, Rofecoxib, Parecoxib, Etoricoxib, L-745337, COX-189, BMS-347070, S-2474, JTE-522, CS-502, P-54, DFP), Anti-interleukin-6 receptor monoclonal antibody (MRA), Glatiramer acetate, Interferon beta 1-a, Interferon beta 1-b, Mitoxantrone, Pimecrolimus, or agents that inhibit cell recruitment mechanisms (eg inhibitors of integrin upregulation or function) or alter leukocyte trafficking.

Experimental

The following examples are put forth so as to provide those of ordinary skill in the art with a disclosure and description of how the compounds, compositions, and methods claimed herein are made and evaluated, and are intended to be purely exemplary of the invention and are not intended to limit the scope of what the inventors regard as their invention. Unless indicated otherwise, percent is percent by weight given the component and the total weight of the composition, temperature is in ° C. or is at ambient temperature, and pressure is at or near atmospheric. Commercial reagents were utilized without further purification. Chromatography refers to column chromatography performed using 32–63 mm silica gel and executed under nitrogen pressure (flash chromatography) conditions. Particle Beam Mass Spectra were recorded on either a Hewlett Packard 59890, utilizing chemical ionization (ammonium), or a Fisons (or MicroMass) Atmospheric Pressure Chemical Ionization (APCI) platform which uses a 50/50 mixture of acetonitrile/water. Room or ambient temperature refers to 20–25° C. All non-aqueous reactions were run under a nitrogen atmosphere for convenience and to maximize yields. Concentration in vacuo means that a rotary evaporator was used. The names for the compounds of the invention were created by the Autonom 2.0 PC-batch version from Beilstein Informationssysteme GmbH (ISBN 3-89536-976-4)

EXAMPLE 1

N-[(2-{3-[4-(4-Fluoro-benzyl)-(2R,5S)-2,5-dimethyl-piperazin-1-yl]-3-oxo-propyl}-5-methyl-phenoxy)-acetyl]-methanesulfonamide (S)-2-(4-Fluoro-benzylamino)-propionic acid methyl ester To a solution of (S)-2-amino-propionic acid methyl ester hydrochloride (25 g, 179 mmol) and 4-fluorobenzaldehyde (23 mL, 215 mmol) in 1,2-dichloroethane (200 mL) was added triethylamine (25 mL, 179 mmol). The resulting mixture was stirred for two hours at ambient temperature followed by addition of sodium triacetoxyborohydride (57 g, 268 mmol) in four portions. The resulting mixture was stirred overnight at ambient temperature. The reaction was neutralized with dilute aqueous sodium hydroxide solution and extracted with dichloromethane. The organic layer was dried over magnesium sulfate, filtered and concentrated in vacuo. Chromatography on silica gel gave the title compound (34.4 g).

(2S)-2-[(2R)-(2-tert-Butoxycarbonylamino-propionyl)-(4-fluoro-benzyl)-amino]-propionic acid methyl ester To a solution of (R)-2-tert-butoxycarbonylamino-propionic acid (37 g, 195 mmol) in dry tetrahydrofuran (250 mL) at 0° C. was added 4-methyl morpholine (21.5 mL, 195 mmol) followed by isobutylchloroformate (25.3 mL, 195 mmol). The reaction was allowed to warm to ambient temperature and stirred for two hours. This was followed by the addition of (S)-2-(4-fluoro-benzylamino)-propionic acid methyl ester (34.4 g, 162 mmol). The resulting mixture was stirred overnight at ambient temperature. The reaction mixture was filtered through a pad of celite and the filter cake was washed with ethyl acetate. The filtrate was concentrated in vacuo, diluted with ethyl acetate and washed with water and brine. The organic layer was dried over magnesium sulfate, filtered and concentrated in vacuo. Chromatography on silica gel gave the title compound (43.2 g).

(3R,6S)-1-(4-Fluoro-benzyl)-3,6-dimethyl-piperazine-2,5-dione

To a solution of (2S)-2-[(2R)-(2-tert-butoxycarbonylamino-propionyl)-(4-fluoro-benzyl)-amino]-propionic acid methyl ester (43 g, 382 mmol) in dichloromethane (120 mL) at 0° C. was added trifluoroacetic acid (60 mL). The reaction was allowed to warm to ambient temperature and stirred for 2 hours. The reaction was cooled to 0° C. and slowly quenched by addition of 3 N sodium hydroxide until basic. The resulting mixture was extracted with dichloromethane. The organic layer was dried over magnesium sulfate, filtered and concentrated in vacuo to give the title compound (22 g).

(2R,5S)-1-(4-Fluoro-benzyl)-2,5-dimethyl-piperazine

To a solution of (3R,6S)-1-(4-fluoro-benzyl)-3,6-dimethyl-piperazine-2,5-dione (22 g, 87.9 mmol) in dry tetrahydrofuran (160 mL) at 0° C. was added a solution of lithium aluminum hydride (1M in tetrahydrofuran, 373 mL, 373 mmol) dropwise over 40 minutes. The reaction mixture was then refluxed for 4 hours, cooled to ambient temperature and slowly quenched with water. The resulting mixture was filtered through a pad of celite and the filter cake was washed with ethyl acetate. The filtrate was then concentrated, diluted with ethyl acetate and washed with saturated aqueous sodium hydrogen carbonate. The organic layer was separated, dried over magnesium sulfate, filtered and concentrated in vacuo to give the title compound (17.7 g).

1-[4-(4-Fluoro-benzyl)-(2R,5S)-2,5-dimethyl-piperazin-1-yl]-3-(2-hydroxy-4-methyl-phenyl)-propan-1-one To a solution of (2R,5S)-1-(4-fluoro-benzyl)-2,5-dimethyl-piperazine (0.25 g, 1.12 mmol) in toluene (10 mL) was added 7-methyl-chroman-2-one (0.25 g, 1.54 mmol) and the resulting solution was heated to reflux for 48 hours. The reaction was cooled, concentrated in vacuo and purified via chromatography on silica gel to give the title compound (0.34 g).

(2-{3-[4-(4-Fluoro-benzyl)-(2R,5S)-2,5-dimethyl-piperazin-1-yl]-3-oxo-propyl}-5-methyl-phenoxy)-acetic acid methyl ester To a solution of 1-[4-(4-fluoro-benzyl)-(2R,5S)-2,5-dimethyl-piperazin-1-yl]-3-(2-hydroxy-4-methyl-phenyl)-propan-1-one, (0.15 g, 0.38 mmol) in tetrahydrofuran (2 mL) at 0° C. was added sodium hydride (0.023 g, 0.57 mmol). The reaction was stirred for 5 minutes, then bromoacetic acid methyl ester (0.043 mL, 0.45 mmol) was added and the reaction was stirred at ambient temperature overnight. The reaction was quenched by the addition of water and the mixture was extracted with ethyl acetate. The organic layer was dried over magnesium sulfate and concentrated in vacuo to give the title compound (0.18 g).

(2-{3-[4-(4-Fluoro-benzyl)-(2R,5S)-2,5-dimethyl-piperazin-1-yl]-3-oxo-propyl}-5-methyl-phenoxy)-acetic acid To a solution of (2-{3-[4-(4-fluoro-benzyl)-(2R,5S)-2,5-dimethyl-piperazin-1-yl]-3-oxo-propyl}-5-methyl-phenoxy)-acetic acid methyl ester (0.18 g, 0.40 mmol) in 2:2:1 tetrahydrofuran:methanol:water (5 mL) was added lithium hydroxide hydrate (0.026 g, 0.62 mmol) and the reaction was stirred at ambient temperature for 2 hours. The reaction was diluted with 0.2 M hydrochloric acid, then extracted with ethyl acetate. The organic layer was dried over magnesium sulfate and concentrated in vacuo. The crude product was purified by trituration in methylene chloride/diethyl ether to give the title compound (0.16 g).

N-[(2-{3-[4-(4-Fluoro-benzyl)-(2R,5S)-2,5-dimethyl-piperazin-1-yl]-3-oxo-propyl}-5-methyl-phenoxy)-acetyl]-methanesulfonamide To a solution of (2-{3-[4-(4-fluoro-benzyl)-(2R,5S)-2,5-dimethyl-piperazin-1-yl]-3-oxo-propyl}-5-methyl-phenoxy)-acetic acid (0.052 g, 0.12 mmol) in methylene chloride (1 mL) was added 4-dimethylaminopyridine (0.022 g, 0.18 mmol), (3-(dimethylamino)propyl)ethyl carbodiimide hydrochloride (0.032 g, 0.17 mmol), methanesulfonamide (0.015 g, 0.16 mmol) and triethylamine (0.035 mL, 0.25 mmol). The reaction was stirred at ambient temperature for 18 hours. The reaction mixture was then diluted with dichloromethane and washed with 0.2 M aqueous hydrochloric acid. The organic layer was dried over magnesium sulfate and concentrated in vacuo. The crude product was purified by trituration in methylene chloride/diethyl ether/hexanes to give the title compound (0.050 g, LRMS: 520.3).

EXAMPLE 2

N-[(5-Chloro-2-{2-[4-(4-fluoro-benzyl)-(2R,5S)-2,5-dimethyl-piperazin-1-yl]-2-oxo-ethoxy}-phenoxy)-acetyl]-methanesulfonamide (4-Chloro-2-methoxy-phenoxy)-acetic acid To a solution of sodium hydroxide (6.6 g, 160 mmol) in water (45 mL) was added 4-chloro-2-methoxy-phenol (2.0 mL, 16 mmol) and chloroacetic acid (7.7 g, 81 mmol). The resulting mixture was heated to 95° C. and stirred for three hours. The reaction was allowed to cool to ambient temperature and slowly acidified with concentrated hydrochloric acid (10 mL) until the mixture became a solution and then extracted with diethyl ether. The organic layer was dried over magnesium sulfate, filtered and concentrated in vacuo to give the title compound (4.16 g).

7-Chloro-benzo[1,4]dioxin-2-one

To a solution of 48% aqueous hyrdrogen bromide (20 mL) was added (4-chloro-2-methoxy-phenoxy)-acetic acid (2.1 g, 9.7 mmol). The resulting mixture was heated to reflux overnight. The mixture was cooled to ambient temperature, diluted with water and extracted with diethyl ether. The organic layer was dried over magnesium sulfate, filtered and concentrated in vacuo to give (4-chloro-2-hydroxy-phenoxy)-acetic acid. The crude product was added to a solution of pyridinium p-toluene sulfonate (0.10 g, 0.40 mmol) in toluene (100 mL). The resulting mixture was heated to reflux for five hours. The reaction was allowed to cool to ambient temperature and concentrated in vacuo. Chromatography on silica gel gave the title compound (0.97 g).

2-(4-Chloro-2-hydroxy-phenoxy)-1-[4-(4-fluoro-benzyl)-(2R,5S)-2,5-dimethyl-piperazin-1-yl]-ethanone To a solution of 7-chloro-benzo[1,4]dioxin-2-one (0.48 g, 2.6 mmol) in toluene (5 mL) was added 1-(4-fluoro-benzyl)-(2R,5S)-2,5-dimethyl-piperazine (0.59 g, 2.6 mmol). The resulting mixture was heated to 95° C. overnight. The reaction was cooled to ambient temperature and concentrated in vacuo. Chromatography on silica gel gave the title compound (0.67 g).

(5-Chloro-2-{2-[4-(4-fluoro-benzyl)-(2R,5S)-2,5-dimethyl-piperazin-1-yl]-2-oxo-ethoxy}-phenoxy)-acetic acid methyl ester To a solution of 2-(4-chloro-2-hydroxy-phenoxy)-1-[4-(4-fluoro-benzyl)-(2R,5S)-2,5-dimethyl-piperazin-1-yl]-ethanone (0.30 g, 0.75 mmol) and bromo-acetic acid methyl ester (0.14 mL, 1.5 mmol) in dioxane (3 mL) was added cesium carbonate (0.50 g, 1.5 mmol). The resulting mixture was stirred at ambient temperature overnight. The reaction was quenched with water and the mixture was extracted with ethyl acetate. The organic layer was washed with brine, dried over magnesium sulfate and concentrated in vacuo to give the title compound (0.61 g).

(5-Chloro-2-{2-[4-(4-fluoro-benzyl)-(2R,5S)-2,5-dimethyl-piperazin-1-yl]-2-oxo-ethoxy}-phenoxy)-acetic acid To a solution of (5-chloro-2-{2-[4-(4-fluoro-benzyl)-(2R,5S)-2,5-dimethyl-piperazin-1-yl]-2-oxo-ethoxy}-phenoxy)-acetic acid methyl ester (0.21 g, 0.46 mmol) in methanol (2 mL), tetrahydrofuran (2 mL) and water (1 mL) was added lithium hydroxide monohydrate (0.039 g, 0.93 mmol). The resulting mixture was stirred at ambient temperature for three hours. The reaction was acidifed to pH 4 with 0.2 N aqueous hydrochloric acid and extracted with ethyl acetate. The organic layer was washed with brine, dried over magnesium sulfate and concentrated in vacuo. The crude product was purified by trituration with methylene chloride/diethyl ether to give the title compound (0.16 g).

N-[(5-Chloro-2-{2-[4-(4-fluoro-benzyl)-(2R,5S)-2,5-dimethyl-piperazin-1-yl]-2-oxo-ethoxy}-phenoxy)-acetyl]-methanesulfonamide To a solution of (5-chloro-2-{2-[4-(4-fluoro-benzyl)-(2R,5S)-2,5-dimethyl-piperazin-1-yl]-2-oxo-ethoxy}-phenoxy)-acetic acid (0.051 g, 0.10 mmol) in methylene chloride (1 mL) was added 4-dimethylaminopyridine (0.022 g, 0.18 mmol), (3-(dimethylamino)propyl)ethyl carbodiimide hydrochloride (0.033 g, 0.17 mmol), methanesulfonamide (0.016 g, 0.17 mmol) and triethylamine (0.040 mL, 0.29 mmol). The reaction was stirred at ambient temperature for 3 days. The reaction mixture was then diluted with dichloromethane and washed with 10% aqueous acetic acid. The organic layer was washed with saturated aqueous sodium hydrogen carbonate, dried over magnesium sulfate and concentrated in vacuo. Chromatography on silica gel followed by trituration with methylene chloride/hydrogen chloride in diethyl ether gave the title compound as the hydrochloride salt (0.015 g, LRMS: 542.1, 544.1).

EXAMPLE 3

2-(5-Chloro-2-{2-[4-(4-fluoro-benzyl)-(2R,5S)-2,5-dimethyl-piperazin-1-yl]-2-oxo-ethoxy}-phenoxy)-propionic acid 2-(5-Chloro-2-{2-[4-(4-fluoro-benzyl)-(2R,5S)-2,5-dimethyl-piperazin-1-yl]-2-oxo-ethoxy}-phenoxy)-propionic acid ethyl ester To a solution of 2-(4-chloro-2-hydroxy-phenoxy)-1-[4-(4-fluoro-benzyl)-(2R,5S)-2,5-dimethyl-piperazin-1-yl]-ethanone (0.076 g, 0.18 mmol), triphenylphosphine (0.076 g, 0.29 mmol) and (2S)-2-hydroxy-propionic acid ethyl ester (0.036 g, 0.31 mmol) in tetrahydrofuran (1 mL) was added diethyl-azodicarboxylate (0.049 g, 0.29 mmol). The resulting mixture was stirred at ambient temperature overnight. The reaction was concentrated in-vacuo. Chromatography on silica gel gave the title compound (0.078 g)

(2-(5-Chloro-2-{2-[4-(4-fluoro-benzyl)-(2R,5S)-2,5-dimethyl-piperazin-1-yl]-2-oxo-ethoxy}-phenoxy)-propionic acid To a solution of 2-(5-chloro-2-{2-[4-(4-fluoro-benzyl)-(2R,5S)-2,5-dimethyl-piperazin-1-yl]-2-oxo-ethoxy}-phenoxy)-propionic acid ethyl ester (0.075 g, 0.15 mmol) in methanol (0.4 mL), tetrahydrofuran (0.4 mL) and water (0.2 mL) was added lithium hydroxide monohydrate (0.010 g, 0.24 mmol). The resulting mixture was stirred at ambient temperature for three hours. The reaction was acidifed to pH 4 with 0.2 N aqueous hydrochloric acid and extracted with ethyl acetate. The organic layer was washed with brine, dried over magnesium sulfate and concentrated in vacuo. The crude product was purified by trituration with methylene chloride/diethyl ether to give the title compound (0.066 g, LRMS: 479.2, 481.2).

EXAMPLE 4

4-(5-Chloro-2-{2-[4-(4-fluoro-benzyl)-(2R,5S)-2,5-dimethyl-piperazin-1-yl]-2-oxo-ethoxy}-phenyl)-4-oxo-butyric acid 4-(5-Chloro-2-hydroxy-phenyl)-4-oxo-butyric acid
To a solution of 1-chloro-4-methoxy-benzene (1.1 g, 8.1 mmol) in 1,2-dichloroethane (8.0 mL) was added succinnic anhydride (0.9 g, 9.0 mmol) and anhydrous aluminum chloride (2.4 g, 18.3 mmol). The resulting mixture was stirred at ambient temperature for 4 days. The reaction was poured into ice and diluted with ethyl acetate and 18% aqueous hydrochloric acid. The aqueous layer was washed with ethyl acetate. The organic layer was washed with brine, dried over magnesium sulfate, filtered and concentrated in vacuo to give a tan solid. The solid was triturated with hexanes and filtered to give the title compound (1.4 g).

4-(5-Chloro-2-hydroxy-phenyl)-4-oxo-butyric acid ethyl ester
A solution of 4-(5-chloro-2-hydroxy-phenyl)-4-oxo-butyric acid (0.25 g, 1.09 mmol) in ethanol (10 mL) saturated with hydrogen chloride (g) was stirred at ambient temperature for 12 hours. The reaction was concentrated in vacuo, dissolved in diethyl ether and washed with saturated aqueous sodium bicarbonate. The organic layer was dried over magnesium sulfate, filtered and concentrated in vacuo to give the title compound (0.259 g).

4-(5-Chloro-2-{2-[4-(4-fluoro-benzyl)-(2R,5S)-2,5-dimethyl-piperazin-1-yl]-2-oxo-ethoxy}-phenyl)-4-oxo-butyric acid ethyl ester
A solution of 2-chloro-1-[4-(4-fluoro-benzyl)-(2R,5S)-2,5-dimethyl-piperazin-1-yl]-ethanone (0.11 g, 0.36 mmol), 4-(5-chloro-2-hydroxy-phenyl)-4-oxo-butyric acid ethyl ester (0.11 g, 0.43 mmol) and 1,5,7-triazabicyclo[4,4,0]dec-5-ene bound to polystyrene crosslinked with 2% DVB (0.21 g, 0.54 mmol) in acetonitrile (1.8 mL) was stirred at ambient temperature for 12 hours. The reaction mixture was filtered through a glass frit, concentrated in vacuo and purified via flash chromatography on silica gel to give the title compound (0.084 g).

4-(5-Chloro-2-{2-[4-(4-fluoro-benzyl)-(2R,5S)-2,5-dimethyl-piperazin-1-yl]-2-oxo-ethoxy}-phenyl)-4-oxo-butyric acid
To a solution of 4-(5-chloro-2-{2-[4-(4-fluoro-benzyl)-(2R,5S)-2,5-dimethyl-piperazin-1-yl]-2-oxo-ethoxy}-phenyl)-4-oxo-butyric acid ethyl ester (0.082 g, 0.16 mmol) in 2:2:1 tetrahydrofuran:methanol:water(1.5 mL) was added lithium hydroxide monohydrate (0.34 g, 0.79 mmol). The resulting solution was stirred 12 hours at ambient temperature, then concentrated in vacuo. The crude product was dissolved in ethyl acetate and washed with 1 M hydrochloric acid. The organics were dried over magnesium sulfate, filtered and concentrated in vacuo to give the title compound (0.072 g, LRMS: 489.4, 491.4).

EXAMPLE 5

3-[3-(5-chloro-2-{2-[4-(4-fluoro-benzyl)-(2R)-2-methyl-piperazin-1-yl]-2-oxo-ethoxy}-phenyl)-ureido]-propionic acid (3R)-1-(4-Fluoro-benzyl)-3-methyl-piperazine
To a solution of (2R)-2-methyl-piperizine (4.5 g, 45 mmol) in ethanol (80 mL) was added 4-fluorobenzyl chloride (5.38 mL, 45.0 mmol) and sodium hydrogen carbonate (11.3 g, 135 mmol). The reaction was refluxed overnight, cooled and concentrated. The remaining residue was diluted with dichloromethane and washed with water. The organic layer was separated and concentrated to give a clear oil. Chromatography on silica gel gave the title compound (5.0 g).

2-Chloro-1-[4-(4-fluoro-benzyl)-(2R)-2-methyl-piperazin-1-yl]-ethanone
To a solution of (3R)-1-(4-fluoro-benzyl)-3-methyl-piperazine (3 g, 14.4 mmol) in dichloromethane (40 mL) was added triethylamine (2.0 mL, 14.4 mmol). The reaction was cooled to 0° C. and chloroacetyl chloride was added (1.1 mL, 14.4 mmol). The reaction was allowed to warm to ambient temperature and stirred for 2 hours. The reaction is diluted with dichloromethane and washed with 10% citric acid. The organic layer was separated, dried over magnesium sulfate, filtered and concentrated in vacuo. Chromatography on silica gel gave the title compound (3.9 g).

2-(4-Chloro-2-nitro-phenoxy)-1-[4-(4-fluoro-benzyl)-(2R)-2-methyl-piperazin-1-yl]-ethanone
To a solution of 2-chloro-1-[4-(4-fluoro-benzyl)-(2R)-2-methyl-piperazin-1-yl]-ethanone (0.40 g, 1.4 mmol) in 2-butanone (14 mL) was added 4-chloro-2-nitro-phenol (0.25 g, 1.4 mmol), potassium carbonate (0.39 g, 2.8 mmol) and potassium iodide (233 mg, 1.4 mmol). The reaction was refluxed overnight, cooled and concentrated in vacuo. Chromatography on silica gel gave the title compound (0.56 g).

2-(2-Amino-4-chloro-phenoxy)-1-[4-(4-fluoro-benzyl)-(2R)-2-methyl-piperazin-1-yl]-ethanone
To a solution of 2-(4-chloro-2-nitro-phenoxy)-1-[4-(4-fluoro-benzyl)-(2R)-2-methyl-piperazin-1-yl]-ethanone (0.55 g, 1.3 mmol) in ethanol (25 mL) was added platinum dioxide on carbon (0.50 g, 5% on carbon). The reaction was subject to 35 psi hydrogen gas for 20 minutes. The reaction was then filtered through celite and the filtrate was concentrated to give the title compound (0.42 g).

(5-Chloro-2-{2-[4-(4-fluoro-benzyl)-(2R)-2-methyl-piperazin-1-yl]-2-oxo-ethoxy}-phenyl)-carbamic acid 4-nitrophenyl ester
To a solution of 2-(2-amino-4-chloro-phenoxy)-1-[4-(4-fluoro-benzyl)-(2R)-2-methyl-piperazin-1-yl]-ethanone (0.14 g, 0.36 mmol) in dichloromethane (5 mL) was added pyridine (0.032 mL, 0.39 mmol) and 4-nitrophenyl chloroformate (0.079 g, 0.39 mmol). The reaction was stirred at ambient temperature for one hour and concentrated in vacuo to give the title compound (0.20 g).

3-[3-(5-Chloro-2-{2-[4-(4-fluoro-benzyl)-(2R)-2-methyl-piperazin-1-yl]-2-oxo-ethoxy}-phenyl)-ureido]-propionic acid methyl ester To a solution of (5-chloro-2-{2-[4-(4-fluoro-benzyl)-(2R)-2-methyl-piperazin-1-yl]-2-oxo-ethoxy}-phenyl)-carbamic acid 4-nitro-phenyl ester (0.10 g, 0.18 mmol) in methanol was added β-alanine methyl ester hydrochloride (0.038 g, 0.27 mmol) and triethylamine (0.038 mL, 0.27 mmol). The reaction was stirred at ambient temperature overnight. The reaction was concentrated and purified via chromatography on silica gel to give the title compound (0.075 g).

3-[3-(5-Chloro-2-{2-[4-(4-fluoro-benzyl)-(2R)-2-methyl-piperazin-1-yl]-2-oxo-ethoxy}-phenyl)-ureido]-propionic acid To a solution of 3-[3-(5-chloro-2-{2-[4-(4-fluoro-benzyl)-(2R)-2-methyl-piperazin-1-yl]-2-oxo-ethoxy}-phenyl)-ureido]-propionic acid methyl ester (0.057 g, 0.11 mmol) in tetrahydrofuran (3 mL), methanol (3 mL) and water (1 mL) was added lithium hydroxide monohydrate (0.023 g, 0.55 mmol). The reaction was stirred at ambient temperature overnight, concentrated in vacuo, taken up in methanol, passed through an ion exchange column and then treated with hydrogen chloride gas to give the title compound as its hydrochloride salt (0.035 g, LRMS: 507.2).

EXAMPLE 6

(5-Chloro-2-{2-[4-(4-fluoro-benzyl)-(2R,5S)-2,5-dimethyl-piperazin-1-yl]-2-oxo-ethoxy}-phenylsulfamoyl)-acetic acid 2-Chloro-1-[4-(4-fluoro-benzyl)-(2R,5S)-2,5-dimethyl-piperazin-1-yl]-ethanone To a solution of (2R,5S)-1-(4-fluoro-benzyl)-2,5-dimethyl-piperazine (2.5 g, 11.2 mmol) in dry dichloromethane (11 mL) at 0° C. was added triethylamine (1.57 mL, 11.2 mmol) followed by chloroacetyl chloride (0.86 mL, 11.2 mmol). The resulting reaction mixture was stirred for 30 minutes. The reaction was then filtered through a pad of celite, washed with dichloromethane and the resulting filtrate was concentrated. Chromatography on silica gel gave the title compound (2.84 g).

2-(4-Chloro-2-nitro-phenoxy)-1-[4-(4-fluoro-benzyl)-(2R,5S)-2,5-dimethyl-piperazin-1-yl]-ethanone To a solution of 2-chloro-1-[4-(4-fluoro-benzyl)-(2R,5S)-2,5-dimethyl-piperazin-1-yl]-ethanone (1.0 g, 3.35 mmol) in butanone (35 mL) was added 2-nitro-4-chlorophenol (0.64 g, 3.69 mmol), potassium carbonate (0.93 g, 6.7mmol) and potassium iodide (0.56 g, 3.35 mmol). The reaction mixture was heated at reflux overnight. The reaction mixture was then cooled, diluted with water and extracted with ethyl acetate. The organic layer was dried over magnesium sulfate, filtered and concentrated to give an orange oil. Chromatography on silica gel gave the title compound (1.35 g).

2-(2-Amino-4-chloro-phenoxy)-1-[4-(4-fluoro-benzyl)-(2R,5S)-2,5-dimethyl-piperazin-1-yl]-ethanone To a solution of 2-(4-chloro-2-nitro-phenoxy)-1-[4-(4-fluoro-benzyl)-(2R,5S)-2,5-dimethyl-piperazin-1-yl]-ethanone (2.2 g, 5.05 mmol) in ethanol (50 mL) in a par bottle was added 5% platinum on carbon (2.2 g). The reaction mixture was subjected to hydrogen gas (35 psi) for 30 minutes. The reaction mixture was filtered through celite and the filter cake was washed with ethanol. The filtrate was concentrated in vacuo. Chromatography on silica gel gave the title compound (1.42 g).

(5-Chloro-2-{2-[4-(4-fluoro-benzyl)-(2R,5S)-2,5-dimethyl-piperazin-1-yl]-2-oxo-ethoxy}-phenylsulfamoyl)-acetic acid To a solution of 2-(2-amino-4-chloro-phenoxy)-1-[4-(4-fluoro-benzyl)-(2R,5S)-2,5-dimethyl-piperazin-1-yl]-ethanone (0.030 g, 0.074 mmol) in dimethylformamide (0.5 ml) was added potassium carbonate (0.030 g, 0.239 mmol), chlorosulfonyl-acetic acid ethyl ester (0.02 g, 0.12 mmol) (for preparation, see: *Helv. Chim. Acta.*, (1997) 80, 671 and *Bull. Soc. Chim. Fr.* (1975), 807) in dimethylformamide (0.5 ml) and finally catalytic dimethylaminopyridine. After 23 hours the reaction was diluted with ethyl acetate and washed with pH 7.0 phosphate buffer (0.05 M). The organic layer was dried over magnesium sulfate, filtered and concentrated. The crude ester was then dissolved in 1:1 tetrahydrofuran: water (0.5 ml) and lithium hydroxide hydrate (0.004 g, 0.095 mmol) was added. After 19 hours the reaction was concentrated and the title compound purified by silica gel chromatography (0.006 g, LRMS: 528.3).

EXAMPLE 7

3-(5-Chloro-2-{2-[4-(4-fluoro-benzyl)-(2R,5S)-2,5-dimethyl-piperazin-1-yl]-2-oxo-ethoxy}-benzylamino)-propionic acid 5-Chloro-2-{2-[4-(4-fluoro-benzyl)-(2R,5S)-2,5-dimethyl-piperazin-1-yl]-2-oxo-ethoxy}-benzaldehyde To a solution of 2-chloro-1-[4-(4-fluoro-benzyl)-(2R,5S)-2,5-dimethyl-piperazin-1-yl]-ethanone (2.87 g, 9.6 mmol) in dimethylformamide (20 mL) was added 5-chlorosalicylaldehyde (1.65 g, 10.5 mmol), potassium carbonate (2.64 g, 19.2 mmol) and potassium iodide (1.59 g, 9.6 mmol). The resulting mixture was heated to 100° C. for 12 hours. The reaction was cooled, diluted with saturated aqueous brine and extracted with ethyl acetate. The organic layer was dried over magnesium sulfate and filtered. The filtrate was concentrated in vacuo to give crude product. Purification via chromatography on silica gel gave the title compound (3.40 g).

3-(5-Chloro-2-{2-[4-(4-fluoro-benzyl)-(2R,5S)-2,5-dimethyl-piperazin-1-yl]-2-oxo-ethoxy}-benzylamino)-propionic acid methyl ester To a solution of 5-chloro-2-{2-[4-(4-fluoro-benzyl)-(2R,5S)-2,5-dimethyl-piperazin-1-yl]-2-oxo-ethoxy}-benzaldehyde (0.075 g, 0.18 mmol) in methanol (2 mL) was added 3-amino-propionic acid methyl ester hydrochloride salt (0.063 g, 0.45 mmol) and the pH of the solution was adjusted to 5–6 with triethylamine and acetic acid. The reaction mixture was stirred at ambient temperature for 1 hour. To the resulting reaction mixture was added sodium cyanoborohydride (0.023 g, 0.36 mmol), and the pH of the solution was again adjusted to pH 5 with acetic acid and triethylamine. The reaction mixture was stirred at ambient temperature overnight, diluted with ethyl acetate and washed with saturated aqueous sodium hydrogen carbonate. The organic layer was dried over magnesium sulfate, filtered and concentrated in vacuo. The crude product was purified by chromatography on silica gel to give the title compound (0.035 g).

3-(5-Chloro-2-{2-[4-(4-fluoro-benzyl)-(2R,5S)-2,5-dimethyl-piperazin-1-yl]-2-oxo-ethoxy}-benzylamino)-propionic acid To a solution of 3-(5-chloro-2-{2-[4-(4-fluoro-benzyl)-(2R,5S)-2,5-dimethyl-piperazin-1-yl]-2-oxo-ethoxy}-benzylamino)-propionic acid methyl ester (0.035 g, 0.069 mmol) in tetrahydrofuran (0.2 mL), methanol (0.2 mL) and water (0.1 mL) was added lithium hydroxide monohydrate (0.015 g, 0.35 mmol). The reaction mixture was stirred at ambient temperature overnight. The reaction mixture was then concentrated in vacuo and the resulting residue was dissolved in dichloromethane and treated with hydrogen chloride gas. The resulting white solid was washed with acetonitrile. The acetonitrile wash was concentrated to give the title compound as its hydrochloride salt (0.010 g, LRMS: 490.3).

EXAMPLE 8

1-(5-Chloro-2-{2-[4-(4-fluoro-benzyl)-(2R,5S)-2,5-dimethyl-piperazin-1-yl]-2-oxo-ethoxy}-benzyl)-3-(2-methylbenzenesulfonyl)-urea 2-(5-Chloro-2-hydroxy-benzyl)-isoindole-1,3-dione
To 4-chlorophenol (2.0 g, 15.5 mmol) and chloromethylphthalamide (2.62 g, 13.4 mmol) was added zinc chloride (3 mL, 0.5 M in tetrahydrofuran, 1.5 mmol). The reaction was stirred at 90° C. for 48 hours. After cooling the reaction was diluted with methanol (15 mL) and brought to reflux. After 30 minutes the hot suspension was filtered through a medium glass frit and concentrated to an off-white solid. Methanol (50 mL) was again added and the reaction brought to reflux. After 3 hours the hot suspension was filtered through a medium glass frit and concentrated to an off-white solid. The crude product was purified via chromatography on silica gel to give the title compound (3.86 g).

2-(5-Chloro-2-{2-[4-(4-fluoro-benzyl)-(2R,5S)-2,5-dimethyl-piperazin-1-yl]-2-oxo-ethoxy}-benzyl)-isoindole-1,3-dione
To a solution of 2-chloro-1-[4-(4-fluoro-benzyl)-(2R,5S)-2,5-dimethyl-piperazin-1-yl]-ethanone (0.75 g, 2.50 mmol) in dry dimethylformamide (25 mL) was added potassium iodide (0.40 g, 2.39 mmol), 2-(5-chloro-2-hydroxy-benzyl)-isoindole-1,3-dione (0.80 g, 2.76 mmol) and potassium carbonate (0.70 g, 5.10 mmol). The resulting mixture was heated to 70° C. for 23 hours. The reaction was cooled to ambient temperature, diluted with water and extracted with 1:1 diethyl ether/hexanes (3×). The organic layers were combined, washed with water and brine, dried over magnesium sulfate, filtered and evaporated to give the title compound (0.87 g).

2-(2-Aminomethyl-4-chloro-phenoxy)-1-[4-(4-fluoro-benzyl)-(2R,5S)-2,5-dimethyl-piperazin-1-yl]-ethanone
To 2-(5-chloro-2-{2-[4-(4-fluoro-benzyl)-(2R,5S)-2,5-dimethyl-piperazin-1-yl]-2-oxo-ethoxy}-benzyl)-isoindole-1,3-dione (0.87 g, 1.59 mmol) in ethanol (20 mL) was added 35% hydrazine (3 mL, 33.1 mmol). After 17 hours, the reaction was filtered and concentrated to a tan solid. This solid was triturated with methylene chloride and the title compound was obtained after filtration, drying over magnesium sulfate and concentrating in vacuo (0.62 g).

(2-methylbenzenesulfonyl)-carbamic acid 5-chloro-2-{2-[4-(4-fluoro-benzyl)-(2R,5S)-2,5-dimethyl-piperazin-1-yl]-2-oxo-ethoxy}-benzyl ester
To a solution of 2-(2-aminomethyl-4-chloro-phenoxy)-1-[4-(4-fluoro-benzyl)-(2R, 5S)-2,5-dimethyl-piperazin-1-yl]-ethanone (0.050 g, 0.12 mmol) in dry toluene (2 mL) was added o-toluenesulfonylisocyanate (0.05 mL, 0.36 mmol). The reaction was concentrated to dryness and purified via chromatography on silica gel to give the title compound (0.048 g, LRMS: 617.2).

EXAMPLE 9

2-(5-Chloro-2-{2-[4-(4-fluoro-benzyl)-(2R,5S)-2,5-dimethyl-piperazin-1-yl]-2-oxo-ethoxy}-benzylsulfamoyl)-propionic acid To a solution of 2-(2-aminomethyl-4-chloro-phenoxy)-1-[4-(4-fluoro-benzyl)-(2R,5S)-2,5-dimethyl-piperazin-1-yl]-ethanone (0.05 g, 0.119 mmol) in tetrahydrofuran (1 ml) at −40° C. was added triethylamine (0.021 ml, 0.151 mmol), catalytic dimethylaminopyridine and finally a solution of 2-chlorosulfonyl-propionic acid ethyl ester (for preparation, see: *Helv. Chim. Acta.*, (1997) 80, 671 and *Bull. Soc. Chim. Fr.* (1975), 807) (0.029 g, 0.145 mmol) in tetrahydrofuran (0.25 ml), added over 5 minutes. The reaction was allowed to warm to ambient temperature. After 23 hours the reaction was diluted with ethyl acetate and washed with pH 7 phosphate buffer (0.5 M). The organic layer was dried over magnesium sulfate, filtered and concentrated. The desired product was isolated via silica gel chromatography (0.047 g). This ester (0.07 mmol) was dissolved in 1:1 tetrahydrofuran:water (1 ml) and lithium hydroxide hydrate (5.8 mg, 0.138 mmol) was added. After 21 hours the reaction was concentrated and the title compound obtained after silica gel chromatography (0.039 g, LRMS: 556.1).

EXAMPLE 10

(5-Chloro-2-{2-[4-(4-fluoro-benzyl)-(2R,5S)-2,5-dimethyl-piperazin-1-yl]-2-oxo-ethoxy}-benzyloxy)-acetyl methanesulfonamide 2-(4-Chloro-2-hydroxymethyl-phenoxy)-1-[4-(4-fluoro-benzyl)-(2R,5S)-2,5-dimethyl-piperazin-1-yl]-ethanone
To a solution of 5-chloro-2-{2-[4-(4-fluoro-benzyl)-(2R,5S)-2,5-dimethyl-piperazin-1-yl]-2-oxo-ethoxy}-benzaldehyde (0.99 g, 2.36 mmol) in dry methanol (25 mL) was added sodium borohydride (0.19 g, 4.92 mmol). After 1 hour the reaction was acidified to pH 2 by the addition of 1N hydrochloric acid. After 5 minutes the reaction was neutralized with 1N sodium hydroxide and the methanol removed by evaporation. The resulting aqueous suspension was extracted with ethyl acetate. The organic layer was washed with brine, dried over magnesium sulfate, filtered and evaporated to give the title compound (0.98 g).

(5-Chloro-2-{2-[4-(4-fluoro-benzyl)-(2R,5S)-2,5-dimethyl-piperazin-1-yl]-2-oxo-ethoxy}-benzyloxy)-acetic acid tert-butyl ester
To a 0° C. solution of sodium hydride (0.025 g, 60% dispersion, 1.0 mmol) in tetrahydrofuran (2 mL) was added a solution of 2-(4-chloro-2-hydroxymethyl-phenoxy)-1-[4-(4-fluoro-benzyl)-(2R,5S)-2,5-dimethyl-piperazin-1-yl]-ethanone (0.17 g, 0.40 mmol) and tert-butyl bromoacetate (0.23 g, 3.0 mmol) in tetrahydrofuran (2 mL). The reaction mixture was warmed to ambient temperature overnight, quenched with water and diluted with ethyl acetate. The organic layer was dried over magnesium sulfate and concentrated in vacuo. The crude product was purified via chromatography on silica gel to give the title compound (0.14 g).

(5-Chloro-2-{2-[4-(4-fluoro-benzyl)-(2R,5S)-2,5-dimethyl-piperazin-1-yl]-2-oxo-ethoxy}-benzyloxy)-acetic acid
To a solution of (5-chloro-2-{2-[4-(4-fluoro-benzyl)-(2R,5S)-2,5-dimethyl-piperazin-1-yl]-2-oxo-ethoxy}-benzyloxy)-acetic acid tert-butyl ester (0.14 g, 0.25 mmol) in dichloromethane (5.0 mL) was added trifluoroacetic acid (0.5 mL). The resulting mixture was stirred at ambient temperature overnight, diluted with dichloromethane and treated with excess hydrogen chloride gas. The mixture was concentrated in vacuo to give the title compound as its hydrochloride salt (0.14 g).

(5-Chloro-2-{2-[4-(4-fluoro-benzyl)-(2R,5S)-2,5-dimethyl-piperazin-1-yl]-2-oxo-ethoxy}-benzyloxy)-acetyl methanesulfonamide To a solution of (5-chloro-2-{2-[4-(4-fluoro-benzyl)-(2R,5S)-2,5-dimethyl-piperazin-1-yl]-2-oxo-ethoxy}-benzyloxy)-acetic acid (0.11 g, 0.22 mmol) in dichloromethane (10 mL) was added 4-dimethylaminopyridine (0.04 g, 0.33 mmol) and 1,3-dicyclohexylcarbodiimide (0.049 g, 0.24 mmol). The resulting reaction mixture was stirred at ambient temperature for 20 minutes and then treated with methanesulfonamide (0.025 g, 0.26 mmol). The reaction was stirred at ambient temperature for 18 hours, filtered through a pad of celite and the resulting filter cake was washed with dichloromethane. The combined organics were concentrated in vacuo and purified via chromatography on silica gel to give the title compound (0.045 g, LRMS: 556.2).

EXAMPLE 11

1-Acetyl-3-(5-chloro-2-{2-[4-(4-fluoro-benzyl)-(2R,5S)-2,5-dimethyl-piperazin-1-yl]-2-oxo-ethoxy}-benzyl)sulfamide 1-(tert-Butoxycarbonyl)-1-(5-chloro-2-{2-[4-(4-fluoro-benzyl)-(2R,5S)-2,5-dimethyl-piperazin-1-yl]-2-oxo-ethoxy}-benzyl)sulfamide To a solution of 2-(4-chloro-2-hydroxymethyl-phenoxy)-1-[4-(4-fluoro-benzyl)-2,5-dimethyl-piperazin-1-yl]-ethanone (0.2 g, 0.48 mmol) in tetrahydrofuran (2 ml) was added tert-butoxycarbonylsulfamide (for preparation, see: EP 557122A1) (0.14 g, 0.71 mmol) and triphenylphosphine (0.16 g, 0.62 mmol). The reaction mixture was cooled to −60° C. and diethyl azodicarboxalate (0.10 ml, 0.64 mmol) was added dropwise. The reaction was warmed to 10° C. over 2 hours and then allowed to warm to room temperature. The reaction was diluted with ethyl acetate and washed with pH 7 phosphate buffer (0.5 M) and brine and then dried over magnesium sulfate. The reaction was concentrated to dryness and purified via chromatography on silica gel to give the title compound (0.28 g).

1-Acetyl-3-(5-chloro-2-{2-[4-(4-fluoro-benzyl)-(2R,5S)-2,5-dimethyl-piperazin-1-yl]-2-oxo-ethoxy}-benzyl)sulfamide To a solution of 1-(tert-butoxycarbonyl)-1-(5-chloro-2-{2-[4-(4-fluoro-benzyl)-(2R,5S)-2,5-dimethyl-piperazin-1-yl]-2-oxo-ethoxy}-benzyl)sulfamide (0.05 g, 0.08 mmol) in methylene chloride (1 ml) was added triethylamine (0.01 ml, 0.09 mmol), acetyl chloride (0.007 ml, 0.098 mmol) and catalytic dimethylaminopyridine. After 18 hours the reaction was diluted with methanol, concentrated to dryness and purified via chromatography on silica gel (0.041 g). This material (0.064 mmol) was dissolved in methylene chloride (1 ml) and trifluoroacetic acid (1 ml). After 3 hours at ambient temperature the reaction was diluted with methylene chloride and quenched with 5% sodium carbonate. The layers were separated and the aqueous layer washed twice with methylene chloride. The organic layers were combined, washed with brine, dried over magnesium sulfate and concentrated to dryness. The title compound was afforded after silica gel chromatography (0.035 g, LRMS: 541.3).

EXAMPLE 12

5-Chloro-2-{2-[4-(4-fluoro-benzyl)-(2R,5S)-2,5-dimethyl-piperazin-1-yl]-2-oxo-ethoxy}-benzylideneaminooxy)-acetic acid To a solution of 5-chloro-2-{2-[4-(4-fluoro-benzyl)-(2R,5S)-2,5-dimethyl-piperazin-1-yl]-2-oxo-ethoxy}-benzaldehyde (0.050 g, 0.12 mmol) in methanol (1 mL) was added triethylamine (excess) and carboxymethoxylamine hemihydrochloride (0.030 g, 0.24 mmol). After 3 hours at ambient temperature the reaction was concentrated and the desired product purified by silica gel chromatography (0.045 g, LRMS: 492.1)

EXAMPLE 13

(2-Methylbenzenesulfonyl)-carbamic acid 5-chloro-2-{2-[4-(4-fluoro-benzyl)-(2R,5S)-2,5-dimethyl-piperazin-1-yl]-2-oxo-ethoxy}-benzyl ester To a solution of 2-(4-chloro-2-hydroxymethyl-phenoxy)-1-[4-(4-fluoro-benzyl)-(2R,5S)-2,5-dimethyl-piperazin-1-yl]-ethanone (0.050 g, 0.12 mmol) in dry toluene (2 mL) was added triethylamine (0.05 mL, 0.36 mmol) followed by o-toluenesulfonylisocyanate (0.05 mL, 0.36 mmol) and catalytic 4-dimethylaminopyridine. After 23 hours the reaction was warmed to 55° C. for 2 hours. After cooling the reaction was evaporated to dryness and the title compound purified by silica gel chromatography (0.074 g, LRMS: 618.1).

EXAMPLE 14

N-[(5-Chloro-2-{2-[4-(4-fluoro-benzyl)-(2R,5S)-2,5-dimethyl-piperazin-1-yl]-2-oxo-ethoxy}-phenyl)-acetyl]-methanesulfonamide (5-Chloro-2-methoxy-phenyl)-methanol To a solution of 5-chloro-2-methoxy-benzoic acid methyl ester (20 g, 9.97 mmol) in THF (100 mL) at 0° C. was added dropwise a solution of lithium aluminum hydride (210 mL, 210 mmol, 1M soln. in THF). The solution was then warmed to reflux for 2 hours. The reaction was cooled to 0° C. and carefully quenched by the addition of cold water. The mixture was filtered through celite and the filter cake was washed with diethyl ether. The filtrate was washed with saturated aqueous sodium hydrogen carbonate then dried over magnesium sulfate. Concentration in vacuo gave the title compound (17.2 g).

(5-Chloro-2-methoxy-phenyl)-acetonitrile

To a solution of (5-chloro-2-methoxy-phenyl)-methanol (17.1 g, 99.1 mmol) in methylene chloride (100 mL) was added thionyl chloride (14.5 mL, 198 mmol). The reaction was stirred at reflux for 3 hours, cooled to room temperature and concentrated in vacuo. The crude product was dissolved in methylene chloride and washed with saturated aqueous sodium hydrogen carbonate then dried over magnesium sulfate. Concentration in vacuo gave 4-chloro-2-chloromethyl-1-methoxy-benzene (18.4 g). To a solution of 4-chloro-2-chloromethyl-1-methoxy-benzene (18.4 g, 96.4 mmol) in acetonitrile (100 mL) was added potassium cyanide (12.5 g, 193 mmol) and 18-crown-6 (2.54 g, 9.64 mmol). The reaction was stirred 12 hours at ambient temperature, diluted with ethyl acetate and washed with aqueous sodium hydrogen carbonate. The organic layer was dried over magnesium sulfate and concentrated in vacuo. The crude product was purified by passing it through a pad of silica gel, eluting with methylene chloride to give the title compound (17.2 g).

(5-Chloro-2-methoxy-phenyl)-acetic acid

To a solution of (5-chloro-2-methoxy-phenyl)-acetonitrile (17.2 g, 96.3 mmol) in ethanol (200 mL) and water (20 mL) was added potassium hydroxide (27 g, 481 mmol). The reaction was heated to reflux for 12 hours, cooled and the ethanol was removed by concentrating in vacuo. The remaining solution was acidified with aqueous hydrochloric acid (3 M) and extracted with diethyl ether. The organic layer was dried over magnesium sulfate and concentrated in vacuo to give the title compound (15.6 g).

(5-Chloro-2-hydroxy-phenyl)-acetic acid ethyl ester

A solution of (5-chloro-2-methoxy-phenyl)-acetic acid (15.5 g, 77.5 mmol) in 48% aqueous hydrogen bromide was heated to reflux for 20 hours. The solution was cooled, diluted with water and extracted with diethyl ether. The organic layer was dried over magnesium sulfate, filtered and concentrated in vacuo. The crude product was purified by trituration in 2:1 methylene chloride:hexanes to give (5-chloro-2-hydroxy-phenyl)-acetic acid (12.8 g). This was dissolved in a solution of ethanol saturated with hydrochloric acid and stirred 12 hours. The reaction was concentrated in vacuo, then the crude product was dissolved in diethyl ether and washed with saturated aqueous sodium hydrogen carbonate. The organic layer was dried over magnesium sulfate, filtered and concentrated in vacuo to give the title compound (12.7 g)

(5-Chloro-2-{2-[4-(4-fluoro-benzyl)-(2R,5S)-2,5-dimethyl-piperazin-1-yl]-2-oxo-ethoxy}-phenyl)-acetic acid ethyl ester To a solution of 2-chloro-1-[4-(4-fluoro-benzyl)-(2R,5S)-2,5-dimethyl-piperazin-1-yl]-ethanone (3.3 g, 11.0 mmol) in 2-butanone (100 mL) was added (5-chloro-2-hydroxy-phenyl)-acetic acid ethyl ester (2.3 g, 11.0 mmol), potassium carbonate (3.05 g, 22.1 mmol), and potassium iodide (1.83 g, 11.0 mmol). The reaction was heated at reflux for 48 hrs. The solution was cooled, diluted with ethyl acetate and washed with brine. The organic layer was dried over magnesium sulfate, filtered and concentrated in vacuo. The crude product was purified by dissolving in dichloromethane and passing through a pad of silica gel. Concentration in vacuo gave the title compound (5.13 g).

(5-Chloro-2-{2-[4-(4-fluoro-benzyl)-(2R,5S)-2,5-dimethyl-piperazin-1-yl]-2-oxo-ethoxy}-phenyl)-acetic acid To a solution of (5-chloro-2-{2-[4-(4-fluoro-benzyl)-(2R,5S)-2,5-dimethyl-piperazin-1-yl]-2-oxo-ethoxy}-phenyl)-acetic acid ethyl ester (5.1 g, 10.7 mmol) in tetrahydrofuran (30 mL), methanol (30 mL) and water (6 mL) was added lithium hydroxide monohydrate (2.2 g, 53.5 mmol). The reaction was stirred for 18 hour at ambient temperature. The reaction was then concentrated in vacuo and the remaining solution was acidified with a 1M aqueous hydrochloric acid and extracted with dichloromethane. The organic layer was dried over magnesium sulfate, filtered and concentrated in vacuo. The crude product was diluted with minimal dichloromethane and diethyl ether was added. A white precipitate was collected by filtration to give the title compound (3.93 g).

N-[(5-Chloro-2-{2-[4-(4-fluoro-benzyl)-(2R,5S)-2,5-dimethyl-piperazin-1-yl]-2-oxo-ethoxy}-phenyl)-acetyl]-methanesulfonamide To a solution of (5-chloro-2-{2-[4-(4-fluoro-benzyl)-(2R,5S)-2,5-dimethyl-piperazin-1-yl]-2-oxo-ethoxy}-phenyl)-acetic acid (0.70 g, 1.44 mmol) was added 4-dimethylaminopyridine (0.26 g, 2.16 mmol), (3-(dimethylamino)propyl) ethyl carbodiimide hydrochloride (0.42 g, 2.16 mmol), methanesulfonamide (0.15 g, 1.58 mmol) and triethylamine (0.40 mL, 2.88 mmol). The reaction was stirred at ambient temperature for 18 hours. The reaction mixture was then diluted with dichloromethane and washed with 1 M aqueous hydrochloric acid. The organic layer was dried over magnesium sulfate, filtered and concentrated in vacuo. The crude product was purified by chromatography on silica gel to give the title compound (0.34 g, LRMS: 526.2).

EXAMPLE 15

N-[(5-Chloro-2-{2-[4-(4-fluoro-benzyl)-(2R,5S)-2,5-dimethyl-piperazin-1-yl]-2-oxo-ethoxy}-phenyl)-acetyl]-sulfamide A solution of (5-chloro-2-{2-[4-(4-fluoro-benzyl)-(2R,5S)-2,5-dimethyl-piperazin-1-yl]-2-oxo-ethoxy}-phenyl)-acetic acid (0.10 g, 0.21 mmol) in thionyl chloride (2 mL) was stirred at ambient temperature for two hours. The reaction was concentrated to dryness and the crude acid chloride was dissolved in 1,4-dioxane (4 mL) followed by addition of sulfamide (0.022 g, 0.23 mmol). The reaction was stirred at ambient temperature for 3 days. The reaction was concentrated and chromatographed on silica gel to give the title compound (0.014 g, LRMS: 525.1).

EXAMPLE 16

N-[3-(5-Chloro-2-{2-[4-(4-fluoro-benzyl)-(2R,5S)-2,5-dimethyl-piperazin-1-yl]-2-oxo-ethoxy}-phenyl)-propionyl]-methanesulfonamide 3-(5-Chloro-2-{2-[4-(4-fluoro-benzyl)-(2R,5S)-2,5-dimethyl-piperazin-1-yl]-2-oxo-ethoxy}-phenyl)-acrylic acid ethyl ester To a solution of 5-chloro-2-{2-[4-(4-fluoro-benzyl)-(2R,5S)-2,5-dimethyl-piperazin-1-yl]-2-oxo-ethoxy}-benzaldehyde (0.50 g, 1.19 mmol) in ethanol (10 mL) at 0° C. was added potassium carbonate (0.4 mL, 2.4 mmol, 6 M solution in water) and triethyl phosphonoacetate (0.47 mL, 2.4 mmol). The reaction was stirred at 0° C. for 2 hours, then at ambient temperature 12 hours. The reaction was diluted with ethyl acetate and filtered through a pad of celite. The filtrate was then washed with saturated aqueous sodium hydrogen carbonate and brine. The organic layer was dried over magnesium sulfate and concentrated in vacuo. The crude product was purified by chromatography on silica gel to give the title compound (0.51 g)

3-(5-Chloro-2-{2-[4-(4-fluoro-benzyl)-(2R,5S)-2,5-dimethyl-piperazin-1-yl]-2-oxo-ethoxy}-phenyl)-propionic acid ethyl ester To a solution of 3-(5-chloro-2-{2-[4-(4-fluoro-benzyl)-(2R,5S)-2,5-dimethyl-piperazin-1-yl]-2-oxo-ethoxy}-phenyl)-acrylic acid ethyl ester (0.50 g, 1.0 mmol) in ethyl acetate(15 mL) in a Parr bottle was added platinum dioxide on carbon (0.25 g, 5% on carbon). The mixture was shaken under a positive pressure of hydrogen at 30 psi for 15 minutes at ambient temperature. The mixture was filtered through a pad of celite and concentrated to give the title compound (0.47 g).

3-(5-Chloro-2-{2-[4-(4-fluoro-benzyl)-(2R,5S)-2,5-dimethyl-piperazin-1-yl]-2-oxo-ethoxy}-phenyl)-propionic acid To a solution of 3-(5-chloro-2-{2-[4-(4-fluoro-benzyl)-(2R,5S)-2,5-dimethyl-piperazin-1-yl]-2-oxo-ethoxy}-phenyl)-propionic acid ethyl ester (1.3 g, 2.7 mmol) in tetrahydrofuran (10 mL), methanol (10 mL) and water (4 mL) was added lithium hydroxide monohydrate (0.57 g, 13.3 mmol). The reaction was stirred at ambient temperature for 12 hours, then made acidic by the addition of 1 M hydrochloric acid. The solution was then extracted with methylene chloride and the organic layer was dried over magnesium sulfate. Concentration in vacuo gave the title compound (1.0 g).

N-[3-(5-Chloro-2-{2-[4-(4-fluoro-benzyl)-(2R,5S)-2,5-dimethyl-piperazin-1-yl]-2-oxo-ethoxy}-phenyl)-propionyl]-methanesulfonamide To a solution of 3-(5-chloro-2-{2-[4-(4-fluoro-benzyl)-(2R,5S)-2,5-dimethyl-piperazin-1-yl]-2-oxo-ethoxy}-phenyl)-propionic acid (0.20 g, 0.40 mmol) was added 4-dimethylaminopyridine (0.075 g, 0.60 mmol), (3-(dimethylamino)propyl)ethyl carbodiimide hydrochloride (0.12 g, 0.60 mmol), methanesulfonamide (0.045 g, 0.48 mmol) and triethylamine (0.12 mL, 0.84 mmol). The reaction was stirred at ambient temperature for 18 hours. The reaction mixture was then diluted with dichloromethane and washed with 10% aqueous acetic acid. The organic layer was dried over magnesium sulfate, filtered and concentrated in vacuo. The crude product was purified by chromatography on silica gel to give the title compound (0.10 g, LRMS: 540.2).

EXAMPLE 17

3-(5-Chloro-2-{2-[4-(4-fluoro-benzyl)-(2R,5S)-2,5-dimethyl-piperazin-1-yl]-2-oxo-ethoxy}-phenyl)-acrylic acid To a solution of 3-(5-chloro-2-{2-[4-(4-fluoro-benzyl)-(2R,5S)-2,5-dimethyl-piperazin-1-yl]-2-oxo-ethoxy}-phenyl)-acrylic acid methyl ester (0.060 g, 0.13 mmol) in tetrahydrofuran, methanol and water (1 ml each) was added lithium hydroxide hydrate (0.020 g, 0.51 mmol). After 1 hour at 50° C. the reaction was concentrated and the title compound was isolated by chromatography on silica gel (0.032 g, LRMS: 461.1).

EXAMPLE 18

(5-Chloro-2-{2-[4-(4-fluoro-benzyl)-(2R,5S)-2,5-dimethyl-piperazin-1-yl]-2-oxo-ethoxy}-benzenesulfonylamino)-acetic acid 5-Chloro-2-methoxy-benzenesulfonamide To a solution of 5-chloro-2-methoxybenzene sulfonyl chloride (1.0 g, 4.15 mmol) in tetrahydrofuran (10 mL) was bubbled ammonia gas until saturated. The reaction was stirred overnight. The white solid that precipitated out of solution was collected by filtration and washed with dichloromethane to give the title compound (0.52 g).

5-Chloro-2-hydroxy-benzenesulfonamide

To a suspension of 5-chloro-2-methoxy-benzenesulfonamide (0.52 g, 2.33 mmol) in dichloromethane (25 mL) at −78° C. was added boron tribromide (1M solution in dichloromethane, 3.5 mL, 3.5 mmol). The reaction was stirred at −78° C. for 30 minutes and then warmed to ambient temperature and stirred overnight. The reaction was quenched with water (0.30 mL) and the precipitate formed was removed by filtration. The filtrate was concentrated in vacuo and the crude product was purified by chromatography on silica gel to give the title compound (0.32 g).

5-Chloro-2-{2-[4-(4-fluoro-benzyl)-(2R,5S)-2,5-dimethyl-piperazin-1-yl]-2-oxo-ethoxy}-benzenesulfonamide To a solution of 2-chloro-1-[4-(4-fluoro-benzyl)-(2R,5S)-2,5-dimethyl-piperazin-1-yl]-ethanone (0.29 g, 0.96 mmol) in 2-butanone (10 mL) was added 5-chloro-2-hydroxy-benzenesulfonamide (0.20 g, 0.96 mmol), potassium carbonate (0.27 g, 1.92 mmol) and potassium iodide (0.16 g, 0.96 mmol). The reaction was refluxed for 4 hours, cooled diluted with ethyl acetate and washed with brine. The organic layer was separated, dried over magnesium sulfate, filtered and concentrated in vacuo. Chromatography on silica gel gave the title compound (0.32 g).

N-tert butyl carbonate (5-chloro-2-{2-[4-(4-fluoro-benzyl)-(2R,5S)-2,5-dimethyl-piperazin-1-yl]-2-oxo-ethoxy}-benzenesulfonylamino To a solution of 5-chloro-2-{2-[4-(4-fluoro-benzyl)-(2R,5S)-2,5-dimethyl-piperazin-1-yl]-2-oxo-ethoxy}-benzenesulfonamide (0.10 g, 0.21 mmol) in dichloromethane (1.0 mL) was added 4-dimethylaminopyridine (0.010 g, 0.08 mmol), triethylamine (0.045 mL, 0.31 mmol), and di-tert butyl dicarbonate (0.056 g, 0.25 mmol). The reaction mixture was stirred at ambient temperature for 1 hour and washed with water and brine. The organic layer was dried over magnesium sulfate, filtered and concentrated in vacuo to give the title compound (0.14 g).

N-tert butyl carbonate (5-Chloro-2-{2-[4-(4-fluoro-benzyl)-(2R,5S)-2,5-dimethyl-piperazin-1-yl]-2-oxo-ethoxy}-benzenesulfonylamino)-acetic acid tert-butyl ester To a solution of N-tert butyl carbonate (5-chloro-2-{2-[4-(4-fluoro-benzyl)-(2R,5S)-2,5-dimethyl-piperazin-1-yl]-2-oxo-ethoxy}-benzenesulfonylamino (0.13 g, 0.22 mmol) in dimethylformamide (1.0 mL) was added bromo-acetic acid tert-butyl ester (0.049 g, 0.25 mmol) and potassium carbonate (0.15 g, 1.10 mmol). The resulting reaction mixture was stirred at ambient temperature overnight, washed with brine, and extracted with ethyl acetate. The organic layer was dried over magnesium sulfate, filtered and concentrated in vacuo. Silica gel chromatography provided the title compound (0.045 g).

(5-Chloro-2-{2-[4-(4-fluoro-benzyl)-(2R,5S)-2,5-dimethyl-piperazin-1-yl]-2-oxo-ethoxy}-benzenesulfonylamino)-acetic acid A solution of N-tert butyl carbonate (5-chloro-2-{2-[4-(4-fluoro-benzyl)-(2R,5S)-2,5-dimethyl-piperazin-1-yl]-2-oxo-ethoxy}-benzenesulfonylamino)-acetic acid tert-butyl ester (0.044 g, 0.064 mmol) in dichloromethane (3.0 mL) and trifluoroacetic acid (1.0 mL) was stirred at ambient temperature, concentrated in vacuo and treated with diethyl ether saturated with hydrochloric acid to give the hydrochloride salt of the title compound (0.040 g, LRMS: 528.3).

EXAMPLE 19

5-Chloro-2-{2-[4-(4-fluoro-benzyl)-(2R,5S)-2,5-dimethyl-piperazin-1-yl]-2-oxo-ethoxy}-N-[(2-propylamino)carbonyl]-benzenesulfonamide 5-Chloro-2-{2-[4-(4-fluoro-benzyl)-(2R,5S)-2,5-dimethyl-piperazin-1-yl]-2-oxo-ethoxy}-N-[(2-propylamino)carbonyl]-benzenesulfonamide To a solution of 5-chloro-2-{2-[4-(4-fluoro-benzyl)-(2R,5S)-2,5-dimethyl-piperazin-1-yl]-2-oxo-ethoxy}-benzenesulfonamide (0.07 g, 0.150 mmol) in tetrahydrofuran (1.5 mL) was added isopropyl isocyanate (0.022 mL, 0.23 mmol) and 1,8-diazabycyclo[5.4.0 ]undec-7-ene (0.034 mL, 0.23 mmol). The reaction was stirred at 60° C. overnight. The reaction was concentrated and purified by chromatography on silica gel to give the title compound (0.06 g, LRMS: 555.2)

EXAMPLE 20

5-Chloro-N-(2,2-dimethyl-propionyl)-2-{2-[4-(4-fluoro-benzyl)-(2R,5S)-2,5-dimethyl-piperazin-1-yl]-2-oxo-ethoxy}-benzenesulfonamide To a solution of 5-chloro-2-{2-[4-(4-fluoro-benzyl)-(2R,5S)-2,5-dimethyl-piperazin-1-yl]-2-oxo-ethoxy}-benzenesulfonamide (0.050 g, 0.11 mmol) in acetonitrile (1.0 mL) was added 2,2-dimethyl-propionyl chloride (0.050 g, 0.47 mmol) and 1,8-diazobicyclo[5.4.0]undec-7-ene (0.25 mL, 1.64 mmol). The resulting reaction mixture was heated to 50° C. for 2 hours, concentrated in vacuo and purified by silica gel chromatography to give the title compound (0.030 g, LRMS: 554.4).

EXAMPLE 21

5-Chloro-2-{2-[4-(4-fluoro-benzyl)-(2R,5S)-2,5-dimethyl-piperazin-1-yl]-2-oxo-ethoxy}-N-(2-hydroxy-2-methyl-propionyl)-benzenesulfonamide Acetic acid 2-(5-chloro-2-{2-[4-(4-fluoro-benzyl)-(2R,5S)-2,5-dimethyl-piperazin-1-yl]-2-oxo-ethoxy}-benzenesulfonylamino)-1,1-dimethyl-2-oxo-ethyl ester To a solution of 5-chloro-2-{2-[4-(4-fluoro-benzyl)-(2R,5S)-2,5-dimethyl-piperazin-1-yl]-2-oxo-ethoxy}-benzenesulfonamide (0.10 g, 0.21 mmol) in dichloromethane (2 mL) was added triethylamine (0.033 mL, 0.23 mmol), 4-dimethylaminopyridine (5 mg, 0.04 mmol) and acetic acid 1-chlorocarbonyl-1-methyl-ethyl ester (0.037 mL, 0.25 mmol). The resulting reaction mixture was stirred at ambient temperature overnight, treated with 0.2 N hydrochloric acid extracted with dichloromethane dried over magnesium sulfate, filtered and concentrated in vacuo to give the crude title compound (0.140 g).

5-Chloro-2-{2-[4-(4-fluoro-benzyl)-(2R,5S)-2,5-dimethyl-piperazin-1-yl]-2-oxo-ethoxy}-N-(2-hydroxy-2-methyl-propionyl)-benzenesulfonamide To a solution of acetic acid 2-(5-chloro-2-{2-[4-(4-fluoro-benzyl)-(2R,5S)-2,5-dimethyl-piperazin-1-yl]-2-oxo-ethoxy}-benzenesulfonylamino)-1,1-dimethyl-2-oxo-ethyl ester (0.14 g, 0.21 mmol) in tetrahydrofuran (2 mL), methanol (0.2 mL) and water (0.4 mL) was added lithium hydroxide monohydrate (0.020 g, 0.48 mmol). The resulting reaction mixture was stirred at ambient temperature overnight. Chromatography on silica gel of the reaction mixture provided the title compound (0.104 g, LRMS: 556.3).

EXAMPLE 22

N-Acetyl-C-(5-chloro-2-{2-[4-(4-fluoro-benzyl)-(2R,5S)-2,5-dimethyl-piperazin-1-yl]-2-oxo-ethoxy}-phenyl)-methanesulfonamide Thioacetic acid S-(5-chloro-2-methoxy-benzyl)ester To a solution of cesium carbonate (0.55 g, 1.70 mmol) in dimethylformamide (13 mL) was added thioacetic acid (0.24 g, 3.14 mmol) followed by addition of 4-chloro-2-chloromethyl-1-methoxybenzene (0.50 g, 2.62 mmol) in one portion. The reaction was stirred in the dark at ambient temperature overnight. The reaction was diluted with ethyl acetate, washed with water, 5% aqueous sodium hydrogen carbonate, and brine. The organic layer was separated, dried over sodium sulfate, filtered and concentrated in vacuo. Chromatography on silica gel gave the title compound (0.58 g).

(5-Chloro-2-methoxy-phenyl)-methanesulfonic acid

To a solution of thioacetic acid S-(5-chloro-2-methoxy-benzyl) ester (0.30 g, 1.3 mmol) in acetic acid (1.5 mL) was added a solution of hydrogen peroxide (1.5 mL, 30% in water) in acetic acid (3 mL). The reaction was stirred overnight at ambient temperature. This was followed by addition of palladium on carbon (0.006 g, 10% on carbon) to break down excess hydrogen peroxide. The reaction was stirred for 10 minutes and filtered through a nylon filter, then azeotroped with toluene (3×) and concentrated in vacuo to give the title compound (0.32 g).

(5-Chloro-2-methoxy-phenyl)-methanesulfonamide

To a solution of (5-chloro-2-methoxy-phenyl)-methanesulfonic acid (0.15 g, 0.63 mmol) in benzene (6 mL) was added phosphorous pentachloride (0.15 g, 0.72 mmol). The reaction was refluxed for 2.5 hours, cooled and concentrated in vacuo. The resulting residue was dissolved in tetrahydrofuran (1 mL) and ammonium hydroxide (1 mL) was added. The reaction was stirred for two days at ambient temperature. The reaction was then diluted with water and extracted with ethyl acetate (3×). The organic layers were combined, dried over sodium sulfate, filtered and concentrated in vacuo. Chromatography on silica gel gave the title compound (0.033 g).

(5-Chloro-2-hydroxy-phenyl)-methanesulfonamide

To a suspension of (5-chloro-2-methoxy-phenyl)-methanesulfonamide (0.03 g, 0.13 mmol) in dichloroethane (1.5 mL) was added boron tribromide solution (1M in dichloromethane, 0.26 mL, 0.26 mmol). The reaction was stirred for one hour at ambient temperature. The reaction was quenched with water, saturated with sodium chloride and extracted with ethyl acetate. The organic layer was dried over sodium sulfate, filtered and concentrated to give the title compound (0.025 g).

(5-Chloro-2-{2-[4-(4-fluoro-benzyl)-(2R,5S)-2,5-dimethyl-piperazin-1-yl]-2-oxo-ethoxy}-phenyl)-methanesulfonamide To a solution of 2-chloro-1-[4-(4-fluoro-benzyl)-(2R,5S)-2,5-dimethyl-piperazin-1-yl]-ethanone (0.028 g, 0.094 mmol) in dimethylformamide (1 mL) was added (5-chloro-2-hydroxy-phenyl)-methanesulfonamide (0.023 g, 0.10 mmol), potassium carbonate (0.026 g, 0.19 mmol) and potassium iodide (0.016 g, 0.094 mmol). The reaction was heated at 60° C. for 17 hours, cooled, diluted with water and extracted with ethyl acetate (3×). The organic layers were combined, dried over sodium sulfate, filtered and concentrated in vacuo. Chromatography on silica gel gave the title compound (0.014 g).

N-Acetyl-C-(5-chloro-2-{2-[4-(4-fluoro-benzyl)-(2R,5S)-2,5-dimethyl-piperazin-1-yl]-2-oxo-ethoxy}-phenyl)-methanesulfonamide To a solution of (5-chloro-2-{2-[4-(4-fluoro-benzyl)-(2R,5S)-2,5-dimethyl-piperazin-1-yl]-2-oxo-ethoxy}-phenyl)-methanesulfonamide (0.05 g, 0.10 mmol) in dichloromethane (1 mL) was added acetic acid (0.007 g, 0.12 mmol), (3-(dimethylamino)propyl)ethyl carbodiimide (0.030 g, 0.16 mmol), 4-dimethylaminopyridine (0.019 g, 0.16 mmol) and triethylamine (0.023 g, 0.23 mmol). The reaction was stirred at ambient temperature overnight. The reaction was diluted with dichloromethane, washed with saturated aqueous sodium bicarbonate solution and the aqueous layer back extracted with dichloromethane (3×). The organics were combined, dried over sodium sulfate, filtered and concentrated in vacuo. Chromatography on silica gel gave the title compound (0.039 g, LRMS: 526.20).

EXAMPLE 23

C-(5-Chloro-2-{2-[4-(4-fluoro-benzyl)-(2R,5S)-2,5-dimethyl-piperazin-1-yl]-2-oxo-ethoxy}-phenyl)-N-(2-hydroxy-2-methyl-propionyl)-methanesulfonamide Acetic acid 2-(5-chloro-2-{2-[4-(4-fluoro-benzyl)-(2R,5S)-2,5-dimethyl-piperazin-1-yl]-2-oxo-ethoxy}-phenylmethanesulfonylamino)-1,1-dimethyl-2-oxo-ethyl ester A solution of 5-Chloro-2-{2-[4-(4-fluoro-benzyl)-(2R,5S)-2,5-dimethyl-piperazin-1-yl]-2-oxo-ethoxy}-phenyl)-methanesulfonamide (50 mg, 0.103 mmol), 1-chlorocarbonyl-1-methylethyl acetate (19 mg, 0.016 mL, 0.114 mmol), triethylamine (13 mg, 0.018 mL, 0.129 mmol) and a catalytic amount of 4-(dimethylamino)pyridine in dichloromethane (1 mL) was stirred at ambient temperature. After 18 h the solution was purified directly using radial chromatography to yield the title compound (0.033 g).

C-(5-Chloro-2-{2-[4-(4-fluoro-benzyl)-(2R,5S)-2,5-dimethyl-piperazin-1-yl]-2-oxo-ethoxy}-phenyl)-N-(2-hydroxy-2-methyl-propionyl)-methanesulfonamide A solution of acetic acid 2-(5-chloro-2-{2-[4-(4-fluoro-benzyl)-(2R,5S)-2,5-dimethyl-perazin-1-yl]-2-oxo-ethoxy}-phenylmethanesulfonylamino)-1,1-dimethyl-2-oxo-ethyl ester (0.030 g, 0.049 mmol) and lithium hydroxide monohydrate (0.004 g, 0.098 mmol) in tetrahydrofuran (0.5 mL), methanol (0.25 mL) and water (0.25 mL) was stirred for 20 h. The resulting solution was concentrated and partitioned between 1M hydrochloric acid and ethyl acetate. The aqueous layer was extracted twice with ethyl acetate. The combined organic layers were washed with saturated aqueous sodium chloride and dried over sodium sulfate. The solution was filtered, concentrated and purified using radial chromatography to yield the title compound (0.022 g, LRMS: 568.2, 570.3).

EXAMPLE 24

C-(5-Chloro-2-{2-[4-(4-fluoro-benzyl)-(2R,5S)-2,5-dimethyl-piperazin-1-yl]-2-oxo-ethoxy}-phenyl)-N-(ethylaminocarbonyl)-methanesulfonamide A solution of 5-chloro-2-{2-[4-(4-fluoro-benzyl)-(2R,5S)-2,5-dimethyl-piperazin-1-yl]-2-oxo-ethoxy}-phenyl)-methanesulfonamide (0.050 g, 0.103 mmol), ethyl isocyanate (0.011 g, 0.012 mL, 0.155 mmol) and 1,8-diazabicyclo[5.4.0]undec-7-ene (0.024 g, 0.023 mL, 0.155 mmol) in tetrahydrofuran (1 mL) was heated on a shaker plate at 60° C. After 5 h the solution was cooled to ambient temperature and purified using radial chromatography to yield the title compound (0.034 g, LRMS: 553.4, 555.4).

EXAMPLE 25

N-(5-Chloro-2-{2-[4-(4-fluoro-benzyl)-(2R)-2-methyl-piperazin-1-yl]-2-oxo-ethoxy}-pyridin-3-yl)-succinamic acid 1-[4-(4-Fluoro-benzyl)-(2R)-2-methyl-piperazin-1-yl]-2-hydroxy-ethanone To a solution of glycolic acid (0.70 g, 9.2 mmol), 4-dimethylaminopyridine (catalytic) and pyridine (1.52 mL, 18.6 mmol) in dry dichloromethane (20 mL) was added trimethylsilylchloride (2.39 mL, 2.05 mmol) dropwise. The reaction was stirred at ambient temperature for 4 hours. The reaction was then cooled to 0° C. and catalytic dimethylformamide (3 drops) was added followed by addition of oxalyl chloride. The reaction was stirred at 0° C. for one hour and then 30 minutes at ambient temperature. The reaction was cooled back to 0° C. and (3R)-1-(4-fluoro-benzyl)-3-methyl-piperazine (2.11 g, 10.12 mmol) was added as a solution in pyridine (2.45 mL, 30.4 mmol). The reaction was allowed to warm to ambient temperature and stirred for 2 hours. The reaction was neutralized with 1N hydrochloric acid and extracted with dichloromethane (2×). The organic layers were combined, dried over magnesium sulfate, filtered and concentrated in vacuo. Chromatography on silica gel gave the title compound (1.84 g).

2-(5-Chloro-3-nitro-pyridin-2-yloxy)-1-[4-(4-fluoro-benzyl)-(2R)-2-methyl-piperazin-1-yl]-ethanone To a solution of 1-[4-(4-fluoro-benzyl)-(2R)-2-methyl-piperazin-1-yl]-2-hydroxy-ethanone (0.77 g, 2.9 mmol) in dry toluene (30 mL) at 0° C. was added sodium hydride (0.13 g, 3.2 mmol, 60% dispersion in mineral oil). The reaction was stirred for 30 minutes at 0° C. followed by addition of 2,5-dichloro-3-nitro-pyridine (0.60 g, 3.18 mmol) as a solution in toluene (5 mL). The reaction was stirred at ambient temperature overnight. The, reaction was concentrated and chromatographed on silica gel to give the title compound (0.96 g).

2-(3-Amino-5-chloro-pyridin-2-yloxy)-1-[4-(4-fluoro-benzyl)-(2R)-2-methyl-piperazin-1-yl]-ethanone To a solution of 2-(5-chloro-3-nitro-pyridin-2-yloxy)-1-[4-(4-fluoro-benzyl)-(2R)-2-methyl-piperazin-1-yl]-ethanone (0.96 g, 2.3 mmol) in ethanol (25 mL) was added platinum dioxide on carbon (0.90 mg, 5% on carbon). The reaction was subject to 35 psi hydrogen gas for 20 minutes. The reaction was filtered through celite, concentrated in vacuo and chromatographed on silica gel to give the title compound (0.78 g).

N-(5-Chloro-2-{2-[4-(4-fluoro-benzyl)-(2R)-2-methyl-piperazin-1-yl]-2-oxo-ethoxy}-pyridin-3-yl)-succinamic acid To a solution of 2-(3-amino-5-chloro-pyridin-2-yloxy)-1-[4-(4-fluoro-benzyl)-(2R)-2-methyl-piperazin-1-yl]-ethanone (0.10 g, 0.26 mmol) in dichloromethane (3 mL) was added N-methylmorpholine (0.028 mL, 0.26 mmol) and succinic anhydride (0.026 g, 0.26 mmol). The reaction was stirred at ambient temperature for 3 days. The reaction was diluted with dichlormethane and washed with 1N hydrochloric acid solution. The organic layer was separated, dried over magnesium sulfate, filtered and concentrated in vacuo. Chromatography on silica gel gave the title compound (0.040 g, LRMS: 493.2).

EXAMPLE 26

N-[(5-Chloro-2-{2-[4-(4-fluoro-benzyl)-(2R,5S)-2,5-dimethyl-piperazin-1-yl]-2-oxo-ethoxy}-pyridin-3-yl)-acetyl]-methanesulfonamide 4-Chloro-but-3-enenitrile To a solution of 1,3-dichloropropene (20.0 g, 180 mmol) in acetonitrile (110 mL) was added potassium iodide (0.75 g, 4.5 mol) and potassium cyanide (70.0 g, 1080 mmol). The reaction mixture was stirred at ambient temperature for 72 hours, filtered through a pad of celite, and the resulting filter cake was washed with diethyl ether. The diethyl ether and acetonitrile were distilled off under atmospheric pressure and the residue was purified by fractional distillation to give the title compound as a mixture of isomers with its regioisomer 4-chloro-but-2-enenitrile (2.2 g).

2,5-Dichloro-pyridine-3-carbaldehyde

To a solution of 4-chloro-but-3-enenitrile (2.25 g, 22.3 mmol) in dimethylformamide (8.6 mL) was added phosphoryl chloride (10.4 mL, 111 mmol). The resulting reaction mixture was heated to 100° C. overnight, cooled to 0° C. and quenched with water. The product was extracted with dichloromethane and the organic layer was dried over magnesium sulfate, filtered and concentrated in vacuo. Recrystallization from hexanes provided the title compound (2.0 g).

(2,5-Dichloro-pyridin-3-yl)-acetic acid methyl ester

To trimethoxyorthoformate (5.47 mL, 50 mmol) was slowly added diphenylphosphine chloride (11.0 g, 50 mmol) at ambient temperature. After the reaction mixture solidified (about 1 hour) the solid was heated to 110° C. for 2 hours. The reaction product was then cooled to ambient temperature and recrystallized from toluene and water to provide dimethoxymethy diphenyl phosphine oxide (12 g).

To a −78° C. solution of diisopropyl amine (1.21 mL, 9.0 mmol) in tetrahydrofuran (100 mL) was added n-butyl lithium (3.45 mL, 2.5 M in hexanes, 9.0 mmol). The reaction mixture was stirred at −78° C. for 20 minute and 0° C. for 15 minutes, and then cooled to −110° C. To the cooled reaction mixture was added dimethoxymethyl diphenyl phosphine oxide (2.18 g, 8.0 mmol) in tetrahydrofuran (120 mL) and then 2,5-dichloro-pyridine-3-carbaldehyde (1.37 g, 8.0 mmol) in tetrahydrofuran (15 mL) while keeping the reaction temperature less than −100° C. The reaction mixture was stirred at −110° C. for 45 minutes and then quenched with water (50 mL), extracted with diethyl ether and washed with brine. The organic layer was dried over magnesium sulfate and concentrated in vacuo. The resulting residue was azeotroped with toluene and then dissolved in tetrahydrofuran (80 mL) and treated with potassium tert-butoxide (0.97 g, 9.0 mmol) at ambient temperature. After stirring for 2 hours the dark solution was treated with 1N hydrochloric acid and extracted with diethyl ether. The organic layer was washed with saturated aqueous sodium hydrogen carbonate, dried over magnesium sulfate, filtered and concentrated in vacuo. Chromatography on silica gel gave the title compound (0.61 g).

(5-Chloro-2-{2-[4-(4-fluoro-benzyl)-(2R,5S)-2,5-dimethyl-piperazin-1-yl]-2-oxo-ethoxy}-pyridin-3-yl)-acetic acid methyl ester To a 0° C. solution of (2,5-dichloro-pyridin-3-yl)-acetic acid methyl ester (0.45 g, 2.05 mmol) and 1-[4-(4-fluoro-benzyl)-(2R,5S)-2,5-dimethyl-piperazin-1-yl]-2-hydroxy-ethanone (0.52 g, 1.86 mmol) in toluene (5.5 mL) was added sodium hydride (0.082 g, 2.05 mmol, 60% dispersion in mineral oil) in toluene (9.3 mL). The reaction mixture was slowly warmed to ambient temperature and then heated to reflux overnight. The resulting reaction mixture was cooled to ambient temperature, quenched with water and extracted with ethyl acetate. The organic layer was washed with saturated aqueous sodium hydrogen carbonate, dried over magnesium sulfate, filtered and concentrated in vacuo. Chromatography on silica gel gave the title compound (0.14 g) and (5-chloro-2-{2-[4-(4-fluoro-benzyl)-(2R,5S)-2,5-dimethyl-piperazin-1-yl]-2-oxo-ethoxy}-pyridin-3-yl)-acetic acid (0.20 g).

(5-Chloro-2-{2-[4-(4-fluoro-benzyl)-(2R,5S)-2,5-dimethyl-piperazin-1-yl]-2-oxo-ethoxyl-pyridin-3-yl)-acetic acid To a solution of (5-chloro-2-{2-[4-(4-fluoro-benzyl)-(2R,5S)-2,5-dimethyl-piperazin-1-yl]-2-oxo-ethoxy}-pyridin-3-yl)-acetic acid methyl ester (0.14 g, 0.3 mmol) in tetrahydrofuran (3.0 mL) and water (0.6 mL) was added lithium hydroxide monohydrate (0.031 g, 0.75 mmol) at ambient temperature. After stirring for 4 hours the reaction mixture was filtered through a pad of silica gel eluting with 10% methanol/dichloromethane. The filtrate was concentrated in vacuo to provide the title compound (0.061 g).

N-[(5-Chloro-2-{2-[4-(4-fluoro-benzyl)-(2R,5S)-2,5-dimethyl-piperazin-1-yl]-2-oxo-ethoxy}-pyridin-3-yl)-acetyl]-methanesulfonamide To a solution of N-[(5-chloro-2-{2-[4-(4-fluoro-benzyl)-(2R,5S)-2,5-dimethyl-piperazin-1-yl]-2-oxo-ethoxy}-pyridin-3-yl)-acetic acid (0.045 g, 0.10 mmol) in dichloromethane (2 mL) was added 4-dimethylaminopyridine (0.018 g, 0.15 mmol), and 1,3-dicyclohexylcarbodiimide (0.023 g, 0.11 mmol). The resulting reaction mixture was stirred at ambient temperature for 20 minutes, and then treated with methanesulfonamide (0.011 g, 0.12 mmol). The reaction was stirred at ambient temperature for 18 hours, filtered through a pad of celite and the resulting filter cake was washed with dichloromethane. The combined organics were concentrated in vacuo and purified by silica gel chromatography followed by trituration with dichloromethane to give the title compound (0.037 g, LRMS: 525.3, 527.2).

EXAMPLE 27

3-(5-Chloro-2-{2-[4-(4-fluoro-benzyl)-(2R,5S)-2,5-dimethyl-piperazin-1-yl]-2-oxo-ethoxy}-pyridin-3-yl)-propionic acid 2,5-Dichloro-pyridine-3-carbaldehyde To a solution of 2,5-Dichloro-nicotinoyl chloride (15 g, 0.071 mol) in tetrahydrofuran was added tributyl-stannane (24.9 g, 0.086 mol) portionwise over 45 minutes. The resulting mixture was stirred at ambient temperature for 50 minutes, and then treated with tetrakis(triphenylphosphine) palladium(0) (0.82 g, 0.00071 mol). The reaction mixture was stirred at ambient temperature for 4 hours, poured into water; the product was extracted with ethylacetate, the combined organics were dried over magnesium sulfate, filtered and concentrated in vacuo. Silica gel chromatography (10% ethyl acetate/hexanes) followed by recrystallization from hexanes/ethylacetate gave the title compound (4.3 g).

5-Chloro-2-{2-[4-(4-fluoro-benzyl)-(2R,5S)-2,5-dimethyl-piperazin-1-yl]-2-oxo-ethoxy}-pyridine-3-carbaldehyde To a 0° C. suspension of sodium hydride (60% dispersion in mineral oil, 0.031 g, 0.78 mmol) in toluene (3 mL) was added 1-[4-(4-fluoro-benzyl)-(2R,5S)-2,5-dimethyl-piperazin-1-yl]-2-hydroxy-ethanone (0.20 g, 0.71 mmol) in toluene (2 mL). The reaction mixture was stirred at 0° C. for 30 minutes, and then treated with 2,5-dichloro-pyridine-3-carbaldehyde (0.14 g, 0.78 mmol). The resulting mixture was refluxed for 4 hours, cooled to ambient temperature and washed with saturated aqueous sodium hydrogen carbonate and brine. The organic layer was dried over magnesium sulfate, filtered and concentrated in vacuo. Silica gel chromatography provided the title compound (0.20 g).

3-(5-Chloro-2-{2-[4-(4-fluoro-benzyl)-(2R,5S)-2,5-dimethyl-piperazin-1-yl]-2-oxo-ethoxy}-pyridin-3-yl)-acrylic acid ethyl ester To a 0° C. solution of 5-chloro-2-{2-[4-(4-fluoro-benzyl)-2,5-dimethyl-piperazin-1-yl]-2-oxo-ethoxy}-pyridine-3-carbaldehyde (0.200 g, 0.47 mmol) in ethanol (5 mL) was added potassium carbonate (0.131 g, 0.95 mmol) in water (0.30 mL) and triethyl phosphonium acetate (0.21 g, 0.19 mL). The reaction mixture was warmed to room temperature over 48 hours, filtered through celite, the filter cake was washed with ethanol and concentrated in vacuo. Purification via chromatography on silica gel gave the title compound (0.102 g).

3-(5-Chloro-2-{2-[4-(4-fluoro-benzyl)-(2R,5S)-2,5-dimethyl-piperazin-1-yl]-2-oxo-ethoxy}-pyridin-3-yl)-propionic acid ethyl ester To a solution of 3-(5-chloro-2-{2-[4-(4-fluoro-benzyl)-(2R,5S)-2,5-dimethyl-piperazin-1-yl]-2-oxo-ethoxy}-pyridin-3-yl)-acrylic acid ethyl ester (0.102 g, 0.21 mmol) in ethanol (20 mL) was added platinum oxide (0.010 g). The reaction mixture was shaken under positive pressure of hydrogen gas (20 psi) for 20 minutes. The resulting mixture was filtered through a pad of celite, the filter cake was washed with ethanol, and the combined filtrate was concentrated in vacuo to give the title compound (0.081 g).

3-(5-Chloro-2-{2-[4-(4-fluoro-benzyl)-(2R,5S)-2,5-dimethyl-piperazin-1-yl]-2-oxo-ethoxy}-pyridin-3-yl)-propionic acid To a solution of 3-(5-chloro-2-{2-[4-(4-fluoro-benzyl)-(2R,5S)-2,5-dimethyl-piperazin-1-yl]-2-oxo-ethoxy}-pyridin-3-yl)-propionic acid ethyl ester (0.081 g, 0.17 mmol) in tetrahydrofuran (2 mL), methanol (2 mL) and water (1 mL) was added lithium hydroxide monohydrate (0.013 g, 0.32 mmol). The reaction mixture was stirred at ambient temperature for 3 hours, neutralized with 0.2M hydrochloric acid and phosphate buffer (pH=7), and extracted with ethyl acetate. The combined organics were dried over magnesium sulfate, filtered and concentrated in vacuo. Purification with via HPLC gave the title compound (0.020 g, LRMS: 464.4).

EXAMPLE 28

[(5-Chloro-2-{2-[4-(4-fluoro-benzyl)-(2R,5S)-2,5-dimethyl-piperazin-1-yl]-2-oxo-ethylamino}-pyridine-3-carbonyl)-amino]-acetic acid {2-[4-(4-Fluoro-benzyl)-(2R,5S)-2,5-dimethyl-piperazin-1-yl]-2-oxo-ethyl}-carbamic acid tert-butyl ester To a solution of tert-butoxycarbonylamino-acetic acid (0.71 g, 4.05 mmol) in dichloromethane (40 mL) was added 4-dimethylaminopyridine (0.74 g, 6.07 mmol), 1-(3-dimethylaminopropyl)-3-ethylcarbodiimide hydrochloride (1.16 g, 6.07 mmol) and 1-(4-fluoro-benzyl)-(2R,5S)-2,5-dimethyl-piperazine (0.90 g, 4.05 mmol). The reaction was stirred overnight at ambient temperature. The reaction was diluted with dichloromethane and washed with brine. The organic layer was separated, dried over magnesium sulfate, filtered and concentrated in vacuo. Chromatography on silica gel gave the title compound (1.45 g).

2-Amino-1-[4-(4-fluoro-benzyl)-(2R,5S)-2,5-dimethyl-piperazin-1-yl]-ethanone

To a solution of {2-[4-(4-fluoro-benzyl)-(2R,5S)-2,5-dimethyl-piperazin-1-yl]-2-oxo-ethyl}-carbamic acid tert-butyl ester (1.45 g, 3.28 mmol) in dichloromethane (38 mL) was added trifluoroacetic acid (20 mL). The reaction was stirred at ambient temperature for two hours. The reaction was diluted with dichloromethane and washed with 1N sodium hydroxide. The organic layer was separated, dried over magnesium sulfate, filtered and concentrated to the give the title compound (1.03 g).

5-Chloro-2-{2-[4-(4-fluoro-benzyl)-(2R,5S)-2,5-dimethyl-piperazin-1-yl]-2-oxo-ethylamino}-nicotinic acid methyl ester To a solution of 2-amino-1-[4-(4-fluoro-benzyl)-(2R,5S)-2,5-dimethyl-piperazin-1-yl]-ethanone (0.27 g, 0.97 mmol) in acetonitrile (5 mL) was added 2,5-dichloro-nicotinic acid methyl ester (0.20 g, 0.97 mmol) and triethylamine (0.135 mL, 0.97 mmol). The reaction was refluxed for 2 hours. The reaction was concentrated and purified by chromatography on silica gel to give the title compound (0.16 g).

5-Chloro-2-{2-[4-(4-fluoro-benzyl)-(2R,5S)-2,5-dimethyl-piperazin-1-yl]-2-oxo-ethylamino}-nicotinic acid To a solution of 5-chloro-2-{2-[4-(4-fluoro-benzyl)-(2R,5S)-2,5-dimethyl-piperazin-1-yl]-2-oxo-ethylamino}-nicotinic acid methyl ester (0.16 g, 0.36 mmol) in tetrahydrofuran (3 mL), methanol (3 mL) and water (1 mL) was added lithium hydroxide monohydrate (0.075 g, 1.78 mmol). The reaction was stirred at ambient temperature overnight, concentrated in vacuo, diluted with dichloromethane and passed through a glass frit. The filtrate was treated with diethyl ether saturated with hydrogen chloride gas, and the white precipitate thus formed was collected by filtration to give the title compound as its hydrochloride salt (0.13 g).

[(5-Chloro-2-{2-[4-(4-fluoro-benzyl)-(2R,5S)-2,5-dimethyl-piperazin-1-yl]-2-oxo-ethylamino}-pyridine-3-carbonyl)-amino]-acetic acid methyl ester To a suspension of 5-chloro-2-{2-[4-(4-fluoro-benzyl)-(2R,5S)-2,5-dimethyl-piperazin-1-yl]-2-oxo-ethylamino}-nicotinic acid hydrochloride salt (0.060 g, 0.12 mmol) in dichloromethane (2 mL) was added 1-(3-dimethylaminopropyl)-3-ethylcarbodiimide hydrochloride (0.034 g, 0.18 mmol). The reaction was stirred at ambient temperature for 5 minutes. This was followed by addition of solution of glycine methyl ester hydrochloride (0.015 g, 0.12 mmol) and triethylamine (0.016 mL, 0.12 mmol) in dichloromethane (0.5 mL). The reaction was then stirred at ambient temperature overnight. The reaction was diluted with dichloromethane and washed with water. The organic layer was separated, dried over magnesium sulfate, filtered and concentrated in vacuo. Chromatography on silica gel gave the title compound (0.030 g).

[(5-Chloro-2-{2-[4-(4-fluoro-benzyl)-(2R,5S)-2,5-dimethyl-piperazin-1-yl]-2-oxo-ethylamino}-pyridine-3-carbonyl)-amino]-acetic acid To a solution of [(5-chloro-2-{2-[4-(4-fluoro-benzyl)-(2R,5S)-2,5-dimethyl-piperazin-1-yl]-2-oxo-ethylamino}-pyridine-3-carbonyl)-amino]-acetic acid methyl ester (0.043 g, 0.085 mmol) in tetrahydrofuran (1 mL), methanol (1 mL) and water (0.25 mL) was added lithium hydroxide monohydrate (0.018 g, 0.43 mmol). The reaction was stirred overnight. The reaction was then concentrated in vacuo, diluted with dichloromethane and passed through a fritted funnel. The filtrate was treated with saturated hydrogen chloride in diethyl ether and the white precipitate formed was collected by filtration to give the title compound (0.022 g, LRMS: 492.2).

EXAMPLE 29

2-(5-Chloro-2-(2-[4-(4-fluoro-benzyl)-(2R,5S)-2,5-dimethyl-piperazin-1-yl]-2-oxo-ethoxy}-phenylsulfanyl)-2-methyl-propionic acid 6-Chloro-3,3-dimethyl-benzo[1,4]oxathiin-2-one To 2-(5-chloro-2-methoxy-phenylsulfanyl)-2-methyl-propionic acid methyl ester (prepared from 5-chloro-2-methoxy-benzenesulfonyl chloride: *Syn. Comm.*, (2001), 31, 505–510) (0.25 g, 0.9 mmol) was added 48% hydrobromic acid (5 ml). The reaction was heated to reflux for 24 hours at which time the solvent was removed by evaporation. To the crude acid phenol was added toluene (5 ml) and catalytic pyridinium p-toluenesulfonate. After 12 hours of heating at reflux the reaction was concentrated and the title compound was isolated by chromatography on silica gel (0.27 g).

2-(5-Chloro-2-{2-[4-(4-fluoro-benzyl)-(2R,5S)-2,5-dimethyl-piperazin-1-yl]-2-oxo-ethoxy}-phenylsulfanyl)-2-methyl-propionic acid ethyl ester To 6-chloro-3,3-dimethyl-benzo[1,4]oxathiin-2-one (0.050 g, 0.22 mmol) in ethanol and tetrahydrofuran (1 ml each) was added potassium carbonate (0.015 g, 0.11 mmol). After 2 hours at 50° C. the reaction was concentrated and the phenol ethyl ester was isolated by chromatography on silica gel (0.043 g).

To the above phenol (0.041 g, 0.15 mmol), triphenylphosphine (0.049 g, 0.19 mmol) and 1-[4-(4-fluoro-benzyl)-(2R,5S)-2,5-dimethyl-piperazin-1-yl]-2-hydroxy-ethanone (0.025 g, 0.13 mmol) in toluene (1.2 ml) was slowly added diethyl azodicarboxylate (0.03 ml, 0.19 mmol). After 14 hours at 50° C. the reaction was cooled to room temperature and diluted with ethyl acetate. After washing with aqueous saturated sodium chloride the organic layer was dried over magnesium sulfate and the title compound isolated by chromatography on silica gel (0.056 g).

2-(5-Chloro-2-{2-[4-(4-fluoro-benzl)-(2R,5S)-2,5-dimethl-piperazin-1-yl]-2-oxo-ethoxy}-phenylsulfanyl)-2-methyl-propionic acid To 2-(5-chloro-2-{2-[4-(4-fluoro-benzyl)-(2R,5S)-2,5-dimethyl-piperazin-1-yl]-2-oxo-ethoxy}-phenylsulfanyl)-2-methyl-propionic acid ethyl ester (0.020 g, 0.4 mmol) in tetrahydrofuran, methanol and water (1 ml each) was added lithium hydroxide hydrate (0.008 g, 0.19 mmol). After 1 hour at 50° C. the reaction was concentrated and the title compound was isolated by chromatography on silica gel (0.010 g, LRMS: 509.4).

EXAMPLE 30

2-(5-Chloro-2-{2-[4-(4-fluoro-benzyl)-(2R,5S)-2,5-dimethyl-piperazin-1-yl]-2-oxo-ethoxy}-benzenesulfonyl)-2-methyl-propionic acid To a solution of 2-(5-chloro-2-{2-[4-(4-fluoro-benzyl)-(2R,5S)-2,5-dimethyl-piperazin-1-yl]-2-oxo-ethoxy}-phenylsulfanyl)-2-methyl-propionic acid ethyl ester (0.020 g, 0.04 mmol) in methanol and water (1 ml each) was added Oxone (0.12 g, 0.19 mmol). After 2 hours the reaction was diluted with methylene chloride and washed with aqueous saturated sodium chloride. The organic layer was dried over magnesium sulfate and the sulfone ester isolated by chromatography on silica gel (0.014 g).

The above ester was dissolved in tetrahydrofuran and water (0.5 ml each) and lithium hydroxide hydrate (0.013 g, 0.33 mmol) was added. After 4 hours the solvent was removed in vacuo and the title compound was isolated by chromatography on silica gel (0.019 g, LRMS: 541.4).

EXAMPLE 31

(5-Chloro-2-{2-[4-(4-fluoro-benzyl)-(2R,5S)-2,5-dimethyl-piperazin-1-yl]-2-oxo-ethoxy}-phenylmethanesulfonyl)-acetic acid (5-Chloro-2-{2-[4-(4-fluoro-benzyl)-(2R,5S)-2,5-dimethyl-piperazin-1-yl]-2-oxo-ethoxy}-benzylsulfanyl)-acetic acid methyl ester To 2-(4-chloro-2-hydroxymethyl-phenoxy)-1-[4-(4-fluoro-benzyl)-(2R,5S)-2,5-dimethyl-piperazin-1-yl]-ethanone (0.50 g, 1.19 mmol) was added thionyl chloride (3 ml). The reaction was heated to reflux for 3 hours. After concentration the benzylic chloride was isolated by chromatography on silica gel (0.27 g).

To 2-(4-chloro-2-chloromethyl-phenoxy)-1-[4-(4-fluoro-benzyl)-(2R,5S)-2,5-dimethyl-piperazin-1-yl]-ethanone (0.10 g, 0.23 mmol) in dimethyl formamide (2 ml) was added potassium carbonate (0.070 g, 0.51 mmol), tetrabutylammonium iodide (0.088 mg, 0.24 mmol) and finally methyl thioglycolate (0.02 ml, 0.25 mmol). The reaction was stirred at 50° C. for 19 hours. The reaction was diluted with ethyl acetate and washed with pH 7 phosphate buffer (0.05 M) and aqueous saturated sodium chloride. The organic layer was dried over magnesium sulfate and the title compound was isolated by chromatography on silica gel (0.046 g).

(5-Chloro-2-{2-[4-(4-fluoro-benzyl)-(2R,5S)-2,5-dimethyl-piperazin-1-yl]-2-oxo-ethoxy}-phenylmethanesulfonyl)-acetic acid To (5-chloro-2-{2-[4-(4-fluoro-benzyl)-(2R,5S)-2,5-dimethyl-piperazin-1-yl]-2-oxo-ethoxy}-benzylsulfanyl)-acetic acid methyl ester (0.046 g, 0.9 mmol) in methanol (1 ml) at 0° C. was added Oxone (0.16 g, 0.27 mmol) followed by the dropwise addition of water (1 ml). The reaction was allowed to warm to room temperature. After 14 hours the reaction was diluted with methylene chloride and washed with aqueous saturated sodium chloride. The organic layer was dried over magnesium sulfate and the sulfone ester isolated by chromatography on silica gel (0.014 g).

The above ester (0.014 g, 0.03 mmol) was dissolved in tetrahydrofuran and water (0.5 ml each) and lithium hydroxide hydrate (0.003 g, 0.08 mmol) was added. After 25 hours the solvent was removed in vacuo and the title compound was isolated by chromatography on silica gel (0.007 g, LRMS: 527.1).

EXAMPLE 32

N-[3-(3-{2-[4-(4-Fluoro-benzyl)-(2R,5S)-2,5-dimethyl-piperazin-1-yl]-2-oxo-ethoxy}-6-methyl-pyridin-2-yl)-propionyl]-methanesulfonamide 3-Hydroxy-6-methyl-pyridine-2-carbaldehyde To a solution of 2-hydroxymethyl-6-methyl-pyridin-3-ol (1.0 g, 7.19 mmol) in methylene chloride (30 mL) at ambient temperature was added manganese dioxide (12.5 g, 143 mmol). The reactions was stirred for 48 hours, then filtered through celite and concentrated to give the title compound (0.070 g).

3-{2-[4-(4-Fluoro-benzyl)-(2R,5S)-2,5-dimethyl-piperazin-1-yl]-2-oxo-ethoxy}-6-methyl-pyridine-2-carbaldehyde To a solution of 3-hydroxy-6-methyl-pyridine-2-carbaldehyde (0.27 g, 1.95 mmol) in dimethylformamide (4 mL) was added 2-chloro-1-[4-(4-fluoro-benzyl)-(2R,5S)-2,5-dimethyl-piperazin-1-yl]-ethanone (0.53 g, 1.77 mmol), potassium carbonate (0.49 g, 3.5 mmol) and potassium iodide (0.29 g, 1.8 mmol). The resulting mixture was stirred at 60° C. overnight, then diluted with EtOAc, washed with brine and the organic layer was dried over magnesium sulfate. Filtration followed by concentration in vacuo gave the title compound (0.85 g)

3-(3-{2-[4-(4-Fluoro-benzyl)-(2R,5S)-2,5-dimethyl-piperazin-1-yl]-2-oxo-ethoxy}-6-methyl-pyridin-2-yl)-acrylic acid ethyl ester To a solution of 3-{2-[4-(4-fluoro-benzyl)-(2R,5S)-2,5-dimethyl-piperazin-1-yl]-2-oxo-ethoxy}-6-methyl-pyridine-2-carbaldehyde (0.58 g, 1.45 mmol) in EtOH (7 mL) at ambient temperature was added triethyl phosphonoacetate (0.65 g, 2.9 mmol) and potassium carbonate (0.4 g in 1.0 mL of water). The reaction was stirred for 12 hours, then filtered through celite and concentrated in vacuo. Chromatography on silica gel gave the title compound (0.55 g).

3-(3-{2-[4-(4-Fluoro-benzyl)-(2R,5S)-2,5-dimethyl-piperazin-1-yl]-2-oxo-ethoxy}-6-methyl-pyridin-2-yl)-propionic acid ethyl ester To a solution of 3-(3-{2-[4-(4-fluoro-benzyl)-(2R,5S)-2,5-dimethyl-piperazin-1-yl]-2-oxo-ethoxy}-6-methyl-pyridin-2-yl)-acrylic acid ethyl ester (0.54 g, 1.15 mmol) in EtOH (5.0 mL) was added platinum oxide (0.050 g) and the mixture was hydrogenated at 45 psi for 90 minutes. The mixture was filtered through celite and concentrated in vacuo to give the title compound (0.50 g).

3-(3-{2-[4-(4-Fluoro-benzyl)-(2R,5S)-2,5-dimethyl-piperazin-1-yl]-2-oxo-ethoxy}-6-methyl-pyridin-2-yl)-propionic acid To a solution of 3-(3-{2-[4-(4-fluoro-benzyl)-(2R,5S)-2,5-dimethyl-piperazin-1-yl]-2-oxo-ethoxy}-6-methyl-pyridin-2-yl)-propionic acid ethyl ester (0.50 g, 1.06 mmol) in 2:2:1 tetrahydrofuran:methanol:water (5.0 mL) was added lithium hydroxide hydrate (0.089 g, 2.12 mmol). The solution was stirred at ambient temperature for 2 hours, concentrated, diluted in ethyl acetate and washed with water. The organic layer was dried over magnesium sulfate, filtered and concentrated in vacuo to give the title compound as a sodium salt (0.22 g).

N-[3-(3-{2-[4-(4-Fluoro-benzyl)-(2R,5S)-2,5-dimethyl-piperazin-1-yl]-2-oxo-ethoxy}-6-methyl-pyridin-2-yl)-propionyl]-methanesulfonamide To a solution of 3-(3-{2-[4-(4-fluoro-benzyl)-(2R,5S)-2,5-dimethyl-piperazin-1-yl]-2-oxo-ethoxy}-6-methyl-pyridin-2-yl)-propionic acid (0.10 g, 0.23 mmol) in methylene chloride (2 mL) was added 4-dimethylaminopyridine (0.032 g, 0.27 mmol), (3-(dimethylamino)propyl)ethyl carbodiimide hydrochloride (0.051 g, 0.27 mmol), methanesulfonamide (0.025 g, 0.27 mmol) and triethylamine (0.037 mL, 0.27 mmol). The reaction was stirred at ambient temperature for 18 hours. The reaction mixture was then diluted with dichloromethane and washed with 0.2 M hydrochloric acid. The organic layer was dried over magnesium sulfate, filtered and concentrated in vacuo. The crude product was purified by chromatography on silica gel to give the title compound (0.051 g, LRMS: 521.5).

EXAMPLE 33

2-Amino-3-(5-chloro-2-{2-[4-(4-fluoro-benzyl)-(2R,5S)-2,5-dimethyl-piperazin-1-yl]-2-oxo-ethoxy}-phenyl)-propionic acid 3-(5-Chloro-2-{2-[4-(4-fluoro-benzyl)-(2R,5S)-2,5-dimethyl-piperazin-1-yl]-2-oxo-ethoxy}-phenyl)-2-nitro-propionic acid ethyl ester To nitro-acetic acid ethyl ester (0.32 g, 2.39 mmol), sodium bicarbonate (0.10 g, 1.19 mmol) and tetrabutyl ammonium iodide (0.088 g, 0.24 mmol) in dimethyl formamide (5 ml) was added 2-(4-chloro-2-chloromethyl-phenoxy)-1-[4-(4-fluoro-benzyl)-(2R,5S)-2,5-dimethyl-piperazin-1-yl]-ethanone (0.52 g, 1.19 mmol). After 1 hour of heating at 60° C. the reaction was concentrated and then diluted with methylene chloride. After washing with aqueous saturated sodium bicarbonate and saturated sodium chloride the organic layer was dried over magnesium sulfate, filtered and concentrated in vacuo. Chromatography on silica gel gave the title compound (0.30 g).

2-Amino-3-(5-chloro-2-{2-[4-(4-fluoro-benzyl)-(2R,5S)-2,5-dimethyl-piperazin-1-yl]-2-oxo-ethoxy}-phenyl)-propionic acid ethyl ester To a solution of 3-(5-chloro-2-{2-[4-(4-fluoro-benzyl)-(2R,5S)-2,5-dimethyl-piperazin-1-yl]-2-oxo-ethoxy}-phenyl)-2-nitro-propionic acid ethyl ester (0.035 g, 0.065 mmol) in acetic acid (1 ml) was added zinc dust (0.085 g, 1.3 mmol). After 2 hours of heating at 60° C. the reaction was filtered and concentrated in vacuo. Chromatography on silica gel gave the title compound (0.033 g).

2-Amino-3-(5-chloro-2-{2-[4-(4-fluoro-benzyl)-(2R,5S)-2,5-dimethyl-piperazin-1-yl]-2-oxo-ethoxy}-phenyl)-propionic acid To a solution of 2-amino-3-(5-chloro-2-{2-[4-(4-fluoro-benzyl)-(2R,5S)-2,5-dimethyl-piperazin-1-yl]-2-oxo-ethoxy}-phenyl)-propionic acid ethyl ester (0.033 g, 0.065 mmol) in tetrahydrofuran, methanol and water (1 ml each) was added lithium hydroxide hydrate (0.014 g, 0.33 mmol). After 3 hours the reaction was concentrated in vacuo and the title compound was isolated by chromatography on silica gel (0.031 g, LRMS 478.5).

EXAMPLE 34

[(5-Chloro-2-{2-[4-(4-fluoro-benzyl)-(2R,5S)-2,5-dimethyl-piperazin-1-yl]-2-oxo-ethoxy}-benzyl)-methyl-amino]-acetic acid

[(5-Chloro-2-{2-[4-(4-fluoro-benzyl)-(2R,5S)-2,5-dimethyl-piperazin-1-yl]-2-oxo-ethoxy}-benzyl)-methyl-amino]-acetic acid methyl ester To a solution of 5-chloro-2-{2-[4-(4-fluoro-benzyl)-(2R,5S)-2,5-dimethyl-piperazin-1-yl]-2-oxo-ethoxy}-benzaldehyde (0.10 g, 0.24 mmol) in methanol (2.5 ml) was added sarcosine methyl ester hydrochloride salt (0.10 g, 0.72 mmol) followed by sodium triacetoxyborohydride (0.155 g, 0.73 mmol). After 15 hours the solvent was removed and the resultant solid taken up in methylene chloride. After washing with pH 7 phosphate buffer (0.05 M) and saturated aqueous sodium chloride the organic layer was dried over magnesium sulfate. After filtration and concentration the title compound was isolated by chromatography on silica gel (0.051 g).

[(5-Chloro-2-{2-[4-(4-fluoro-benzyl)-(2R,5S)-2,5-dimethyl-piperazin-1-yl]-2-oxo-ethoxy}-benzyl)-methyl-amino]-acetic acid To a solution of [(5-chloro-2-{2-[4-(4-fluoro-benzyl)-(2R,5S)-2,5-dimethyl-piperazin-1-yl]-2-oxo-ethoxy}-benzyl)-methyl-amino]-acetic acid methyl ester (0.051 g, 0.10 mmol) in 1:1 tetrahydrofuran:water (1 ml) and lithium hydroxide hydrate (0.016 g, 0.38 mmol) was added. After 1.5 hours the reaction was concentrated and the title compound isolated by chromatography on silica gel (0.045 g, LRMS: 492.4).

EXAMPLE 35

2-[4-Chloro-2-(2H-tetrazol-5-ylmethoxy)-phenoxy]-1-[4-(4-fluoro-benzyl)-(2R,5S)-2,5-dimethyl-piperazin-1-yl]-ethanone (5-Chloro-2-{2-[4-(4-fluoro-benzyl)-(2R,5S)-2,5-dimethyl-piperazin-1-yl]-2-oxo-ethoxy}-phenoxy)-acetonitrile To a solution of 2-(4-chloro-2-hydroxy-phenoxy)-1-[4-(4-fluoro-benzyl)-(2R,5S)-2,5-dimethyl-piperazin-1-yl]-ethanone (0.10 g, 0.24 mmol), and cesium carbonate (0.12 g, 0.38 mmol) in dioxane (1 mL) was added bromoacetonitrile (0.034 g, 0.28 mmol). The resulting mixture was stirred at ambient temperature overnight. The reaction was diluted with ethyl acetate and washed with water. The organic layer was washed with saturated aqueous sodium chloride, dried over magnesium sulfate and concentrated in vacuo to give the title compound (0.11 g).

2-[4-Chloro-2-(2H-tetrazol-5-ylmethoxy)-phenoxy]-1-[4-(4-fluoro-benzyl)-(2R,5S)-2,5-dimethyl-piperazin-1-yl]-ethanone To a solution of (5-chloro-2-{2-[4-(4-fluoro-benzyl)-(2R,5S)-2,5-dimethyl-piperazin-1-yl]-2-oxo-ethoxy}-phenoxy)-acetonitrile (0.11 g, 0.25 mmol) in dimethylformamide (0.50 mL) was added ammonium chloride (0.058 g, 1.1 mmol) and sodium azide (0.055 g, 0.85 mmol). The resulting mixture was stirred at 100° C. for 12 hours. The reaction was cooled and diluted with ethyl acetate and washed with water. The organic layer was washed with saturated aqueous sodium chloride, dried over magnesium sulfate and concentrated in vacuo. Trituration with diethyl ether and methylene chloride gave the title compound (0.018 g, LRMS 489.4, 491.5).

EXAMPLE 36

2-(5-Chloro-2-{2-[4-(4-fluoro-benzyl)-(2R,5S)-2,5-dimethyl-piperazin-1-yl]-2-oxo-ethoxy}-phenoxy)-nicotinic acid To a solution of 2-(4-chloro-2-hydroxy-phenoxy)-1-[4-(4-fluoro-benzyl)-(2R,5S)-2,5-dimethyl-piperazin-1-yl]-ethanone (0.10 g, 0.25 mmol), and 2-chloro-nicotinic acid (0.045 g, 0.28 mmol) in dimethylformamide (0.75 mL) were added potassium carbonate (0.084 g, 0.60 mmol), copper (0.0050 g, 0.078 mmol) and copper (I) iodide (0.0050 g, 0.0.026 mmol). The resulting mixture was stirred at 145° C. for 2 hours. The reaction was cooled and diluted with ethyl acetate and washed with water. The organic layer was washed with saturated aqueous sodium chloride, dried over magnesium sulfate and concentrated in vacuo. Chromatography on silica gel followed by trituration with methylene chloride/hydrogen chloride in diethyl ether gave the title compound as the hydrochloride salt (0.022 g, LRMS 528.4, 530.4).

EXAMPLE 37

(2-{2-[(2R)-2-Carbamoylmethyl-4-(4-fluoro-benzyl)-piperazin-1-yl]-2-oxo-ethoxy}-5-chloro-phenoxy)-acetic acid

[2-(4-fluoro-benzylamino)-ethyl]-carbamic acid tert-butyl ester (2-Amino-ethyl)-carbamic acid tert-butyl ester (5.95 g, 37.1 mmol), 4-fluorobenzaldehyde (5.07 g, 40.9 mmol, 4.4 mL), triethylamine (1.50 g, 14.9 mmol, 2.1 mL) and magnesium sulfate (6.71 g, 55.7 mmol) were stirred in methanol (50 mL). After 1.5 h the solution was cooled to 0° C. and sodium borohydride (8.4 g, 223 mmol) was added in portions. After 2 h the reaction was quenched with water and extracted three times with ethyl acetate. The combined organic layers were washed three times with water and the desired product extracted into the aqueous layer with 0.5 M hydrochloric acid (4×50 mL). The combined acid wash was cooled to 0° C. and basified with saturated aqueous ammonium hydroxide. The aqueous layer was extracted three times with chloroform and the combined chloroform layer washed three times with water, dried over sodium sulfate and concentrated to yield the title compound as a colorless oil (7.49 g).

4-[(2-tert-butoxycarbonylamino-ethyl)-(4-fluoro-benzyl)-amino]-but-2-enoic acid methyl ester

[2-(4-Fluoro-benzylamino)-ethyl]-carbamic acid tert-butyl ester (7.0 g, 26.1 mmol) and potassium carbonate (7.2 g, 52.2 mmol) were stirred in acetone (150 mL). A mixture of methyl 4-bromocrotonate (4.7 g, 26.1 mmol, 3.1 mL) in acetone (50 mL) was added to this solution dropwise using an addition funnel. After 18 h the solution was filtered, concentrated and chromatographed on silica gel to yield the title compound as a yellow oil (8.53 g).

[(4R)-4-(4-Fluoro-benzyl)-piperazin-2-yl]-acetic acid methyl ester

A solution of 4-[(2-tert-butoxycarbonylamino-ethyl)-(4-fluoro-benzyl)-amino]-but-2-enoic acid methyl ester (8.5 g, 23.2 mmol) in dichloromethane (250 mL) and trifluoroacetic acid (25 mL) was stirred for 5 h and then concentrated. The resulting residue was diluted with dichloromethane and the pH was adjusted to 10 with saturated aqueous sodium carbonate. The aqueous layer was extracted three times with ethyl acetate and the combined organic layers were dried over sodium sulfate, filtered and concentrated to give 6.05 g of a pale yellow oil. The racemic mixture was separated on a chiral column using prep HPLC to give the title compound as a white solid.

(2R)-2-[1-[(4-Chloro-2-hydroxy-phenoxy)-acetyl]-4-(4-fluoro-benzyl)-piperazin-2-yl]-acetamide

[(4R)-4-(4-Fluoro-benzyl)-piperazin-2-yl]-acetic acid methyl ester (0.25 g, 0.94 mmol) was dissolved in methanol (10 mL) and ammonia gas was bubbled into the solution for 10 minutes. The reaction flask was tightly capped and the reaction stirred overnight. After thin layer chromatography indicated the reaction was complete, the solution was concentrated and the residue dissolved in toluene (9 mL). 7-chloro-benzo[1,4]dioxin-2-one (0.17 g, 0.94 mmol) was added and the solution heated to 95° C. for 16 h. The reaction was cooled to ambient temperature, concentrated in vacuo and the resulting oil chromatographed on silica gel to yield the title compound (0.19 g).

(2-{2-[(2R)-2-carbamoylmethyl-4-(4-fluoro-benzyl)-piperazin-1-yl]-2-oxo-ethoxy}-5-chloro-phenoxy)-acetic acid tert-butyl ester (2R)-2-[1-[(4-Chloro-2-hydroxy-phenoxy)-acetyl]-4-(4-fluoro-benzyl)-piperazin-2-yl]-acetamide (0.070 g, 0.16 mmol), cesium carbonate (0.078 g, 0.24 mmol) and tert-butyl bromoacetate (0.038 g, 0.028 mL, 0.193 mmol) were stirred in dioxane (2 mL). After 2.5 days, the solution was filtered, concentrated and chromatographed on silica gel to yield the title compound as a white solid (0.077 g).

(2-{2-[(2R)-2-Carbamoylmethyl-4-(4-fluoro-benzyl)-piperazin-1-yl]-2-oxo-ethoxy}-5-chloro-phenoxy)-acetic acid A solution of (2-{2-[(2R)-2-carbamoylmethyl-4-(4-fluoro-benzyl)-piperazin-1-yl]-2-oxo-ethoxy}-5-chloro-phenoxy)-acetic acid tert-butyl ester (0.070 g, 0.13 mmol) in dichloromethane (1 mL) and trifluoroacetic acid (0.10 mL) was stirred for 3.5 h and then concentrated. The resulting residue was diluted with dichloromethane and the excess trifluoroacetic acid was quenched with saturated aqueous sodium carbonate. The aqueous layer was neutralized with 0.1N hydrochloric acid and extracted one time with dichloromethane/methanol (1:1) and twice with ethyl acetate. The combined organic layers were dried over magnesium sulfate, filtered and concentrated to give the title compound (0.054 g, LRMS: 492.4, 494.4).

EXAMPLE 38

(4S)-4-(5-Chloro-2-{2-[4-(4-fluoro-benzyl)-(2R,5S)-2,5-dimethyl-piperazin-1-yl]-2-oxo-ethoxy}-phenoxy)-1-methyl-pyrrolidine-(2S)-2-carboxylic acid (4S)-4-(5-Chloro-2-{2-[4-(4-fluoro-benzyl)-(2R,5S)-2,5-dimethyl-piperazin-1-yl]-2-oxo-ethoxy}-phenoxy)-pyrrolidine-1,2S-dicarboxylic acid di-tert-butyl ester To a solution of 2-(4-chloro-2-hydroxy-phenoxy)-1-[4-(4-fluoro-benzyl)-(2R,5S)-2,5-dimethyl-piperazin-1-yl]-ethanone (0.51 g, 1.2 mmol), triphenylphosphine (0.51 g, 1.9 mmol) and (2S,4R)-4-hydroxy-pyrrolidine-1,2-dicarboxylic acid di-tert-butyl ester (0.56 g, 1.9 mmol) in tetrahydrofuran (12 mL) was added diethyl-azodicarboxylate (0.34 g, 1.9 mmol). The resulting mixture was stirred at ambient temperature overnight. The reaction was concentrated in vacuo. Chromatography on silica gel gave the title compound (0.76 g).

(4S)-4-(5-Chloro-2-{2-[4-(4-fluoro-benzyl)-(2R,5S)-2,5-dimethyl-piperazin-1-yl]-2-oxo-ethoxy}-phenoxy)-pyrrolidine-(2S)-2-carboxylic acid (4S)-4-(5-Chloro-2-{2-[4-(4-fluoro-benzyl)-(2R,5S)-2,5-dimethyl-piperazin-1-yl]-2-oxo-ethoxy}-phenoxy)-pyrrolidine-1,2S-dicarboxylic acid di-tert-butyl ester (0.76 g, 1.1 mmol) was dissolved in 4 N hydrogen chloride in dioxane (20 mL). The resulting mixture was stirred at ambient temperature for six hours. The reaction was concentrated in vacuo. The crude product was purified by trituration with diethyl ether to give the title compound as the bis-hydrochloride salt (0.76 g).

(4S)-4-(5-Chloro-2-{2-[4-(4-fluoro-benzyl)-(2R,5S)-2,5-dimethyl-piperazin-1-yl]-2-oxo-ethoxy}-phenoxy)-1-methyl-pyrrolidine-(2S)-2-carboxylic acid To a solution of (4S)-4-(5-chloro-2-{2-[4-(4-fluoro-benzyl)-(2R,5S)-2,5-dimethyl-piperazin-1-yl]-2-oxo-ethoxy}-phenoxy)-pyrrolidine-(2S)-2-carboxylic acid bis-hydrochloride (0.030 g, 0.051 mmol) in ethanol (6 mL) was added 37% aqueous formaldehyde (0.10 mL), and 10% palladium on carbon (0.010 g). The resulting mixture was hydrogenated on a Parr shaker at 30 psi of hydrogen for 12 hours at ambient temperature. The mixture was filtered through a 0.45 µm filter and concentrated in vacuo. The crude product was purified by trituration with methylene chloride/hydrogen chloride in diethyl ether to give the title compound as the bis-hydrochloride salt (0.030 g, LRMS 534.5, 536.5).

EXAMPLE 39

C-(5-Chloro-2-{2-[4-(4-fluoro-benzyl)-(2R,5S)-2,5-dimethyl-piperazin-1-yl]-2-oxo-ethoxy}-phenyl)-N-(methoxycarbonyl)-methanesulfonamide (5-Chloro-2-{2-[4-(4-fluoro-benzyl)-(2R,5S)-2,5-dimethyl-piperazin-1-yl]-2-ethoxy}-phenyl)-methanesulfonamide (0.050 g, 0.103 mmol), N,N-diisopropylethylamine (0.020 g, 0.155 mmol, 0.027 mL) and methyl chloroformate (0.012 g, 0.124 mmol, 0.010 mL) were stirred in dichloromethane (1 mL). After 3.5 hours the solution was purified directly using radial chromatography to yield the title compound (0.021 g, LRMS: 542.1, 540.2).

EXAMPLE 40

6-(5-Chloro-2-{2-[4-(4-fluoro-benzyl)-(2R,5S)-2,5-dimethyl-piperazin-1-yl]-2-oxo-ethoxy}-phenoxymethyl)-nicotinic acid 6-Bromomethyl-nicotinic acid methyl ester To a solution of 6-methyl-nicotinic acid methyl ester (0.54 g, 3.57 mmol) in carbon tetrachloride (10 mL) was added 2,2'-azobis(2-methyl-proprionitrile) (0.030 g, 0.18 mmol) and N-bromosuccinimide (0.703 g, 3.95 mmol). The solution was stirred at reflux for 12 hours, cooled and concentrated in vacuo. Flash chromatography on silica gel provided the title compound (0.28 g).

6-(5-Chloro-2-{2-[4-(4-fluoro-benzyl)-(2R,5S)-2,5-dimethyl-piperazin-1-yl]-2-oxo-ethoxy}-phenoxymethyl)-nicotinic acid methyl ester To a solution of 2-(4-chloro-2-hydroxy-phenoxy)-1-[4-(4-fluoro-benzyl)-(2R,5S)-2,5-dimethyl-piperazin-1-yl]-ethanone (0.11 g, 0.27 mmol) in dioxane (1 mL) was added 6-bromomethyl-nicotinic acid methyl ester (0.075 g, 0.32 mmol) and cesium carbonate (0.15 g, 0.47 mmol). The reaction was stirred at ambient temperature for 6 days, then concentrated. Chromatography on silica gel gave the title compound (0.13 g).

6-(5-Chloro-2-{2-[4-(4-fluoro-benzyl)-(2R,5S)-2,5-dimethyl-piperazin-1-yl]-2-oxo-ethoxy}-phenoxymethyl)-nicotinic acid To a solution of 6-(5-chloro-2-{2-[4-(4-fluoro-benzyl)-(2R,5S)-2,5-dimethyl-piperazin-1-yl]-2-oxo-ethoxy}-phenoxymethyl)-nicotinic acid methyl ester (0.13 g, 0.23 mmol) in 2:2:1 tetrahydrofuran:methanol:$H_2O$ (2 mL) was added lithium hydroxide hydrate (0.020 g, 0.48 mmol). The reaction was stirred at ambient temperature for 3 hours, the pH was then adjusted to 4 with 0.2 M hydrochloric acid. The solution was extracted with ethyl acetate and the organic layer was dried over magnesium sulfate, filtered and concentrated in vacuo. Trituration in diethyl ether provided the title compound (0.034 g, LRMS: 542.4, 544.5).

EXAMPLE 41

5-(5-Chloro-2-{2-[4-(4-fluoro-benzyl)-(2R,5S)-2,5-dimethyl-piperazin-1-yl]-2-oxo-ethoxy}-phenyl)-5-oxo-pentanoic acid 5-(5-chloro-2-hydroxy-phenyl)-5-oxo-pentanoic acid ethyl ester To a solution of 5-(5-chloro-2-hydroxy-phenyl)-5-oxo-pentanoic acid (0.38 g, 0.23 mmol, this compound was prepared by methods described in: *Eur. J. Med. Chem.* 1990, 25, 749) in ethanol was bubbled hydrogen chloride (g) for 10 minutes. The resulting solution was stirred for 3 days at ambient temperature. Concentration gave the title compound (0.39 g).

5-(5-Chloro-2-{2-[4-(4-fluoro-benzyl)-(2R,5S)-2,5-dimethyl-piperazin-1-yl]-2-oxo-ethoxy}-phenyl)-5-oxo-pentanoic acid ethyl ester To a solution of (2-chloro-1-[4-(4-fluoro-benzyl)-2,5-dimethyl-piperazin-1-yl]-ethanone (0.10 g, 0.35 mmol) in 2-butanone (1 mL) was added potassium carbonate (0.13 g, 0.90 mmol), potassium iodide (0.065 g, 0.39 mmol) and 5-(5-chloro-2-hydroxy-phenyl)-5-oxo-pentanoic acid ethyl ester (0.11 g, 0.39 mmol). The reaction was stirred at 60° C. for 12 hours, then cooled and concentrated. Chromatography on silica gel gave the title compound (0.089 g).

5-(5-Chloro-2-{2-[4-(4-fluoro-benzyl)-(2R,5S)-2,5-dimethyl-piperazin-1-yl]-2-oxo-ethoxy}-phenyl)-5-oxo-pentanoic acid To a solution of 5-(5-chloro-2-{2-[4-(4-fluoro-benzyl)-(2R,5S)-2,5-dimethyl-piperazin-1-yl]-2-oxo-ethoxy}-phenyl)-5-oxo-pentanoic acid ethyl ester (0.089 g, 0.17 mmol) in 2:2:1 tetrahydrofuran:methanol:$H_2O$ (2 mL) was added lithium hydroxide hydrate (0.025 g, 0.60 mmol). The reaction was stirred at ambient temperature for 4 hours. The pH was then adjusted to 4 with 0.2 M hydrochloric acid. The solution was extracted with ethyl acetate and the organic layer was dried over magnesium sulfate, filtered and concentrated in vacuo. Anion exchange chromatography (MCX) provided the title compound (0.014 g, LRMS: 505.5, 507.5).

EXAMPLE 42

5-(5-Chloro-2-{2-[4-(4-fluoro-benzyl)-(2R,5S)-2,5-dimethyl-piperazin-1-yl]-2-oxo-ethoxy}-phenyl)-dihydro-furan-2-one 4-(5-Chloro-2-{2-[4-(4-fluoro-benzyl)-(2R,5S)-2,5-dimethyl-piperazin-1-yl]-2-oxo-ethoxy}-phenyl)-4-hydroxy-butyric acid To a solution of 4-(5-chloro-2-{2-[4-(4-fluoro-benzyl)-(2R,5S)-2,5-dimethyl-piperazin-1-yl]-2-oxo-ethoxy}-phenyl)-4-oxo-butyric acid (0.10 g, 0.20 mmol) in methanol (4 mL) was added sodium borohydride (0.012 g, 0.32 mmol). The reaction was stirred at ambient temperature for 3 hours. The reaction was then diluted with brine and extracted with ethyl acetate. The organic layer was dried over magnesium sulfate, filtered and concentrated in vacuo. Trituration in diethyl ether/methylene chloride/hexanes gave the title compound (0.095 g, LRMS: 493.2, 495.3).

5-(5-Chloro-2-{2-[4-(4-fluoro-benzyl)-(2R,5S)-2,5-dimethyl-piperazin-1-yl]-2-oxo-ethoxy}-phenyl)-dihydro-furan-2-one To a solution of 4-(5-chloro-2-{2-[4-(4-fluoro-benzyl)-(2R,5S)-2,5-dimethyl-piperazin-1-yl]-2-oxo-ethoxy}-phenyl)-4-hydroxy-butyric acid (0.050 g, 0.10 mmol) in toluene (5 mL) was added p-toluene sulfonic acid (0.040 g) and the reaction was stirred at reflux for 4 hours. The reaction was cooled, diluted with saturated aqueous sodium bicarbonate and extracted with ethyl acetate. The organic layer was dried over magnesium sulfate, filtered and concentrated in vacuo. Trituration in diethyl ether/hexanes gave the title compound (0.052 g, LRMS: 475.2, 477.3).

EXAMPLE 43

4-(5-Chloro-2-{2-[4-(4-fluoro-benzyl)-(2R,5S)-2,5-dimethyl-piperazin-1-yl]-2-oxo-ethoxy}-pyridin-3-ylamino)-butyric acid 2-(5-Chloro-3-nitro-pyridin-2-yloxy)-1-[4-(4-fluoro-benzyl)-(2R,5S)-2,5-dimethyl-piperazin-1-yl]-ethanone To a solution of 1-[4-(4-fluoro-benzyl)-(2R,5S)-2,5-dimethyl-piperazin-1-yl]-2-hydroxy-ethanone (0.90 g, 3.2 mmol) in toluene (20 mL) at 0° C. was added sodium hydride (0.18 g, 4.5 mmol, 60% dispersion in mineral oil). The reaction was stirred for 15 minutes, then 2,5-dichloro-3-nitro-pyridine (0.65 g, 3.38 mmol) was added and the solution was stirred at ambient temperature for 18 hours. The reaction was quenched by the slow addition of water (5 mL) then extracted with ethyl acetate. The organic layer was washed with brine, dried over magnesium sulfate, filtered and concentrated in vacuo. Flash chromatography on silica gel gave the title compound (1.25 g).

2-(3-Amino-5-chloro-pyridin-2-yloxy)-1-[4-(4-fluoro-benzyl)-(2R,5S)-2,5-dimethyl-piperazin-1-yl]-ethanone To a solution of 2-(5-chloro-3-nitro-pyridin-2-yloxy)-1-[4-(4-fluoro-benzyl)-(2R,5S)-2,5-dimethyl-piperazin-1-yl]-ethanone (1.25 g, 2.86 mmol) in ethanol (50 mL) was added platinum dioxide (0.92 g). The mixture was hydrogenated on a Parr shaker at 35 psi of hydrogen for 5 minutes at ambient temperature. The reaction was then purged with nitrogen and filtered through celite. The filtrate was concentrated in vacuo to give the title compound (1.08 g).

4-(5-Chloro-2-{2-[4-(4-fluoro-benzyl)-(2R,5S)-2,5-dimethl-piperazin-1-yl]-2-oxo-ethoxy}-pyridin-3-ylamino)-butyric acid ethyl ester To a solution of 2-(3-amino-5-chloro-pyridin-2-yloxy)-1-[4-(4-fluoro-benzyl)-(2R,5S)-2,5-dimethyl-piperazin-1-yl]-ethanone (0.072 g, 0.18 mmol) in ethanol (1 mL) was added 4-bromo-butyric acid ethyl ester (0.030 mL, 0.21 mmol), sodium bicarbonate (0.031 g, 0.37 mmol) and potassium iodide (~0.030 g). The resulting solution was stirred at 70° C. for 18 hours. Additional bromo-butyric acid ethyl ester (0.030 mL, 0.21 mmol) was added and the reaction was stirred at 70° C. for 18 hours. The reaction was cooled, concentrated in vacuo and purified via flash chromatography on silica gel to give the title compound (0.034 g).

4-(5-Chloro-2-{2-[4-(4-fluoro-benzyl)-(2R,5S)-2,5-dimethyl-piperazin-1-yl]-2-oxo-ethoxy}-pyridin-3-ylamino)-butyric acid To a solution of 4-(5-chloro-2-{2-[4-(4-fluoro-benzyl)-(2R,5S)-2,5-dimethyl-piperazin-1-yl]-2-oxo-ethoxy}-pyridin-3-ylamino)-butyric acid ethyl ester (0.034 g, 0.065 mmol) in 2:2:1 methanol:tetrahydrofuran:water (1 mL) was added lithium hydroxide monohydrate (0.010 g, 0.24 mmol). The reaction was stirred at ambient temperature for 3 hours. The pH of the solution was adjusted to ~4 by the addition of 0.2 M hydrochloric acid, then diluted with brine and extracted with ethyl acetate. The organic layer was dried over magnesium sulfate, filtered and concentrated in vacuo. The product was purified by anion exchange chromatography to give the title compound as its acetic acid addition salt (0.020 g, LRMS: 493.1, 495.3)

EXAMPLE 44

(5-Chloro-2-{2-[4-(4-fluoro-benzyl)-(2R,5S)-2,5-dimethyl-piperazin-1-yl]-2-oxo-ethoxy}-pyridin-3-ylamino)-acetic acid (5-Chloro-2-{2-[4-(4-fluoro-benzyl)-(2R,5S)-2,5-dimethyl-piperazin-1-yl]-2-oxo-ethoxy}-pyridin-3-ylamino)-acetic acid ethyl ester To a solution of 2-(3-amino-5-chloro-pyridin-2-yloxy)-1-[4-(4-fluoro-benzyl)-(2R,5S)-2,5-dimethyl-piperazin-1-yl]-ethanone (0.105 g, 0.26 mmol) in 1,2-dichloroethane (2 mL) was added ethyl glyoxylate (0.050 mL, ~0.5 mmol, 50% solution in toluene), acetic acid (0.016 mL, 0.28 mmol) and sodium triacetoxyborohydride (0.085 g, 0.40 mmol). The reaction was stirred at ambient temperature for 18 hours. Additional ethyl glyoxylate (0.050 mL, ~0.5 mmol, 50% solution in toluene) and acetic acid (0.016 mL, 0.28 mmol) were added and the reaction was warmed to reflux for 3 hours. The reaction was then cooled to ambient temperature, sodium cyanoborohydride (~0.030 g, 0.48 mmol) was added and the reaction was stirred at ambient temperature for 18 hours. The reaction was diluted with water and extracted with methylene chloride. The organic layer was dried over magnesium sulfate, filtered and concentrated in vacuo. Flash chromatography on silica gel provided the title compound (0.085 g).

(5-Chloro-2-{2-[4-(4-fluoro-benzyl)-(2R,5S)-2,5-dimethyl-piperazin-1-yl]-2-oxo-ethoxy}-pyridin-3-ylamino)-acetic acid To a solution of (5-chloro-2-{2-[4-(4-fluoro-benzyl)-(2R,5S)-2,5-dimethyl-piperazin-1-yl]-2-oxo-ethoxy}-pyridin-3-ylamino)-acetic acid ethyl ester (0.080, 0.16 mmol) in 2:2:1 methanol:tetrahydrofuran:water (1.5 mL) was added lithium hydroxide monohydrate (0.015 g, 0.36 mmol). The reaction was stirred at ambient temperature for 3 hours. The pH of the solution was adjusted to ~4 by the addition of 0.2 M hydrochlroric acid, then diluted with brine and extracted with ethyl acetate. The organic layer was dried over magnesium sulfate, filtered and concentrated in vacuo. The product was purified by anion exchange chromatography to give the title compound as its acetic acid addition salt (0.058 g, LRMS: 465.1, 467.2).

EXAMPLE 45

2-[4-Chloro-2-(2H-tetrazol-5-yloxy)-phenoxy]-1-[4-(4-fluoro-benzyl)-(2R)-2-methyl-piperazin-1-yl]-ethanone 2-(4-Chloro-2-hydroxy-phenoxy)-1-[4-(4-fluoro-benzyl)-(2R)-2-methyl-piperazin-1-yl]-ethanone To a solution of 7-chloro-benzo[1,4]dioxin-2-one (0.845 g, 4.81 mmol) in toluene (25 mL) was added (3R)-1-(4-fluoro-benzyl)-3-methyl-piperazine (1.003 g, 4.81 mmol). The resulting mixture was heated to 95° C. overnight. The reaction was cooled to ambient temperature, filtered and concentrated in vacuo. Chromatography on silica gel gave the title compound (~1 g).

2-(4-Chloro-2-cyanato-phenoxy)-1-[4-(4-fluoro-benzyl)-(2R)-2-methyl-piperazin-1-yl]-ethanone To a solution of 2-(4-chloro-2-hydroxy-phenoxy)-1-[4-(4-fluoro-benzyl)-(2R)-2-methyl-piperazin-1-yl]-ethanone (0.168 g, 0.427 mmol) in methylene chloride (2 mL) was added triethylamine (0.12 mL, 0.86 mmol). The solution was cooled to −5° C. via an acetone/ice bath then cyanogen bromide was added (0.22 mL, 0.66 mmol). The reaction was stirred at −5° C. for 30 minutes then concentrated in vacuo to give the crude title compound which was taken directly on to the next step (0.17 g).

2-[4-Chloro-2-(2H-tetrazol-5-yloxy)-phenoxy]-1-[4-(4-fluoro-benzyl)-(2R)-2-methyl-piperazin-1-yl]-ethanone To a solution of 2-(4-chloro-2-cyanato-phenoxy)-1-[4-(4-fluoro-benzyl)-(2R)-2-methyl-piperazin-1-yl]-ethanone (0.17 g, 0.427 mmol) in acetone (2 mL) was added sodium azide (0.061 g, 0.94 mmol) and the reaction was stirred at reflux for 3 hours, then cooled to ambient temperature and stirred 18 hours. The reaction was diluted with water and extracted with ethyl acetate. The organic layer was dried over magnesium sulfate, filtered and concentrated in vacuo. The product was purified by anion exchange chromatography to give the title compound as its acetic acid addition salt (0.073 g, LRMS: 461.2, 463.3).

EXAMPLE 46

1-(5-Chloro-2-{2-[4-(4-fluoro-benzyl)-(2R,5S)-2,5-dimethyl-piperazin-1-yl]-2-oxo-ethoxy}-phenyl)-2-(1H-tetrazol-5-yl)-ethanone 2-(4-Chloro-2-isoxazol-5-yl-phenoxy)-1-[4-(4-fluoro-benzyl)-(2R,5S)-2,5-dimethyl-piperazin-1-yl]-ethanone To a solution of (2-chloro-1-[4-(4-fluoro-benzyl)-2,5-dimethyl-piperazin-1-yl]-ethanone (0.30 g, 1.0 mmol) in acetonitrile (10 mL) was added potassium carbonate (0.207 g, 1.5 mmol), potassium iodide (0.033 g, 0.20 mmol) and 4-chloro-2-isoxazol-5-yl-phenol (0.215 g, 1.1 mmol). The resulting mixture was stirred for 18 hours at ambient temperature. The reaction was diluted with tetrahydrofuran (10 mL), filtered and concentrated in vacuo to give the title compound (0.465 g).

3-(5-Chloro-2-{2-[4-(4-fluoro-benzyl)-(2R,5S)-2,5-dimethyl-piperazin-1-yl]-2-oxo-ethoxy}-phenyl)-3-oxo-propionitrile To a stirred mixture of sodium ethoxide (0.14 g, 1.0 mmol) in ethanol (2 mL) was added 2-(4-chloro-2-isoxazol-5-yl-phenoxy)-1-[4-(4-fluoro-benzyl)-(2R,5S)-2,5-dimethyl-piperazin-1-yl]-ethanone (0.465 g, 1.0 mmol) in ethanol (3 mL). The resulting mixture was stirred at ambient temperature for 3 hours. To the reaction was then added 3M hydrochloric acid (2 mL) and the resulting solution was poured into water (30 mL). This was extracted with ethyl acetate and the organic layer was washed with brine, dried over magnesium sulfate, filtered and concentrated in vacuo. Flash chromatography on silica gel gave the title compound (0.34 g).

1-(5-Chloro-2-{2-[4-(4-fluoro-benzyl)-(2R,5S)-2,5-dimethyl-piperazin-1-yl]-2-oxo-ethoxy}-phenyl)-2-(1H-tetrazol-5-yl)-ethanone To a mixture of sodium azide (0.061 g, 0.95 mmol) and aluminum trichloride (0.042 g, 0.31 mmol) was added 3-(5-chloro-2-{2-[4-(4-fluoro-benzyl)-(2R,5S)-2,5-dimethyl-piperazin-1-yl]-2-oxo-ethoxy}-phenyl)-3-oxo-propionitrile (0.035 g, 0.076 mmol) in tetrahydrofuran (2 mL). The reaction was warmed to 70° C. and stirred for 18 hours. To this was added saturated aqueous sodium bicarbonate (0.5 mL) and dimethylsulfoxide (0.5 mL) and the solution was stirred for 1 hour at ambient temperature. The solids were removed by filtration and the filtrate was concentrated in vacuo. The crude product was purified by reverse phase HPLC to give the title compound which was converted to its hydrochloride salt (0.020 g, LRMS: 501.2).

EXAMPLE 47

1-(5-Chloro-2-{2-[4-(4-fluoro-benzyl)-(2R,5S)-2,5-dimethyl-piperazin-1-yl]-2-oxo-ethoxy}-phenyl)-3-(1H-tetrazol-5-yl)-propan-1-one 4-(5-Chloro-2-hydroxy-phenyl)-4-oxo-butyronitrile A solution of 1-(5-chloro-2-hydroxy-phenyl)-ethanone (1.0 g, 5.86 mmol) and magnesium methylcarbonate (13 mL, 32.5 mmol, 2.5 M solution in DMF) was stirred at 120° C. for 3 hours. The mixture was cooled to ambient temperature followed by the addition of bromoacetonitrile (1.22 mL, 17.6 mmol). The resulting solution was stirred at 90° C. for 3 hours. The reaction was cooled to ambient temperature then slowly poured into 1 M hydrochloric acid (200 mL). This was extracted with ethyl acetate, washed with brine, dried over magnesium sulfate, filtered and concentrated. Flash chromatography on silica gel gave the title compound (0.72 g).

4-(5-Chloro-2-{2-[4-(4-fluoro-benzyl)-(2R,5S)-2,5-dimethyl-piperazin-1-yl]-2-oxo-ethoxy}-phenyl)-4-oxo-butyronitrile To a solution of 4-(5-chloro-2-hydroxy-phenyl)-4-oxo-butyronitrile (0.15 g, 0.70 mmol) in acetonitrile (4 mL) was added potassium carbonate (0.16 g, 1.16 mmol), potassium iodide (0.040 g, 0.24 mmol) and (2-chloro-1-[4-(4-fluoro-benzyl)-2,5-dimethyl-piperazin-1-yl]-ethanone (0.21 g, 0.70 mmol). The reaction was stirred for 20 hours at ambient temperature. Tetrahydrofuran (8 mL) was added and solids were removed by filtration. The filtrate was concentrated and the crude product purified by flash chromatography to give the title compound (0.31 g).

1-(5-Chloro-2-{2-[4-(4-fluoro-benzyl)-(2R,5S)-2,5-dimethyl-piperazin-1-yl]-2-oxo-ethoxy}-phenyl)-3-(1H-tetrazol-5-yl)-propan-1-one To a mixture of sodium azide (0.061 g, 0.95 mmol) and aluminum trichloride (0.042 g, 0.31 mmol) was added 3-(5-chloro-2-{2-[4-(4-fluoro-benzyl)-(2R,5S)-2,5-dimethyl-piperazin-1-yl]-2-oxo-ethoxy}-phenyl)-3-oxo-propionitrile (0.036 g, 0.076 mmol) in tetrahydrofuran (2 mL). The reaction was warmed to 70° C. and stirred for 18 hours. To this was added saturated aqueous sodium bicarbonate (0.5 mL) and dimethylsulfoxide (0.5 mL) and the solution was stirred for 1 hour at ambient temperature. The solids were removed by filtration and the filtrate was concentrated in vacuo. The crude product purified by reverse phase HPLC to give the title compound which was converted to its hydrochloride salt (0.008 g, LRMS: 515.2, 517.3). The compounds from Table 1 were prepared according to the methods described above in Examples 1–47.

TABLE 1

Example compounds prepared

| Example | Name | LRMS |
|---|---|---|
| 48 | (2-{3-[4-(4-Fluoro-benzyl)-(2R,5S)-2,5-dimethyl-piperazin-1-I]-3-oxo-propyl}-5-methoxy-phenoxy)-acetic acid | 457.4 |
| 49 | (2-{3-[4-(4-Fluoro-benzyl)-(2R,5S)-2,5-dimethyl-piperazin-1-yl]-3-oxo-propyl}-5-methyl-phenoxy)-acetic acid | 441.4 |
| 50 | N-[(2-{3-[4-(4-Fluoro-benzyl)-(2R,5S)-2,5-dimethyl-piperazin-1-yl]-3-oxo-propyl}-5-methoxy-phenoxy)-acetyl]-methanesulfonamide | 536.3 |
| 51 | (5-Chloro-2-{3-[4-(4-fluoro-benzyl)-(2R,5S)-2,5-dimethyl-piperazin-1-yl]-3-oxo-propyl}-phenoxy)-acetic acid | 463.1, 465.1 |
| 52 | (5-Chloro-2-{2-[4-(4-fluoro-benzyl)-(2R,5S)-2,5-dimethyl-piperazin-1-yl]-2-oxo-ethoxy}-phenyl)-oxo-acetic acid | 461.2 |
| 53 | (5-Chloro-2-{2-[4-(4-fluoro-benzyl)-(2R,5S)-2,5-dimethyl-piperazin-1-yl]-2-oxo-ethoxy}-phenoxy)-acetic acid | 465.2, 467.2 |
| 54 | (5-Chloro-2-{2-[4-(4-fluoro-benzyl)-(2R)-2-methyl-piperazin-1-yl]-2-oxo-ethoxy}-phenoxy)-acetic acid | 451.1, 453.2 |
| 55 | N-[(5-Chloro-2-{2-[4-(4-fluoro-benzyl)-(2R)-2-methyl-piperazin-1-yl]-2-oxo-ethoxy}-phenoxy)-acetyl]-methanesulfonamide | 528.1, 530.1 |

TABLE 1-continued

Example compounds prepared

| Example | Name | LRMS |
|---|---|---|
| 56 | (5-Bromo-2-{2-[4-(4-fluoro-benzyl)-(2R,5S)-2,5-dimethyl-piperazin-1-yl]-2-oxo-ethoxy}-phenoxy)-acetic acid | 509.1, 511.1 |
| 57 | (5-Bromo-2-{2-[4-(4-fluoro-benzyl)-(2R)-2-methyl-piperazin-1-yl]-2-oxo-ethoxy}-phenoxy)-acetic acid | 495.2, 497.2 |
| 58 | (5-Chloro-2-{2-[(2R)-2-ethyl-4-(4-fluoro-benzyl)-piperazin-1-yl]-2-oxo-ethoxy}-phenoxy)-acetic acid | 465.1, 467.2 |
| 59 | N-[(5-Bromo-2-{2-[4-(4-fluoro-benzyl)-(2R,5S)-2,5-dimethyl-piperazin-1-yl]-2-oxo-ethoxy}-phenoxy)-acetyl]-methanesulfonamide | 586.0, 588.0 |
| 60 | N-[(5-Bromo-2-{2-[4-(4-fluoro-benzyl)-(2R)-2-methyl-piperazin-1-yl]-2-oxo-ethoxy}-phenoxy)-acetyl]-methanesulfonamide | 572.0, 574.0 |
| 61 | N-[(5-Chloro-2-{2-[(2R)-2-ethyl-4-(4-fluoro-benzyl)-piperazin-1-yl]-2-oxo-ethoxy)-phenoxy)-acetyl]-methanesulfonamide | 542.1 |
| 62 | 2-(5-Chloro-2-{2-[4-(4-fluoro-benzyl)-(2R,5S)-2,5-dimethyl-piperazin-1-yl]-2-oxo-ethoxy}-phenoxy)-2-methyl-propionic acid | 493.2, 495.2 |
| 63 | 4-(5-Chloro-2-{2-[4-(4-fluoro-benzyl)-(2R,5S)-2,5-dimethyl-piperazin-1-yl]-2-oxo-ethoxy}-phenoxy)-butyric acid | 493.2, 495.2 |
| 64 | 6-(5-Chloro-2-{2-[4-(4-fluoro-benzyl)-(2R,5S)-2,5-dimethyl-piperazin-1-yl]-2-oxo-ethoxy}-phenoxy)-pyridine-2-carboxylic acid | 528.2, 530.2 |
| 65 | (5-Chloro-2-{2-[4-(4-fluoro-benzyl)-(2R,5S)-2,5-dimethyl-piperazin-1-yl]-2-oxo-ethoxy}-phenoxy)-difluoro-acetic acid | 501.4, 503.5 |
| 66 | (2R)-2-Amino-4-(5-chloro-2-{2-[4-(4-fluoro-benzyl)-(2R,5S)-2,5-dimethyl-piperazin-1-yl]-2-oxo-ethoxy}-phenoxy)-butyric acid | 508.4 |
| 67 | (5-Chloro-2-{2-[4-(4-fluoro-benzyl)-(2R)-2-methyl-piperazin-1-yl]-2-oxo-ethoxy}-phenoxy)-difluoro-acetic acid | 487.4, 489.3 |
| 68 | 4-(5-Chloro-2-{2-[4-(4-fluoro-benzyl)-(2R)-2-methyl-piperazin-1-yl]-2-oxo-ethoxy}-phenoxy)-butyric acid | 479.5, 481.5 |
| 69 | 2-(5-Chloro-2-{2-[4-(4-fluoro-benzyl)-(2R)-2-methyl-piperazin-1-yl]-2-oxo-ethoxy}-phenoxy)-2-methyl-propionic acid | 479.5, 481.5 |
| 70 | (2S)-2-Amino-4-(5-chloro-2-{2-[4-(4-fluoro-benzyl)-(2R,5S)-2,5-dimethyl-piperazin-1-yl]-2-oxo-ethoxy}-phenoxy)-butyric acid | 508.5 |
| 71 | 2-(5-Bromo-2-{2-[4-(4-fluoro-benzyl)-(2R,5S)-2,5-dimethyl-piperazin-1-yl]-2-oxo-ethoxy}-phenoxy)-2-methyl-propionic acid | 537.2, 539.2 |
| 72 | (5-Bromo-2-{2-[4-(4-fluoro-benzyl)-(2R,5S)-2,5-dimethyl-piperazin-1-yl]-2-oxo-ethoxy}-phenoxy)-difluoro-acetic acid | 545.1, 547.1 |
| 73 | 2-(5-Bromo-2-{2-[4-(4-fluoro-benzyl)-(2R)-2-methyl-piperazin-1-yl]-2-oxo-ethoxy}-phenoxy)-2-methyl-propionic acid | 523.2, 525.2 |
| 74 | (5-Bromo-2-{2-[4-(4-fluoro-benzyl)-(2R)-2-methyl-piperazin-1-yl]-2-oxo-ethoxy}-phenoxy)-difluoro-acetic acid | 531.1, 533.1 |
| 75 | (2S)-2-Amino-4-(5-chloro-2-{2-[4-(4-fluoro-benzyl)-(2R)-2-methyl-piperazin-1-yl]-2-oxo-ethoxy}-phenoxy)-butyric acid | 494.4 |
| 76 | (2S)-2-Amino-4-(5-bromo-2-{2-[4-(4-fluoro-benzyl)-(2R,5S)-2,5-dimethyl-piperazin-1-yl]-2-oxo-ethoxy}-phenoxy)-butyric acid | 550.2, 552.2 |
| 77 | 4-(5-Chloro-2-{2-[4-(4-fluoro-bnzyl)-(2R,5S)-2,5-dimethyl-piperazin-1-yl]-2-oxo-ethoxy}-phenoxy)-pyridine-2-carboxylic acid | 521.5 |
| 78 | N-[(2R)-2-Amino-4-(5-chloro-2-{2-[4-(4-fluoro-benzyl)-(2R,5S),-2,5-dimethyl-piperazin-1-yl]-2-oxo-ethoxy}-phenoxy)-butyryl]-methanesulfonamide | 585.5, 587.5 |
| 79 | 2-(5-Chloro-2-{2-[4-(4-fluoro-benzyl)-(2R,5S)-2,5-dimethyl-piperazin-1-yl]-2-oxo-ethoxy}-phenoxymethyl)-thiazole-4-carboxylic acid | 548.2, 550.3 |
| 80 | 3-(5-Chloro-2-{2-[4-(4-fluoro-benzyl)-(2R,5S)-2,5-dimethyl-piperazin-1-yl]-2-oxo-ethoxy}-phenoxymethyl)-furan-2-carboxylic acid | 531.2, 533.2 |
| 81 | 5-(5-Chloro-2-{2-[4-(4-fluoro-benzyl)-(2R,5S)-2,5-dimethyl-piperazin-1-yl]-2-oxo-ethoxy}-phenoxymethyl)-furan-2-carboxylic acid | 531.3, 533.3 |
| 82 | 3-(5-Chloro-2-{2-[4-(4-fluoro-benzyl)-(2R,5S)-2,5-dimethyl-piperazin-1-yl]-2-oxo-ethoxy}-phenoxymethyl)-thiophene-2-carboxylic acid | 547.2, 549.3 |
| 83 | 2-(5-Chloro-2-{2-[4-(4-fluoro-benzyl)-(2R,5S)-2,5-dimethyl-piperain-1-yl]-2-oxo-ethoxy}-phenoxymethyl)-furan-3-carboxylic acid | 531.2, 533.3 |
| 84 | 5-(5-Chloro-2-{2-[4-(4-fluoro-benzyl)-(2R,5S)-2,5-dimethyl-piperazin-1-yl]-2-oxo-ethoxy}-phenoxymethyl)-thiophene-2-carboxylic acid | 547.2, 549.2 |
| 85 | 3-(5-Chloro-2-{2-[4-(4-fluoro-benzyl)-(2R)-2-methyl-piperazin-1-yl]-2-oxo-ethoxy}-phenoxymethyl)-furan-2-carboxylic acid | 517.1, 519.2 |
| 86 | 3-(5-Bromo-2-{2-[4-(4-fluoro-benzyl)-2-methyl-piperazin-1-yl]-2-oxo-ethoxy}-phenoxymethyl)-furan-2-carboxylic acid | 561.1, 563.1 |
| 87 | 5-(5-Chloro-2-{2-[4-(4-fluoro-benzyl)-(2R,5S)-2,5-dimethyl-piperazin-1-yl]-2-oxo-ethoxy}-phenoxy)-5-(2-methoxy-ethyl)-pyrimidine-2,4,6-trione | 591.1, 593.3 |
| 88 | 5-(5-Chloro-2-{2-[4-(4-fluoro-benzyl)-(2R,5S)-2,5-dimethyl-piperazin-1-yl]-2-oxo-ethoxy}-phenoxy)-5-methyl-pyrimidine-2,4,6-trione | 547.0 |

TABLE 1-continued

Example compounds prepared

| Example | Name | LRMS |
|---|---|---|
| 89 | 5-(5-Chloro-2-{2-[4-(4-fluoro-benzyl)-(2R,5S)-2,5-dimethyl-piperazin-1-yl]-2-oxo-ethoxy}-phenoxy)-5-ethyl-pyrimidine-2,4,6-trione | 561.0 |
| 90 | (2S)-2-(5-Chloro-2-{2-[4-(4-fluoro-benzyl)-(2R,5S)-2,5-dimethyl-piperazin-1-yl]-2-oxo-ethoxy}-phenoxy)-propionic acid | 479.2, 481.2 |
| 91 | (2R)-2-(5-Chloro-2-{2-[4-(4-fluoro-benzyl)-(2R)-2-methyl-piperazin-1-yl]-2-oxo-ethoxy}-phenoxy)-propionic acid | 465.2, 467.2 |
| 92 | (2S)-2-(5-Chloro-2-{2-[4-(4-fluoro-benzyl)-(2R)-2-methyl-piperazin-1-yl]-2-oxo-ethoxy}-phenoxy)-propionic acid | 465.2, 467.3 |
| 93 | (4S)-2-(5-Chloro-2-{2-[4-(4-fluoro-benzyl)-(2R,5S)-2,5-dimethyl-piperazin-1-yl]-2-oxo-ethoxy}-phenoxy)-pyrrolidine-2-carboxylic acid | 520.4 |
| 94 | 3-(5-Chloro-2-{2-[4-(4-fluoro-benzyl)-(2R,5S)-2,5-dimethyl-piperazin-1-yl]-2-oxo-ethoxy}-phenoxy)-2,2-dimethyl-propionic acid | 507.5, 509.7 |
| 95 | (4S)-4-(5-Bromo-2-{2-[4-(4-fluoro-benzyl)-(2R,5S)-2,5-dimethyl-piperazin-1-yl]-2-oxo-ethoxy}-phenoxy)-pyrrolidine-(2S)-2-carboxylic acid | 564.4, 566.4 |
| 96 | (4S)-4-(5-Bromo-2-{2-[4-(4-fluoro-benzyl)-(2R)-2-methyl-piperazin-1-yl]-2-oxo-ethoxy}-phenoxy)-pyrrolidine-(2S)-2-carboxylic acid | 550.4, 552.4 |
| 97 | (4S)-4-(5-Chloro-2-{2-[4-(4-fluoro-benzyl)-(2R,5S)-2,5-dimethyl-piperazin-1-yl]-2-oxo-ethoxy}-phenoxy)-pyrrolidine-(2S)-2-carboxylic acid | 520.4 |
| 98 | N-[(4S)-4-(5-Chloro-2-{2-[4-(4-fluoro-benzyl)-(2R,5S)-2,5-dimethyl-piperazin-1-yl]-2-oxo-ethoxy}-phenoxy)-pyrrolidine-(2S)-2-carbonyl]-methanesulfonamide | 597.5 |
| 99 | [3-(5-Chloro-2-{2-[4-(4-fluoro-benzyl)-(2R,5S)-2,5-dimethyl-piperazin-1-yl]-2-oxo-ethoxy}-phenyl)-ureido]-acetic acid | 507.2 |
| 100 | 3-[3-(5-Chloro-2-{2-[4-(4-fluoro-benzyl)-(2R,5S)-2,5-dimethyl-piperazin-1-yl]-2-oxo-ethoxy}-phenyl)-ureido]-propionic acid | 521.2 |
| 101 | 3-[3-(4-Chloro-2-{2-[4-(4-fluoro-benzyl)-(2R,5S)-2,5-dimethyl-piperazin-1-yl]-2-oxo-ethoxy}-phenyl)-ureido]-propionic acid | 521.2 |
| 102 | [3-(4-Chloro-2-{2-[4-(4-fluoro-benzyl)-(2R,5S)-2,5-dimethyl-piperazin-1-yl]-2-oxo-ethoxy}-phenyl)-ureido]-acetic acid | 507.2 |
| 103 | 1-(5-Chloro-2-{2-[4-(4-fluoro-benzyl)-(2R,5S)-2,5-dimethyl-piperazin-1-yl]-2-oxo-ethoxy}-phenyl)-3-(methylsulfonyl)-urea | 527.2 |
| 104 | (5-Chloro-2-{2-[4-(4-fluoro-benzyl)-(2R,5S)-2,5-dimethyl-piperazin-1-yl]-2-oxo-ethoxy}-benzylsulfamoyl)-acetic acid | 542.3 |
| 105 | 1-(5-Chloro-2-{2-[4-(4-fluoro-benzyl)-(2R,5S)-2,5-dimethyl-piperazin-1-yl]-2-oxo-ethoxy}-benzyl)-3-(methylsulfonyl)-urea | 541.2 |
| 106 | 1-[(5-chloro-2-{2-[4-(4-fluoro-benzyl)-(2R,5S)-2,5-dimethyl-piperazin-1-yl]-2-oxo-ethoxy}-benzyl)]-3-(2-methylbenzoyl)sulfamide | 617.2 |
| 107 | (5-Bromo-2-{2-[4-(4-fluoro-benzyl)-(2R,5S)-2,5-dimethyl-piperazin-1-yl]-2-oxo-ethoxy}-benzylideneaminooxy)-acetic acid | 538.2 |
| 108 | [1-(5-Chloro-2-{2-[4-(4-fluoro-benzyl)-(2R,5S)-2,5-dimethyl-piperazin-1-yl]-2-oxo-ethoxy}-phenyl)-ethylideneaminooxy]-acetic acid | 506.2 |
| 109 | [1-(5-Bromo-2-{2-[4-(4-fluoro-benzyl)-(2R,5S)-2,5-dimethyl-piperazin-1-yl]-2-oxo-ethoxy}-phenyl)-ethylideneaminooxy]-acetic acid | 552.1 |
| 110 | [(5-Chloro-2-{2-[4-(4-fluoro-benzyl)-(2R,5S)-2,5-dimethyl-piperazin-1-yl]-2-oxo-ethoxy}-phenyl)-phenyl-methyleneaminooxy]-acetic acid | 568.0 |
| 111 | (2-{2-[4-(4-Fluoro-benzyl)-(2R,5S)-2,5-dimethyl-piperazin-1-yl]-2-oxo-ethoxy}-5-methyl-benzylideneaminooxy)-acetic acid | 471.5 |
| 112 | (2S)-2-(5-Chloro-2-{2-[4-(4-fluoro-benzyl)-(2R,5S)-2,5-dimethyl-piperazin-1-yl]-2-oxo-ethoxy}-benzyloxy)-propionic acid | 493 |
| 113 | (2R)-2-(5-Chloro-2-{2-[4-(4-fluoro-benzyl)-(2R,5S)-2,5-dimethyl-piperazin-1-yl]-2-oxo-ethoxy]-benzyloxy)-propionic acid | 493 |
| 114 | 2-(5-Chloro-2-{2-[4-(4-fluoro-benzyl)-(2R,5S)-2,5-dimethyl-piperazin-1-yl]-2-oxo-ethoxy}-benzyloxy)-2-methyl-propionic acid | 507.6 |
| 115 | methylsulfonyl-carbamic acid 5-chloro-2-{2-[4-(4-fluoro-benzyl)-(2R,5S)-2,5-dimethyl-piperazin-1-yl]-2-oxo-ethoxy}-benzyl ester | 540.3, 542.2 |
| 116 | N-(5-Chloro-2-{2-[4-(4-fluoro-benzyl)-(2R,5S)-2,5-dimethyl-piperazin-1-yl]-2-oxo-ethoxy}-benzoyl)-methanesulfonamide | 512.2 |
| 117 | N-(5-Chloro-2-{2-[4-(4-fluoro-benzyl)-(2R)-2-methyl-piperazin-1-yl]-2-oxo-ethoxy}-benzoyl)-methanesulfonamide | 498.1 |
| 118 | N-[(5-Bromo-2-{2-[4-(4-fluoro-benzyl)-(2R,5S)-2,5-dimethyl-piperazin-1-yl]-2-oxo-ethoxy}-phenyl)acetyl]-methanesulfonamide | 570.0, 572.1 |
| 119 | N-[(5-Chloro-2-{2-[4-(4-fluoro-benzyl)-piperazin-1-yl]-2-oxo-ethoxy}-phenyl)-acetyl]-methanesulfonamide | 498.1 |
| 120 | N-[(5-Chloro-2-{2-[4-(4-fluoro-benzyl)-(2R,5S)-2,5-dimethyl-piperazin-1-yl]-2-oxo-ethoxy}-phenyl)-acetyl]-C,C,C-trifluoro-methanesulfonamide | 579.3 |
| 121 | N-[(5-Chloro-2-{2-[4-(4-fluoro-benzyl)-(2R,5S)-2,5-dimethyl-piperazin-1-yl]-2-oxo-ethoxy}-phenyl)-acetyl]-4-fluoro-benzenesulfonamide | 607.1 |

TABLE 1-continued

Example compounds prepared

| Example | Name | LRMS |
|---|---|---|
| 122 | N-[(2-{2-[4-(4-Fluoro-benzyl)-(2R,5S)-2,5-dimethyl-piperazin-1-yl]-2-oxo-ethoxy}-4-methoxy-phenyl)-acetyl]-methanesulfonamide | 522.3 |
| 123 | N-[(5-Chloro-2-{2-[4-(4-fluoro-benzyl)-(2R,5S)-2,5-dimethyl-piperazin-1-yl]-2-oxo-ethoxy}-phenyl)-acetyl]-benzenesulfonamide | 588.4 |
| 124 | N-[(5-Chloro-2-{2-[4-(4-fluoro-benzyl)-(2R,5S)-2,5-dimethyl-piperazin-1-yl]-2-oxo-ethoxy}-phenyl)-acetyl]-2-methyl-benzenesulfonamide | 602.4 |
| 125 | Ethanesulfonic acid [(5-chloro-2-{2-[4-(4-fluoro-benzyl)-(2R,5S)-2,5-dimethyl-piperazin-1-yl]-2-oxo-ethoxy}-phenyl)-acetyl]-amide | 540.3 |
| 126 | 3,5-Dimethyl-isoxazole-4-sulfonic acid [(5-chloro-2-{2-[4-(4-fluoro-benzyl)-(2R,5S)-2,5-dimethyl-piperazin-1-yl]-2-oxo-ethoxy}-phenyl)-acetyl]-amide | 607.2 |
| 127 | N-[(5-Bromo-2-{2-[4-(4-fluoro-benzyl)-piperazin-1-yl]-2-oxo-ethoxy}-phenyl)-acetyl]-methanesulfonamide | 542.1, 544.1 |
| 128 | N-[(5-Chloro-2-{2-[4-(4-fluoro-benzyl)-(2R)-2-methyl-piperazin-1-yl]-2-oxo-ethoxy}-phenyl)-acetyl]-methanesulfonamide | 512.0 |
| 129 | N-[(5-Bromo-2-{2-[4-(4-fluoro-benzyl)-(2R)-2-methyl-piperazin-1-yl]-2-oxo-ethoxy}-phenyl)-acetyl]-methanesulfonamide | 556.2, 558.1 |
| 130 | N-[(5-Chloro-2-{2-[4-(4-fluoro-benzyl)-(2R,5S)-2,5-dimethyl-piperazin-1-yl]-2-oxo-ethoxy}-phenyl)-acetyl]-4-methoxy-benzenesulfonamide | 618.2 |
| 131 | 2-Chloro-N-[(5-chloro-2-{2-[4-(4-fluoro-benzyl)-(2R,5S)-2,5-dimethyl-piperazin-1-yl]-2-oxo-ethoxy}-phenyl)-acetyl]-benzenesulfonamide | 622.1 |
| 132 | N-[(5-Chloro-2-{2-[4-(4-fluoro-benzyl)-(2R,5S)-2,5-dimethyl-piperazin-1-yl]-2-oxo-ethoxy}-phenyl)-acetyl]-2-fluoro-benzenesulfonamide | 606.1 |
| 133 | N-[(5-Chloro-2-{2-[4-(4-fluoro-benzyl)-(2R,5S)-2,5-dimethyl-piperazin-1-yl]-2-oxo-ethoxy}-phenyl)-acetyl]-4-methyl-benzenesulfonamide | 602.2 |
| 134 | Propane-2-sulfonic acid [(5-chloro-2-{2-[4-(4-fluoro-benzyl)-(2R,5S)-2,5-dimethyl-piperazin-1-yl]-2-oxo-ethoxy}-phenyl)-acetyl]-amide | 544.2 |
| 135 | Propane-1-sulfonic acid [(5-chloro-2-{2-[4-(4-fluoro-benzyl)-(2R,5S)-2,5-dimethyl-piperazin-1-yl]-2-oxo-ethoxy}-phenyl)-acetyl]-amide | 544.2 |
| 136 | [(4-Chloro-2-{2-[4-(4-fluoro-benzyl)-(2R,5S)-2,5-dimethyl-piperazin-1-yl]-2-oxo-ethoxy}-phenyl)]-N-cyanoacetamide | 473.2 |
| 137 | N-[(4-Chloro-2-{2-[4-(4-fluoro-benzyl)-(2R,5S)-2,5-dimethyl-piperazin-1-yl]-2-oxo-ethoxy}-phenyl)-acetyl]-methanesulfonamide | 526.2 |
| 138 | N-[(4-Chloro-2-{2-[4-(4-fluoro-benzyl)-(2R)-2-methyl-piperazin-1-yl]-2-oxo-ethoxy}-phenyl)-acetyl]-methanesulfonamide | 512.2, 510.3 |
| 139 | N-[(5-Chloro-2-{2-[4-(3,4-difluoro-benzyl)-(2R,5S)-2,5-dimethyl-piperazin-1-yl]-2-oxo-ethoxy}-phenyl)-acetyl]-methanesulfonamide | 544.2 |
| 140 | N-[(5-Chloro-2-{2-[4-(4-chloro-benzyl)-(2R,5S)-2,5-dimethyl-piperazin-1-yl]-2-oxo-ethoxy}-phenyl)-acetyl]-methanesulfonamide | 542.3 |
| 141 | N-[(2-{2-[4-(4-Fluoro-benzyl)-(2R,5S)-2,5-dimethyl-piperazin-1-yl]-2-oxo-ethoxy}-phenyl)-acetyl]-methanesulfonamide | 492.2 |
| 142 | N-[(5-Chloro-2-{2-[4-(4-fluoro-benzyl)-(2R,5S)-2,5-dimethyl-piperazin-1-yl]-2-oxo-ethoxy}-phenyl)-acetyl]-C-phenyl-methanesulfonamide | 602.1 |
| 143 | N-[3-(2-{2-[4-(4-Fluoro-benzyl)-(2R,5S)-2,5-dimethyl-piperazin-1-yl]-2-oxo-ethoxy}-phenyl)-propionyl]-methanesulfonamide | 506.5 |
| 144 | N-[(5-Chloro-2-{2-[4-(4-chloro-benzyl)-(2R)-2-methyl-piperazin-1-yl]-2-oxo-ethoxy}-phenyl)-acetyl]-methanesulfonamide | 528.1 |
| 145 | N-[(5-Chloro-2-{2-[4-(3,4-difluoro-benzyl)-(2R)-2-methyl-piperazin-1-yl]-2-oxo-ethoxy}-phenyl)-acetyl]-methansulfonamide | 530.2 |
| 146 | N-[(5-Chloro-2-{2-[(2R)-2-ethyl-4-(4-fluoro-benzyl)-piperazin-1-yl]-2-oxo-ethoxy}-phenyl)-acetyl]-methansulfonamide | 526.2, 528.2 |
| 147 | N-[(5-Bromo-2-{(2R)-2-2-ethyl-4-(4-fluoro-benzyl)-piperazin-1-yl]-2-oxo-ethoxy}-phenyl)-acetyl]-methanesulfonamide | 568.2, 570.2 |
| 148 | N-[(2-{2-[(2R)-2-Ethyl-4-(4-fluoro-benzyl)-piperazin-1-yl]-2-oxo-ethoxy}-5-methyl-phenyl)-acetyl]-methanesulfonamide | 506.2 |
| 149 | N-[3-(5-Chloro-2-{2-[4-(4-fluoro-benzyl)-(2R)-2-methyl-piperazin-1-yl]-2-oxo-ethoxy}-phenyl)-propionyl]-methanesulfonamide | 526.1 |
| 150 | N-[3-(2-{2-[4-(4-Fluoro-benzyl)-(2R)-2-methyl-piperazin-1-yl]-2-oxo-ethoxy}-5-methyl-phenyl)-propionyl]-methanesulfonamide | 506.2 |
| 151 | N-[3-(2-{2-[4-(4-Fluoro-benzyl)-(2R,5S)-2,5-dimethyl-piperazin-1-yl]-2-oxo-ethopxy}-5-methylphenyl)-propionyl]-methanesulfonamide | 520.2 |
| 152 | N-[3-(5-Bromo-2-{2-[4-(4-fluoro-benzyl)-(2R)-2-methylpiperazin-1-yl]-2-oxo-ethoxy}-phenyl)-propionyl]-methanesulfonamide | 570.1, 572.1 |
| 153 | N-[3-(5-Bromo-2-{2-[4-(4-fluoro-benzyl)-(2R,5S)-2,5-dimethyl-piperazin-1-yl]-2-oxo-ethoxy}-phenyl)-propionyl]-methanesulfonamide | 584.1, 586.1 |
| 154 | N-[3-(3-{2-[(2R)-2-Ethyl-4-(4-fluoro-benzyl)-piperazin-1-yl]-2-oxo-ethoxy}-5-methylphenyl)-propionyl]-methansulfonamide | 520.2 |

TABLE 1-continued

Example compounds prepared

| Example | Name | LRMS |
|---|---|---|
| 155 | (5-Chloro-2-{2-[4-(4-fluoro-benzyl)-(2R,5S)-2,5-dimethyl-piperazin-1-yl]-2-oxo-ethoxy}-benzylamino)-acetic acid | 478.5 |
| 156 | 3-(5-Bromo-2-{2-[4-(4-fluoro-benzyl)-(2R,5S)-2,5-dimethyl-piperazin-1-yl]-2-oxo-ethoxy}-phenyl)-acrylic acid | 505.1 |
| 157 | 3-(2-{2-[4-(4-Fluoro-benzyl)-(2R,5S)-2,5-dimethyl-piperazin-1-yl]-2-oxo-ethoxy}-5-methyl-phenyl)-acrylic acid | 441.4 |
| 158 | 3-(5-Chloro-2-{2-[4-(4-fluoro-benzyl)-(2R)-2-methyl-piperazin-1-yl]-2-oxo-ethoxy}-phenyl)-acetic acid | 446.1 |
| 159 | 3-(5-Bromo-2-{2-[4-(4-fluoro-benzyl)-(2R)-2-methyl-piperazin-1-yl]-2-oxo-ethoxy}-phenyl)-acrylic acid | 490.1 |
| 160 | 5-Chloro-2-{2-[4-(4-fluoro-benzyl)-(2R,5S)-2,5-dimethyl-piperazin-1-yl]-2-oxo-ethoxy}-N-(ethylamino)carbonyl]-benzenesulfonamide | 541.2 |
| 161 | 5-Chloro-2-{2-[4-(4-fluoro-benzyl)-(2R,5S)-2,5-dimethyl-piperazin-1-yl]-2-oxo-ethoxy}-N-(phenylamino)carbonyl]-benzenesulfonamide | 589.1 |
| 162 | 5-Chloro-2-{2-[4-(4-fluoro-benzyl)-(2R,5S)-2,5-dimethyl-piperazin-1-yl]-2-oxo-ethoxy}-N-(2-methyl phenylamino)carbonyl]-benzenesulfonamide | 603.1 |
| 163 | 5-Chloro-2-{2-[4-(4-fluoro-benzyl)-(2R,5S)-2,5-dimethyl-piperazin-1-yl]-2-oxo-ethoxy}-N-(4-fluoro-phenylamino)carbonyl]-benzenesulfonamide | 607.1 |
| 164 | 5-Chloro-2-{2-[4-(4-fluoro-benzyl)-(2R,5S)-2,5-dimethyl-piperazin-1-yl]-2-oxo-ethoxy}-N-(methoxycarbonyl)-benzenesulfonamide | 470.3 |
| 165 | 5-Chloro-2-{2-[4-(4-fluoro-benzyl)-(2R,5S)-2,5-dimethyl-piperazin-1-yl]-2-oxo-ethoxy}-N-(ethoxycarbonyl)-benzenesulfonamide | 470.3 |
| 166 | 5-Chloro-2-{2-[4-(4-fluoro-benzyl)-(2R,5S)-2,5-dimethyl-piperazin-1-yl]-2-oxo-ethoxy}-N-isobutyryl-benzenesulfonamide | 540.4 |
| 167 | 5-Chloro-N-cyclopropanecarbonyl-2-{2-[4-(4-fluoro-benzyl)-(2R,5S)-2,5-dimethyl-piperazin-1-yl]-2-oxo-ethoxy}-benzenesulfonamide | 538.4 |
| 168 | N-Acetyl-5-chloro-2-{2-[4-(4-fluoro-benzyl)-(2R,5S)-2,5-dimethyl-piperazin-1-yl]-2-oxo-ethoxy}-benzenesulfonamide | 512.2 |
| 169 | 5-Chloro-N-cylopropanecarbonyl-2-{2-[4-(4-fluoro-benzyl)-(2R,5S)-2,5-dimethyl-piperazin-1-yl]-2-oxo-ethoxy}-benzenesulfonamide | 566.2 |
| 170 | (5-Chloro-2-{2-[4-(4-fluoro-benzyl)-(2R,5S)-2,5-dimethyl-piperazin-1-yl]-2-oxo-ethoxy}-benzenesulfonamino)-oxo-acetic acid | 542.3 |
| 171 | 5-Chloro-2-{2-[4-(4-fluoro-benzyl)-(2R,5S)-2,5-dimethyl-piperazin-1-yl]-2-oxo-ethoxy}-N-hydroxyacetyl-benzenesulfonamide | 528.2 |
| 172 | N-Acetyl-C-(5-chloro-2-{2-[4-(4-fluoro-benzyl)-(2R)-2-methyl-piperazin-1-yl]-2-oxo-ethoxy}-phenyl)-methanesulfonamide | 510.2, 512.1 |
| 173 | N-Acetyl-C-(5-chloro-2-{2-[4-(3,4-difluoro-benzyl)-(2R)-2-methyl-piperazin-1-yl]-2-oxo-ethoxy}-phenyl)-methanesulfonamide | 530.2 |
| 174 | N-Acetyl-C-(5-chloro-2-{2-[4-(4-chloro-benzyl)-(2R)-2-methyl-piperazin-1-yl]-2-oxo-ethoxy}-phenyl)-methanesulfonamide | 528.2 |
| 175 | (5-Chloro-2-{2-[3,4-difluoro-benzyl)-(2R)-2-methyl-piperazin-1-yl]-2-oxo-ethoxy}-phenyl)-methanesulfonamide | 488.1 |
| 176 | (5-Chloro-2-{2-[4-(4-chloro-benzyl)-(2R)-2-methyl-piperazin-1-yl]-2-oxo-ethoxy}-phenyl)-methanesulfonamide | 486.1 |
| 177 | (5-Chloro-2-{2-[4-(4-fluoro-benzyl)-(2R)-2-methyl-piperazin-1-yl]-2-oxo-ethoxy}-phenyl)-methanesulfonamide | 470.1 |
| 178 | C-(5-Chloro-2-{2-[4-(3,4-difluoro-benzyl)-(2R)-2-methyl-piperazin-1-yl]-2-oxo-ethoxy}-phenyl)-N-cyclopropanecarbonyl-methanesulfonamide | 556.2 |
| 179 | C-(5-Chloro-2-{2-[4-(4-chloro-benzyl)-(2R)-2-methyl-piperazin-1-yl]-2-oxo-ethoxy}-phenyl)-N-trifluoroacetyl-methanesulfonamide | 582.1 |
| 180 | (5-Chloro-2-{2-[(2R)-2-ethyl-4-(4-fluoro-benzyl)-piperazin-1-yl]-2-oxo-ethoxy}-phenyl)-methanesulfonamide | 484.1, 486.1 |
| 181 | (5-Bromo-2-{2-[4-(4-fluoro-benzyl)-(2R,5S)-2,5-dimethyl-piperazin-1-yl]-2-oxo-ethoxy}-phenyl)-methanesulfonamide | 528.1, 530.1 |
| 182 | (5-Bromo-2-{2-[4-(4-fluoro-benzyl)-(2R)-2-methyl-piperazin-1-yl]-2-oxo-ethoxy}-phenyl)-methanesulfonamide | 514.1, 516.1 |
| 183 | (5-Bromo-2-{2-[(2R)-2-ethyl-4-(4-fluoro-benzyl)-piperazin-1-yl]-2-oxo-ethoxy}-phenyl)-methanesulfonamide | 528.1, 530.1 |
| 184 | N-Acetyl-C-(5-chloro-2-{2-[(2R)-2-ethyl-4-(4-fluoro-benzyl)-piperazin-1-yl]-2-oxo-ethoxy}-phenyl)-methanesulfonamide | 526.1, 528.1 |
| 185 | N-Acetyl-C-(5-bromo-2-{2-[4-(4-fluoro-benzyl)-(2R,5S)-2,5-dimethyl-piperazin-1-yl]-2-oxo-ethoxy}-phenyl)-methanesulfonamide | 570.1, 572.1 |
| 186 | N-Acetyl-C-(5-bromo-2-{2-[4-(4-fluoro-benzyl)-(2R)-2-methyl-piperazin-1-yl]-2-oxo-ethoxy}-phenyl)-methanesulfonamide | 556.0, 558.0 |
| 187 | N-Acetyl-C-(5-bromo-2-{2-[(2R)-2-ethyl-4-(4-fluoro-benzyl)-piperazin-1-yl]-2-oxo-ethoxy}-phenyl)-methanesulfonamide | 570.1, 572.1 |
| 188 | C-(5-Chloro-2-{2-[4-(4-fluoro-benzyl)-(2R,5S)-2,5-dimethyl-piperazin-1-yl]-2-oxo-ethoxy}-phenyl)-N-(2,2-dimethyl-propionyl)-methanesulfonamide | 566.3, 568.2 |
| 189 | (5-Chloro-2-{2-[4-(3,4-difluoro-benzyl)-(2R,5S)-2,5-dimethyl-piperazin-1-yl]-2-oxo-ethoxy}-phenyl)-methanesulfonamide | 502.4 |

TABLE 1-continued

Example compounds prepared

| Example | Name | LRMS |
|---|---|---|
| 190 | (5-Chloro-2-{2-[4-(4-chloro-benzyl)-(2R,5S)-2,5-dimethyl-piperazin-1-yl]-2-oxo-ethoxy}-phenyl)-methanesulfonamide | 501.8 |
| 191 | N-Acetyl-C-(5-chloro-2-{2-[4-(4-chloro-benzyl)-(2R,5S)-2,5-dimethyl-piperazin-1-yl]-2-oxo-ethoxy}-phenyl)-methanesulfonamide | 542.3 |
| 192 | C-(5-Chloro-2-{2-[4-(4-chloro-benzyl)-(2R,5S)-2,5-dimethyl-piperazin-1-yl]-2-oxo-ethoxy}-phenyl)-N-cyclopropanecarbonyl-methanesulfonamide | 568.3 |
| 193 | C-(5-Chloro-2-{2-[4-(4-chloro-benzyl)-(2R,5S)-2,5-dimethyl-piperazin-1-yl]-2-oxo-ethoxy}-phenyl)-N-trifluoroacetyl-methanesulfonamide | 596.2 |
| 194 | N-Acetyl-C-(5-chloro-2-{2-[4-(3,4-difluoro-benzyl)-(2R,5S)-2,5-dimethyl-piperazin-1-yl]-2-oxo-ethoxy}-phenyl)-methanesulfonamide | 544.3 |
| 195 | C-(5-Chloro-2-{2-[4-(3,4-difluoro-benzyl)-(2R,5S)-2,5-dimethyl-piperazin-1-yl]-2-oxo-ethoxy}-phenyl)-N-cyclopropanecarbonyl-methanesulfonamide | 570.3 |
| 196 | (5-Bromo-2-{2-[4-(4-chloro-benzyl)-(2R)-2-methyl-piperazin-1-yl]-2-oxo-ethoxy}phenyl)methanesulfonamide | 530.0 |
| 197 | N-Acetyl-C-(5-bromo-2-{2-[4-(4-chloro-benzyl)-(2R)-2-methyl-piperazin-1-yl]-2-oxo-ethoxy}-phenyl)-methanesulfonamide | 573.9 |
| 198 | N-Acetyl-C-(5-bromo-2-{2-[4-(4-chloro-benzyl)-(2R,5S)-2,5-dimethyl-piperazin-1-yl]-2-oxo-ethoxy}-phenyl)-methanesulfonamide | 586.2 |
| 199 | (5-Bromo-2-{2-[4-(4-chloro-benzyl)-(2R,5S)-2,5-dimethyl-piperazin-1-yl]-2-oxo-ethoxy}-phenyl)-methanesulfonamide | 544.2 |
| 200 | (5-Chloro-2-{2-[4-(4-fluoro-benzyl)-(2R,5S)-2,5-dimethyl-piperazin-1-yl]-2-oxo-ethoxy}-phenylmethanesulfonamino)-oxo-acetic acid | 556.3, 554.4 |
| 201 | C-(5-Chloro-2-{2-[4-(4-fluoro-benzyl)-(2R,5S)-2,5-dimethyl-piperazin-1-yl]-2-oxo-ethoxy}-phenyl)-N-(1-hydroxy-cyclopropanecarbonyl)-methanesulfonamide | 568.4, 566.3 |
| 202 | (5-Chloro-2-{2-[4-(4-fluoro-benzyl)-(2R)-2-methyl-piperazin-1-yl]-2-oxo-ethoxy}-phenylmethanesulfonamino)-oxo-acetic acid | 542.3, 540.2 |
| 203 | C-(5-Chloro-2-{2-[4-(4-fluoro-benzyl)-(2R,5S)-2,5-dimethyl-piperazin-1-yl]-2-oxo-ethoxy}-phenyl)-N-methoxyacetyl-methanesulfonamide | 556.4, 554.3 |
| 204 | N-Acetyl-C-(2-{2-[4-(4-fluoro-benzyl)-(2R)-2-methyl-piperazin-1-yl]-2-oxo-ethoxy}-5-trifluoromethyl-phenyl)-methanesulfonamide | 546.2 |
| 205 | N-Acetyl-C-(2-{2-[4-(4-fluoro-benzyl)-(2R,5S)-2,5-dimethyl-piperazin-1-yl]-2-oxo-ethoxy}-5-trifluoromethyl-phenyl)-methanesulfonamide | 560.2 |
| 206 | (2-{2-[4-(4-Fluoro-benzyl)-(2R,5S)-,2,5-dimethyl-piperazin-1-yl]-2-oxo-ethoxy}-5-trifluoromethyl-phenyl)-methanesulfonamide | 518.2 |
| 207 | (2-{2-[4-(4-Fluoro-benzyl)-(2R)-2-methyl-piperazin-1-yl]-2-oxo-ethoxy}-5-trifluoromethyl-phenyl)-methanesulfonamide | 504.1 |
| 208 | C-(5-Chloro-2-{2-[4-(4-fluoro-benzyl)-(2R,5S)-2,5-dimethyl-piperazin-1-yl]-2-oxo-ethoxy}-phenyl)-N-hydroxyacetyl-methanesulfonamide | 540.2, 542.4 |
| 209 | C-(5-Chloro-2-{2-[4-(4-fluoro-benzyl)-(2R,5S)-2,5-dimethyl-piperazin-1-yl]-2-oxo-ethoxy}-phenyl)-N-(3-hydroxy-3-methyl-butyryl)-methanesulfonamide | 582.3, 584.4 |
| 210 | C-(5-Chloro-2-{2-[4-(4-fluoro-benzyl)-(2R)-2-methyl-piperazin-1-yl]-2-oxo-ethoxy}-phenyl)-N-(2-hydroxy-2-methyl-propionyl)-methanesulfonamide | 554.2, 556.4 |
| 211 | C-(5-Chloro-2-{2-[4-(4-fluoro-benzyl)-(2R)-2-methyl-piperazin-1-yl]-2-oxo-ethoxy}-phenyl)-N-hydroxyacetyl-methanesulfonamide | 526.2, 528.3 |
| 212 | C-(5-Chloro-2-{2-[4-(4-chloro-benzyl)-(2R,5S)-2,5-dimethyl-piperazin-1-yl]-2-oxo-ethoxy}-phenyl)-N-(2-hydroxy-2-methyl-propionyl)-methanesulfonamide | 588.2 |
| 213 | C-(5-Chloro-2-{2-[4-(3,4-difluoro-benzyl)-2R,5S)-2,5-dimethyl-piperazin-1-yl]-2-oxo-ethoxy}-phenyl)-N-(2-hydroxy-2-methyl-propionyl)-methanesulfonamide | 586.2 |
| 214 | C-(5-Chloro-2-{2-[4-(4-chloro-benzyl)-(2R,5S)-2,5-dimethyl-piperazin-1-yl]-2-oxo-ethoxy}-phenyl)-N-hydroxyacetyl-methanesulfonamide | 558.1 |
| 215 | C-(5-Chloro-2-{2-[4-(3,4-dilfluoro-benzyl)-(2R,5S)-2,5-dimethyl-piperazin-1-yl]-2-oxo-ethoxy}-phenyl)-N-hydroxyacetyl-methanesulfonamide | 560.1 |
| 216 | C-(5-Chloro-2-{2-[4-(4-fluoro-benzyl)-(2R)-2-methyl-piperazin-1-yl]-2-oxo-ethoxy}-phenyl)-N-(3-hydroxy-3-methyl-butyryl)-methanesulfonamide | 570.2, 568.3 |
| 217 | C-(5-Chloro-2-{2-[4-(4-fluoro-benzyl)-(2R)-2-methyl-piperazin-1-yl]-2-oxo-ethoxy}-phenyl)-N-(1-hydroxy-cyclopropanecarbonyl)-methanesulfonamide | 554.4, 552.3 |
| 218 | C-(2-{2-[4-(4-Fluoro-benzyl)-(2R,5S)-2,5-dimethyl-piperazin-1-yl]-2-oxo-ethoxy}-5-trifluoromethyl-phenyl)-N-hydroxyacetyl-methanesulfonamide | 576.3 |

TABLE 1-continued

Example compounds prepared

| Example | Name | LRMS |
|---|---|---|
| 219 | C-(2-{2-[4-(4-Fluoro-benzyl)-(2R,5S)-2,5-dimethyl-piperazin-1-yl]-2-oxo-ethoxy}-5-trifluoromethyl-phenyl)-N-(2-hydroxy-2-methyl-propionyl)-methanesulfonamide | 604.1 |
| 220 | C-(2-{2-[4-(4-Fluoro-benzyl)-(2R)-2-methyl-piperazin-1-yl]-2-oxo-ethoxy)-2-trifluoromethyl-phenyl)-N-(2-hydroxy-2-methyl-propionyl)-methanesulfonamide | 590.2 |
| 221 | C-(5-Chloro-2-{2-[4-(4-fluoro-benzyl)-(2R)-2-methyl-piperazin-1-yl]-2-oxo-ethoxy}-phenyl)-N-(methoxycarbonyl)-methanesulfonamide | 526.2, 528.3 |
| 222 | C-(5-Chloro-2-{2-[4-(4-chloro-benzyl)-(2R,5S)-2,5-dimethyl-piperazin-1-yl]-2-oxo-ethoxy}-N-(methoxycarbonyl)-methanesulfonamide | 558.1 |
| 223 | C-(5-Chloro-2-{2-[4-(3,4-difluoro-benzyl)-(2R,5S)-2,5-dimethyl-piperazin-1-yl]-2-oxo-ethoxy}-phenyl)-N-(methoxycarbonyl)-methanesulfonamide | 560.1 |
| 224 | N-(5-Chloro-2-{2-[4-(4-fluoro-benzyl)-(2R)-2-methyl-piperazin-1-yl]-2-oxo-ethoxy}-pyridin-3-yl)-2,2-dimethyl-succinamic acid | 521.2 |
| 225 | [(5-Chloro-2-{2-[4-(4-fluoro-benzyl)-(2R,5S)-2,5-dimethyl-piperazin-1-yl]-2-oxo-ethoxy}-pyridine-2-carbonyl)-amino]-acetic acid | 493.2 |
| 226 | N-(5-Chloro-2-{2-[4-(4-fluoro-benzyl)-(2R,5S)-2,5-dimethyl-piperzin-1-yl]-2-oxo-ethoxy}-pyridin-2-yl)-succinamic acid | 507.2 |
| 227 | 3-(5-Chloro-2-{2-[4-(4-fluoro-benzyl)-(2R,5S)-2,5-dimethyl-piperazin-1-yl]-2-oxo-ethoxy}-pyridin-3-yl)-succinamic acid | 462.2 |
| 228 | 3-(5-Chloro-2-{2-[4-(4-fluoro-benzyl)-(2R,5S)-2,5-dimethyl-piperazin-1-yl]-2-oxo-ethylamino}-pyridin-3-yl)-propionic acid | 463.4, 461.4 |
| 229 | N-[3-(5-Chloro-2-{2-[4-(4-fluoro-benzyl)-(2R,5S)-2,5-dimethyl-piperazin-1-yl]-2-oxo-ethoxy}-pyridin-3-yl)-propionyl]-methanesulfonamide | 541 |
| 230 | 2-Amino-3-(5-chloro-2-{2-[4-(4-fluoro-benzyl)-(2R,5S)-2,5-dimethyl-piperazin-1-yl]-2-oxo-ethoxy}-pyridin-3-yl)-propionic acid | 479.4, 477.7 |
| 231 | [(5-Chloro-2-{2-[4-(4-fluorobenzyl)-(2R,5S)-2,5-dimethyl-piperazin-1-yl]-2-oxo-ethoxy}-pyridin-2-ylmethyl)-amino]-acetic acid | 479.2, 477.5 |
| 232 | 2-(5-Chloro-2-{2-[4-(4-fluoro-benzyl)-(2R,5S)-2,5-dimethyl-piperazin-1-yl]-2-oxo-ethoxy}-phenyoxy)-6-methyl-pyrimidine-4-carboxylic acid | 543.2, 545.3 |
| 233 | 2-(5-Chloro-2-{2-[4-(4-fluoro-benzyl)-(2R,5S)-2,5-dimethyl-piperazin-1-yl]-2-oxo-ethoxy}-phenoxy)-4-methyl-thiazol-5-carboxylic acid | 548.1, 550.2 |
| 234 | 6-(5-Chloro-2-{2-[4-(4-fluoro-benzyl)-(2R,5S)-2,5-dimethyl-piperazin-1-yl]-2-oxo-ethoxy}-phenoxy)-nicotinic acid | 528.1, 530.2 |
| 235 | 2-(5-Chloro-2-{2-[4-(4-fluoro-benzyl)-(2R,5S)-2,5-dimethyl-piperazin-1-yl]-2-oxo-ethoxy}-phenoxymethyl)-nicotinic acid | 542.4, 544.5 |
| 236 | 6-[(5-Chloro-2-{2-[4-(4-fluoro-benzyl)-(2R,5S)-2,5-dimethyl-piperazin-1-yl]-2-oxo-ethoxy}-pyridin-3-ylamino)-methyl]-nicotinic acid | 542.0 |
| 237 | 2-[4-Chloro-2-(2H-tetrazol-5-yloxy)-phenoxy]-1-[4-(4-fluoro-benzyl)-(2R,5S)-2,5-dimethyl-piperazin-1-yl]-ethanone | 473.4, 475.4 |
| 238 | 2-[4-Bromo-2-(2H-tetrazol-5-yloxy)-phenoxy]-1-[4-(4-fluoro-benzyl)-(2R)-2-methyl-piperazin-1-yl]-ethanone | 505.2, 507.2 |
| 239 | (5-Chloro-2-{2-[4-(4-fluoro-benzyl)-(2R)-2-methyl-piperazin-1-yl]-2-oxo-ethoxy}-phenyl)-acetic acid | 435 |
| 240 | (5-Bromo-2-{2-[4-(4-fluoro-benzyl)-(2R,5S)-2,5-dimethyl-piperazin-1-yl]-2-oxo-ethoxy}-phenyl)-acetic acid | 495.1, 493.1 |
| 241 | (5-Bromo-2-{2-[4-(4-fluoro-benzyl)-(2R)-2-methyl-piperazin-1-yl]-2-oxo-ethoxy}-phenyl)-acetic acid | 479.1 |
| 242 | (2-{2-[4-(4-Fluoro-benzyl)-(2R,5S)-2,5-dimethyl-piperazin-1-yl]-2-oxo-ethoxy}-4-methoxy-phenyl)-acetic acid | 445.4 |
| 243 | 3-(5-Chloro-2-{2-[4-(4-fluoro-benzyl)-(2R)-2-methyl-piperazin-1-yl]-2-oxo-ethoxy}-phenyl)-propionic acid | 449.1, 447.3 |
| 244 | (4-Chloro-2-{2-[4-(4-fluoro-benzyl)-(2R,5S)-2,5-dimethyl-piperazin-1-yl]-2-oxo-ethoxy}-phenyl)-acetic acid | 449.2, 447.4 |
| 245 | (4-Chloro-2-{2-[4-(4-fluoro-benzyl)-(2R)-2-methyl-piperazin-1-yl]-2-oxo-ethoxy}-phenyl)-acetic acid | 435.2, 433.4 |
| 246 | 3-(2-{2-[4-(4-Fluoro-benzyl)-(2R)-2-methyl-piperazin-1-yl]-2-oxo-ethoxy}-5-methyl-phenyl)-propionic acid | 429.3 |
| 247 | 3-(2-{2-[4-(4-Fluoro-benzyl)-(2R,5S)-2,5-dimethyl-piperazin-1-yl]-2-oxo-ethoxy}-5-methyl-phenyl)-propionic acid | 443.3 |
| 248 | 3-(5-Bromo-2-{2-[4-(4-fluoro-benzyl)-(2R)-2-methyl-piperazin-1-yl]-2-oxo-ethoxy}-phenyl)-propionic acid | 493.1, 495.1 |
| 249 | 3-(5-Bromo-2-{2-[4-(4-fluoro-benzyl)-(2R,5S)-2,5-dimethyl-piperazin-1-yl]-2-oxo-ethoxy}-phenyl)-propionic acid | 507.1, 509.1 |
| 250 | (5-Chloro-2-{2-[4-(3,4-difluoro-benzyl)-(2R,5S)-2,5-dimethyl-piperazin-1-yl]-2-oxo-ethoxy}-phenyl)-acetic acid | 465.2 |
| 251 | (5-Chloro-2-{2-[4-(4-chloro-benzyl)-(2R,5S)-2,5-dimethyl-piperazin-1-yl]-2-oxo-ethoxy}-phenyl)-acetic acid | 467.2 |

TABLE 1-continued

Example compounds prepared

| Example | Name | LRMS |
|---|---|---|
| 252 | (5-Chloro-2-{2-[(2R)-2-ethyl-4-(4-fluoro-benzyl)-piperazin-1-yl]-2-oxo-ethoxy}-phenyl)-acetic acid | 449.2, 451.2 |
| 253 | (5-Bromo-2-{2-[(2R)-2-ethyl-4-(4-fluoro-benzyl)-piperazin-1-yl]-2-oxo-ethoxy}-phenyl)-acetic acid | 493.2, 495.2 |
| 254 | (5-Chloro-2-{2-[4-(4-chloro-benzyl)-(2R)-2-methyl-piperazin-1-yl]-2-oxo-ethoxy}-phenyl)-acetic acid | 451.1 |
| 255 | (5-Chloro-2-{2-[4-(3,4-difluoro-benzyl)-(2R)-2-methyl-piperazin-1-yl]-2-oxo-ethoxy}-phenyl)-acetic acid | 453.1 |
| 256 | (2-{2-[(2R)-2-Ethyl-4-(4-fluoro-benzyl)-piperazin-1-yl]-2-oxo-ethoxy}-5-methyl-phenyl)-acetic acid | 429.2 |
| 257 | (2-{2-[4-(4-Fluoro-benzyl)-(2R)-2-methyl-piperazin-1-yl]-2-oxo-ethoxy}-5-methyl-phenyl)-acetic acid | 415.2, 413.3 |
| 258 | (2-{2-[4-(4-Fluoro-benzyl)-(2R,5S)-2,5-dimethyl-piperazin-1-yl]-2-oxo-ethoxy}-5-methyl-phenyl)-acetic acid | 429.2, 427.3 |
| 259 | 3-(2-{2-[(2R)-2-Ethyl-4-(4-fluoro-benzyl)-piperazin-1-yl]-2-oxo-ethoxy}-5-methyl-phenyl)-propionic acid | 443.2 |

Throughout this application, various publications are referenced. The disclosures of these publications in their entireties are hereby incorporated by reference into this application for all purposes.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound of the formula I

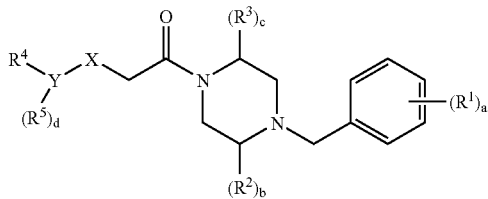

or a pharmaceutically acceptable form thereof; wherein
a is 0, 1, 2, 3, 4, or 5;
b is 0, 1, or 2;
c is 0, 1, or 2;
d is 0, 1, 2, 3, or 4;
X is —O—, —S—, —CH$_2$—, or —NR$^6$—;
Y is (C$_6$–C$_{10}$)aryl;
each R$^1$ is independently H—, HO—, halo-, (C$_1$–C$_8$)alkyl-, (C$_1$–C$_8$)alkyl-O—, HO—(C$_1$–C$_8$)alkyl-, NC—, H$_2$N—, H$_2$N—(C$_1$–C$_8$)alkyl-, HO—(C=O)—, (C$_1$–C$_8$)alkyl-(C=O)—, (C$_1$–C$_8$)alkyl-(C=O)—(C$_1$–C$_8$)alkyl-, H$_2$N—(C=O)—, or H$_2$N—(C=O)—(C$_1$–C$_8$)alkyl-;

each R$^2$ and R$^3$ are independently H—, oxo, (C$_1$–C$_8$)alkyl-, (C$_3$–C$_8$)cycloalkyl-(C$_1$–C$_8$)alkyl-, (C$_6$–C$_{10}$)aryl-, (C$_6$–C$_{10}$)aryl-(C$_1$–C$_8$)alkyl-, HO—(C$_1$–C$_8$)alkyl-, (C$_1$–C$_8$)alkyl-O—(C$_1$–C$_8$)alkyl-, H$_2$N—(C$_1$–C$_8$)alkyl-, (C$_1$–C$_8$)alkyl-NH—(C$_1$–C$_8$)alkyl-, [(C$_1$–C$_8$)alkyl]$_2$N—(C$_1$–C$_8$)alkyl-, (C$_2$–C$_9$)heterocyclyl-(C$_1$–C$_8$)alkyl-, (C$_3$–C$_8$)cycloalkyl-NH—(C$_1$–C$_8$)alkyl-, (C$_1$–C$_8$)alkyl-(C=O)—NH—(C$_1$–C$_8$)alkyl-, (C$_1$–C$_8$)alkyl-O—(C=O)—NH—(C$_1$–C$_8$)alkyl-, H$_2$N—(C=O)—NH—(C$_1$–C$_8$)alkyl-, (C$_1$–C$_8$)alkyl-SO$_2$—NH—(C$_1$–C$_8$)alkyl-, (C$_2$–C$_9$)heteroaryl-(C$_1$–C$_8$)alkyl-, H$_2$N—(C=O)—, or H$_2$N—(C=O)—(C$_1$–C$_8$)alkyl-;
R$^4$ is —HO—(C=O)—(C$_1$–C$_8$)alkyl][(C$_1$–C$_8$)alkyl]N—(C$_1$–C$_8$)alkyl-, HO—(C=O)—(C$_1$–C$_8$)alkyl-O—N=(C$_1$–C$_8$)alkyl-, HO—(C=O)—(C$_1$–C$_8$)alkyl-SO$_2$—, HO—(C=O)—(C$_1$–C$_8$)alkyl-SO$_2$—(C$_1$–C$_8$)alkyl-, HO—(C=O)—(C$_1$–C$_8$)alkyl-SO$_2$—NH—, HO—(C=O)—(C$_1$–C$_8$)alkyl-SO$_2$—NH—(C$_1$–C$_8$)alkyl-, HO—(C=O)—(C$_1$–C$_8$)alkyl-NH—SO$_2$—, HO—(C=O)—(C=O)—NH—SO$_2$—, HO—(C=O)—(C=O)—NH—SO$_2$—(C$_1$–C$_8$)alkyl-, HO—(C=O)—(C$_1$–C$_8$)alkyl-NH—(C=O)—NH—, HO—(C=O)—(C$_1$–C$_8$)alkyl-O—, HO—(C=O)—(C$_1$–C$_8$)alkyl-O—(C$_1$–C$_8$)alkyl-, HO—(C=O)—(C$_2$–C$_8$)alkenyl-, (C$_1$–C$_9$)heteroaryl-(C$_1$–C$_8$)alkyl-O—, (C$_1$–C$_9$)heteroaryl-O—, HO—(C=O)—(C$_1$–C$_8$)alkyl-S—, HO—(C=O)—(C=O)—, HO—(C=O)—(C$_1$–C$_8$)alkyl-(C=O)—, NC—NH—(C=O)—(C$_1$–C$_8$)alkyl, (C$_1$–C$_8$)alkyl-SO$_2$—NH—(C=O)—(C$_1$–C$_8$)alkyl-, (C$_6$–C$_{10}$)aryl-SO$_2$—NH—(C=O)—C$_1$–C$_8$)alkyl-, (C$_1$–C$_9$)heteroaryl-SO$_2$—NH—(C=O)—(C$_1$–C$_8$)alkyl-, H$_2$N—SO$_2$—NH—(C=O)—(C$_1$–C$_8$)alkyl-, (C$_1$–C$_8$)alkyl-SO$_2$—NH—(C=O)—(C$_1$–C$_8$)alkyl-O—, (C$_1$–C$_8$)alkyl-SO$_2$—NH—(C=O)—(C$_1$–C$_8$)alkyl-O—(C$_1$–C$_8$)alkyl-, H$_2$N—SO$_2$—(C$_1$–C$_8$)alkyl-, (C$_1$–C$_8$)alkyl-(C=O)—NH—SO$_2$—(C$_1$–C$_8$)alkyl-, HO—(C$_1$–C$_8$)alkyl-(C=O)—NH—SO$_2$—(C$_1$–C$_8$)alkyl-, (C$_1$–C$_8$)alkyl-NH—(C=O)—NH—SO$_2$—(C$_1$–C$_8$)alkyl-, (C$_6$–C$_{10}$)aryl-NH—(C=O)—NH—

SO$_2$—, (C$_1$–C$_8$)alkyl-O—(C═O)—NH—SO$_2$—, (C$_1$–C$_8$)alkyl-O—(C═O)—NH—SO$_2$—(C$_1$–C$_8$) alkyl-, (C$_1$–C$_8$)alkyl-SO$_2$—NH—(C═O)—O—(C$_1$–C$_8$)alkyl-, (C$_1$–C$_8$)alkyl-SO$_2$—NH—(C═O)—NH—(C$_1$–C$_8$)alkyl-, (C$_6$–C$_{10}$)aryl-SO$_2$—NH—(C═O)—O—(C$_1$–C$_8$)alkyl-, (C$_6$–C$_{10}$)aryl-SO$_2$—NH—(C═O)—NH—(C$_1$–C$_8$)alkyl-, (C$_1$–C$_8$)alkyl-(C═O)—NH—SO$_2$—NH—(C$_1$–C$_8$)alkyl, (C$_6$–C$_{10}$)aryl-(C═O)—NH—SO$_2$—NH—(C$_1$–C$_8$)alkyl, or (C$_1$–C$_9$)heteroaryl-(C$_1$–C$_8$)alkyl-(C═O)—;

each R$^5$ is independently H—, HO—, halo-, NC—, HO—(C═O)—, H$_2$N—, (C$_1$–C$_8$)alkyl-NH—, [(C$_1$–C$_8$)alkyl]$_2$N—, (C$_1$–C$_8$)alkyl-, (C$_1$–C$_8$)alkyl-O—, HO—(C$_1$–C$_8$)alkyl-, (C$_1$–C$_8$)alkyl-O—(C$_1$–C$_8$)alkyl-, H$_2$N—(C$_1$–C$_8$)alkyl-, (C$_1$–C$_8$)alkyl-NH—(C$_1$–C$_8$)alkyl-, [(C$_1$–C$_8$)alkyl]$_2$N—(C$_1$–C$_8$)alkyl-, (C$_1$–C$_8$)alkyl-(C═O)—, (C$_1$–C$_8$)alkyl-(C═O)—(C$_1$–C$_8$)alkyl-, (C$_6$–C$_{10}$)aryl-, (C$_2$–C$_9$)heteroaryl-, (C$_6$–C$_{10}$)aryloxy-, H$_2$N—(C═O)—, H$_2$N—(C═O)—(C$_1$–C$_8$)alkyl-, (C$_1$–C$_8$)alkyl-NH—(C═O)—, (C$_1$–C$_8$)alkyl-NH—(C═O)—(C$_1$–C$_8$)alkyl-, [(C$_1$–C$_8$)alkyl]$_2$N—(C═O)—, [(C$_1$–C$_8$)alkyl]$_2$—N—(C═O)—(C$_1$–C$_8$)alkyl-, (C$_3$–C$_8$)cycloalkyl-, (C$_1$–C$_8$)alkyl-SO$_2$—, NC—(C$_1$–C$_8$)alkyl-, (C$_1$–C$_8$)alkyl-(C═O)—NH—, H$_2$N—(C═O)—NH—, or H$_2$N—(C═O)—NH—(C$_1$–C$_8$)alkyl-; and R$^6$ is H, (C$_1$–C$_8$)alkyl-, (C$_1$–C$_8$)alkyl-(C═O)—, (C$_6$–C$_{10}$)aryl-(C═O)—, (C$_2$–C$_9$)heteroaryl-(C═O)—, H$_2$N—(C═O)—, (C$_1$–C$_8$)alkyl-NH—(C═O)—, [(C$_1$–C$_8$)alkyl]$_2$N—(C═O)—, (C$_1$–C$_8$)alkyl-O—(C═O)—, or (C$_1$–C$_8$)alkyl-SO$_2$—.

2. A compound according to claim 1, wherein R$^4$ is [HO—(C═O)—(C$_1$–C$_8$)alkyl][(C$_1$–C$_8$)alkyl]N—(C$_1$–C$_8$)alkyl-, HO—(C═O)—(C$_1$–C$_8$)alkyl-O—N═(C$_1$–C$_8$)alkyl-, HO—(C═O)—(C$_1$–C$_8$)alkyl-SO$_2$—, HO—(C═O)—(C$_1$–C$_8$)alkyl-SO$_2$—(C$_1$–C$_8$)alkyl-, HO—(C═O)—(C$_1$–C$_8$)alkyl-SO$_2$—NH—, HO—(C═O)—(C$_1$–C$_8$)alkyl-SO$_2$—NH—(C$_1$–C$_8$)alkyl-, HO—(C═O)—(C$_1$–C$_8$)alkyl-NH—SO$_2$—, HO—(C═O)—(C═O)—NH—SO$_2$—, HO—(C═O)—(C═O)—NH—SO$_2$—(C$_1$–C$_8$)alkyl-, HO—(C═O)—(C$_1$–C$_8$)alkyl-NH—(C═O)—NH—, HO—(C═O)—(C$_1$–C$_8$)alkyl-O—, HO—(C═O)—(C$_1$–C$_8$)alkyl-O—(C$_1$–C$_8$)alkyl-, HO—(C═O)—(C$_2$–C$_8$)alkenyl-, HO—(C═O)—(C$_1$–C$_8$)alkyl-S—, HO—(C═O)—(C═O)—, HO—(C═O)—(C$_1$–C$_8$)alkyl-(C═O)—, NC—NH—(C═O)—(C$_1$–C$_8$)alkyl, (C$_1$–C$_8$)alkyl-SO$_2$—NH—(C═O)—(C$_1$–C$_8$)alkyl-, (C$_6$–C$_{10}$)aryl-SO$_2$—NH—(C═O)—(C$_1$–C$_8$)alkyl-, H$_2$N—SO$_2$—NH—(C═O)—(C$_1$–C$_8$)alkyl-, (C$_1$–C$_8$)alkyl-SO$_2$—NH—(C═O)—(C$_1$–C$_8$)alkyl-O—, (C$_1$–C$_8$)alkyl-SO$_2$—NH—(C═O)—(C$_1$–C$_8$)alkyl-O—(C$_1$–C$_8$)alkyl-, H$_2$N—SO$_2$—(C$_1$–C$_8$)alkyl-, (C$_1$–C$_8$)alkyl-(C═O)—NH—SO$_2$—(C$_1$–C$_8$)alkyl-, HO—(C$_1$–C$_8$)alkyl-(C═O)—NH—SO$_2$—(C$_1$–C$_8$)alkyl-, (C$_1$–C$_8$)alkyl-NH—(C═O)—NH—SO$_2$—(C$_1$–C$_8$)alkyl-, (C$_6$–C$_{10}$)aryl-NH—(C═O)—NH—SO$_2$—, (C$_1$–C$_8$)alkyl-O—(C═O)—NH—SO$_2$—, (C$_1$–C$_8$)alkyl-O—(C═O)—NH—SO$_2$—(C$_1$–C$_8$)alkyl-, (C$_1$–C$_8$)alkyl-SO$_2$—NH—(C═O)—O—(C$_1$–C$_8$)alkyl-, (C$_1$–C$_8$)alkyl-SO$_2$—NH—(C═O)—NH—(C$_1$–C$_8$)alkyl-, (C$_6$–C$_{10}$)aryl-SO$_2$—NH—(C═O)—O—(C$_1$–C$_8$)alkyl-, (C$_6$–C$_{10}$)aryl-SO$_2$—NH—(C═O)—NH—(C$_1$–C$_8$)alkyl-, (C$_6$–C$_{10}$)aryl-(C═O)—NH—SO$_2$—NH—(C$_1$–C$_8$)alkyl, (C$_6$–C$_{10}$)aryl-(C═O)—NH—SO$_2$—NH—(C$_1$–C$_8$)alkyl.

3. A compound according to claim 1, wherein the pharmaceutically acceptable form is a pharmaceutically acceptable salt thereof.

4. A compound according to claim 1, wherein the stereochemistry is as depicted in formula Ia and b is 0 or 1 and c is 1:

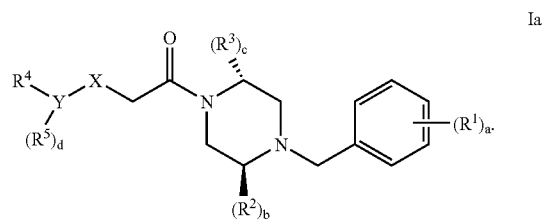

Ia

5. A compound according to claim 4, wherein each R$^1$ is independently H—, HO—, halo, NC—, (C$_1$–C$_8$)alkyl, or (C$_1$–C$_8$)alkyl-O—; and a is 1 or 2.

6. A compound according to claim 5, wherein R$^2$ is H— or (C$_1$–C$_8$)alkyl- and R$^3$ is (C$_1$–C$_8$)alkyl-.

7. A compound according to claim 6, wherein X is —O— or —NR$^6$— and R$^6$ is H—.

8. A compound according to claim 7, wherein d is 1 or 2, and R$^5$ is H—, HO—, NC—, (C$_1$–C$_8$)alkyl-, (C$_1$–C$_8$)alkyl-O—, (C$_1$–C$_8$)alkyl-(C═O)—, or halo.

9. A compound according to claim 8, wherein R$^4$ is [HO—(C═O)—(C$_1$–C$_8$)alkyl][(C$_1$–C$_8$)alkyl]N—(C$_1$–C$_8$)alkyl-, (C$_1$–C$_8$)alkyl-SO$_2$—NH—(C═O)—(C$_1$–C$_8$)alkyl-, (C$_1$–C$_9$)heterocyclyl-SO$_2$—NH—(C═O)—(C$_1$–C$_8$)alkyl-, H$_2$N—SO$_2$—NH—(C═O)—(C$_1$–C$_8$)alkyl-, (C$_1$–C$_8$)alkyl-SO$_2$—NH—(C═O)—(C$_1$–C$_8$)alkyl-O—, (C$_1$–C$_8$)alkyl-SO$_2$—NH—(C═O)—(C$_1$–C$_8$)alkyl-O—(C$_1$–C$_8$)alkyl-, H$_2$N—SO$_2$—(C$_1$–C$_8$)alkyl-, (C$_1$–C$_8$)alkyl-(C═O)—NH—SO$_2$—(C$_1$–C$_8$)alkyl-, HO—(C$_1$–C$_8$)alkyl-(C═O)—NH—SO$_2$—(C$_1$–C$_8$)alkyl-, (C$_1$–C$_8$)alkyl-NH—(C═O)—NH—SO$_2$-(C$_1$–C$_8$)alkyl-, (C$_1$–C$_8$)alkyl-SO$_2$—NH—(C═O)—NH—(C$_1$–C$_8$)alkyl-, (C$_1$–C$_8$)alkyl-(C═O)—NH—SO$_2$—NH—(C$_1$–C$_8$)alkyl, HO—(C═O)—(C$_1$–C$_8$)alkyl-O—, HO—(C═O)—(C$_1$–C$_8$)alkyl-O—(C$_1$–C$_8$)alkyl-, (C$_1$–C$_9$)heteroaryl-(C$_1$–C$_8$)alkyl-O—, (C$_1$–C$_9$)heterocyclyl-O—, (C$_1$–C$_9$)heteroaryl-O—, HO—(C═O)—(C$_1$–C$_8$)alkyl-S—, HO—(C═O)—(C$_1$–C$_8$)alkyl-SO$_2$—, HO—(C═O)—(C$_1$–C$_8$)alkyl-SO$_2$—(C$_1$–C$_8$)alkyl-, HO—(C═O)—(C$_1$–C$_8$)alkyl-(C═O)—, or (C$_1$–C$_9$)heteroaryl-(C$_1$–C$_8$)alkyl-(C═O)—.

10. A compound according to claim 9, wherein Y is (C$_6$–C$_{10}$)aryl.

11. A compound according to claim 4, wherein R$^4$ is [HO—(C═O)—(C$_1$–C$_8$)alkyl][(C$_1$–C$_8$)alkyl]N—(C$_1$–C$_8$)alkyl-, (C$_1$–C$_9$)heteroaryl-SO$_2$—NH—(C═O)—(C$_1$–C$_8$)alkyl-, H$_2$N—SO$_2$—NH—(C═O)—(C$_1$–C$_8$)alkyl-, (C$_1$–C$_8$)alkyl-SO$_2$—NH—(C═O)—(C$_1$–C$_8$)alkyl-O—, (C$_1$–C$_8$)alkyl-SO$_2$—NH—(C═O)—(C$_1$–C$_8$)alkyl-O—(C$_1$–C$_8$)alkyl-, H$_2$N—SO$_2$—(C$_1$–C$_8$)alkyl-, (C$_1$–C$_8$)alkyl-(C═O)—NH—SO$_2$—(C$_1$–C$_8$)alkyl-, HO—(C$_1$–C$_8$)alkyl-(C═O)—NH—SO$_2$—(C$_1$–C$_8$)alkyl-, (C$_1$–C$_8$)alkyl-NH—(C═O)—NH—SO$_2$-(C$_1$–C$_8$)alkyl-, (C$_1$–C$_8$)alkyl-SO$_2$—NH—(C═O)—NH—(C$_1$–C$_8$)alkyl-, (C$_1$–C$_8$)alkyl-(C═O)—NH—SO$_2$—NH—(C$_1$–C$_8$)alkyl, HO—(C═O)—(C$_1$–C$_8$)alkyl-O—, HO—(C═O)—(C$_1$–C$_8$)alkyl-O—(C$_1$–C$_8$)alkyl-, (C$_1$–C$_9$)heteroaryl-(C$_1$–C$_8$)alkyl-O—, (C$_1$–C$_9$)heterocyclyl-O—, (C$_1$–C$_9$)heteroaryl-O—, HO—(C═O)—(C$_1$–C$_8$)alkyl-S—, HO—(C═O)—(C$_1$–C$_8$)alkyl-SO$_2$—, HO—(C═O)—(C$_1$–C$_8$)alkyl-SO$_2$-(C$_1$–C$_8$)alkyl-, HO—(C═O)—(C$_1$–C$_8$)alkyl-(C═O)—, or (C$_1$–C$_9$)heteroaryl-(C$_1$–C$_8$)alkyl-(C═O).

12. A compound according to claim 11, wherein a is 1 or 2;

X is —O— or —NR$^6$—;

each R$^1$ is independently H—, HO—, halo, NC—, $(C_1-C_8)$alkyl, or $(C_1-C_8)$alkyl-O—;

R$^2$ and R$^3$ are each independently H—, $(C_1-C_8)$alkyl-, $(C_3-C_8)$cycloalkyl-, $(C_3-C_8)$cycloalkyl-$(C_1-C_8)$alkyl-, $(C_6-C_{10})$aryl-, $(C_6-C_{10})$aryl-$(C_1-C_8)$alkyl-, HO—$(C_1-C_8)$alkyl-, H$_2$N—$(C_1-C_8)$alkyl-, $(C_1-C_9)$heterocyclyl-$(C_1-C_8)$alkyl-, $(C_1-C_8)$alkyl-O—(C=O)—NH—$(C_1-C_8)$alkyl-, H$_2$N—(C=O)—NH—$(C_1-C_8)$alkyl-, $(C_1-C_8)$alkyl-SO$_2$—NH—$(C_1-C_8)$alkyl-, $(C_1-C_9)$heteroaryl-$(C_1-C_8)$alkyl-, H$_2$N—(C=O)—, or H$_2$N—(C=O)—$(C_1-C_8)$alkyl-; and R$^5$ is H—, HO—, NC—, $(C_1-C_8)$alkyl-, $(C_1-C_8)$alkyl-O—, $(C_1-C_8)$alkyl-(C=O)—, or halo.

13. A compound according to claim 12, wherein a is 1 or 2;

d is 1 or 2;

X is —O—;

Y is $(C_6-C_{10})$aryl;

R$^1$ is halo;

R$^2$ is H— or $(C_1-C_8)$alkyl-;

R$^3$ is $(C_1-C_8)$alkyl-; and

R$^5$ is H—, halo, $(C_1-C_8)$alkyl-, or$(C_1-C_8)$alkyl-O—.

14. A compound according to claim 13, wherein R$^4$ is $(C_1-C_9)$heteroaryl-SO$_2$—NH—(C=O)—$(C_1-C_8)$alkyl-, H$_2$N—SO$_2$—NH—(C=O)—$(C_1-C_8)$alkyl-, $(C_1-C_8)$alkyl-SO$_2$—NH—(C=O)—$(C_1-C_8)$alkyl-O—, $(C_1-C_8)$alkyl-SO$_2$—NH—(C=O)—$(C_1-C_8)$alkyl-O—$(C_1-C_8)$alkyl-, $(C_1-C_8)$alkyl-NH—(C=O)—NH—SO$_2$—$(C_1-C_8)$alkyl-, $(C_1-C_8)$alkyl-SO$_2$—NH—(C=O)—NH—$(C_1-C_8)$alkyl-, $(C_1-C_8)$alkyl-(C=O)—NH—SO$_2$—NH—$(C_1-C_8)$alkyl, HO—(C=O)—$(C_1-C_8)$alkyl-SO$_2$—, HO—(C=O)—$(C_1-C_8)$alkyl-SO$_2$—$(C_1-C_8)$alkyl-, HO—(C=O)—$(C_1-C_8)$alkyl-(C=O)—, HO—(C=O)—$(C_1-C_8)$alkyl-O—N=$(C_1-C_8)$alkyl-, HO—(C=O)—$(C_1-C_8)$alkyl-SO$_2$—NH—, or HO—(C=O)—$(C_1-C_8)$alkyl-NH—SO$_2$—.

15. A compound selected from the group consisting of:

(2-{2-[4-(4-Fluoro-benzyl)-(2R)-2-methyl-piperazin-1-yl]-2-oxo-ethoxy}-5-trifluoromethyl-phenyl)-methanesulfonamide;

(2-{3-[4-(4-Fluoro-benzyl)-(2R,5S)-2,5-dimethyl-piperazin-1-yl]-3-oxo-propyl}-5-methyl-phenoxy)-acetic acid;

(5-Bromo-2-{2-[(2R)-2-ethyl-4-(4-fluoro-benzyl)-piperazin-1-yl]-2-oxo-ethoxy}-phenyl)-methanesulfonamide;

(5-Bromo-2-{2-[4-(4-chloro-benzyl)-(2R)-2-methyl-piperazin-1-yl]-2-oxo-ethoxy}phenyl)methanesulfonamide;

(5-Chloro-2-{2-[4-(4-fluoro-benzyl)-(2R,5S)-2,5-dimethyl-piperazin-1-yl]-2-oxo-ethoxy}-benzyloxy)-acetyl methanesulfonamide;

2-(5-Chloro-2-{2-[4-(4-fluoro-benzyl)-(2R,5S)-2,5-dimethyl-piperazin-1-yl]-2-oxo-ethoxy}-phenoxy)-4-methyl-thiazole-5-carboxylic acid;

3-(5-Chloro-2-{2-[4-(4-fluoro-benzyl)-(2R)-2-methyl-piperazin-1-yl]-2-oxo-ethoxy}-phenyl)-acrylic acid;

4-(5-Chloro-2-{2-[4-(4-fluoro-benzyl)-(2R)-2-methyl-piperazin-1-yl]-2-oxo-ethoxy}-phenyl)-4-oxo-butyric acid;

5-(5-Chloro-2-{2-[4-(4-fluoro-benzyl)-(2R,5S)-2,5-dimethyl-piperazin-1-yl]-2-oxo-ethoxy}-phenoxy)-5-methyl-pyrimidine-2,4,6-trione;

6-(5-Chloro-2-{2-[4-(4-fluoro-benzyl)-(2R,5S)-2,5-dimethyl-piperazin-1-yl]-2-oxo-ethoxy}-phenoxymethyl)-nicotinic acid;

C-(5-Chloro-2-{2-[4-(4-fluoro-benzyl)-(2R)-2-methyl-piperazin-1-yl]-2-oxo-ethoxy}-phenyl)-N-(3-hydroxy-3-methyl-butyryl)-methanesulfonamide;

C-(5-Chloro-2-{2-[4-(4-fluoro-benzyl)-(2R,5S)-2,5-dimethyl-piperazin-1-yl]-2-oxo-ethoxy}-phenyl)-N-hydroxyacetyl-methanesulfonamide;

N-[(2-{2-[4-(4-Fluoro-benzyl)-(2R,5S)-2,5-dimethyl-piperazin-1-yl]-2-oxo-ethoxy}-4-methoxy-phenyl)-acetyl]-methanesulfonamide; and N-[(5-Chloro-2-{2-[4-(4-fluoro-benzyl)-(2R,5S)-2,5-dimethyl-piperazin-1-yl]-2-oxo-ethoxy}-phenyl)-acetyl]-4-fluoro-benzenesulfonamide;

or a pharmaceutically acceptable form thereof.

16. A compound selected from the group consisting of:

(2S)-2-Amino-4-(5-chloro-2-{2-[4-(4-fluoro-benzyl)-(2R,5S)-2,5-dimethyl-piperazin-1-yl]-2-oxo-ethoxy}-phenoxy)-butyric acid;

(4S)-4-(5-Chloro-2-{2-[4-(4-fluoro-benzyl)-(2R,5S)-2,5-dimethyl-piperazin-1-yl]-2-oxo-ethoxy}-phenoxy)-pyrrolidine-(2S)-2-carboxylic acid;

(5-Bromo-2-{2-[4-(4-fluoro-benzyl)-(2R,5S)-2,5-dimethyl-piperazin-1-yl]-2-oxo-ethoxy}-benzylideneaminooxy)-acetic acid;

(5-Bromo-2-{2-[4-(4-fluoro-benzyl)-(2R,5S)-2,5-dimethyl-piperazin-1-yl]-2-oxo-ethoxy}-phenoxy)-acetic acid;

(5-Chloro-2-{2-[4-(4-fluoro-benzyl)-(2R,5S)-2,5-dimethyl-piperazin-1-yl]-2-oxo-ethoxy}-benzylsulfamoyl)-acetic acid;

3-(5-Chloro-2-{2-[4-(4-fluoro-benzyl)-(2R,5S)-2,5-dimethyl-piperazin-1-yl]-2-oxo-ethoxy}-phenyl)-acrylic acid;

4-(5-Chloro-2-{2-[4-(4-fluoro-benzyl)-(2R,5S)-2,5-dimethyl-piperazin-1-yl]-2-oxo-ethoxy}-phenyl)-4-oxo-butyric acid;

5-(5-Chloro-2-{2-[4-(4-fluoro-benzyl)-(2R,5S)-2,5-dimethyl-piperazin-1-yl]-2-oxo-ethoxy}-phenyl)-5-oxo-pentanoic acid;

(5-Chloro-2{-2-[4-(4-fluoro-benzyl)-(2R,5S)-2,5-dimethyl-piperazin-1-yl]-2-oxo-ethoxy}-benzylideneaminooxy)-acetic acid;

6-(5-Chloro-2-{2-[4-(4-fluoro-benzyl)-(2R,5S)-2,5-dimethyl-piperazin-1-yl]-2-oxo-ethoxy}-phenoxy)-nicotinic acid;

C-(5-Chloro-2-{2-[4-(4-fluoro-benzyl)-(2R,5S)-2,5-dimethyl-piperazin-1-yl]-2-oxo-ethoxy}-phenyl)-N-hydroxyacetyl-methanesulfonamide;

N-[(5-Bromo-2-{2-[4-(4-fluoro-benzyl)-(2R)-2-methyl-piperazin-1-yl]-2-oxo-ethoxy}-phenyl)-acetyl]-methanesulfonamide;

N-[(5-Chloro-2-{2-[4-(4-fluoro-benzyl)-(2R)-2-methyl-piperazin-1-yl]-2-oxo-ethoxy}-phenyl)-acetyl]-methanesulfonamide; and N-[(5-Chloro-2-{2-[4-(4-fluoro-benzyl)-(2R,5S)-2,5-dimethyl-piperazin-1-yl]-2-oxo-ethoxy}-phenyl)-acetyl]-methanesulfonamide;

or a pharmaceutically acceptable form thereof.

17. A compound selected from the group consisting of:

(2R)-2-(5-Chloro-2-{2-[4-(4-fluoro-benzyl)-(2R)-2-methyl-piperazin-1-yl]-2-oxo-ethoxy}-phenoxy)-propionic acid;

(4S)-4-(5-Chloro-2-{2-[4-(4-fluoro-benzyl)-(2R,5S)-2,5-dimethyl-piperazin-1-yl]-2-oxo-ethoxy}-phenoxy)-pyrrolidine-2-carboxylic acid;

(5-Chloro-2-{2-[4-(4-fluoro-benzyl)-(2R,5S)-2,5-dimethyl-piperazin-1-yl]-2-oxo-ethoxy}-phenylsulfamoyl)-acetic acid;

4-(5-Chloro-2-{2-[4-(4-fluoro-benzyl)-(2R,5S)-2,5-dimethyl-piperazin-1-yl]-2-oxo-ethoxy}-phenoxy)-pyridine-2-carboxylic acid;

4-(5-Chloro-2-{2-[4-(4-fluoro-benzyl)-(2R,5S)-2,5-dimethyl-piperazin-1-yl]-2-oxo-ethoxy}-phenyl)-but-3-enoic acid;

4-(5-Chloro-2-{2-[4-(4-fluoro-benzyl)-(2R,5S)-2,5-dimethyl-piperazin-1-yl]-2-oxo-ethoxy}-phenyl)-4-hydroxy-but-3-enoic acid;

N-[(5-Bromo-2-{2-[4-(4-fluoro-benzyl)-(2R,5S)-2,5-dimethyl-piperazin-1-yl]-2-oxo-ethoxy}-phenyl)-acetyl]-methanesulfonamide;

N-[(5-Chloro-2-{2-[4-(4-fluoro-benzyl)-(2R,5S)-2,5-dimethyl-piperazin-1-yl]-2-oxo-ethoxy}-phenyl)-acetyl]-sulfamide;

N-Acetyl-C-(5-bromo-2-{2-[4-(4-chloro-benzyl)-(2R)-2-methyl-piperazin-1-yl]-2-oxo-ethoxy}-phenyl)-methanesulfonamide;

N-Acetyl-C-(5-chloro-2-{2-[(2R)-2-ethyl-4-(4-fluoro-benzyl)-piperazin-1-yl]-2-oxo-ethoxy}-phenyl)-methanesulfonamide;

N-Acetyl-C-(5-chloro-2-{2-[4-(4-chloro-benzyl)-(2R,5S)-2,5-dimethyl-piperazin-1-yl]-2-oxo-ethoxy}-phenyl)-methanesulfonamide; and Propane-1-sulfonic acid [(5-chloro-2-{2-[4-(4-fluoro-benzyl)-(2R,5S)-2,5-dimethyl-piperazin-1-yl]-2-oxo-ethoxy}-phenyl)-acetyl]-amide;

or a pharmaceutically acceptable form thereof.

18. A pharmaceutical composition comprising a pharmaceutically effective amount of a compound according to any of claims 1 to 15 to 17, or a pharmaceutically acceptable form thereof, and a pharmaceutically acceptable carrier.

19. A compound of 4-(5-Chloro-2-{2-[4-(4-fluoro-benzyl)-(2R,5S)-2,5-dimethylpiperazin-1-yl]-2-oxo-ethoxy}-phenyl)-4-oxo-butyric acid or a pharmaceutically acceptable form thereof.

20. A compound of 4-(5-Chloro-2-{2-[4-(4-fluoro-benzyl)-(2R,5S)-2,5-dimethylpiperazin-1-yl]-2-oxo-ethoxy}-phenyl)-4-oxo-butyric acid or a pharmaceutically acceptable salt thereof.

* * * * *

UNITED STATES PATENT AND TRADEMARK OFFICE
CERTIFICATE OF CORRECTION

PATENT NO.        : 7,098,212 B2                                 Page 1 of 1
APPLICATION NO.   : 10/273658
DATED             : August 29, 2006
INVENTOR(S)       : Laura C. Blumberg et al.

It is certified that error appears in the above-identified patent and that said Letters Patent is hereby corrected as shown below:

Column 104, line 13:

please replace "1 to 15 to 17" with -- 1 to 17--.

Signed and Sealed this

Nineteenth Day of December, 2006

JON W. DUDAS
*Director of the United States Patent and Trademark Office*